US005510320A

United States Patent [19]

Tseng

[11] Patent Number: 5,510,320

[45] Date of Patent: Apr. 23, 1996

[54] HERBICIDAL TRIAZOLECARBOXAMIDES

[75] Inventor: Chi-Ping Tseng, Wilmington, Del.

[73] Assignee: E. I. Du Pont de Nemours and Company, Wilmington, Del.

[21] Appl. No.: 211,721

[22] PCT Filed: Oct. 22, 1992

[86] PCT No.: PCT/US92/08822

§ 371 Date: Apr. 26, 1994

§ 102(e) Date: Apr. 26, 1994

[87] PCT Pub. No.: WO93/09100

PCT Pub. Date: May 13, 1993

Related U.S. Application Data

[63] Continuation-in-part of Ser. No. 784,343, Oct. 29, 1991, abandoned.

[51] Int. Cl.$^6$ ........................ A01N 43/653; C07D 249/12

[52] U.S. Cl. .................... 504/273; 548/264.2; 548/264.4

[58] Field of Search ........................ 504/273; 548/264.2, 548/264.4

[56] References Cited

U.S. PATENT DOCUMENTS

| | | | |
|---|---|---|---|
| 3,952,001 | 4/1976 | Brookes et al. | 260/308 R |
| 4,087,269 | 5/1978 | Brookes et al. | 71/92 |
| 4,148,626 | 4/1979 | Brookes et al. | 71/92 |
| 4,251,262 | 2/1981 | Brookes et al. | 71/92 |
| 4,702,764 | 10/1987 | Nakayama et al. | 71/92 |

FOREIGN PATENT DOCUMENTS

| | | |
|---|---|---|
| 331072 | 8/1976 | Austria . |
| 0332133 | 9/1989 | European Pat. Off. . |
| 0422369 | 4/1991 | European Pat. Off. . |
| 0433804 | 6/1992 | European Pat. Off. . |
| 3929673 | 9/1989 | Germany . |
| 6-116263 | 4/1994 | Japan . |

*Primary Examiner*—Patricia L. Morris

[57] ABSTRACT

Herbicidal triazolecarboxamides are useful as agricultural chemicals. In particular the compounds are useful as herbicides, both general and selective, both post-emergent and pre-emergent. Examples of selective activity include excellent control of blackgrass and wild oats with outstanding wheat tolerance, and control of crabgrass, giant foxtail, barnyardgrass and blackgrass with outstanding tolerance to corn, soybeans, rice, cotton, wheat, sugarbeets and rape.

8 Claims, No Drawings

HERBICIDAL TRIAZOLECARBOXAMIDES

CROSS-REFERENCE TO RELATED APPLICATION

This application is a continuation-in-part of U.S. patent application Ser. No. 07/784,343, filed Oct. 29, 1991, now abandoned.

BACKGROUND OF THE INVENTION

This invention relates to certain substituted triazolecarboxamides which are useful as herbicides and their agriculturally suitable compositions as well as methods for their use as general or selective preemergent or postemergent herbicides or as plant growth regulants.

New compounds effective for controlling the growth of undesired vegetation are in constant demand. In the most common situation, such compounds are sought to selectively control the growth of weeds in useful crops such as cotton, rice, corn, wheat and soybeans, to name a few. Unchecked weed growth in such crops can cause significant losses, reducing profit to the farmer and increasing costs to the consumer. In other situations, herbicides are desired which will control all plant growth. Examples of areas in which complete control of all vegetation is desired are areas around railroad tracks, storage tanks and industrial storage areas. There are many products commercially available for these purposes, but the search continues for products which are more effective, less costly and environmentally safe.

EP-A-332,133 discloses triazole compounds of the formula:

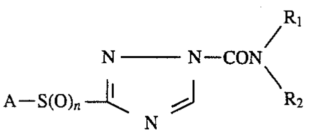

wherein
A is

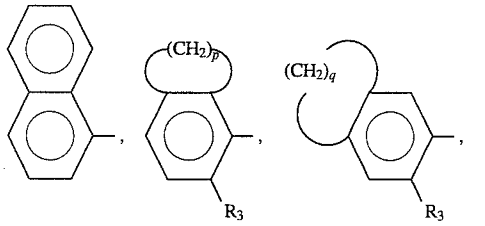

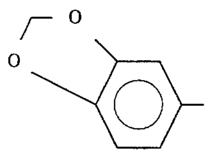

or

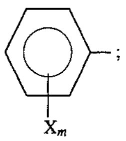

JP 1-106,883 discloses herbicides of the formula

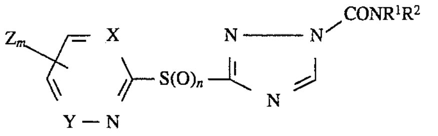

wherein, inter alia, X and Y are independently CH or N.

SUMMARY OF THE INVENTION

This invention comprises novel compounds of Formula I, agriculturally suitable compositions containing them, and their method-of-use as preemergent and/or postemergent herbicides or plant growth regulants.

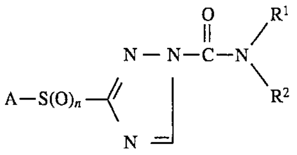

I wherein

A is a 5-membered heterocyclic ring containing 1 to 3 heteroatoms selected from the group 0–3 nitrogens, 0–1 oxygen and 0–1 sulfur, and is substituted with 1 to 4 substituents selected from $R^3$, $R^4$, $R^5$ and $R^6$;

$R^1$ is H; $C_1$–$C_6$ alkyl optionally substituted with $C_1$–$C_3$ alkoxy or 1 to 5 halogens; $C_3$–$C_6$ cycloalkyl; $C_2$–$C_6$ alkenyl optionally substituted with 1 to 3 halogens; $C_3$–$C_6$ alkynyl; or $C_1$–$C_3$ alkoxy;

$R^2$ is $C_1$–$C_6$ alkyl optionally substituted with $C_1$–$C_3$ alkoxy or 1 to 5 halogens; $C_3$–$C_6$ cycloalkyl; $C_2$–$C_6$ alkenyl optionally substituted with 1 to 3 halogens; or $C_3$–$C_6$ alkynyl;

$R^1$ and $R^2$may be taken together to form $—(CH_2)_3—$, $—(CH_2)_4—$, $—(CH_2)_5—$ or $—(CH_2)_6—$, each ring optionally substituted with 1 to 3 substituents selected from halogen and $C_1$–$C_3$ alkyl;

$R^3$, $R^4$ and $R^5$ are independently H; halogen; $C_1$–$C_6$ alkyl optionally substituted with one or more halogen, $C_1$–$C_6$ alkoxy, CN, $CO_2R^7$, $S(O)_mR^8$, $C(O)NR^9R^{10}$ or $SO_2NR^{13}R^{14}$; $C_3$–$C_6$ cycloalkyl; $C_2$–$C_6$ alkenyl; $C_2$–$C_6$ haloalkenyl; $C_2$–$C_6$ alkynyl; $C_1$–$C_6$ alkoxy; CN; $CO_2R^{11}$; $S(O)_pR^{12}$; $C(O)NR^{15}R^{16}$; $SO_2NR^{17}R^{18}$; $C(O)R^{19}$, $C(OR^{20})(OR^{21})R^{22}$; $CR^{23}{=}NOR^{24}$; $NO_2$; $NR^{25}R^{26}$; or phenyl or benzyl, each ring optionally substituted with 1 to 3 substituents selected from halogen, $C_1$–$C_3$ alkyl, $C_1$–$C_3$ haloalkyl and $C_1$–$C_3$ alkoxy;

$R^6$ is H; $C_1$–$C_6$ alkyl optionally substituted with one or more halogen, $C_1$–$C_6$ alkoxy, CN, $CO_2R^7$, $S(O)_mR^8$, $C(O)NR^9R^{10}$ or $SO_2NR^{13}R^{14}$; $C_2$–$C_6$ alkenyl; $C_2$–$C_6$ haloalkenyl; $C_2$–$C_6$ alkynyl; CN; $CO_2R^{11}$; $SO_2R^{12}$; $C(O)NR^{15}R^{16}$; $SO_2NR^{17}R^{18}$; phenyl or benzyl, each ring optionally substituted with 1 to 3 substituents selected from halogen, $C_1$–$C_3$ alkyl, $C_1$–$C_3$ haloalkyl and $C_1$–$C_3$ alkoxy; or pyridine, pyrimidine, thiazole, thiophene or pyrazole, each ring optionally substituted with 1 to 3 substituents selected from halogen, $C_1$–$C_3$ alkyl, $C_1$–$C_3$ haloalkyl and $C_1$–$C_3$ alkoxy; and when A is

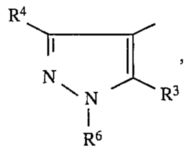

then $R^3$ and $R^6$ may be taken together as $—(CH_2)_3—$ or $—(CH_2)_4—$;

$R^7$ and $R^{11}$ are independently H, $C_1$–$C_3$ alkyl or allyl;

$R^8$ and $R^{12}$ are independently $C_1$–$C_3$ alkyl;

$R^9$, $R^{10}$, $R^{13}$, $R^{14}$, $R^{15}$, $R^{16}$, $R^{17}$ and $R^{18}$ are independently H or $C_1$–$C_3$ alkyl;

$R^9$ and $R^{10}$ may be taken together to form a 5- or 6-membered ring; $R^{13}$ and $R^{14}$ may be taken together to form a 5- or 6-membered ring: $R^{15}$ and $R^{16}$ may be taken together to form a 5- or 6-membered ring; and $R^{17}$ and $R^{18}$ may be taken together to form a 5- or 6-membered ring;

$R^{19}$, $R^{22}$ and $R^{23}$ are independently H or $C_1$–$C_3$ alkyl;

$R^{20}$ and $R^{21}$ are independently $C_1$–$C_3$ alkyl or may be taken together to form a 5- or 6-membered ring;

$R^{24}$ is H or $C_1$–$C_3$ alkyl;

$R^{25}$ and $R^{26}$ are independently H, $C_1$–$C_3$ alkyl or may be taken together to form a 5- or 6-membered ring;

m, n and p are independently 0, 1 or 2;

provided that a) $R^3$, $R^4$ and $R^5$ are independently bonded to carbon, and $R^6$ is bonded to nitrogen; and b) when $S(O)_n$ is bonded to nitrogen then n is 2.

In the above definitions, the term "alkyl" includes straight chain or branched alkyl, e.g., methyl, ethyl, n-propyl, isopropyl or the different butyl isomers. Alkoxy includes methoxy, ethoxy, n-propyloxy, isopropyloxy, etc. Alkenyl includes straight chain or branched alkenes, e.g., 1-propenyl, 2-propenyl, 3-propenyl and the different butenyl isomers. Cycloalkyl includes cyclopropyl, cyclobutyl, cyclopentyl and cyclohexyl. The term "halogen", either alone or in compound words such as "haloalkenyl", means fluorine, chlorine, bromine or iodine. Further, when used in compound words said alkyl or alkenyl may be partially or fully substituted with halogen atoms, which may be the same or different.

Preferred for reasons including ease of synthesis and/or greater herbicidal efficacy are:

1. A compound of Formula I whereto n is 1 or 2.

2. A compound of Preferred 1 wherein A is

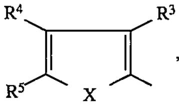,
A-1

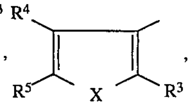,
A-2

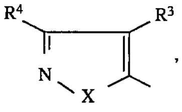,
A-3

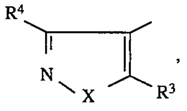,
A-4

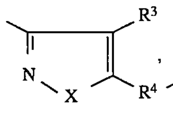,
A-5

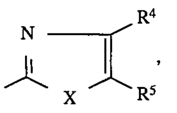,
A-6

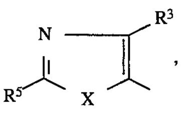,
A-7

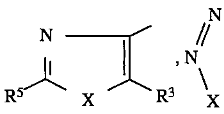,
A-8

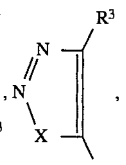,
A-9

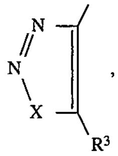,
A-10

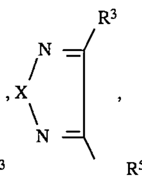,
A-11

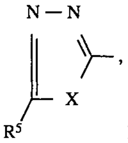,
A-12

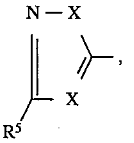,
A-13

-continued

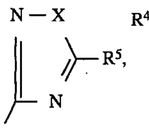
A-14

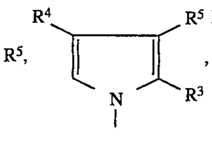,
A-15

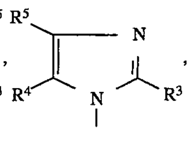,
A-16

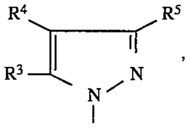,
A-17

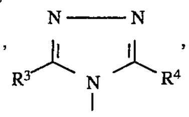,
A-18

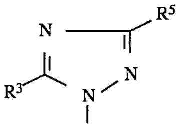
A-19 or

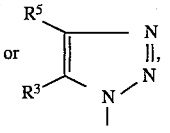,
A-20 wherein

X is $NR^6$, O or S.

3. A compound of Preferred 2 wherein n is 2 and $R^1$ and $R^2$ are independently $C_1$–$C_3$ alkyl or $C_2$–$C_3$ alkenyl.

4. A compound of Preferred 3 wherein A is selected from A-3, A-4, A-5 and A-17, and X is $NR^6$.

5. A compound of Preferred 4 wherein $R^3$, $R^4$ and $R^5$ are independently H; F; Cl; Br; $C_1$–$C_3$ alkyl optionally substituted with one or more F, Cl, Br or $C_1$–$C_3$ alkoxy; cyclopropyl; $C_2$–$C_3$ alkenyl; $C_2$–$C_3$ haloalkenyl; $C_2$–$C_3$ alkenyl; $C_1$–$C_3$ alkoxy; CN; $CO_2(C_1$–$C_2$ alkyl); $S(O)_p(C_1$–$C_2$ alkyl); $C(O)NR^{15}R^{16}$; $SO_2NR^{17}R^{18}$; $C(O)R^{19}$; $C(OR^{20})(OR^{21})R^{22}$; $CR^{23}$=$NOR^{24}$; $NO_2$; $NR^{25}R^{26}$; or phenyl optionally substituted with 1 to 3 substituents selected from halogen, $C_1$–$C_3$ alkyl, $C_1$–$C_3$ haloalkyl and $C_1$–$C_3$ alkoxy;

$R^6$ is H, $C_1$–$C_4$ alkyl optionally substituted with one or more F, Cl, Br. $C_1$–$C_3$ alkoxy, CN, $CO_2(C_1$–$C_2$ alkyl), $S(O)_m(C_1$–$C_2$ alkyl), $C(O)NR^9R^{10}$ or $SO_2NR^{13}R^{14}$; $C_2$–$C_4$ alkenyl; $C_2$–$C_4$ haloalkenyl; $C_2$–$C_4$ alkynyl; $CO_2R^{11}$; $SO_2(C_1$–$C_2$ alkyl); $C(O)NR^{15}R^{16}$; $SO_2NR^{17}R^{18}$; phenyl or benzyl, each ring optionally substituted with 1 to 3 substituents selected from halogen, $C_1$–$C_3$ alkyl, $C_1$–$C_3$ haloalkyl and $C_1$–$C_3$ alkoxy; or pyridine, pyrimidine or thiazole, each ring optionally substituted with 1 to 3 substituents selected from halogen, $C_1$–$C_3$ alkyl, $C_1$–$C_3$ haloalkyl and $C_1$–$C_3$ alkoxy;

$R^9$, $R^{10}$, $R^{13}$ and $R^{14}$ are independently $C_1$–$C_2$ alkyl;

$R^{11}$ is $C_1$–$C_2$ alkyl or allyl;

$R^{15}$, $R^{16}$, $R^{17}$, $R^{18}$, $R^{25}$ and $R^{26}$ are independently $C_1$–$C_3$ alkyl; and $R^{19}$, $R^{22}$ and $R^{23}$ are independently H or $C_1$–$C_2$ alkyl.

6. A compound of Preferred 5 wherein $R^1$ and $R^2$ are independently ethyl or allyl; and $R^5$ is H, cyclopropyl, Cl, $CH_3$, $C_2H_5$ or $CF_3$.

7. A compound of Preferred 6 wherein $R^3$ and $R^4$ are independently H, Cl, $C_1$–$C_3$ alkyl, $CF_3$, $C_1$–$C_2$ alkoxy or $C_2$–$C_3$ alkenyl; and $R^6$ is $C_1$–$C_3$ alkyl optionally substituted with 1 to 3 F, Cl, Br, $C_1$–$C_2$ alkoxy, CN, $CO_2(C_1$–$C_2$ alkyl)or $C(O)NR^9R^{10}$; allyl; propargyl; $C(O)NR^{15}R^{16}$; phenyl; pyridine; pyrimidine; or thiazole.

8. A compound of Preferred 7 selected from:

3-[(5-chloro-1-ethyl-3-methyl-1H-pyrazol-4-yl)sulfonyl]-N,N-diethyl-1H-1,2,4-triazole-1-carboxamide;

3-[(3,5-diethyl-1-methyl-1H -pyrazol-4-yl)sulfonyl]-N,N-diethyl-1 H-1,2,4-triazole-1-carboxamide; and 3-[[5-chloro-3-methyl-1-(2,2,2-trifluoroethyl)-1H-pyrazol-4-yl] sulfonyl]-N,N-diethyl-1H-1,2,4-triazole-1-carboxamide.

DETAILED DESCRIPTION OF THE INVENTION

Compounds of General Formula I can be readily prepared by one skilled in the art by using the reactions and techniques described in Scheme 1 to Scheme 29 below. In cases where the substituent of a starting material is not compatible with the reaction conditions described for any of the reaction schemes, it can be assumed that the substituent is convened to a protected form prior to the described reaction scheme and then deprotected after the reaction using commonly accepted protecting/deprotecting techniques (as an example, see T. W. Greene and P. G. M. Wuts, "Protective Groups in Organic Synthesis", 2nd Edition, John Wiley and Sons. Inc., New York, 1991). Otherwise alternative approaches known to one skilled in the art are available.

Scheme 1 illustrates the preparation of compounds of General Formula I (where n, A, $R^1$ and $R^2$ are defined as above) whereby the triazole derivative of General Formula II (where n and A are defined as above) is allowed to react with the carbamoyl halide of General Formula III (where $R^1$ and $R^2$ are defined as above; W is a halogen atom).

SCHEME 1

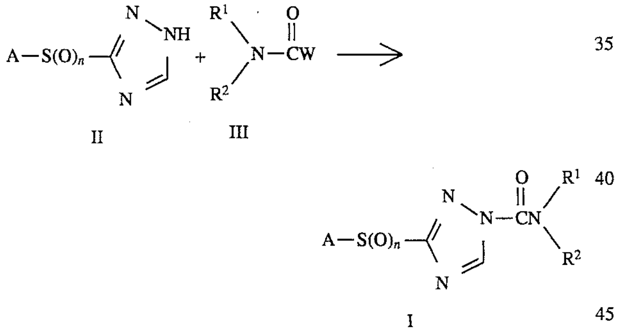

II III

I

This reaction is performed in an inert solvent such as acetonitrile, acetone. N,N-dimethylformamide, benzene, toluene, xylene, chloroform, dichloroethane, dioxane, tetrahydrofuran or methylethylketone and in the presence of a hydrogen halide removing agent such as trimethylamine, pyridine, sodium carbonate, potassium carbonate, sodium ethoxide, potassium t-butoxide or sodium hydride with the reaction temperature being between 0° and 140° C. and the reaction time being between 10 minutes and 100 hours.

One to 5 equivalents of hydrogen halide removing agent and 1 to 4 equivalents of carbamoyl halide of General Formula III are usually used per one equivalent of the triazole derivative of Formula II.

Upon completion of the reaction, the reaction mixture is concentrated under reduced pressure and water is added to the residue. The aqueous layer is then extracted with organic solvent. The organic extract is then dried and concentrated. The crude product can be further purified by means of flash column chromatography, recrystallization, or a similar operation if needed.

Scheme 2 illustrates the preparation of compounds of General Formula Ia (which are compounds of General Formula I where $R^1$ is H; A, n and $R^2$ are defined as above) whereby the triazole derivative of General Formula II (wherein A and n are defined as above) is allowed to react with an isocyanate of General Formula IV (wherein $R^2$ is defined as above).

SCHEME 2

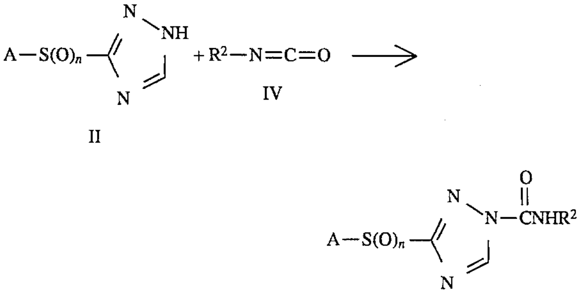

II IV

Ia

This reaction is performed in an inert solvent such as acetonitrile, N,N-dimethylformamide, benzene, toluene, xylene, chloroform, dichloroethane, dioxane, tetrahydrofuran or methylethylketone with or without a catalyst such as methylamine, pyridine, potassium t-butoxide or 1,8-diazabicyclo[5.4.0]-undec-7-ene (DBU). The reaction temperature ranges from 0° to 140° C. and the reaction time is between 10 minutes and 100 hours.

Upon completion of the reaction, the reaction mixture is concentrated under reduced pressure. Water is then added to the residue and the aqueous layer is extracted with organic solvent. The organic extract is dried and concentrated to give the crude product. This crude product can be further purified by flash column chromatography if needed.

Compounds of General Formula Ib (which are compounds of General Formula I where n is 1 or 2; A, $R^1$ and $R^2$ are defined as above; m is the same as n if applicable) can also be prepared by oxidizing the compounds of General Formula Ic (which are compounds of General Formula I where n is 0; A, $R^1$ and $R^2$ are defined as above) as illustrated in Scheme 3.

SCHEME 3

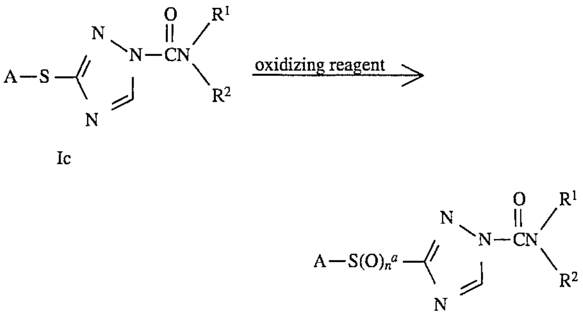

Ic

Ib wherein $n^a$ is 1 or 2

The oxidizing reagents that can be used in the process of Scheme 3 include 3-chloroperoxybenzoic acid, peracetic acid, trifluoroperacetic acid and hydrogen peroxide. This oxidation is normally performed in a solvent and the solvents that can be used will vary depending on the type of oxidizing reagent used. For example, if the oxidizing reagent is 3-chloroperoxybenzoic acid, benzene, methylene chloride, chloroform or other halogenated hydrocarbons can be used as solvent. If peracetic acid or trifluoroperacetic acid is used as the oxidizing reagent, halogenated hydrocarbons or the corresponding acid can be used as solvent. If the oxidant is hydrogen peroxide, water, acetone, acetic acid or the like can be used.

The reaction temperature range is normally 0° to 80° C. while the reaction time ranges from 10 minutes to 100 hours. In general, 0.9 to 1.2 equivalents of the oxidizing reagent are used for the preparation of compounds of General Formula Ib where n is 1. Two to five equivalents of oxidant are used for preparing compounds of General Formula Ib where n is 2. When substituent(s) on A contains sulfur atom(s), additional amounts of oxidant will be needed for the oxidation of the additional sulfur atom(s) on the substituent(s) to the desired oxidation state.

Upon completion of the reaction, methylsulfide or other reducing agents are added to destroy the unreacted oxidant. Water is then added followed by organic solvent extraction. If 3-chloroperoxybenzoic acid is used as the oxidant, the organic extract is washed with dilute basic aqueous solution such as sodium bicarbonate aqueous solution. The organic extract is then dried and concentrated to give the crude product. Flash column chromatography, recrystallization or a similar operation may be performed to further purify the crude product if needed.

Scheme 4 illustrates the preparation of compounds of General Formula Id (which are compounds of General Formula I where A is A-2; X is O; n is defined as above; $R^1$ is defined as above, other than H; $R^2$ is defined as above; $R^3$ is H, $C_3$–$C_6$ cycloalkyl, $C_2$–$C_6$ alkenyl, $C_2$–$C_6$ alkynyl, $C_1$–$C_6$ alkoxy or $C_1$–$C_6$ alkyl optionally substituted with one or more F, Cl, Br or $C_1$–$C_3$ alkoxy; $R^4$ is $C_1$–$C_6$ alkyl; $R^5$ is H or $C_1$–$C_6$ alkyl) whereby a triazolecarboxamide derivative of General Formula V is allowed to react with an acetylenic sulphonium salt of General Formula VI in the presence of a base.

SCHEME 4

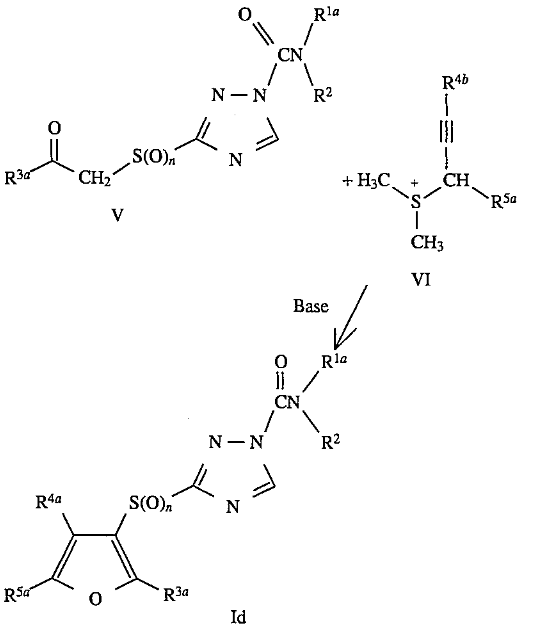

V

VI

Id wherein $R^{1a}$ is $R^1$ except H;

$R^{3a}$ is H, $C_3$–$C_6$ cycloalkyl, $C_2$–$C_6$ alkenyl, $C_2$–$C_6$ alkynyl, $C_1$–$C_6$ alkoxy or $C_1$–$C_6$ alkyl optionally substituted with one or more F, Cl, Br or $C_1$–$C_3$ alkoxy;

$R^{4a}$ is $C_1$–$C_6$ alkyl;

$R^{5a}$ is H or $C_1$–$C_6$ alkyl;

$R^{4b}$ is H or $C_1$–$C_5$ alkyl.

This reaction is carried out in a solvent such as acetonitrile, methylene chloride, N,N-dimethylformamide, dioxane, tetrahydrofuran, ethyl alcohol or t-butyl alcohol with reaction temperature ranging from 0° to 120° C. and reaction time being between 10 minutes and 100 hours.

One to two equivalents of base such as 1,8-diazabicyclo [5.4.0]-undec-7-ene (DBU), triethylamine, diisopropylethylamine, sodium ethoxide or potassium t-butoxide and 1 to 1.2 equivalents of the acetylenic sulphonium salt of General Formula VI are used per equivalent of the triazolecarboxamide derivative of General Formula V.

Upon completion of the reaction, the reaction mixture is concentrated under reduced pressure. The desired product is isolated from the residue by flash column chromatography.

Compounds of General Formula IIa (which are compounds of General Formula II where n is 2; A is defined as above) can be prepared by reacting the sulfonyl fluoride of General Formula VII with the lithium salt generated in situ from compounds of General Formula VIII (where $R^{28}$ is $C_1$–$C_4$ alkyl and the two $R^{28}$ groups may be taken together to form $—(CH_2)_3—$, $—(CH_2)_4—$, $—(CH_2)_5—$ or $—(CH_2)_6)—$ as illustrated in Scheme 5.

SCHEME 5

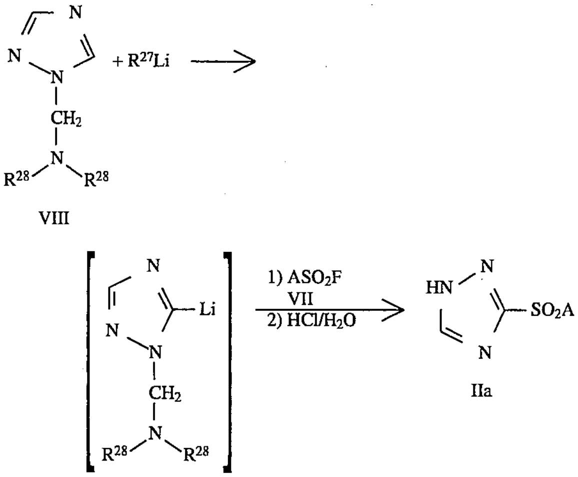

VIII

IIa wherein $R^{27}$ is n-butyl, 2-butyl or t-butyl;

A is defined as above.

In this reaction, the compound of General Formula VIII in an inert solvent such as diethylether, dimethoxyethane or tetrahydrofuran is cooled under $N_2$ to –60° C. to –100° C. and the solution of an alkyl Lithium such as n-butyllithium or t-butyllithium in an inert solvent such as hexane is slowly added dropwise to it. The resulting mixture is kept at –50° to –100° C. for a period of time ranging from 10 minutes to 2 hours. The sulfonyl fluoride of General Formula VII in an inert solvent such as diethylether or dimethoxyethane or tetrahydrofuran is then added while the reaction temperature is kept at –50° to –100° C. After the addition, the reaction mixture is allowed to warm up to room temperature and stirred at that temperature for 10 minutes to 5 hours. Aqueous hydrochloric acid is then added. The resulting mixture is allowed to stir for 10 minutes to 2 hours. Aqueous $NaHCO_3$ solution is then added to this mixture until a pH between 4 and 7 is reached. Organic solvent such as methylene chloride is then added. The mixture is then shaken in a separatory funnel. The organic layer is separated, dried over sodium sulfate or magnesium sulfate and concentrated to give the crude product. This crude product can be further purified through flash column chromatography, recrystallization or other similar operations. Alternatively, the reaction procedures taught by A. R. Katritzky et al., *Tetrahedron* 46(2), 641 (1990), or slight modifications thereof, can also be used for the reaction of Scheme 5. Compounds IIa can also be prepared from compounds I through alkaline hydrolysis by one skilled in the art.

Compounds of General Formula IIb (which are compounds of General Formula II where n is 0, A is defined as above) can be prepared by reacting the disulfide of General Formula IX (where A is defined as above) with the lithium salt generated in situ from compounds of General Formula VIII (where $R^{28}$ is $C_1$–$C_4$ alkyl) as illustrated in Scheme 6.

SCHEME 6

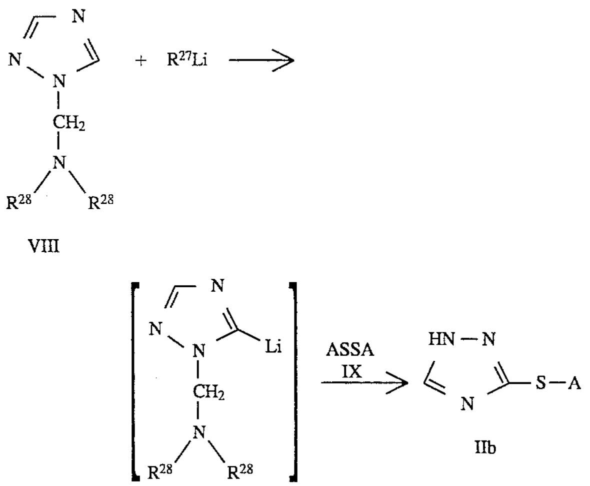

VIII

IIb wherein $R^{27}$ is n-butyl, 2-butyl or t-butyl.

In this reaction, the compound of General Formula VIII in an inert solvent such as diethylether, dimethoxyethane or tetrahydrofuran is cooled under $N_2$ to −60° C. to −100° C. and the solution of an alkyl lithium such n-butyl lithium or t-butyl lithium in an inert solvent such as hexane is slowly added dropwise to it. The resulting mixture is kept at −50° to −100° C. for a period of time ranging from 10 minutes to 2 hours. The disulfide of Genera/Formula IX in an inert solvent such as diethylether, dimethoxyethane or tetrahydrofuran is then added while the reaction temperature is kept at −50° to −100° C. After the addition, the reaction mixture is allowed to warm up to a temperature ranging from 20° C. to 60° C. and stirred at that temperature for 10 minutes to 5 hours. Aqueous hydrochloric acid is then added. The resulting mixture is allowed to stir for 10 minutes to 2 hours. Aqueous $NaHCO_3$ solution is then added to this mixture until a pH between 5 and 7 is reached. Organic solvent such as methylene chloride is then added. The mixture is then shaken in a separatory funnel. The organic layer is separated, dried over sodium sulfate or magnesium sulfate and concentrated to give the crude product. The crude product can be further purified by flash column chromatography, recrystallization or other similar operation. Alternatively, the reaction procedures taught by A. R. Katritzky et al., *Tetrahedron* 46(2), 641 (1990), or slight modifications thereof, can also be used for the reaction of Scheme 6.

Scheme 7 illustrates the preparation of compounds of General Formula IIc (which are compounds of Genera/ Formula II where n is 0, A is A-4; $R^3$ and $R^4$ are independently $C_1$–$C_6$ alkyl or $C_3$–$C_6$ cycloalkyl, X is O or $NR^6$) whereby a triazolylthiodiketone of Genera/Formula X is reacted with a hydrazinc or a hydroxylamine of General Formula XI.

SCHEME 7

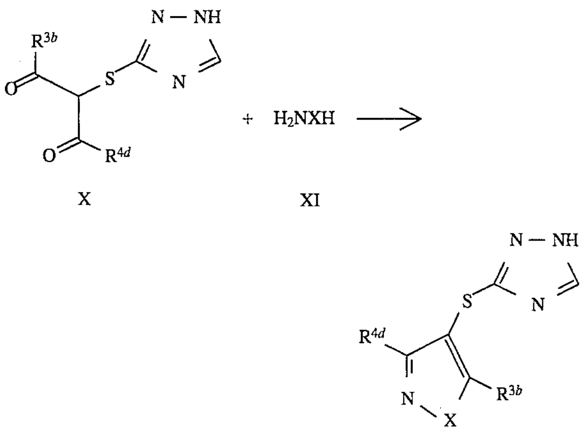

X

XI

IIc wherein $R^{4d}$ is $C_1$–$C_6$ alkyl or $C_3$–$C_6$ cycloalkyl;

$R^{3b}$ is $C_1$–$C_6$ alkyl or $C_3$–$C_6$ cycloalkyl;

X is O or $NR^6$.

This reaction is carried out in a solvent such as methanol, ethanol, isopropanol, N-N-dimethylformamide or acetonitrile with the reaction temperature between 25° C. and 140° C. for a period of time ranging from 0.5 to 500 hours. One to 3 equivalents of XI are usually used per equivalent of X.

Upon completion of the reaction, the reaction mixture is concentrated. Water is added to the residue. The aqueous layer is then extracted with organic solvent such as hexane, ether or methylene chloride. The organic extract is then dried over sodium sulfate or magnesium sulfate and concentrated under reduced pressure to give the desired product. This crude product may be further purified by flash column chromatography, recrystallization or other similar operation.

Scheme 8 illustrates the preparation of compounds of General Formula IId (which are compounds of General Formula II where n is 0, A is A-4; $R^3$ is Cl or Br; $R^4$ is $R^{4d}$; X is $NR^6$) whereby a triazolylthioheterocycle of General Formula XII (wherein $R^{4d}$ and $R^6$ are defined as above) is allowed to react with a halogenating agent such as phosphorous oxychloride or phosphorous oxybromide.

SCHEME 8

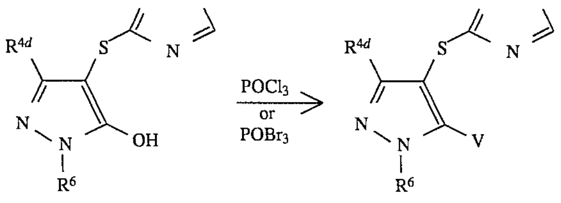

XII

IId wherein $R^{4d}$ is defined as above;

$R^6$ is defined as above;

V is Cl or Br.

This reaction is carried out in the absence of a solvent or in an inert solvent such as dioxane, chloroform, dichloroethane or toluene in a sealed tube or under atmospheric pressure. The reaction temperature is between 50° C. and 170° C. and the reaction time ranges from 2 to 50 hours. One to 100 equivalents of halogenating agent such as phosphorus oxychloride or phosphorus oxybromide are used per equivalent of the compound of General Formula XII.

Upon completion of the reaction, the solvent and/or the excess halogenating agent are evaporated under reduced pressure. Water is then added to the residue. The aqueous layer is then extracted with organic solvent such as ether or methylene chloride. The organic extract is dried over magnesium sulfate or sodium sulfate and then concentrated under reduced pressure to give the desired product. This crude product can be further purified by flash column chromatography, recrystallization or other similar operation.

Scheme 8a illustrates the preparation of compounds of General Formula IIg (which are compounds of General Formula II where n is 0, A is A-4; $R^3$ is $C_1$–$C_6$ alkoxy; $R^4$ is $R^{4d}$; X is $NR^6$) whereby a triazolylthioheterocycle of General Formula XII (wherein $R^{4d}$ and $R^6$ are defined as above) is allowed to react with an alkylating agent such as dialkylsulfate, alkyliodide, alkylbromide, or alkylsulfonate in the presence of a base such as potassium carbonate, sodium carbonate, potassium bicarbonate, triethylamine, or 1,8-diazabicyclo[5.4.0]-undec-7-ene (DBU).

SCHEME 8a

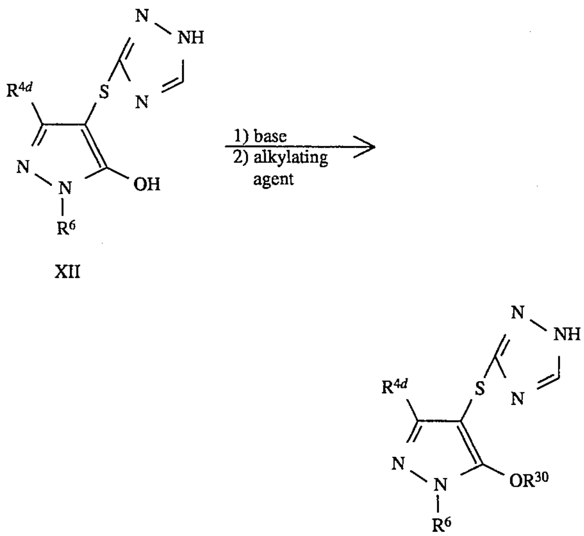

XII

IIg wherein $R^{4d}$ is defined as above;

$R^6$ is defined as above;

$R^{30}$ is $C_1$–$C_6$ alkyl.

To one equivalent of the compound of General Formula XII in an inert solvent such as acetone, dioxane, N,N-dimethylformamide is added one to twenty equivalents of a base. The resulting mixture is stirred at temperature between 0° C. and 150° C. for 1 to 150 hours. One to five equivalents of an alkylating agent is then added. The resulting mixture is stirred for another 1 to 100 hours at temperature between 0° C. and 150° C. The solvent is then evaporated. To the residue is added water. The aqueous solution is then extracted with an organic solvent such as methylene chloride or ethyl acetate. The organic extract is then dried over sodium sulfate or magnesium sulfate and concentrated under reduced pressure to give the desired product. This crude product may be further purified by flash column chromatography, recrystallization or other similar operation.

Scheme 9 illustrates the preparation of compounds of General Formula IIe (which are compounds of General Formula II where A is A-1 to A-14); whereby a halogen substituted heterocycle of General Formula XIII (wherein V is Cl or Br; $A^a$ is A-1 to A-14) is allowed to react with the anion of 1,2,4-triazole-3-thiol (Formula XIV).

SCHEME 9

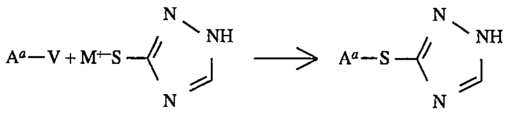

XIII XIV IIe wherein

M is Na, Li or K.

This reaction is carried out in a solvent such as N,N-dimethylformamide, ethanol, isopropanol or t-butyl alcohol at temperatures between 50° C. and 140° C. for a period of time between 30 minutes and 48 hours. One to 2 equivalents of XIV are usually used per equivalent of XIII.

Upon completion of the reaction, the reaction solvent is evaporated under reduced pressure and water is added to the residue. Aqueous hydrochloric acid is then added until the solution pH reaches about 7.

If the desired product precipitated out from the water, it is collected by filtration, air dried and then dried in an oven. Alternatively, organic solvent such as methylene chloride or ethyl acetate is added to extract the product out of the aqueous layer. The organic extract is then dried over sodium sulfate or magnesium sulfate and then concentrated to give the desired product. The crude product can be further purified by recrystallization, flash column chromatography or other similar operation.

Compounds of Genera/Formula III and General Formula IV are either commercially available or can be prepared by one skilled in the an.

Compounds of General Formula Va (which are compounds of Genera/ Formula V where n is 1 or 2; $R^1$, $R^2$ and $R^{3a}$ are defined as above) can be prepared by allowing compounds of General Formula Vb (which are compounds of General Formula V where n is 0; $R^1$, $R^2$ and $R^{3a}$ are defined as above) to react with the appropriate amount of an oxidizing reagent such as 3-chloroperoxybenzoic acid, peracetic acid, trifluoroperacetic acid or hydrogen peroxide as illustrated in Scheme 10.

SCHEME 10

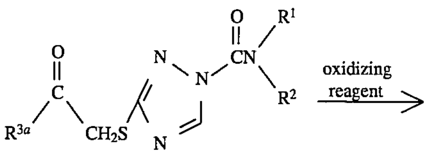

Vb

-continued

SCHEME 10

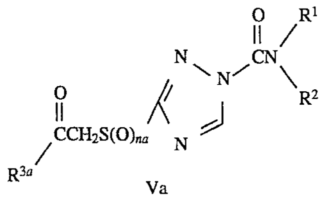

Va

The reaction conditions for Scheme 10 are very similar to those described for Scheme 3 with the exception that Vb is used instead of Ic.

Scheme 11 illustrates the preparation of compounds of General Formula Vb hereby the α-triazolylthioketone of General Formula XV (wherein $R^{3a}$ is defined as above) is allowed to react with the carbamoyl halide of General Formula III.

SCHEME 11

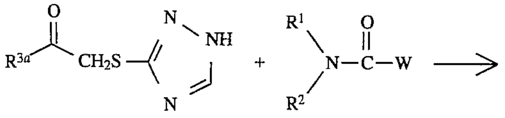

XV III

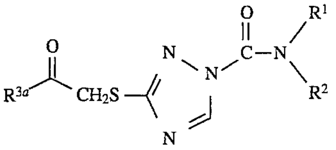

Vb

This reaction is performed in an inert solvent such as acetonitrile, N,N-dimethylformamide, toluene, chloroform or tetrahydrofuran and in the presence of a hydrogen halide removing agent such as triethylamine, pyridine or sodium carbonate at a temperature between 0° and 140° C. for a period of time ranging from 10 minutes to 100 hours. One to 5 equivalents of hydrogen halide removing agent and 1 to 4 equivalents of carbamoyl halide of General Formula III are usually used per equivalent of the triazole derivative of Formula XV.

Upon completion of the reaction, the reaction mixture is concentrated under reduced pressure and water is added to the residue. The product can be collected by filtration if it precipitates.

Alternatively, the aqueous solution is extracted with organic solvent. The organic extract is then dried and concentrated to give the desired product. The crude product can be further purified by means of recrystallization, flash column chromatography or a similar operation if needed.

Compounds of General Formula VI can be prepared using methods taught by G. D. Appleyard and C. J. M. Stirling in *J. Chem. Soc.* (C), 1904 (1969); and by J. W. Batty, P. D. Howes and C. J. M. Stirling in *J.C.S., Perkin I*, 65 (1973) or using slight modifications of the above-mentioned method.

Compounds of General Formula VIII can be prepared from 1,2,4-triazole, dialkylamine (or its hydrochloride salt) and formaldehyde using methods taught by Alan R. Katritzky, Gordon W. Rewcastle and Wei-Giang Fan in *J. Org. Chem.*, 53 5685 (1988); by F. B. Stocker J. L. Kurtz, B. L. Gilman and D. A. Forsyth in *J. Org. Chem.* 35 883 (1970); by K. Hideg and H. O. Hankovsky in *Acta. Chim. Acad. Sci. Hung (Budapest)* 53 271 (1967); by Alan R. Katritzky, Andrzej Jozwiak, Ping Lue, Konstantina Yannakopoulou, Gus J. Palenik and Ze Ying Zhang in *Tetrahedron* 46 (2), 633 (1990); and by S. Oeckl, H. G. Schmitt, W. Pattius, and H. Genth in German. Patent DE 3,238,006, Apr. 19, 1984, or using slight modification of the above-mentioned methods.

Compounds of General Formula VII can be prepared from sulfonyl chlorides of General Formula XVI (where A is defined as above) as illustrated in Scheme 12.

SCHEME 12

$$ASO_2Cl \xrightarrow{F^-} ASO_2F$$

XVI VII

Reaction conditions taught by J. Ichihara, T. Matsuo, T. Hanafusa and T. Ando in *J. Chem. Soc. Chem. Comm.*, No. 10, 793 (1986); by H. G. Liu, P. Wang and P. N. Sun in *J. Fluorine Chem.*, 43(3), 429 (1989); by C. L. Borders, Jr., D. L. Macdonell, and J. L. Chambers, Jr., in *J. Org. Chem.* 37 3549 (1972); by T. A. Blanchi and L. A. Cate, in *J. Org. Chem.*, 42 2031 (1977); and by T. Kitazume and N. Ishikawa, in *Chem. Lett.*, 283 (1978) or slight modifications thereof can be used for reactions of Scheme 12.

Compounds of General Formula IX can be prepared by reacting thiols of General Formula XVII (wherein A is defined as above) with bromine, chlorine or sulfuryl chloride as illustrated in Scheme 13.

SCHEME 13

$$ASH + Br_2 \longrightarrow ASSA$$

XVII (or $Cl_2$ or $SO_2Cl_2$) IX

This reaction is carried out in a solvent such as methylene chloride, chloroform or methanol in the presence of 1 to 3 equivalents of hydrogen halide removing agent such as triethylamine or sodium methoxide (per equivalent of the thiol of General Formula XVII) at temperature between 0° and 60° C. for a period of time ranging from 10 minutes to 20 hours. Per equivalent of the thiol of Formula XVII, 0.5 to 1.2 equivalents of the halogenating agent such as bromine, chlorine or sulfuryl chloride are usually used. The product can be isolated by filtration if it precipitates out of the reaction solution. Otherwise the reaction mixture is concentrated under reduced pressure. To the residue is added water and the aqueous layer is then extracted with organic solvent such as ether, hexane or methylene chloride. The organic extract is dried over sodium sulfate or magnesium sulfate and then concentrated under reduced pressure to give the desired product. The crude product can be further purified by recrystallization, flash column chromatography or other similar operation.

Scheme 14 illustrates the preparation of compounds of General Formula X whereby compounds of General Formula XVIII (wherein $R^{3b}$ and $R^{4d}$ are defined as above: V is Cl or Br) are allowed to react with 1,2,4-triazole-3-thiol.

SCHEME 14

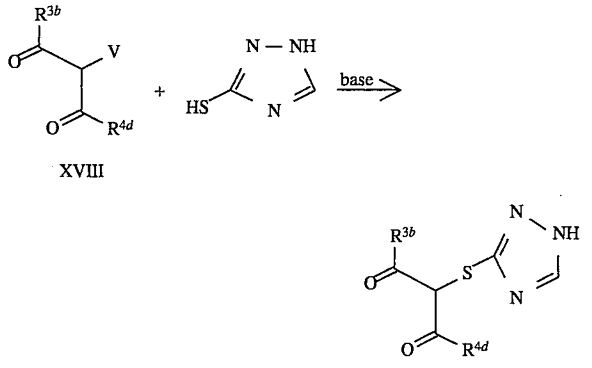

XVIII

X

This reaction is performed in a solvent such as N,N-dimethylformamide, acetonitrile, tetrahydrofuran or methanol in the presence of a base such as methylamine, sodium methoxide, potassium hydroxide or sodium hydride at temperature between 25° C. and 140° C. for a period of time ranging from 30 minutes to 70 hours.

One to 2 equivalents of 1,2,4-triazole-3-thiol and 1 to 3 equivalents of the base is usually used per equivalent of XVIII.

Upon completion of the reaction, the reaction mixture is concentrated under reduced pressure. Water is added to the residue. The product can be isolated by filtration if it precipitates. Otherwise the aqueous solution is extracted with organic solvent. The organic solvent is dried over magnesium sulfate (or sodium sulfate) and concentrated under reduced pressure to give the desired product. The crude product can be further purified by recrystallization, flash column chromatography or other similar operation.

Compounds of General Formula XI are either commercially available or can be prepared by one skilled in the art.

Scheme 15 illustrates the preparation of compounds of General Formula XII whereby a triazolylthioketoester of General Formula XIX (wherein $R^{4d}$ is defined as above; $R^{29}$ is $C_1$–$C_2$ alkyl) is allowed to react with hydrazines of General Formula XX (wherein $R^6$ is defined as above).

SCHEME 15

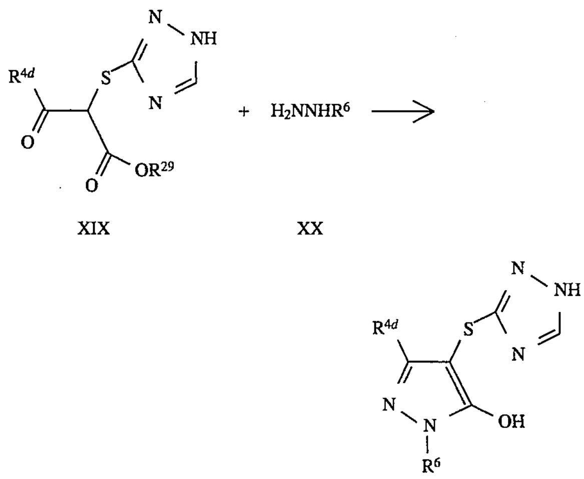

XIX XX

XII

The reaction conditions for Scheme 15 are very similar to those described for Scheme 7 with the exception that XIX is used instead of X.

Compounds of General Formula XIII are either commercially available or can be prepared by one skilled in the art using literature methods or slight modification thereof.

Some examples of the above-mentioned literature methods are:

Dario Chiarino et al., *J. Med. Chem.*,34(2),600(1991)

Kenzi Makino et al., *J. Fluorine Chem.*, 39 (3), 435 (1988)

Robert Kenneth Howe et al., EP 27020

Dietmar Seyferth et al., *J. Am. Chem. Soc.*, 95 (25), 84645 (1973)

Len F. Lee et al., *J. Heterocycl. Chem.*,22(6), 1621 (1985)

V. S. Korsunskii et al., *Khim.-Farm. Zh.*,23(2),249(1989)

Jerzy Suwinski et al., *Pol. J., Chem.*,56(10–12),1261 (1982)

Patricia Demaree et al., *Can. J. Chem.*, 55 (2).243 (1977)

Yu. N. Bulychev et al., *Khim. Geterotsikl. Soedin.*, (7) 920 (1988)

L. I. Bagal et al., *Khim. Geterotsikl. Soedin.*, (12) 1701 (1970)

Ian J. Ferguson et al., *J. Chem. Soc., Perkin Trans.* 1, (6) 672 (1977)

Zdislaw Machon et al., *Acta Pol. Pharm.*,45(1) 18(1988)

Norio Sasaki et al., *Yakugaicu Zasshi*, 90(1)32(1970)

Tadaski Sasaki et al., *J. Chem. Soc.* C, (11) 2147 (1971)

Frartz Effenberger et al., *Chem. Ber.*, 120 (1) 45 (1987)

Richard C. Larock et al., *J. Org. Chem.*,48,(13) 215i (1983)

Michael E. Sitzmann., *J. Heterocycl. Chem.*, 16 (3) 477 (1979)

Scheme 16 illustrates the preparation of compounds of General Formula XV whereby a haloketone of General Formula XXI (wherein V is Cl or Br; $R^{3a}$ is defined as above) is allowed to react with 1,2,4-triazole-3-thiol.

SCHEME 16

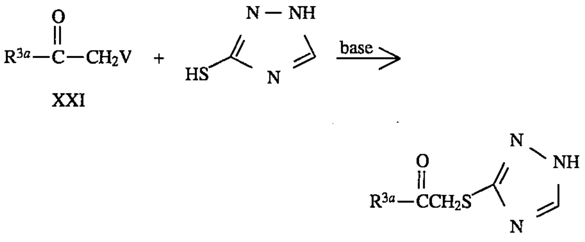

XXI

XV

The reaction conditions for Scheme 16 are very similar to those described for Scheme 14 with the exception that XXI is used instead of XVIII.

Compounds of General Formula XVI and General Formula XVII are either commercially available or can be prepared by one skilled in the art using literature methods or slight modifications thereof.

The literature methods include:

George Levitt et al., U.S. H504 (published 8/2/88)

R. G. Jones et al., *J. Am. Chem. Soc.*,72,4000(1949)

Paolo Gnmanger and Paola Vita-Finzi, "Heterocyclic Compounds", Vol. 49 p. 337 and p. 391

Geoffrey A. Carter et al., *Pestic. Sci.*,6(1),43 (1975)

Tyo Sone et al., *Bull. Chem. Soc. Jap.*, 58 (3), 1063 (1985),

L. S. Abovyan et al., *Kim.-Farm. Zh.*, 17 (6), 685 (1983)

Giovanni Consiglio et al., *J. Chem. Soc., Perkin Trans.* 2, (5), 625 (1982)

Phillip A. Rossy et al., *J. Org. Chem.*, 45 (4) 617 (1980)

Robert Bellemin et at., *J. Heterocycl. Chem.*, 21 (4), 1017 (1984)

Fritz Eiden et at., *Arch. Pharm. (Weinheim)*, 322 (11 ), 807 (1989)

Kenneth Clarke et at., *J. Chem. Soc., Perkin Trans.* 1, (4), 1029 (1980)

Manfred Regitz et al., *Chem. Ber.*, 102 (2), 417 (1969)

Manfred Regitz et at., *Justus Liebigs Ann. Chem.*, 710, 118 (1967)

Marcel Pesson et al., *C. R. Acad Sci., Paris, Ser.* C, 267 (25), 1726 (1968)

Marcel Pesson et al., *Bull. Soc. Chim. Fr.*, (4), 1590(1970)

Ludwig Nuesslein et al., DE 2853196

Charles A. R. Baxter et al., DE 2612761

Marc Montavon et al., EP-A-75 104

M. Liliana Graziano et al., *J. Chem. Res., Synop.*, (2) 42 (1989)

Alfred Treibo et al., *Jusms Liebigs Ann. Chem.*, (2), 207 (1973)

R. L. N. Harris, *Aust. J. Chem.*, 25 (5), 985 (1972)

Ya. L. Goldfarb et at., *Izv. Akad. Nauk SSSR, Ser. Khim.*, (10) 2260 (1969)

L. A. Boilco et al., *Khim. Geterotsikl. Soedin.*, (6), 723 (1970)

Nobuyuki Okajima et at., *Synthesis*, (5), 398 (1989)

I. M. Bazavova et al., *Zh. Org. Khim.*, 17 (1), 200 (1981)

P. Manolova et al., *Farmatsiya (Sofia)*, 29 (6), 1 (1979)

V. Buran et al., *Boll. Chim. Farm.*, 119 (12), 725 (1980)

Surendra Kulkami et al., *Aust. J. Chem.*, 40 (8) 1415 (1987)

T. K. Vinogradova et al., *Zh. Org. Khim.*, 18 (9), 1864 (1982)

Benjamin Blank et al., *J. Med. Chem.*, 20 (4), 572 (1977)

Manfred Regitz et al., *Liebigs Ann. Chem.*, (2), 305 (1980)

R. Alan Jones; "Heterocyclic Compounds", Vol. 48 p. 235

Compounds of General Formula XVIII are either commercially available or can be prepared by one skilled in the art by well-known methods.

Scheme 17 illustrates the preparation of compounds of General Formula XIX whereby a haloketoester of General Formula XXII (wherein V is Cl or Br; $R^{4d}$ and $R^{29}$ are defined as above) is allowed to react with 1,2,4-triazole-3-thiol.

SCHEME 17

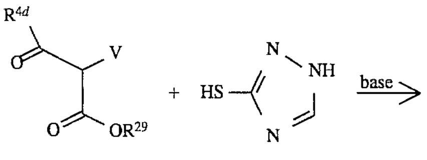

XXII

-continued
SCHEME 17

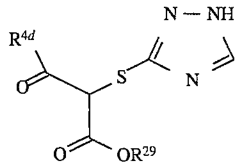

XIX

The reaction conditions for Scheme 17 are very similar to those described for Scheme 14 with the exception that XXII is used instead of XVIII.

Compounds of General Formula XXI and General Formula XXII are either commercially available or can be prepared by one skilled in the an using well-known methods such as N. DeKimpe et at., Synthesis, 2, 188 (1987).

Scheme 18 illustrates an alternative method for preparing compounds of General Formula IIf (which are compounds of General Formula II where A is A-4; n is 0; X is $NR^{6a}$ and $R^{6a}$ is $C_1$–$C_6$ alkyl or $C_3$–$C_6$ cycloalkyl; $R^3$ is $R^{3b}$; $R^4$ is $R^{4d}$) whereby an amine of General Formula XXIII is allowed to react with hydroxylamine-O-sulfonic acid and the reaction product formed in situ is then allowed to react with a tnazolylthiodiketone of General Formula X.

SCHEME 18

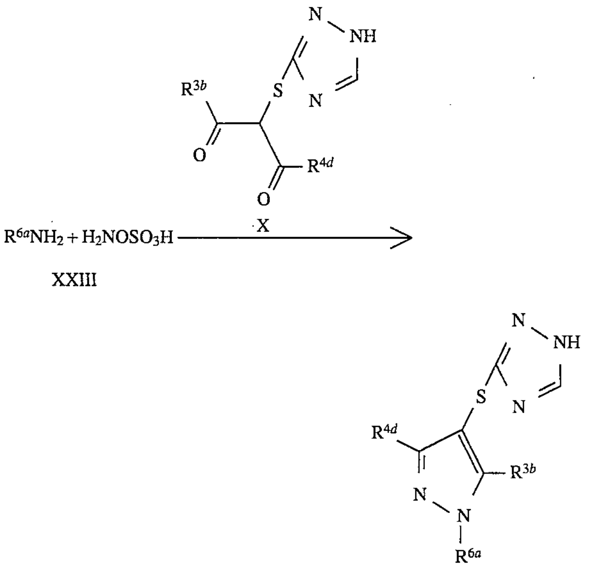

XXIII

IIf wherein $R^{3b}$ and $R^{4d}$ are defined as above;

$R^{6a}$ is $C_1$–$C_6$ alkyl or $C_3$–$C_6$ cycloalkyl.

This reaction is carried out by adding hydroxylamine-O-sulfonic acid in a solvent such as water to an amine of General Formula XXIII in a solvent such as water or in the absence of a solvent. The mixture is stirred at temperature between 0° C. and 8)° C. for a period of time between 1 minute and 24 hours. Most of the unreacted amine of General Formula XXIII is then distilled away under reduced pressure. To the residue is then added the triazolylthiodiketone of General Formula X in a solvent such as methanol, acetonitrile or N,N-dimethylformamide. The resulting mixture is then stirred at a temperature between 0° C. for a period of time between 1 and 200 hours.

One to ten thousand equivalents of the amine of General Formula XXIII and one to five equivalents of hydroxylamine-O-sulfonic acid per equivalent of the triazolylthiodicetone of General Formula X are usually used.

Upon completion of the reaction, the solvent is evaporated under reduced pressure. The residue is partitioned between water and an organic solvent such as dichloromethane. The organic extract is then separated, dried over magnesium sulfate (or sodium sulfate) and concentrated under reduced pressure. This crude product can be further purified by flash column chromatography, recrystallization or other similar operations.

The amines of General Formula XXIII are either commercially available or can be prepared by one skilled in the an using well-known methods.

Scheme 19 illustrates the preparation of compounds of General Formula Ie (which are compounds of General Formula I where A is A-15, A-16, A-17, A-18, A-19 or A-20; n is 2; R is $R^{1a}$, $R^2$ is defined as above) whereby a 1-amino-carbonyltriazole-3-sulfonyl chloride of General Formula XXIV is allowed to react with a heterocycle of General Formula XXV in the presence of a base.

SCHEME 19

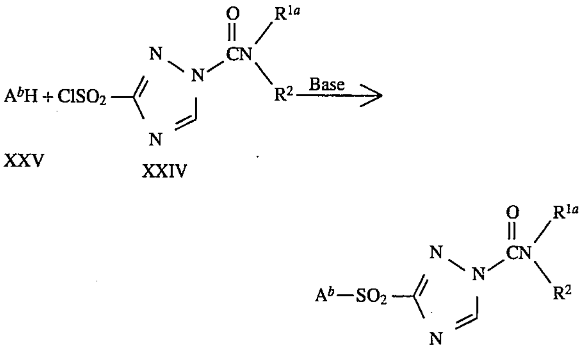

XXV XXIV

Ie wherein $A^b$ is A-15, A-16, A-17, A-18, A-19 or A-20.

This reaction is carried out in a solvent such as acetonitrile, methylene chloride, N,N-dimethylformamide, dioxane, tetrahydrofuran or toluene with reaction temperature ranging from 0° to 120° C. and reaction time between 10 minutes and 100 hours.

In general, 0.5 to 5 equivalents of base such as triethylamine, diisopropylethylmine, sodium hydride or potassium t-butoxide and 0.5 to 2 equivalents of 1-aminocarbonyltriazole-3-sulfonyl chloride of General Formula XXIV are used per equivalent of the heterocycle of General Formula XXV. Compounds of General Formula XXV are either commercially available or can be prepared by one skilled in the art.

Upon completion of the reaction, the reaction mixture is concentrated under reduced pressure. The desired product is isolated from the residue by flash column chromatography, recrystallization or a similar operation.

The 1-aminocarbonyltriazole-3-sulfonyl chlorides of General Formula XXIV can be prepared from the thioether of General Formula XXVI as depicted in Scheme 20.

SCHEME 20

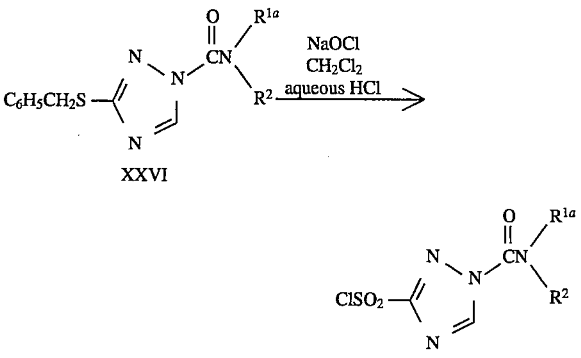

XXVI

XXIV

In this reaction, hypochlorite solution, i.e., NaOCl, is contacted with thioether of General Formula XXVI in a two-phase solvent system buffered with a suitable inorganic acid such as aqueous hydrochloric acid to provide XXIV. The reaction temperature can be from about −10° to about 10° C., preferably from about −5° to about 5° C., and the reaction time from about 0.5 to 3 hours, preferably from 0.5 to 1 hour. Suitable solvents are water and an men organic solvent such as methylene chloride or 1,2-dichlorobenzene, with methylene chloride being preferred. Following completion of the reaction, the organic phase is isolated, washed with aqueous sodium bisulfite solution, dried (e.g., $MgSO_4$) and concentrated in vacuo at about 25° to 35° C. to provide a residue containing XXIV. The impure residue containing XXIV can be further purified by slurrying with hexane and/or flash chromatography on silica gel, and/or recrystallization if a solid. For further details, see analogous reactions in South African Patent Application No. 84/8845 and 84/8844.

Intermediate thioether of General Formula XXVI can be prepared as depicted in Scheme 21.

SCHEME 21

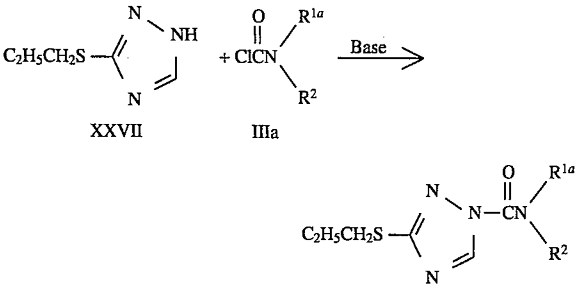

XXVII IIIa

XXVI

The reaction of Scheme 21 can be carried out according to the teachings of U.S. Pat. No. 4,280,83 1, DE 3,929,673 A1 and U.S. Pat. No. 3,962,001. Thus, XXVI can be obtained by contacting 3-benzylthio-1,2,4-triazole (XXVII) with carbamoyl chloride of General Formula IIIa (which are compounds of General Formula III where $R^1$ is $R^{1a}$; W is Cl; $R^2$ is defined as above) in excess pyridine at from about 20° to about 30° C.; or by contacting XXVII with IIIa and a tertiary amine base such as triethylamine in an inert organic solvent such as tetrahydrofuran at about 25° C. to reflux.

Intermediate carbamyl chloride IIIa can be prepared by contacting appropriate secondary amines with phosgene in an inert organic solvent such as refluxing ethyl acetate, according to the teachings of U.S. Pat. No. 3,952,001. The preparation of 3-benzylthio-1,2,4-triazole XXVII is taught in U.S. Pat. No. 4,280,831.

Alternatively, thioethers of General Formula XXVI can be prepared according to the teachings of U.S. Pat. No. 3,952,001. Thus, contacting triazole of General Formula XXVII with phosgene and a tertiary amine base such as pyridine or methylamine in an inert organic solvent such tetrahydrofuran at from about 0° to about 30° C. can provide the corresponding carbamyl chloride. Subsequent reaction of the carbamyl chloride with an appropriate secondary amine in the presence of a suitable base such as pyridine or triethylamine in an inert organic solvent such as tetrahydrofuran at from about 0° to about 30° C. can provide XXVI. Appropriate secondary amines axe known or can be prepared by methods generally known to those skilled in the art; see. e.g., U.S. Pat. No. 3,952,001.

Scheme 22 illustrates the preparation of compounds of General Formula If (which are compounds of General Formula I where A is A-2; X is $NR^6$; n is 2; $R^1$ is $R^{1a}$; $R^2$ is defined as above; $R^3$ is H or $C_1$–$C_6$ alkyl optionally substituted with one or more F, Cl, Br or $C_1$–$C_3$ alkoxy; $R^4$ is $R^{4a}$; $R^5$ is H or $C_1$–$C_6$ alkyl optionally substituted with one or more halogen) whereby a mesoionic oxazolones of Gemeral Formula XXVIII (which may be prepared in situ) is allowed to react with an 1,2-propaclienylsulfone of General Formula XXIX.

SCHEME 22

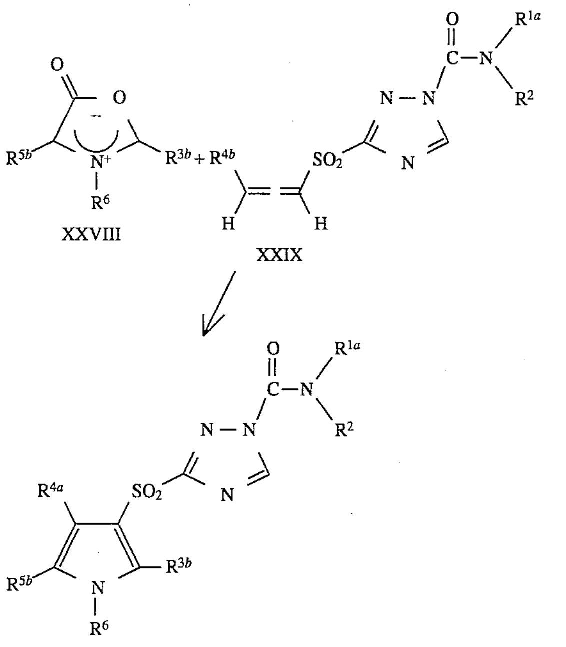

XXVIII XXIX If wherein $R^{3b}$ is H or $C_1$–$C_6$ alkyl optionally substituted with one or more F, Cl, Br or $C_1$–$C_3$ alkoxy;

$R^{5b}$ is H or $C_1$–$C_6$ alkyl optionally substituted with one or more halogen.

This reaction is carried out in a solvent such as xylene, toluene, 1,2-dichlorobenzene, 1,3-dichlorobenzene or an anhydride of Formula $(R^{3b}CO)_2O$ with the reaction temperature ranging from 0° to 200° C. and the reaction time being between 10 minutes and 100 hours. One to twenty equivalents of the mesoionic oxazolone of General Formula XXVIII is used per equivalent of the 1,2-propadienylsulfone of General Formula XXIX.

Upon completion of the reaction, the reaction mixture is concentrated. The desired product is isolated from the residue by flash column chromatography, recrystallization or other similar operation.

Scheme 23 illustrates the preparation of compounds of General Formula Ig (which are compounds of General Formula I where A is A-2, X is $NR^6$; n is 2; $R^1$ is $R^{1a}$; $R^2$ is defined as above; $R^3$ is $R^{3b}$; $R^4$ is H, $C_1$–$C_6$ alkyl optionally substituted with one or more halogen, $C_1$–$C_6$ alkoxy, CN, $CO_2R^7$, $S(O)_mR^8$, $CONR^9R^{10}$, or $SO_2NR^{13}R^{14}$; $C_3$–$C_6$ cycloalkyl; $C_1$–$C_6$ alkoxy; or phenyl or benzyl, each ring optionally substituted with 1 to 3 substituents selected from halogen, $C_1$–$C_3$ alkyl, $C_1$–$C_3$ haloalkyl and $C_1$–$C_3$ alkoxy) whereby a mesoionic oxazolones of General Formula XXVIII (which may be prepared in situ) is allowed to react with an alkynylsulfone of General Formula XXX.

SCHEME 23

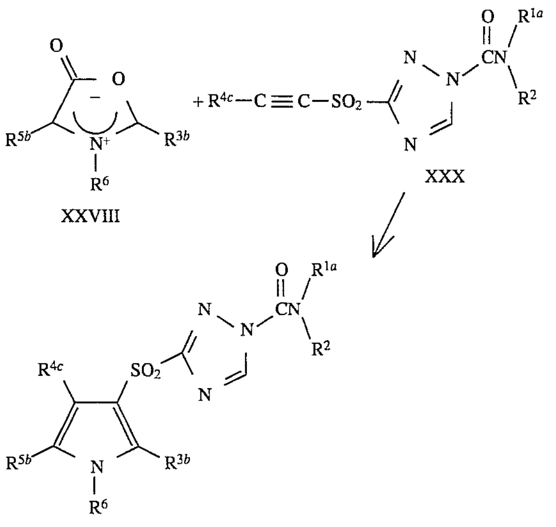

XXVIII XXX Ig wherein $R^{4c}$ is H, $C_1$–$C_6$ alkyl optionally substituted with one or more halogen, $C_1$–$C_6$ alkoxy, CN, $CO_2R^7$, $S(O)_mR^8$, $C(O)NR^9R^{10}$ or $SO_2NR^{13}R^{14}$, $C_3$–$C_6$ cycloalkyl; $C_1$–$C_6$ alkoxy; or phenyl or benzyl, each ring optionally substituted with 1 to 3 substituents selected from halogen, $C_1$–$C_3$ alkyl, $C_1$–$C_3$ haloalkyl and $C_1$–$C_3$ alkoxy.

This reaction is carried out in a solvent such as xylene, toluene, 1,2-dichlorobenzene, 1.3-dichlorobenzene or an anhydride of Formula $(R^{3b}CO)_2O$ with the reaction temperature ranging from 0° to 200° C. and the reaction time being between 10 minutes and 100 hours. One to twenty equivalents of mesoionic oxazolone of General Formula XXVIII is used per equivalent of the alkynyl sulfone of General Formula XXX. Upon completion of the reaction, the reaction mixture is concentrated. The desired product is isolated from the residue by flash column chromatography, recrystallization or other similar operation.

Scheme 24 illustrates the preparation of compounds of General Formula Ih (which are compounds of General Formula I where A is A-4, X is $NR^6$, n is 2; $R^1$ is $R^{1a}$, $R^2$ is defined as above; $R^3$ is $R^{3b}$, $R^4$ is $R^{4a}$; $R^{3b}$ and $R^6$ may be taken together as $-(CH_2)_3-$ or $-(CH_2)_4-$ whereby a sydnone of General Formula XXXI is allowed to react with a 1,2-propadienylsulfone of General Formula XXIX.

SCHEME 24

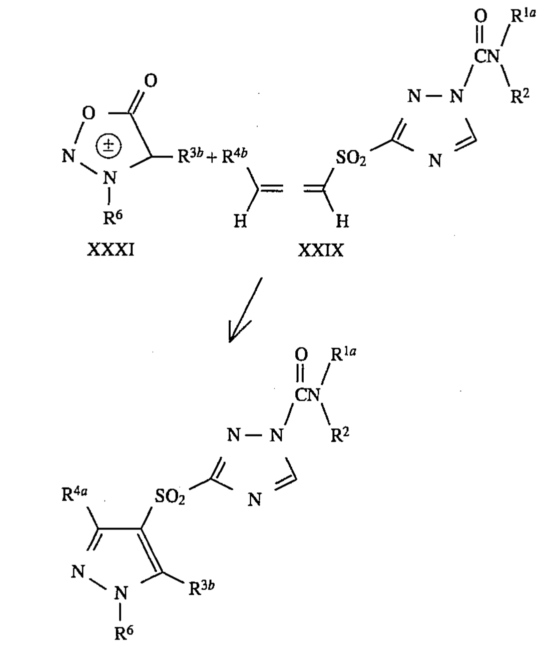

XXXI XXIX

Ih wherein $R^{3b}$ and $R^6$ may be taken together as $-(CH_2)_3-$ or $-(CH_2)_4-$.

This reaction is carried out in a solvent such as xylene, 1,2-dichlorobenzene. 1,3-dichlorobenzene, toluene, nitrobenzene, 1,2-dimethoxyethane or N,N-dimethylformamide with the reaction temperature ranging from 0° to 200° C. and the reaction time being between 10 minutes and 100 hours. One to twenty equivalents of the sydnone of General Formula XXXI is used per equivalent of 1,2-propaclienylsulfone of General Formula XXIX. Upon completion of the reaction, the reaction mixture is concentrated. The desired product is isolated from the residue by flash column chromatography, recrystallization or other similar operation.

Scheme 25 illustrates the preparation of compounds of General Formula Ii (which are compounds of General Formula I where A is A-4, X is $NR^6$, n is 2; $R^1$ is $R^{1a}$, $R^2$ is defined as above, $R^3$ is $R^{3b}$, $R^4$ is $R^{4c}$, $R^{3b}$ and $R^6$ may be taken together as $-(CH_2)_3-$ or $-(CH_2)_4-$) whereby a sydnone of General Formula XXXI is allowed to react with an alkynylsulfone of General Formula XXX.

SCHEME 25

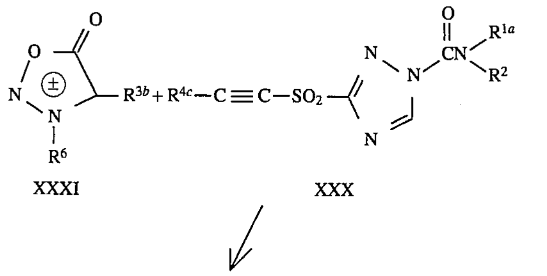

XXXI XXX

-continued

SCHEME 25

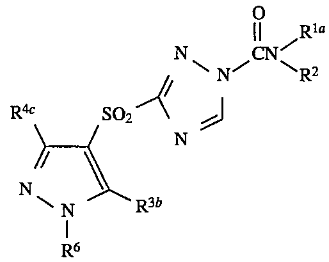

Ii wherein $R^{3b}$ and $R^6$ may be taken together as $-(CH_2)_3-$ or $-(CH_2)_4-$.

This reaction is carried out in a solvent such as xylene, 1,2-dichlorobenzene, 1,3-dichlorobenzene, toluene, nitrobenzene, 1,2-dimethoxyethane or N,N-dimethylformamide with the reaction temperature ranging from 0° to 200° C. and the reaction time being between 10 minutes and 100 hours. One to twenty equivalents of the sydnone of General Formula XXXI are used per equivalent of alkynylsulfone of General Formula XXX.

The 1,2-propadienylsulfones of General Formula XXIX can be prepared by oxidizing the compounds of General Formula XXXII followed by treatment of a base such as sodium bicarbonate aqueous solution sodium carbonate aqueous solution, triethylamine, 1,8-diazobicyclo[5.4.0]-undec-7-ene (DBU)or potassium t-butoxide as illustrated in Scheme 26.

SCHEME 26

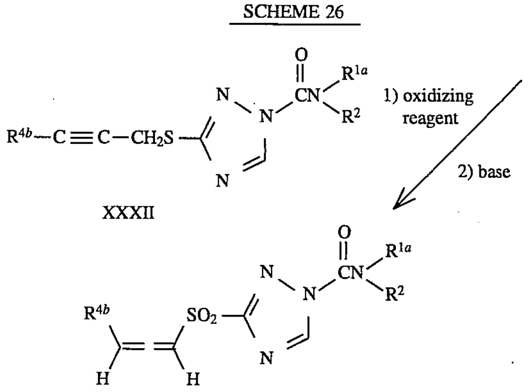

XXXII

XXIX

The oxidizing reagents that can be used in the process of Scheme 26 include 3-chloroperoxybenzoic acid, peracetic acid, trifluoroperacetic acid, and hydrogen peroxide. The oxidation is normally performed in a solvent and solvents that can be used will vary depending on the type of oxidizing reagent used. For example, if the oxidizing reagent is 3-chloroperoxybenzoic acid, benzene, methylene chloride, chloroform or other halogenated hydrocarbons can be used as solvent. If peracetic acid or trifluoroperacetic acid is used as the oxidizing reagent, halogenated hydrocarbon or the corresponding acid can be used as solvent. If the oxidant is hydrogen peroxide, water, acetone, acetic acid or the like can be used.

The reaction temperature range is normally 0° to 80° C. while the reaction time ranges from 10 minutes to 100 hours. In general, two to five equivalents of oxidant are used per equivalent of the compound of General Formula XXXII.

Upon completion of the reaction, methylsulfide or other reducing agents are added to destroy the unreacted oxidant. Additional organic solvent such as methylene chloride or chloroform was then added. The reaction mixture was then washed or treated with the above mentioned base. The organic layer is dried and concentrated. The crude product is then purified by flash column chromatography over silica gel.

Scheme 27 illustrates the preparation of compounds of General Formula XXXII whereby the thiotriazole of General Formula XXXIII is allowed to react with the carbamyl chloride of General Formula IIIa.

SCHEME 27

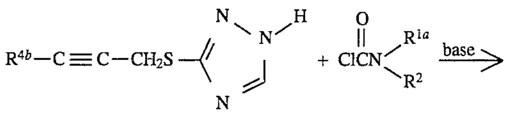

XXXIII IIIa

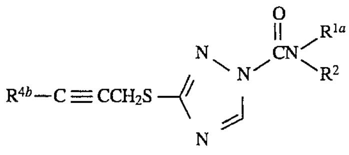

XXXII

The reaction conditions for Scheme 27 are very similar to those described for Scheme 21 with the exception that XXXIII is used instead of XXVII.

Scheme 28 illustrates the preparation of compounds of General Formula XXXIII whereby a 2-propynyl halide of General Formula XXXIV (wherein V is Cl or Br; $R^{4b}$ is defined as above) is allowed to react with 1,2,4-triazole-3-thiol.

SCHEME 28

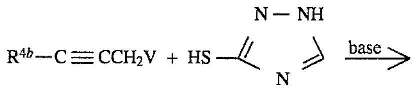

XXXIV

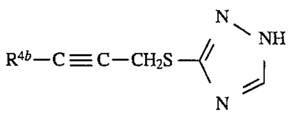

XXXIII

The reaction conditions for Scheme 28 are very similar to those described for Scheme 14 with the exception that XXXIV is used instead of XVIII.

The alkynylsulfones of General Formula XXX can be prepared by reacting the 1-aminocarbonyltriazole-3-sulfonyl chlorides of General Formula XXIV with a trimethylsilylalkyne of General Formula XXXV or an alkyne of General Formula XXXVI as depicted in Scheme 29.

SCHEME 29

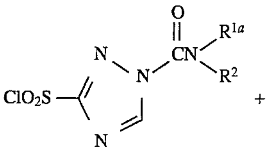

XXIV $R^{4c}-C\equiv CSi(CH_3)_3$
(or $R^{4c}-C\equiv CH$)

XXXVI base
or
Lewis acid

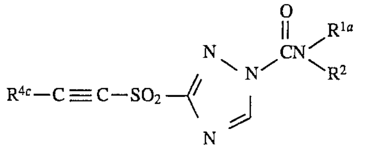

XXX

The reaction conditions (including the catalysts which may be needed) for Scheme 29 are very similar to those reaction conditions for the synthesis of alkynylsulfones taught by J. Dunogues et al., in *J. Chem. Res.* (S) 16 (1982) and K. Schank in *The Chemistry of Sulfones and Sulfoxide* (edited by S. Patai et al.; published by John-WHey & Sons; pp. 190–202) with the exception that XXIV is used instead of other sulfonyl chlorides.

Compounds of General Formula XXXIV, XXXV and XXXVI are either commercially available or can be prepared by one skilled in the art.

The sydnones of General Formula XXXI can be prepared by one skilled in the art using literature methods or slight modifications thereof.

Some examples of the above mentioned literature methods are:

F. H. C. Stewart, *Chemical Reviews* 64 129 (1964)

H. J. Tien et al., *Bull. Chem. Soc. of Japan* 45 2944 (1972)

C. V. Greco et al., *J. Heterocycl. Chem.*,3(3) 391 (1966)

The mesoiordc oxazolone of General Formula XXVIII can be prepared (in situ in most cases) by one skilled in the art using literature methods of slight modifications thereof.

Some examples of the above mentioned literature methods are:

R. Huisgen et at., *Chem. Ber.* 103,2611 (I970)

M. T. Pizzomo et al., *J. Org. Chem.*, 42(5) 909 (1977)

K. T. Potts et al., *J. Org. Chem.*, 44(6) 977(1979)

The following are non-limiting examples illustrating the preparation of compounds of this invention Chemical shits in the proton nuclear magnetic resonance (NMR) spectra are reported as parts per million downfield from the internal standard tetramethylsilanes. Melting points are uncorrected.

EXAMPLE 1

Preparation of 3-[(4H-1,2,4-triazol-3-yl)thio]-2,4-pentanedione

Under $N_2$, 1.25 g of sodium was added to 100 ml of methanol. This mixture was stirred at ambient temperature for 15 minutes and 5.7 g of 1,2,4-triazole-3-thiol was then added. The reaction solution was then stirred at ambient temperature for 45 minutes. To this reaction solution was then added 6.7 g of 3-chloro-2,4-pentanedione. The resulting mixture was refluxed for ~4 hours and was then concentrated under reduced pressure. The residue was stirred in water. The solid precipitated was collected by filtration, washed with water, air dried, and then dried in a vacuum oven to give 3.53 g of the title product as a solid, m.p. 114°–115° C. The aqueous filtrate was concentrated under reduced pressure to a smaller volume. The precipitate was collected by filtration, air dried and then dried in a vacuum oven to give an additional 3.35 g of the title product, m.p. 114°–115° C. NMR ($CDCl_3$): 2.42 (s, 6H); 8.19 (s, 1H).

EXAMPLE 2

Preparation of
3-[(1-ethyl-3,5-dimethyl-1H-pyrazol-4-yl)thio]-1H-1,2,4-triazole

Under $N_2$, 0.56 g of sodium was added to 100 ml of methanol. This mixture was stirred at ambient temperature for 15 minutes and 2.8 g of ethylhydrazine oxalate was added. The reaction mixture was stirred at ambient temperature for another 15 minutes. To the reaction solution was then added 2.5 g of 3-[(4H-1,2,4-triazol-3-yl)thio]- 2,4-pentanedione.

The resulting mixture was refluxed overnight and was then concentrated under reduced pressure. The residue was dissolved in 200 ml of water and the aqueous solution was extracted with methylene chloride (4×100 ml). The methylene chloride extracts were combined, dried over magnesium sulfate and concentrated under reduced pressure to give 2 g of the titled product as a solid, m.p. 127°–129° C. NMR ($CDCl_3$): 1.38 (t, 3H); 2.24 (s, 3H); 2.32 (s, 3H); 4.04 (q, 2H); 7.98 (s, 1H).

EXAMPLE 3

Preparation of
N,N-diethyl-3-[(1-ethyl-3,5-dimethyl-1 H-pyrazol-4-yl)thio]1H-1,2,4-triazole-1-carboxamide To 34 ml of acetonitrile was added 1.1 g of 3-[(1-ethyl-3,5-dimethyl-1 H-pyrazol-4-yl)thio]-1H-1,2,4-triazole, 1.9 ml of diethylcarbamyl chloride and 2.2 ml of triethylamine. The resulting mixture was refluxed under nitrogen for 24 hours and was then concentrated under reduced pressure. To the residue was added 100 ml of water. The aqueous layer was then extracted with a solution of 150 ml of diethylether and 150 ml of hexane twice. The organic extracts were then combined, dried over magnesium sulfate and concentrated under reduced pressure to give 1.2 g of the title product as a solid, m.p. 67°–69° C. NMR ($CDCl_3$): 1.18 (bt, 6H); 1.39 (t, 3H); 2.25 (s, 3H); 2.3 (s, 3H); 3.64 (q, 4H); 4.05 (q, 2H); 8.69 (s, 1H).

EXAMPLE 4

Preparation of
N,N-diethyl-3-[(1-ethyl-3,5-dimethyl-1 H-pyrazol-4-yl)sulfonyl]-1H-1,2,4-triazole-1-carboxamide To a solution of 0.82 g of N,N-diethyl-3[(1-ethyl-3,5-dimethyl-1 H-pyrazol-4-yl)thio] -1H-1,2,4-triazole-1-carboxamide in 16 ml of methylene chloride at room temperature was added 2.8 g of 3-chloroperoxybenzoic acid (50%–60% pure; from Aldrich Chemical Co., Inc., Milwaukee, Wis.). The resulting mixture was stirred at room temperature for ~58 hours. To this reaction mixture was then added 1.5 ml of methylsulfide. The resulting mixture was stirred for another 5 minutes and 100 ml of methylene chloride was added. The methylene chloride solution was then washed with dilute sodium bicarbonate aqueous solution (3×150 ml), dried over magnesium sulfate and concentrated under reduced pressure .to give 0.5 g of the title product as a solid, m.p. 90°–96° C. NMR ($CDCl_3$): 1.3 (t, 6H); 1.4 (t, 3H); 2.45 (s, 3H); 2.58 (s, 3H); 3.6 (b, 4H); 4.03 (q, 2H); 8.8 (s, 1H).

EXAMPLE 5

Preparation of
3-[(3,5-dimethyl-1-propyl-1H-pyrazol-4-yl)thio]-1H-1,2,4-triazole Under $N_2$, 0.69 g of sodium was added to 100 ml of methanol. The mixture was stirred at ambient temperature for 10 minutes and 3.4 g of n-propylhydrazine oxalate was then added. The resulting mixture was stirred at room temperature for another 15 minutes and 3 g of 3-[(4H-1,2,4-triazol-3-yl)thio]-2,4-pentanedione was then added. The reaction mixture was refluxed for 48 hours and was then concentrated under reduced pressure. To the residue was added 200 ml of water and the aqueous layer was extracted with methylene chloride (4×100 ml). The methylene chloride extracts were combined, dried over magnesium sulfate and concentrated under reduced pressure. The residue was triturated in 10 ml of 1-chlorobutane. The precipitate was collected by filtration and dried in a vacuum oven to give 1.3 g of the title compound as a solid, m.p. 106°–108° C. NMR ($CDCl_3$): 0.9 (t, 3H); 1.8 (m, 2H); 2.24 (s, 3H); 2.31 (s, 3H); 3.93 (t, 3H); 7.98 (s, 1H).

EXAMPLE 6

Preparation of
3-[(3,5-dimethyl-1-propyl-1H-pyrazol-4-yl)thio]-N,N-diethyl-1 H-1,2,4-triazole-1-carboxamide To a solution of 1.1 g of 3-[(3,5-dimethyl1-propyl-1H-pyrazol-4-yl)thio] 1H-1,2,4-triazole in 34 ml of acetonitrile was added 1.9 ml of diethylcarbamyl chloride and then 2.2 ml of triethylamine. The resulting mixture was refluxed under nitrogen for 18 hours and was then concentrated under reduced pressure. To the residue was added 100 ml of water. The aqueous layer was extracted with a solution of 150 ml of diethylether and 150 ml of hexane twice. The organic extracts were then combined, dried over magnesium sulfate and concentrated under reduced pressure to give 1.15 g of the title product as a solid, m.p. 81°–83° C. NMR ($CDCl_3$): 0.93 (t, 3H); 1.2 (m, 6H); 1.82 (m, 2H); 2.25 (s, 3H); 2.30 (s, 3H); 3.48 (q, 4H); 3.97 (t, 2H); 8.89 (s, 1H).

EXAMPLE 7

Preparation of
3-[(3,5-dimethyl-1-propyl-1H-pyrazol-4-yl)sulfonyl]-N,N-diethyl-1 H-1,2,4-triazole-1-carboxamide To a solution of 1.1 g of 3-[(3,5-dimethyl-1-propyl-1H-pyrazol-4-yl)thio]-N,N-diethyl-1 H-1,2,4-triazole-1-carboxamide in 24 ml of methylene chloride was added 3.8 g of 3-chloroperoxybenzoic acid (50–60% pure; from Aldrich Chemical Co., Inc.). The resulting mixture was stirred at room temperature overnight. To this reaction mixture was then added 1.5 ml of methylsulfide. The resulting mixture was stirred for another 5 minutes and 100 ml of methylene chloride was added. The methylene chloride solution was then washed with dilute sodium bicarbonate aqueous solution (3×150 ml), dried over magnesium sulfate and concentrated under reduced pressure to give 0.78 g of the title compound as an oil. NMR ($CDCl_3$): 0.92 (t, 3H); 1.29 (t, 6H); 1.8 (m, 2H); 2.45 (s, 3H); 2.57 (s, 3H); 3.6 (m, 4H); 3.95 (t, 2H); 8.8 (s, 1H).

EXAMPLE 8

Preparation of 3-[(3,5-dimethyl-4-isoxazolyl)thio]-1H-1,2,4-triazole

Under nitrogen, 0.6 g of sodium was added to 50 ml of methanol. This mixture was stirred at ambient temperature for 15 minutes and 2.4 g of hydroxylamine hydrochloride was added. The resulting mixture was then stirred for another hour. To it was added 3 g of 3-[(4H-1,2,4-triazol-3-yl)thio]-2,4-pentanedione. The reaction mixture was refluxed for 2 weeks and then concentrated under reduced pressure. The residue was triturated in 300 ml of hexane which was then decanted away. The residue was then triturated in 150 ml of water. The precipitate was collected by filtration to give 2.3 g of the title compound as a solid, m.p. 129°–131° C. NMR ($CDCl_3$): 2.28 (s, 3H); 2.5 (s, 3H); 8.15 (s, 1H).

EXAMPLE 9

Preparation of 3-[(3,5-dimethyl-4-isoxazolyl)thio]-N,N-diethyl]-1H-1,2,4-triazole-1-carboxamide To a solution of 1.2 g of 3-[(3,5-dimethyl-4-isoxazolyl)thio]-1H-1,2,4-triazole in 34 ml of acetonitrile was added 2.5 ml of diethylcarbamyl chloride and then 3 ml of triethylamine. The resulting mixture was refluxed under nitrogen for 21 hours and was then concentrated. To the residue was added 100 ml of water. The aqueous layer was then extracted with a solution of 150 ml of diethylether and 150 ml of hexane twice. The organic extracts were combined, dried over magnesium sulfate and concentrated under reduced pressure to give 1.15 g of the title compound as an oil. NMR ($CDCl_3$): 1.2 (m, 6H); 2.27 (s, 3H); 2.48 (s, 3H); 3.48 (q, 4H); 8.72 (s, 1H).

EXAMPLE 10

Preparation of 3-[(3,5-dimethyl-4-isoxazolyl)sulfonyl]-N,N-diethyl-1 H-1,2,4-triazole-1-carboxamide To a solution of 0.7 g of 3-[(3,5-dimethyl-4-isoxazolyl)thio]-N,N-diethyl-1 H-1,2,4-triazole-1-carboxamide in 16 ml of methylene chloride was added 2.8 g of 3-chloroperoxybenzoic acid (50–60% pure; from Aldrich Chemical Co., Inc.). The resulting mixture was stirred at room temperature for 14 hours. To this reaction mixture was then added 1.5 ml of methylsulfide. The resulting mixture was stirred for another 5 minutes and 100 ml of methylene chloride was added. The methylene chloride solution was then washed with dilute sodium bicarbonate aqueous solution (3 ×150 ml), dried over magnesium sulfate and concentrated under reduced pressure to give 0.58 g of the title compound as a solid, m.p. 108°–10° C. NMR ($CDCl_3$): 1.3 (t, 6H); 2.49 (s, 3H); 2.76 (s, 3H); 3.6 (m, 4H); 8.86 (s, 1H).

EXAMPLE 11

Preparation of 1-[5 -chloro-2-[(1H-1,2,4-triazol-3-yl)thio]3-thienyl]ethanone

To a solution of 4.5 g of 1,2,4-triazole-3-thiol in 100 ml N,N-dimethylformamide under $N_2$ was added 2 g of sodium hydride (60% dispersion in mineral oil). The resulting mixture was stirred at ambient temperature for 15 minutes and 7.8 g of 3-acetyl-2,5-dichlorothiophene was then added to it. The resulting mixture was heated at 90° C. for 2 hours and was then concentrated under reduced pressure. To the residue was added 100 ml of water. Aqueous hydrochloric acid (1 normal) was then added with stirring until the pH was 7. The precipitate was collected by filtration, washed with water, air dried and dried in a vacuum oven to give 10.45 g of the title product as a solid, m.p. 187°–189° C. NMR ($CDCl_3$): 2.51 (s, 3H); 7.64 (s, 1H); 8.8 (s, 1H).

EXAMPLE 12

Preparation of 3-[(3-acetyl-5-chloro-2-thienyl)thio]-N,N-diethyl-1 H-1,2,4-triazole-1-carboxamide To a solution of 5.5 g of 1-[5-chloro-2-[(1H-1,2,4-triazol-3-yl)thio]3-thienyl] ethanone in 75 ml of acetonitrile was added 4.4 ml of diethylcarbamyl chloride and then 5.3 ml of triethylamine. The resulting mixture was refluxed under nitrogen overnight and was then concentrated. The residue was stirred in 100 ml of water for 15 minutes. The precipitate was collected by filtration, washed with water and dried in a vacuum oven to give 6.8 g of the title product as a solid, m.p. 103°– 105° C. NMR ($CDCl_3$): 1.28 (t, 6H); 2.54 (s, 3H); 3.6 (m, 4H); 7.24 (s, 1H); 8.87 (s, 1H).

EXAMPLE 13

Preparation of 3-[(3-acetyl-5-chloro-2-thienyl)sulfonyl]-N,N-diethyl-1 H-1,2,4-triazole-1-carboxamide To a solution of 0.98 g of 3-[(3-acetyl-5-chloro-2-thienyl)thio]-N,N-diethyl- 1H-1,2,4-triazole-1-carboxamide in 21 ml of methylene chloride was added 3 g of 3-chloroperoxybenzoic acid (50–60% pure; from Aldrich Chemical Co., Inc.). The resulting mixture was stirred at ambient temperature for 20 hours and 1.5 ml of methylsulfide was then added. The reaction mixture was stirred for mother 5 minutes and 100 ml of methylene chloride was then added. The methylene chloride solution was washed with dilute sodium bicarbonate aqueous solution (3×150 ml), dried over magnesium sulfate and concentrated under reduced pressure to give 0.79 g of the title product as a solid, m.p. 128°–130° C. NMR ($CDCl_3$): 1.29 (t, 6H); 2.52 (s,3 H); 3.6 (b, 4H); 7.27 (s, 1H); 8.83 (s, 1H). IR (Nujol): 1700, 1328, 1130$cm^{-1}$.

EXAMPLE 14

Preparation of methyl 3-oxo-2-[(1H-1,2,4-triazol-3yl)thio]butanoate

Under nitrogen, 7 g of sodium was added to 300 ml of methanol. This mixture was stirred at ambient temperature for 30 minutes and 30 g of 1,2,4-triazol-3-thiol was then added. The reaction mixture was then stirred at ambient temperature for 15 minutes. To this reaction mixture with stirring was then added 50 ml of methyl 2-chloroacetoacetate dropwise. The resulting mixture was stirred at ambient temperature for 1 hour and was then concentrated under reduced pressure. To the residue was added 200 ml of water. The precipitate was collected by filtration, washed with 100 ml of water, air dried and then dried in oven to give 50.5 g of the title compound as a solid. m.p. 63°–65° C. NMR ($CDCl_3$): 2.39 (s, 3H); 3.75 (s, 3H); 8.14 (s, 1H); 13.7 (bs, 1H).

EXAMPLE 15

Preparation of
1,2-hydro-5-methyl-4-[(1H-1,2,4-triazol-3-yl)thio]-2-(2.2.2-trifluoroethyl)-3H-pyrazol-3-one To a solution of 4 g of methyl 3-oxo-2-[(1H-1,2,4-triazol-3-yl)thio]butanoate in 100 ml of methanol was added 2.8 ml of 2,2,2-trifluoroethylhydrazine. The resulting solution was refluxed under nitrogen for 20 hours and was then concentrated under reduced pressure. The residue was triturated in 200 ml of diethylether for ten minutes. The precipitate was collected by filtration, air dried and dried in oven to give a solid. This solid was then stirred in 400 ml of diethylether for 4 hours. The precipitate was then collected by filtration, washed with diethylether and dried in oven to give 3 g of the title compound as a solid, m.p. 196°–200° C. NMR (DMSO-$d_6$): 2.02 (s, 3H); 4.58 (q, 2H); 8.18 (s, 1H) with impurity peas.

EXAMPLE 16

Preparation of
3-[[5-chloro-3-methyl-1(2.2.2-trifluoroethyl)-1H-pyrazol- 4yl)thio]-1H-1,2,4-triazole To a heavy walled glass tube with a magnetic stirring bar and a screw teflon cap was added 40 ml of phosphorus oxychloride and then 2 g of 1,2-dihydro-5-methyl-4-[(1 H-1,2,4-triazol-3-yl)thio]-2-(2,2,2-trifluoroethyl)-3H-pyrazol-3-one. The tube was purged with nitrogen and was then sealed with a teflon cap. The sealed glass tube was put into a silicon oil bath (~⅔ of the tube was under the oil surface) with the magnetic bar stirring. The oil bath was heated at ~160° C. for 5 hours and was then cooled down to room temperature. The resulting reaction mixture was then concentrated under reduced pressure. To the residue was added 40 ml of water. The resulting mixture was stirred for 10 minutes and was then extracted with methylene chloride (3×100 ml). The methylene chloride extracts were combined, dried over magnesium sulfate, and concentrated under reduced pressure to give 0.56 g of the title compound as a solid, m.p. 112°–114° C. NMR ($CDCl_3$): 2.31 (s, 3H); 4.7 (q, 2H); 8.13 (s, 1H).

EXAMPLE 17

Preparation of
3-[[5-chloro-3-methyl-1-(2.2.2-trifluoroethyl)-1H-pyrazol- 4-yl]thio]-N,N-diethyl-1H-1,2,4-triazole-1-carboxamide To a solution of 0.56 g of 3-[[5-chloro-3-methyl-1-(2,2,2-trifluoroethyl)-1H-pyrazol- 4-yl)thio]-1H-1,2,4-triazole in 21 ml of acetonitrile was added 1 ml of diethylcarbamyl chloride and then 1.1 ml of methylmine. The resulting mixture was refluxed under nitrogen for 20 hours and was then concentrated under reduced pressure. To the residue was added 100 ml of water. The resulting mixture was stirred at ambient temperature for 10 minutes. The precipitate was collected by filtration, washed with water, air dried, and then dried in oven to give 0.64 g of the title product as a solid, m.p. 112°–114° C. NMR ($CDCl_3$): 1.15 (m, 6H); 2.3 (s, 3H); 3.48 (q, 4H); 4.72 (q, 2H); 8.73 (s, 1H).

EXAMPLE 18

Preparation of
3-[[5-chloro-3-methyl-1-(2.2.2-trifluoroethyl)-1H-pyrazol- 4-yl]-sulfonyl]-N,N-diethyl-1H-1,2,4-triazole-1-carboxamide To a solution of 0.6 g of 3-[[5-chloro-3-methyl-1-(2,2,2-trifluoroethyl)-1 H-pyrazol-4-yl)thio]-N,N-diethyl-1H-1,2,4-triazole-1-carboxamide in 16 ml of methylene chloride was added 2 g of 3-chloroperoxybenzoic acid (50–60% pure; from Aldrich Chemical Co., Inc.). The resulting mixture was stirred at ambient temperature for 20 hours. To this reaction mixture was then added 1.5 ml of methylsulfide. The resulting mixture was stirred for another 5 minutes and 100 ml of methylene chloride was added. The methylene chloride solution was then washed with dilute sodium bicarbonate aqueous solution (3×150 ml), dried over magnesium sulfate and concentrated under reduced pressure to give 0.44 g of the title compound as a solid, m.p. 103°–105° C. NMR ($CDCl_3$): 1.29 (t, 6H); 2.53 (s, 3H); 3.6 (bs, 4H); 4.7 (q, 2H); 8.86 (s, 1H).

EXAMPLE 19

Preparation of
3-[[phenylmethyl]thio]-N,N-diethyl-1H-1,2,4-triazole-1-carboxamide To a solution of 3-benzylthio-1H-1,2,4-triazole (98.4 g, 0.52 mol) (U.S. Pat. No. 4,280,831) in pyridine (350 mL) was added dropwise diethylcarbamyl chloride (73.5 g, 0.54 mol) at ambient temperature. The solution was stirred overnight (ca. 16 h), then poured into excess water (1500 mL). The suspension was stirred until a precipitate formed, then filtered, and the residue was suction-dried overnight to provide the title compound (98.0 g) as a solid melting at 50°–55° C. IR (mineral oil): 1690 $cm^{-1}$; $^1H$-NMR ($CDCl_3$): δ1.25 (t, 6H), 3.6 (bs, 4H), 4.4 (s, 2H), 7.2–7.4 (m, 5H), 8.75 (s, 1H).

EXAMPLE 20

Preparation of 1-[(diethylamino)carbonyl-1H-1,2,4-triazole-3-sulfonyl chloride

To a solution of 40.0 g of 3-[(phenylmethyl)thio]-N,N-diethyl-1H-1,2,4-triazole-1-carboxamide in methylene chloride (606 mL) was added water (318 mL), and the suspension was cooled with external cooling to about 0° to 5° C. Concentrated hydrochloric acid (41 mL) was added followed by dropwise addition of Clorox® (658 mL, active ingredient 5.25% sodium hypochlorite) while maintaining the reaction temperature at 0° to 5° C. with external cooling and occasional addition of wet ice to the reaction suspension. After stirring at 0° to 5° C. for 1 h, the organic layer was separated, washed with saturated aqueous sodium bisulfite (150–175 mL ). then dried ($MgSO_4$) and concentrated in vacuo (25°–35° C.) to an oil. On standing overnight the oil partially crystallized. The suspension was slurried with hexane (75 mL), filtered and the residue suction-dried to provide the title compound as a solid (26.0 g). The solid was further purified by flash chromatography (silica gel with 1:1 hexane:ethyl acetate) to provide the title compound (23.0 g), melting at 44°–47° C. IR (mineral oil): 1160, 1270–1290, 1720 $cm^{-1}$; $^1$H-NMR ($CDCl_3$): δ1.35 (t, 6H), 3.6 (bs, 4H), 9.0 (s, 1H).

EXAMPLE 21

Preparation of 3-[(3,5-diethyl-1H-pyrazol-1-yl)sulfonyl)-N,N-diethyl-1 H-1,2,4-triazole-1-carboxamide To a solution of 0.62 g of 3,5-diethyl-1H-pyrazole in 22 ml of anhydrous tetrahydrofuran under nitrogen with stirring was added 0.62 g of 60% sodium hydride (dispersion in mineral oil; from Aldrich Chemical Co., Inc.). The resulting mixture was stirred at ambient temperature for 1 hour. To this mixture was then added 1.36 g of 1-[(diethylamino)carbonyl]-1H-1,2,4-triazole-3-sulfonyl chloride. The resulting mixture was stirred at ambient temperature for another 2 hours and was then concentrated under reduced pressure. The residue was flash column chromatographed (silica gel with 1:9 ethyl acetate/hexane and 1:2 ethyl acetate/hexane as eluents) to provide 1.0 g of the title compound as a solid, m.p. 70°–71° C. NMR ($CDCl_3$): 1.15–1.4 (m. 12H); 2.6 (q, 2H); 3.03 (q, 2H); 3.6 (m, 4H); 6.1 (s, 1H); 8.82 (s, 1H).

EXAMPLE 22

Preparation of 3-(2-propynylthio)-1H-1,2,4-triazole

To a solution of 21.8 g of potassium hydroxide in 400 ml of methanol under nitrogen was added 33.37 g of 1,2,4-triazole-3-thiol. The resulting mixture was stirred at ambient temperature for ~1 hour. To this mixture was added 33.4 ml of propargyl bromide dropwise while keeping the reaction temperature below 30° C. After the addition, the resulting mixture was stirred at ambient temperature for ~4 hours and was then concentrated under reduced pressure. The residue was triturated in 300 ml of water. The precipitate was collected by filtration, washed with water and then hexanes, air dried and then dried in oven to give 24.6 g of the title product as a solid, m.p. 102°–104° C. NMR (DMSO-d6): 3.14 (t, 1H); 3.92 (d, 2H); 8.48 (s, 1H); 14.2 (bs, 1H).

EXAMPLE 23

Preparation of N,N-diethyl-3-(2-propynylthio)-1H-1,2,4-triazol-1-carboxamide

To 31.5 ml of pyridine was added 5.56 g of 3-(2-propynylthio)-1H-1,2,4-triazole and then 6.3 ml of diethylcarbamyl chloride. The resulting mixture was stirred under nitrogen at ambient temperature for 3 days and was then poured into 350 ml of cold water with agitation. The precipitate was collected by filtration, washed with water air dried and then dried in oven to give 8.1 g of the title compound as a solid. m.p. 67°–69° C. NMR ($CDCl_3$): 1.3 (t, 6H); 2,21 (t. 1H); 3.62 (m, 4H); 3.88 (d, 2H); 8.78 (s, 1H).

EXAMPLE 24

Preparation of N,N-diethyl-3-(1,2-propadienylsulfonyl)-1H-1,2,4-triazole-1-carboxamide To a solution of 2 g of N,N-diethyl-3-(2-propynylthio)-1H-1,2,4-triazole-1-carboxamide in 40 ml of methylene chloride was added 10 g of 3-chloroperoxybenzoic acid (50–60%; from Aldrich Chemical Co., Inc.). The resulting mixture was stirred at ambient temperature for 22 hours. To this reaction mixture was then added 3 ml of methylsulfide. The resulting mixture was stirred for mother 15 minutes and 50 ml of methylene chloride was added. The methylene chloride solution was then washed with 5% sodium bicarbonate aqueous solution (3×150 ml), dried over magnesium sulfate and concentrated under reduced pressure. The residue was then flash column chromatographed (silica gel with 1:2 ethyl acetate/hexanes as eluent) to provide 1.87 g of the title compound as a solid, m.p. 98°–100° C. NMR ($CDCl_3$): 1.32 (t, 6H); 3.6 (m, 4H); 5.62 (d, 2H); 6.46 (t, 1H); 8.89 (s, 1H). IR (neat): 1966 $cm^{-1}$, 1712 $cm^{-1}$, 1334 $cm^{-1}$, 1140 $cm^{-1}$.

EXAMPLE 25

Preparation of N,N-diethyl-3-[(1,2,4-trimethyl-1H-pyrrol-3-yl)-sulfonyl]-1 H-1,2,4-triazole-1-carboxamide To 20 ml of acetic anhydride was added 0.9 g of sarcosin. The resulting mixture as heated under nitrogen to 98° C. and was stirred at 98° C. for 10 minutes. To this reaction solution at 98° C. was then added a solution of 0.6 g of N,N-diethyl-3-(1,2-propadienylsulfonyl)-1H-1,2,4-triazole-1-carboxamide in 5 ml of methylene chloride dropwise. The resulting mixture was then heated to 110° C. and was stirred at 110° C. for 1.5 hours. The reaction mixture was then concentrated under reduced pressure. The residue was then purified by flash column chromatography twice (silica gel with 2:3 ethyl acetate/hexane as eluent were employed for the first flash column chromatography; silica gel with 2%, 4%, 6%, 8% and 10% ether in methylene chloride as eluents were employed for the second flash column chromatography) to provide 0.308 g of the title compound as an oil. NMR ($CDCl_3$): 1.3 (m, 6H); 2.23 (s, 3H); 2.53 (s, 3H); 3.48 (s, 3H); 3.6 (m, 4H); 6.32 (s, 1H): 8.78 (s, 1H).

By the general procedures described in Schemes 1–29 and Examples 1–25 or by obvious modifications thereof one skilled in the art can prepare the compounds of Tables 1–20.

TABLES 1–20

The following tables pertain to compounds of Formula I:

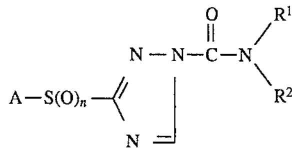

I wherein A is

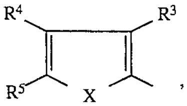

A-1,

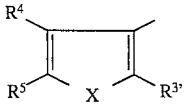

A-2,

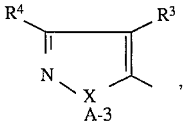

A-3,

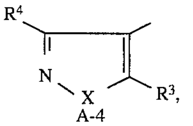

A-4,

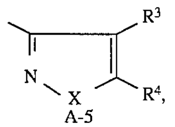

A-5,

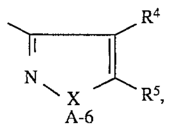

A-6,

TABLES 1-20-continued

The following tables pertain to compounds of Formula I:

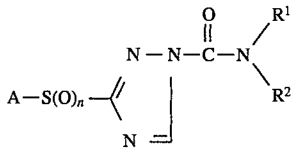

I

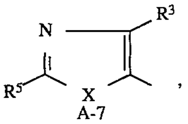

, A-7

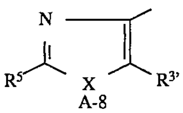

, A-8

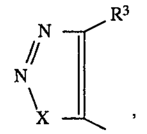

, A-9

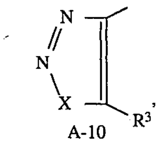

, A-10

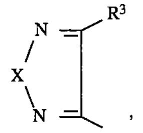

, A-11

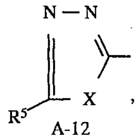

, A-12

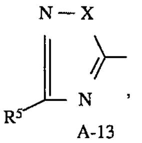

, A-13

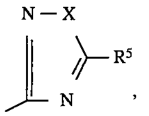

, A-14

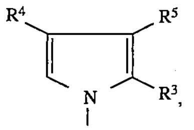

, A-15

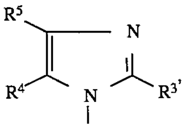

A-16

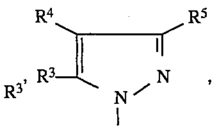

, A-17

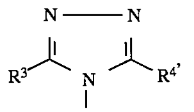

A-18

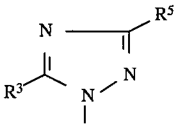

A-19 or

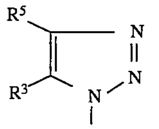

A-20

In the following tables, each page or section is read in the order of the columns to the left of the vertical dividing line, in their entirety, followed by the columns to the fight of the line, and then followed again by the columns to the left of the line on the next page or section.

TABLE 1

A = A-1; X = O; $R^1$ = $C_2H_5$; $R^2$ = $C_2H_5$

| n | $R^3$ | $R^4$ | $R^5$ |
|---|---|---|---|
| 2 | H | H | H |
| 2 | H | H | $CH_3$ |
| 2 | H | H | $C_2H_5$ |
| 2 | H | H | $CH_2CH_2CH_3$ |
| 2 | H | Cl | H |
| 2 | H | Cl | $CH_3$ |
| 2 | H | Cl | $C_2H_5$ |
| 2 | H | Cl | $CH_2CH_2CH_3$ |
| 2 | H | $OCH_3$ | H |
| 2 | H | $OCH_3$ | $CH_3$ |
| 2 | H | $OCH_3$ | $C_2H_5$ |
| 2 | H | $OCH_3$ | $CH_2CH_2CH_3$ |
| 2 | H | $CH_3$ | H |
| 2 | H | $CH_3$ | $CH_3$ |
| 2 | H | $CH_3$ | $C_2H_5$ |

TABLE 1-continued

| | | | |
|---|---|---|---|
| 2 | H | $CH_3$ | $CH_2CH_2CH_3$ |
| 2 | H | $C_2H_5$ | H |
| 2 | H | $C_2H_5$ | $CH_3$ |
| 2 | H | $C_2H_5$ | $C_2H_5$ |
| 2 | H | $C_2H_5$ | $CH_2CH_2CH_3$ |
| 2 | Cl | H | H |
| 2 | Cl | H | $CH_3$ |
| 2 | Cl | H | $C_2H_5$ |
| 2 | Cl | H | $CH_2CH_2CH_3$ |
| 2 | Cl | Cl | H |
| 2 | Cl | Cl | $CH_3$ |
| 2 | Cl | Cl | $C_2H_5$ |
| 2 | Cl | Cl | $CH_2CH_2CH_3$ |
| 2 | Cl | $OCH_3$ | H |
| 2 | Cl | $OCH_3$ | $CH_3$ |
| 2 | Cl | $OCH_3$ | $C_2H_5$ |
| 2 | Cl | $OCH_3$ | $CH_2CH_2CH_3$ |
| 2 | Cl | $CH_3$ | H |
| 2 | Cl | $CH_3$ | $CH_3$ |
| 2 | Cl | $CH_3$ | $C_2H_5$ |
| 2 | Cl | $CH_3$ | $CH_2CH_2CH_3$ |
| 2 | Cl | $C_2H_5$ | H |
| 2 | Cl | $C_2H_5$ | $CH_3$ |
| 2 | Cl | $C_2H_5$ | $C_2H_5$ |
| 2 | Cl | $C_2H_5$ | $CH_2CH_2CH_3$ |
| 2 | $OCH_3$ | H | H |
| 2 | $OCH_3$ | H | $CH_3$ |
| 2 | $OCH_3$ | H | $C_2H_5$ |
| 2 | $OCH_3$ | H | $CH_2CH_2CH_3$ |
| 2 | $OCH_3$ | Cl | H |
| 2 | $OCH_3$ | Cl | $CH_3$ |
| 2 | $OCH_3$ | Cl | $C_2H_5$ |
| 2 | $OCH_3$ | Cl | $CH_2CH_2CH_3$ |
| 2 | $OCH_3$ | $OCH_3$ | H |
| 2 | $OCH_3$ | $OCH_3$ | $CH_3$ |
| 2 | $OCH_3$ | $OCH_3$ | $C_2H_5$ |
| 2 | $OCH_3$ | $OCH_3$ | $CH_2CH_2CH_3$ |
| 2 | $OCH_3$ | $CH_3$ | H |
| 2 | $OCH_3$ | $CH_3$ | $CH_3$ |
| 2 | $OCH_3$ | $CH_3$ | $C_2H_5$ |
| 2 | $OCH_3$ | $CH_3$ | $CH_2CH_2CH_3$ |
| 2 | $OCH_3$ | $C_2H_5$ | H |
| 2 | $OCH_3$ | $C_2H_5$ | $CH_3$ |
| 2 | $OCH_3$ | $C_2H_5$ | $C_2H_5$ |
| 2 | $OCH_3$ | $C_2H_5$ | $CH_2CH_2CH_3$ |
| 2 | $CH_3$ | H | H |
| 2 | $CH_3$ | H | $CH_3$ |
| 2 | $CH_3$ | H | $C_2H_5$ |
| 2 | $CH_3$ | H | $CH_2CH_2CH_3$ |
| 2 | $CH_3$ | Cl | H |
| 2 | $CH_3$ | Cl | $CH_3$ |
| 2 | $CH_3$ | Cl | $C_2H_5$ |
| 2 | $CH_3$ | Cl | $CH_2CH_2CH_3$ |
| 2 | $CH_3$ | $OCH_3$ | H |
| 2 | $CH_3$ | $OCH_3$ | $CH_3$ |
| 2 | $CH_3$ | $OCH_3$ | $C_2H_5$ |
| 2 | $CH_3$ | $OCH_3$ | $CH_2CH_2CH_3$ |
| 2 | $CH_3$ | $CH_3$ | H |
| 2 | $CH_3$ | $CH_3$ | $CH_3$ |
| 2 | $CH_3$ | $CH_3$ | $C_2H_5$ |
| 2 | $CH_3$ | $CH_3$ | $CH_2CH_2CH_3$ |
| 2 | $CH_3$ | $C_2H_5$ | H |
| 2 | $CH_3$ | $C_2H_5$ | $CH_3$ |
| 2 | $CH_3$ | $C_2H_5$ | $C_2H_5$ |
| 2 | $CH_3$ | $C_2H_5$ | $CH_2CH_2CH_3$ |
| 2 | $C_2H_5$ | H | H |
| 2 | $C_2H_5$ | H | $CH_3$ |
| 2 | $C_2H_5$ | H | $C_2H_5$ |
| 2 | $C_2H_5$ | H | $CH_2CH_2CH_3$ |
| 2 | $C_2H_5$ | Cl | H |
| 2 | $C_2H_5$ | Cl | $CH_3$ |
| 2 | $C_2H_5$ | Cl | $C_2H_5$ |
| 2 | $C_2H_5$ | Cl | $CH_2CH_2CH_3$ |
| 2 | $C_2H_5$ | $OCH_3$ | H |
| 2 | $C_2H_5$ | $OCH_3$ | $CH_3$ |
| 2 | $C_2H_5$ | $OCH_3$ | $C_2H_5$ |
| 2 | $C_2H_5$ | $OCH_3$ | $CH_2CH_2CH_3$ |
| 2 | $C_2H_5$ | $CH_3$ | H |
| 2 | $C_2H_5$ | $CH_3$ | $CH_3$ |

TABLE 1-continued

| | | | |
|---|---|---|---|
| 2 | $C_2H_5$ | $CH_3$ | $C_2H_5$ |
| 2 | $C_2H_5$ | $CH_3$ | $CH_2CH_2CH_3$ |
| 2 | $C_2H_5$ | $C_2H_5$ | H |
| 2 | $C_2H_5$ | $C_2H_5$ | $CH_3$ |
| 2 | $C_2H_5$ | $C_2H_5$ | $C_2H_5$ |
| 2 | $C_2H_5$ | $C_2H_5$ | $CH_2CH_2CH_3$ |
| 2 | $CH_2CH_2CH_3$ | H | H |
| 2 | $CH_2CH_2CH_3$ | H | $CH_3$ |
| 2 | $CH_2CH_2CH_3$ | H | $C_2H_5$ |
| 2 | $CH_2CH_2CH_3$ | H | $CH_2CH_2CH_3$ |
| 2 | $CH_2CH_2CH_3$ | Cl | H |
| 2 | $CH_2CH_2CH_3$ | Cl | $CH_3$ |
| 2 | $CH_2CH_2CH_3$ | Cl | $C_2H_5$ |
| 2 | $CH_2CH_2CH_3$ | Cl | $CH_2CH_2CH_3$ |
| 2 | $CH_2CH_2CH_3$ | $OCH_3$ | H |
| 2 | $CH_2CH_2CH_3$ | $OCH_3$ | $CH_3$ |
| 2 | $CH_2CH_2CH_3$ | $OCH_3$ | $C_2H_5$ |
| 2 | $CH_2CH_2CH_3$ | $OCH_3$ | $CH_2CH_2CH_3$ |
| 2 | $CH_2CH_2CH_3$ | $CH_3$ | H |
| 2 | $CH_2CH_2CH_3$ | $CH_3$ | $CH_3$ |
| 2 | $CH_2CH_2CH_3$ | $CH_3$ | $C_2H_5$ |
| 2 | $CH_2CH_2CH_3$ | $CH_3$ | $CH_2CH_2CH_3$ |
| 2 | $CH_2CH_2CH_3$ | $C_2H_5$ | H |
| 2 | $CH_2CH_2CH_3$ | $C_2H_5$ | $CH_3$ |
| 2 | $CH_2CH_2CH_3$ | $C_2H_5$ | $C_2H_5$ |
| 2 | $CH_2CH_2CH_3$ | $C_2H_5$ | $CH_2CH_2CH_3$ |
| 2 | $CH_3$ | $CH_3$ | Cl |
| 2 | $CH_3$ | $CH_3$ | $OCH_3$ |
| 2 | $CH_3$ | $CH_3$ | F |
| 2 | $CH_3$ | $CH_3$ | Br |
| 2 | $CH_3$ | $CH_3$ | $CO_2CH_3$ |
| 2 | $CH_3$ | $CH_3$ | $CO_2C_2H_5$ |
| 2 | $CH_3$ | $CH_3$ | $CH_2OCH_3$ |
| 2 | $CH_3$ | $CH_3$ | $CON(CH_3)_2$ |
| 2 | $CH_3$ | $CH_3$ | $SCH_3$ |
| 2 | $CH_3$ | $CH_3$ | $SO_2CH_3$ |
| 2 | $CH_3$ | $CH_3$ | $NO_2$ |
| 2 | $CH_3$ | $CH_3$ | $N(CH_3)_2$ |
| 2 | $CH_3$ | $CH_3$ | $NH_2$ |
| 2 | $CH_3$ | $CH_3$ | $C_6H_5$ |
| 2 | $CH_3$ | $C_6H_5$ | H |
| 2 | $C_6H_5$ | $CH_3$ | H |
| 2 | $CH_3$ | $CF_3$ | H |
| 2 | $CF_3$ | $CH_3$ | H |
| 2 | $COCH_3$ | H | H |
| 2 | $CH{=}CH_2$ | $CH_3$ | H |
| 2 | $CH_3$ | $CH{=}CH_2$ | H |
| 2 | $SCH_3$ | $CH_3$ | H |
| 2 | $CH_3$ | $SCH_3$ | H |
| 2 | $NO_2$ | $CH_3$ | H |
| 2 | $NH_2$ | $CH_3$ | H |
| 2 | CHO | $CH_3$ | H |
| 2 | $CO_2CH_3$ | H | H |
| 2 | $CH(OCH_3)_2$ | H | H |
| 2 | $COCH_3$ | H | Cl |
| 2 | $C_2H_5$ | H | Cl |
| 2 | $CO_2CH_3$ | H | Cl |

A = A-1; X = O; $R^3 = CH_3$; $R^4 = CH_3$

| n | $R^1$ | $R^2$ | $R^5$ |
|---|---|---|---|
| 2 | $CH_3$ | $CH_3$ | H |
| 2 | $C_2H_5$ | $CH_3$ | H |
| 2 | H | $CH_3$ | H |
| 2 | H | $C_2H_5$ | H |
| 2 | H | $CH_2CH_2CH_3$ | H |
| 2 | $OCH_3$ | $CH_3$ | H |
| 2 | $OCH_3$ | $C_2H_5$ | H |
| 2 | $CH_2CH{=}CH_2$ | $CH_2CH{=}CH_2$ | H |
| 2 | $CH_2C{\equiv}CH$ | $CH_2C{\equiv}CH$ | H |
| 2 | $CH(CH_3)_2$ | $CH(CH_3)_2$ | H |
| 2 | $-(CH_2)_5-$ | | H |
| 2 | $-(CH_2)_4-$ | | H |
| 2 | $CH_2CH{=}CH_2$ | $C_2H_5$ | H |
| 2 | $CH_2C{\equiv}CH$ | $C_2H_5$ | H |

TABLE 1-continued

| | | | |
|---|---|---|---|
| 2 | $OC_2H_5$ | $CH_3$ | H |
| 2 | $OC_2H_5$ | $C_2H_5$ | H |
| 2 | H | 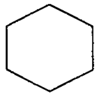 | H |
| 2 | 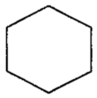 | 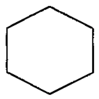 | H |
| 2 | H | $CH_2CH{=}CH_2$ | H |
| 2 | $CH_2CH_2CH_3$ | $CH_3$ | H |
| 2 | $CH_2CH{=}CH_2$ | $CH_3$ | $CH_3$ |
| 2 | $CH_2CH{=}CH_2$ | $C_2H_5$ | $CH_3$ |
| 2 | $CH_2CH{=}CH_2$ | $CH_2CH{=}CH_2$ | $CH_3$ |
| 2 | $CH_2CH_2CH_3$ | $CH_2CH_2CH_3$ | $CH_3$ |
| 2 | $CH_2CH_2CH_3$ | $C_2H_5$ | $CH_3$ |
| 2 | $-(CH_2)_5-$ | | $CH_3$ |
| 0 | $CH_3$ | $CH_3$ | H |
| 1 | $CH_3$ | $CH_3$ | H |

A = A-1; X = S; $R^1 = C_2H_5$; $R^2 = C_2H_5$

| n | $R^3$ | $R^4$ | $R^5$ |
|---|---|---|---|
| 2 | H | H | H |
| 2 | H | H | $CH_3$ |
| 2 | H | H | $C_2H_5$ |
| 2 | H | H | $CH_2CH_2CH_3$ |
| 2 | H | Cl | H |
| 2 | H | Cl | $CH_3$ |
| 2 | H | Cl | $C_2H_5$ |
| 2 | H | Cl | $CH_2CH_2CH_3$ |
| 2 | H | $OCH_3$ | H |
| 2 | H | $OCH_3$ | $CH_3$ |
| 2 | H | $OCH_3$ | $C_2H_5$ |
| 2 | H | $OCH_3$ | $CH_2CH_2CH_3$ |
| 2 | H | $CH_3$ | H |
| 2 | H | $CH_3$ | $CH_3$ |
| 2 | H | $CH_3$ | $C_2H_5$ |
| 2 | H | $CH_3$ | $CH_2CH_2CH_3$ |
| 2 | H | $C_2H_5$ | H |
| 2 | H | $C_2H_5$ | $CH_3$ |
| 2 | H | $C_2H_5$ | $C_2H_5$ |
| 2 | H | $C_2H_5$ | $CH_2CH_2CH_3$ |
| 0 | $CH_3$ | $CH_3$ | H |
| 2 | Cl | H | H |
| 2 | Cl | H | $CH_3$ |
| 2 | Cl | H | $C_2H_5$ |
| 2 | Cl | H | $CH_2CH_2CH_3$ |
| 2 | Cl | Cl | H |
| 2 | Cl | Cl | $CH_3$ |
| 2 | Cl | Cl | $C_2H_5$ |
| 2 | Cl | Cl | $CH_2CH_2CH_3$ |
| 2 | Cl | $OCH_3$ | H |
| 2 | Cl | $OCH_3$ | $CH_3$ |
| 2 | Cl | $OCH_3$ | $C_2H_5$ |
| 2 | Cl | $OCH_3$ | $CH_2CH_2CH_3$ |
| 2 | Cl | $CH_3$ | H |
| 2 | Cl | $CH_3$ | $CH_3$ |
| 2 | Cl | $CH_3$ | $C_2H_5$ |
| 2 | Cl | $CH_3$ | $CH_2CH_2CH_3$ |
| 2 | Cl | $C_2H_5$ | H |
| 2 | Cl | $C_2H_5$ | $CH_3$ |
| 2 | Cl | $C_2H_5$ | $C_2H_5$ |
| 2 | Cl | $C_2H_5$ | $CH_2CH_2CH_3$ |
| 1 | $CH_3$ | $CH_3$ | H |
| 2 | $OCH_3$ | H | H |
| 2 | $OCH_3$ | H | $CH_3$ |
| 2 | $OCH_3$ | H | $C_2H_5$ |
| 2 | $OCH_3$ | H | $CH_2CH_2CH_3$ |
| 2 | $OCH_3$ | Cl | H |
| 2 | $OCH_3$ | Cl | $CH_3$ |
| 2 | $OCH_3$ | Cl | $C_2H_5$ |

TABLE 1-continued

| | | | |
|---|---|---|---|
| 2 | $OCH_3$ | Cl | $CH_2CH_2CH_3$ |
| 2 | $OCH_3$ | $OCH_3$ | H |
| 2 | $OCH_3$ | $OCH_3$ | $CH_3$ |
| 2 | $OCH_3$ | $OCH_3$ | $C_2H_5$ |
| 2 | $OCH_3$ | $OCH_3$ | $CH_2CH_2CH_3$ |
| 2 | $OCH_3$ | $CH_3$ | H |
| 2 | $OCH_3$ | $CH_3$ | $CH_3$ |
| 2 | $OCH_3$ | $CH_3$ | $C_2H_5$ |
| 2 | $OCH_3$ | $CH_3$ | $CH_2CH_2CH_3$ |
| 2 | $OCH_3$ | $C_2H_5$ | H |
| 2 | $OCH_3$ | $C_2H_5$ | $CH_3$ |
| 2 | $OCH_3$ | $C_2H_5$ | $C_2H_5$ |
| 2 | $OCH_3$ | $C_2H_5$ | $CH_2CH_2CH_3$ |
| 2 | $CH_3$ | H | H |
| 2 | $CH_3$ | H | $CH_3$ |
| 2 | $CH_3$ | H | $C_2H_5$ |
| 2 | $CH_3$ | H | $CH_2CH_2CH_3$ |
| 2 | $CH_3$ | Cl | H |
| 2 | $CH_3$ | Cl | $CH_3$ |
| 2 | $CH_3$ | Cl | $C_2H_5$ |
| 2 | $CH_3$ | Cl | $CH_2CH_2CH_3$ |
| 2 | $CH_3$ | $OCH_3$ | H |
| 2 | $CH_3$ | $OCH_3$ | $CH_3$ |
| 2 | $CH_3$ | $OCH_3$ | $C_2H_5$ |
| 2 | $CH_3$ | $OCH_3$ | $CH_2CH_2CH_3$ |
| 2 | $CH_3$ | $CH_3$ | H |
| 2 | $CH_3$ | $CH_3$ | $CH_3$ |
| 2 | $CH_3$ | $CH_3$ | $C_2H_5$ |
| 2 | $CH_3$ | $CH_3$ | $CH_2CH_2CH_3$ |
| 2 | $CH_3$ | $C_2H_5$ | H |
| 2 | $CH_3$ | $C_2H_5$ | $CH_3$ |
| 2 | $CH_3$ | $C_2H_5$ | $C_2H_5$ |
| 2 | $CH_3$ | $C_2H_5$ | $CH_2CH_2CH_3$ |
| 2 | $C_2H_5$ | H | H |
| 2 | $C_2H_5$ | H | $CH_3$ |
| 2 | $C_2H_5$ | H | $C_2H_5$ |
| 2 | $C_2H_5$ | H | $CH_2CH_2CH_3$ |
| 2 | $C_2H_5$ | Cl | H |
| 2 | $C_2H_5$ | Cl | $CH_3$ |
| 2 | $C_2H_5$ | Cl | $C_2H_5$ |
| 2 | $C_2H_5$ | Cl | $CH_2CH_2CH_3$ |
| 2 | $C_2H_5$ | $OCH_3$ | H |
| 2 | $C_2H_5$ | $OCH_3$ | $CH_3$ |
| 2 | $C_2H_5$ | $OCH_3$ | $C_2H_5$ |
| 2 | $C_2H_5$ | $OCH_3$ | $CH_2CH_2CH_3$ |
| 2 | $C_2H_5$ | $CH_3$ | H |
| 2 | $C_2H_5$ | $CH_3$ | $CH_3$ |
| 2 | $C_2H_5$ | $CH_3$ | $C_2H_5$ |
| 2 | $C_2H_5$ | $CH_3$ | $CH_2CH_2CH_3$ |
| 2 | $C_2H_5$ | $C_2H_5$ | H |
| 2 | $C_2H_5$ | $C_2H_5$ | $CH_3$ |
| 2 | $C_2H_5$ | $C_2H_5$ | $C_2H_5$ |
| 2 | $C_2H_5$ | $C_2H_5$ | $CH_2CH_2CH_3$ |
| 2 | $CH(CH_3)_2$ | $C_2H_5$ | $CH_3$ |
| 2 | $CH(CH_3)_2$ | $C_2H_5$ | $C_2H_5$ |
| 2 | $CH(CH_3)_2$ | $C_2H_5$ | $CH_2CH_2CH_3$ |
| 2 | $CH_3$ | $CH_3$ | Cl |
| 2 | $CH_3$ | $CH_3$ | $OCH_3$ |
| 2 | $CH_3$ | $CH_3$ | F |
| 2 | $CH_3$ | $CH_3$ | Br |
| 2 | $CH_3$ | $CH_3$ | $CO_2CH_3$ |
| 2 | $CH_3$ | $CH_3$ | $CO_2C_2H_5$ |
| 2 | $CH_3$ | $CH_3$ | $CH_2OCH_3$ |
| 2 | $CH_3$ | $CH_3$ | $CON(CH_3)_2$ |
| 2 | $CH_3$ | $CH_3$ | $SCH_3$ |
| 2 | $CH_3$ | $CH_3$ | $SO_2CH_3$ |
| 2 | $CH_3$ | $CH_3$ | $NO_2$ |
| 2 | $CH_3$ | $CH_3$ | $N(CH_3)_2$ |
| 2 | $CH_3$ | $CH_3$ | $NH_2$ |
| 2 | $CH_3$ | $CH_3$ | $C_6H_5$ |
| 2 | $CH_3$ | $C_6H_5$ | H |
| 2 | $C_6H_5$ | $CH_3$ | H |
| 2 | $CH_3$ | $CF_3$ | H |
| 2 | $CF_3$ | $CH_3$ | H |
| 2 | $COCH_3$ | H | H |
| 2 | $CH=CH_2$ | $CH_3$ | H |
| 2 | $CH_3$ | $CH=CH_2$ | H |
| 2 | $SCH_3$ | $CH_3$ | H |
| 2 | $CH_3$ | $SCH_3$ | H |

TABLE 1-continued

| | | | |
|---|---|---|---|
| 2 | $NO_2$ | $CH_3$ | H |
| 2 | $NH_2$ | $CH_3$ | H |
| 2 | CHO | $CH_3$ | H |
| 2 | $CO_2CH_3$ | H | H |
| 2 | $CH(OCH_3)_2$ | H | H |
| 2 | C(O)$CH_3$ | H | Cl |
| 2 | $C_2H_5$ | H | Cl |
| 2 | $CO_2CH_3$ | H | Cl |
| 0 | C(O)$CH_3$ | H | Cl |

A = A-1; X = S; $R^3 = CH_3$; $R^4 = CH_3$

| n | $R^1$ | $R^2$ | $R^5$ |
|---|---|---|---|
| 2 | $CH_3$ | $CH_3$ | H |
| 2 | $C_2H_5$ | $CH_3$ | H |
| 2 | H | $CH_3$ | H |
| 2 | H | $C_2H_5$ | H |
| 2 | H | $CH_2CH_2CH_3$ | H |
| 2 | $OCH_3$ | $CH_3$ | H |
| 2 | $OCH_3$ | $C_2H_5$ | H |
| 2 | $CH_2CH_2CH_3$ | $CH_2CH_2CH_3$ | H |
| 2 | $CH_2CH=CH_2$ | $CH_2CH=CH_2$ | H |
| 2 | $CH_2C\equiv CH$ | $CH_2C\equiv CH$ | H |
| 2 | $CH(CH_3)_2$ | $CH(CH_3)_2$ | H |
| 2 | $-(CH_2)_5-$ | | H |
| 2 | $-(CH_2)_4-$ | | H |
| 2 | $CH_2CH=CH_2$ | $C_2H_5$ | H |
| 2 | $CH_2C\equiv CH$ | $C_2H_5$ | H |
| 2 | $OC_2H_5$ | $CH_3$ | H |
| 2 | $OC_2H_5$ | $C_2H_5$ | H |
| 2 | H | 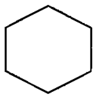 | H |
| 2 | 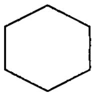 | 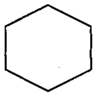 | H |
| 2 | H | $CH_2CH=CH_2$ | H |
| 2 | $CH_2CH_2CH_3$ | $CH_3$ | H |
| 2 | $CH_2CH=CH_2$ | $CH_3$ | $CH_3$ |
| 2 | $CH_2CH=CH_2$ | $C_2H_5$ | $CH_3$ |
| 2 | $CH_2CH=CH_2$ | $CH_2CH=CH_2$ | $CH_3$ |
| 2 | $CH_2CH_2CH_3$ | $CH_2CH_2CH_3$ | $CH_3$ |
| 2 | $CH_2CH_2CH_3$ | $C_2H_5$ | $CH_3$ |
| 2 | $-(CH_2)_5-$ | | $CH_3$ |
| 0 | $CH_3$ | $CH_3$ | H |
| 1 | $CH_3$ | $CH_3$ | H |

A = A-1; X = $NCH_3$; $R^1 = C_2H_5$; $R^2 = C_2H_5$

| n | $R^3$ | $R^4$ | $R^5$ |
|---|---|---|---|
| 2 | H | H | H |
| 2 | H | H | $CH_3$ |
| 2 | H | H | $C_2H_5$ |
| 2 | H | H | $CH_2CH_2CH_3$ |
| 2 | H | H | H |
| 2 | H | H | $CH_3$ |
| 2 | H | H | $C_2H_5$ |
| 2 | H | H | $CH_2CH_2CH_3$ |
| 2 | H | Cl | H |
| 2 | H | Cl | $CH_3$ |
| 2 | H | Cl | $C_2H_5$ |
| 2 | H | Cl | $CH_2CH_2CH_3$ |
| 2 | H | $OCH_3$ | H |
| 2 | H | $OCH_3$ | $CH_3$ |
| 2 | H | $OCH_3$ | $C_2H_5$ |
| 2 | H | $OCH_3$ | $CH_2CH_2CH_3$ |
| 2 | H | $CH_3$ | H |
| 2 | H | $CH_3$ | $CH_3$ |
| 2 | H | $CH_3$ | $C_2H_5$ |
| 2 | H | $CH_3$ | $CH_2CH_2CH_3$ |

TABLE 1-continued

| | | | |
|---|---|---|---|
| 2 | H | $C_2H_5$ | H |
| 2 | H | $C_2H_5$ | $CH_3$ |
| 2 | H | $C_2H_5$ | $C_2H_5$ |
| 2 | H | $C_2H_5$ | $CH_2CH_2CH_3$ |
| 2 | H | $CH(CH_3)_2$ | H |
| 2 | H | $CH(CH_3)_2$ | $CH_3$ |
| 2 | H | $CH(CH_3)_2$ | $C_2H_5$ |
| 2 | H | $CH(CH_3)_2$ | $CH_2CH_2CH_3$ |
| 2 | H | $CH_2CH_2CH_3$ | H |
| 2 | H | $CH_2CH_2CH_3$ | $CH_3$ |
| 2 | H | $CH_2CH_2CH_3$ | $C_2H_5$ |
| 2 | H | $CH_2CH_2CH_3$ | $CH_2CH_2CH_3$ |
| 0 | $CH_3$ | $CH_3$ | H |
| 2 | Cl | H | H |
| 2 | Cl | H | $CH_3$ |
| 2 | Cl | H | $C_2H_5$ |
| 2 | Cl | H | $CH_2CH_2CH_3$ |
| 2 | Cl | Cl | H |
| 2 | Cl | Cl | $CH_3$ |
| 2 | Cl | Cl | $C_2H_5$ |
| 2 | Cl | Cl | $CH_2CH_2CH_3$ |
| 2 | Cl | $OCH_3$ | H |
| 2 | Cl | $OCH_3$ | $CH_3$ |
| 2 | Cl | $OCH_3$ | $C_2H_5$ |
| 2 | Cl | $OCH_3$ | $CH_2CH_2CH_3$ |
| 2 | Cl | $CH_3$ | H |
| 2 | Cl | $CH_3$ | $CH_3$ |
| 2 | Cl | $CH_3$ | $C_2H_5$ |
| 2 | Cl | $CH_3$ | $CH_2CH_2CH_3$ |
| 2 | Cl | $C_2H_5$ | H |
| 2 | Cl | $C_2H_5$ | $CH_3$ |
| 2 | Cl | $C_2H_5$ | $C_2H_5$ |
| 2 | Cl | $C_2H_5$ | $CH_2CH_2CH_3$ |
| 1 | $CH_3$ | $CH_3$ | H |
| 2 | $OCH_3$ | H | H |
| 2 | $OCH_3$ | H | $CH_3$ |
| 2 | $OCH_3$ | H | $C_2H_5$ |
| 2 | $OCH_3$ | H | $CH_2CH_2CH_3$ |
| 2 | $OCH_3$ | Cl | H |
| 2 | $OCH_3$ | Cl | $CH_3$ |
| 2 | $OCH_3$ | Cl | $C_2H_5$ |
| 2 | $OCH_3$ | Cl | $CH_2CH_2CH_3$ |
| 2 | $OCH_3$ | $OCH_3$ | H |
| 2 | $OCH_3$ | $OCH_3$ | $CH_3$ |
| 2 | $OCH_3$ | $OCH_3$ | $C_2H_5$ |
| 2 | $OCH_3$ | $OCH_3$ | $CH_2CH_2CH_3$ |
| 2 | $OCH_3$ | $CH_3$ | H |
| 2 | $OCH_3$ | $CH_3$ | $CH_3$ |
| 2 | $OCH_3$ | $CH_3$ | $C_2H_5$ |
| 2 | $OCH_3$ | $CH_3$ | $CH_2CH_2CH_3$ |
| 2 | $OCH_3$ | $C_2H_5$ | H |
| 2 | $OCH_3$ | $C_2H_5$ | $CH_3$ |
| 2 | $OCH_3$ | $C_2H_5$ | $C_2H_5$ |
| 2 | $OCH_3$ | $C_2H_5$ | $CH_2CH_2CH_3$ |
| 2 | $CH_3$ | H | H |
| 2 | $CH_3$ | H | $CH_3$ |
| 2 | $CH_3$ | H | $C_2H_5$ |
| 2 | $CH_3$ | H | $CH_2CH_2CH_3$ |
| 2 | $CH_3$ | Cl | H |
| 2 | $CH_3$ | Cl | $CH_3$ |
| 2 | $CH_3$ | Cl | $C_2H_5$ |
| 2 | $CH_3$ | Cl | $CH_2CH_2CH_3$ |
| 2 | $CH_3$ | $OCH_3$ | H |
| 2 | $CH_3$ | $OCH_3$ | $CH_3$ |
| 2 | $CH_3$ | $OCH_3$ | $C_2H_5$ |
| 2 | $CH_3$ | $OCH_3$ | $CH_2CH_2CH_3$ |
| 2 | $CH_3$ | $CH_3$ | H |
| 2 | $CH_3$ | $CH_3$ | $CH_3$ |
| 2 | $CH_3$ | $CH_3$ | $C_2H_5$ |
| 2 | $CH_3$ | $CH_3$ | $CH_2CH_2CH_3$ |
| 2 | $CH_3$ | $C_2H_5$ | H |
| 2 | $CH_3$ | $C_2H_5$ | $CH_3$ |
| 2 | $CH_3$ | $C_2H_5$ | $C_2H_5$ |
| 2 | $CH_3$ | $C_2H_5$ | $CH_2CH_2CH_3$ |
| 2 | $C_2H_5$ | H | H |
| 2 | $C_2H_5$ | H | $CH_3$ |
| 2 | $C_2H_5$ | H | $C_2H_5$ |
| 2 | $C_2H_5$ | H | $CH_2CH_2CH_3$ |
| 2 | $C_2H_5$ | Cl | H |
| 2 | $C_2H_5$ | Cl | $CH_3$ |
| 2 | $C_2H_5$ | Cl | $C_2H_5$ |
| 2 | $C_2H_5$ | Cl | $CH_2CH_2CH_3$ |
| 2 | $C_2H_5$ | $OCH_3$ | H |
| 2 | $C_2H_5$ | $OCH_3$ | $CH_3$ |
| 2 | $C_2H_5$ | $OCH_3$ | $C_2H_5$ |
| 2 | $C_2H_5$ | $OCH_3$ | $CH_2CH_2CH_3$ |
| 2 | $C_2H_5$ | $CH_3$ | H |
| 2 | $C_2H_5$ | $CH_3$ | $CH_3$ |
| 2 | $C_2H_5$ | $CH_3$ | $C_2H_5$ |
| 2 | $C_2H_5$ | $CH_3$ | $CH_2CH_2CH_3$ |
| 2 | $C_2H_5$ | $C_2H_5$ | H |
| 2 | $C_2H_5$ | $C_2H_5$ | $CH_3$ |
| 2 | $C_2H_5$ | $C_2H_5$ | $C_2H_5$ |
| 2 | $C_2H_5$ | $C_2H_5$ | $CH_2CH_2CH_3$ |
| 2 | $CH_3$ | $CH_3$ | Cl |
| 2 | $CH_3$ | $CH_3$ | $OCH_3$ |
| 2 | $CH_3$ | $CH_3$ | F |
| 2 | $CH_3$ | $CH_3$ | Br |
| 2 | $CH_3$ | $CH_3$ | $CO_2CH_3$ |
| 2 | $CH_3$ | $CH_3$ | $CO_2C_2H_5$ |
| 2 | $CH_3$ | $CH_3$ | $CH_2OCH_3$ |
| 2 | $CH_3$ | $CH_3$ | $CON(CH_3)_2$ |
| 2 | $CH_3$ | $CH_3$ | $SCH_3$ |
| 2 | $CH_3$ | $CH_3$ | $SO_2CH_3$ |
| 2 | $CH_3$ | $CH_3$ | $NO_2$ |
| 2 | $CH_3$ | $CH_3$ | $N(CH_3)_2$ |
| 2 | $CH_3$ | $CH_3$ | $NH_2$ |
| 2 | $CH_3$ | $CH_3$ | $C_6H_5$ |
| 2 | $CH_3$ | $C_6H_5$ | H |
| 2 | $C_6H_5$ | $CH_3$ | H |
| 2 | $CH_3$ | $CF_3$ | H |
| 2 | $CF_3$ | $CH_3$ | H |
| 2 | $COCH_3$ | H | H |
| 2 | $CH=CH_2$ | $CH_3$ | H |
| 2 | $CH_3$ | $CH=CH_2$ | H |
| 2 | $SCH_3$ | $CH_3$ | H |
| 2 | $CH_3$ | $SCH_3$ | H |
| 2 | $NO_2$ | $CH_3$ | H |
| 2 | $NH_2$ | $CH_3$ | H |
| 2 | CHO | $CH_3$ | H |
| 2 | $CO_2CH_3$ | H | H |
| 2 | $CH(CH_3)_2$ | H | H |
| 2 | $COCH_3$ | H | C |
| 2 | $C_2H_5$ | H | Cl |
| 2 | $CO_2CH_3$ | H | Cl |

A = A-1; X = $NCH_3$; $R^3 = CH_3$; $R^4 = CH_3$

| n | $R^1$ | $R^2$ | $R^5$ |
|---|---|---|---|
| 2 | $CH_3$ | $CH_3$ | H |
| 2 | $C_2H_5$ | $CH_3$ | H |
| 2 | H | $CH_3$ | H |
| 2 | H | $C_2H_5$ | H |
| 2 | H | $CH_2CH_2CH_3$ | H |
| 2 | $OCH_3$ | $CH_3$ | H |
| 2 | $OCH_3$ | $C_2H_5$ | H |
| 2 | $CH_2CH_2CH_3$ | $CH_2CH_2CH_3$ | H |
| 2 | $CH_2CH=CH_2$ | $CH_2CH=CH_2$ | H |
| 2 | $CH_2C\equiv CH$ | $CH_2C\equiv CH$ | H |
| 2 | $CH(CH_3)_2$ | $CH(CH_3)_2$ | H |
| 2 | $-(CH_2)_5-$ | | H |
| 2 | $-(CH_2)_4-$ | | H |
| 2 | $CH_2CH=CH_2$ | $C_2H_5$ | H |
| 2 | $CH_2C\equiv CH$ | $C_2H_5$ | H |
| 2 | $OC_2H_5$ | $CH_3$ | H |
| 2 | $OC_2H_5$ | $C_2H_5$ | H |
| 2 | H | 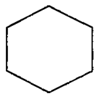 | H |

TABLE 1-continued

| | | | |
|---|---|---|---|
| 2 | 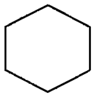 | 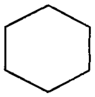 | H |
| 2 | H | $CH_2CH{=}CH_2$ | H |
| 2 | $CH_2CH_2CH_3$ | $CH_3$ | H |
| 2 | $CH_2CH{=}CH_2$ | $CH_3$ | $CH_3$ |
| 2 | $CH_2CH{=}CH_2$ | $C_2H_5$ | $CH_3$ |
| 2 | $CH_2CH{=}CH_2$ | $CH_2CH{=}CH_2$ | $CH_3$ |
| 2 | $CH_2CH_2CH_3$ | $CH_2CH_2CH_3$ | $CH_3$ |
| 2 | $CH_2CH_2CH_3$ | $C_2H_5$ | $CH_3$ |
| 2 | $-(CH_2)_5-$ | | $CH_3$ |
| 2 | $CH_3$ | $CH_3$ | H |

| n | $R^3$ | $R^4$ | $R^5$ |
|---|---|---|---|
| 2 | H | H | H |
| 2 | H | H | $CH_3$ |
| 2 | H | H | $C_2H_5$ |
| 2 | H | H | $CH_2CH_2CH_3$ |
| 2 | H | Cl | H |
| 2 | H | Cl | $CH_3$ |
| 2 | H | Cl | $C_2H_5$ |
| 2 | H | Cl | $CH_2CH_2CH_3$ |
| 2 | H | $OCH_3$ | H |
| 2 | H | $OCH_3$ | $CH_3$ |
| 2 | H | $OCH_3$ | $C_2H_5$ |
| 2 | H | $OCH_3$ | $CH_2CH_2CH_3$ |
| 2 | H | $CH_3$ | H |
| 2 | H | $CH_3$ | $CH_3$ |
| 2 | H | $CH_3$ | $C_2H_5$ |
| 2 | H | $CH_3$ | $CH_2CH_2CH_3$ |
| 2 | H | $C_2H_5$ | H |
| 2 | H | $C_2H_5$ | $CH_3$ |
| 2 | H | $C_2H_5$ | $C_2H_5$ |
| 2 | H | $C_2H_5$ | $CH_2CH_2CH_3$ |
| 2 | H | $CH(CH_3)_2$ | H |
| 2 | H | $CH(CH_3)_2$ | $CH_3$ |
| 2 | H | $CH(CH_3)_2$ | $C_2H_5$ |
| 2 | H | $CH(CH_3)_2$ | $CH_2CH_2CH_3$ |
| 2 | H | $CH_2CH_2CH_3$ | H |
| 2 | H | $CH_2CH_2CH_3$ | $CH_3$ |
| 2 | H | $CH_2CH_2CH_3$ | $C_2H_5$ |
| 2 | H | $CH_2CH_2CH_3$ | $CH_2CH_2CH_3$ |
| 0 | $CH_3$ | $CH_3$ | H |
| 2 | Cl | H | H |
| 2 | Cl | H | $CH_3$ |
| 2 | Cl | H | $C_2H_5$ |
| 2 | Cl | H | $CH_2CH_2CH_3$ |
| 2 | Cl | Cl | H |
| 2 | Cl | Cl | $CH_3$ |
| 2 | Cl | Cl | $C_2H_5$ |
| 2 | Cl | Cl | $CH_2CH_2CH_3$ |
| 2 | Cl | $OCH_3$ | H |
| 2 | Cl | $OCH_3$ | $CH_3$ |
| 2 | Cl | $OCH_3$ | $C_2H_5$ |
| 2 | Cl | $OCH_3$ | $CH_2CH_2CH_3$ |
| 2 | Cl | $CH_3$ | H |
| 2 | Cl | $CH_3$ | $CH_3$ |
| 2 | Cl | $CH_3$ | $C_2H_5$ |
| 2 | Cl | $CH_3$ | $CH_2CH_2CH_3$ |
| 2 | Cl | $C_2H_5$ | H |
| 2 | Cl | $C_2H_5$ | $CH_3$ |
| 2 | Cl | $C_2H_5$ | $C_2H_5$ |
| 2 | Cl | $C_2H_5$ | $CH_2CH_2CH_3$ |
| 1 | $CH_3$ | $CH_3$ | H |
| 2 | $OCH_3$ | H | H |
| 2 | $OCH_3$ | H | $CH_3$ |
| 2 | $OCH_3$ | H | $C_2H_5$ |
| 2 | $OCH_3$ | H | $CH_2CH_2CH_3$ |
| 2 | $OCH_3$ | Cl | H |
| 2 | $OCH_3$ | Cl | $CH_3$ |
| 2 | $OCH_3$ | Cl | $C_2H_5$ |
| 2 | $OCH_3$ | Cl | $CH_2CH_2CH_3$ |
| 2 | $OCH_3$ | $OCH_3$ | H |
| 2 | $OCH_3$ | $OCH_3$ | $CH_3$ |
| 2 | $OCH_3$ | $OCH_3$ | $C_2H_5$ |

TABLE 1-continued

| | | | |
|---|---|---|---|
| 2 | $OCH_3$ | $OCH_3$ | $CH_2CH_2CH_3$ |
| 2 | $OCH_3$ | $CH_3$ | H |
| 2 | $OCH_3$ | $CH_3$ | $CH_3$ |
| 2 | $OCH_3$ | $CH_3$ | $C_2H_5$ |
| 2 | $OCH_3$ | $CH_3$ | $CH_2CH_2CH_3$ |
| 2 | $OCH_3$ | $C_2H_5$ | H |
| 2 | $OCH_3$ | $C_2H_5$ | $CH_3$ |
| 2 | $OCH_3$ | $C_2H_5$ | $C_2H_5$ |
| 2 | $OCH_3$ | $C_2H_5$ | $CH_2CH_2CH_3$ |
| 2 | $CH_3$ | H | H |
| 2 | $CH_3$ | H | $CH_3$ |
| 2 | $CH_3$ | H | $C_2H_5$ |
| 2 | $CH_3$ | H | $CH_2CH_2CH_3$ |
| 2 | $CH_3$ | Cl | H |
| 2 | $CH_3$ | Cl | $CH_3$ |
| 2 | $CH_3$ | Cl | $C_2H_5$ |
| 2 | $CH_3$ | Cl | $CH_2CH_2CH_3$ |
| 2 | $CH_3$ | $OCH_3$ | H |
| 2 | $CH_3$ | $OCH_3$ | $CH_3$ |
| 2 | $CH_3$ | $OCH_3$ | $C_2H_5$ |
| 2 | $CH_3$ | $OCH_3$ | $CH_2CH_2CH_3$ |
| 2 | $CH_3$ | $CH_3$ | H |
| 2 | $CH_3$ | $CH_3$ | $CH_3$ |
| 2 | $CH_3$ | $CH_3$ | $C_2H_5$ |
| 2 | $CH_3$ | $CH_3$ | $CH_2CH_2CH_3$ |
| 2 | $CH_3$ | $C_2H_5$ | H |
| 2 | $CH_3$ | $C_2H_5$ | $CH_3$ |
| 2 | $CH_3$ | $C_2H_5$ | $C_2H_5$ |
| 2 | $CH_3$ | $C_2H_5$ | $CH_2CH_2CH_3$ |
| 2 | $C_2H_5$ | H | H |
| 2 | $C_2H_5$ | H | $CH_3$ |
| 2 | $C_2H_5$ | H | $C_2H_5$ |
| 2 | $C_2H_5$ | H | $CH_2CH_2CH_3$ |
| 2 | $C_2H_5$ | Cl | H |
| 2 | $C_2H_5$ | Cl | $CH_3$ |
| 2 | $C_2H_5$ | Cl | $C_2H_5$ |
| 2 | $C_2H_5$ | Cl | $CH_2CH_2CH_3$ |
| 2 | $C_2H_5$ | $OCH_3$ | H |
| 2 | $C_2H_5$ | $OCH_3$ | $CH_3$ |
| 2 | $C_2H_5$ | $OCH_3$ | $C_2H_5$ |
| 2 | $C_2H_5$ | $OCH_3$ | $CH_2CH_2CH_3$ |
| 2 | $C_2H_5$ | $CH_3$ | H |
| 2 | $C_2H_5$ | $CH_3$ | $CH_3$ |
| 2 | $C_2H_5$ | $CH_3$ | $C_2H_5$ |
| 2 | $C_2H_5$ | $CH_3$ | $CH_2CH_2CH_3$ |
| 2 | $C_2H_5$ | $C_2H_5$ | H |
| 2 | $C_2H_5$ | $C_2H_5$ | $CH_3$ |
| 2 | $C_2H_5$ | $C_2H_5$ | $C_2H_5$ |
| 2 | $C_2H_5$ | $C_2H_5$ | $CH_2CH_2CH_3$ |
| 2 | $CH_3$ | $CH_3$ | Cl |
| 2 | $CH_3$ | $CH_3$ | $OCH_3$ |
| 2 | $CH_3$ | $CH_3$ | F |
| 2 | $CH_3$ | $CH_3$ | Br |
| 2 | $CH_3$ | $CH_3$ | $CO_2CH_3$ |
| 2 | $CH_3$ | $CH_3$ | $CO_2C_2H_5$ |
| 2 | $CH_3$ | $CH_3$ | $CH_2OCH_3$ |
| 2 | $CH_3$ | $CH_3$ | $CON(CH_3)_2$ |
| 2 | $CH_3$ | $CH_3$ | $SCH_3$ |
| 2 | $CH_3$ | $CH_3$ | $SO_2CH_3$ |
| 2 | $CH_3$ | $CH_3$ | $NO_2$ |
| 2 | $CH_3$ | $CH_3$ | $N(CH_3)_2$ |
| 2 | $CH_3$ | $CH_3$ | $NH_2$ |
| 2 | $CH_3$ | $CH_3$ | $C_6H_5$ |
| 2 | $CH_3$ | $C_6H_5$ | H |
| 2 | $C_6H_5$ | $CH_3$ | H |
| 2 | $CH_3$ | $CF_3$ | H |
| 2 | $CF_3$ | $CH_3$ | H |
| 2 | $COCH_3$ | H | H |
| 2 | $CH{=}CH_2$ | $CH_3$ | H |
| 2 | $CH_3$ | $CH{=}CH_2$ | H |
| 2 | $SCH_3$ | $CH_3$ | H |
| 2 | $CH_3$ | $SCH_3$ | H |
| 2 | $NO_2$ | $CH_3$ | H |
| 2 | $NH_2$ | $CH_3$ | H |
| 2 | CHO | $CH_3$ | H |
| 2 | $CO_2CH_3$ | H | H |
| 2 | $CH(OCH_3)_2$ | H | H |
| 2 | $COCH_3$ | H | Cl |

TABLE 1-continued

| | | | |
|---|---|---|---|
| 2 | $C_2H_5$ | H | Cl |
| 2 | $CO_2CH_3$ | H | Cl |

A = A-1; X = $NC_2H_5$; $R^3 = CH_3$; $R^4 = CH_3$

| n | $R^1$ | $R^2$ | $R^5$ |
|---|---|---|---|
| 2 | $CH_3$ | $CH_3$ | H |
| 2 | $C_2H_5$ | $CH_3$ | H |
| 2 | H | $CH_3$ | H |
| 2 | H | $C_2H_5$ | H |
| 2 | H | $CH_2CH_2CH_3$ | H |
| 2 | $OCH_3$ | $CH_3$ | H |
| 2 | $OCH_3$ | $C_2H_5$ | H |
| 2 | $CH_2CH_2CH_3$ | $CH_2CH_2CH_3$ | H |
| 2 | $CH_2CH{=}CH_2$ | $CH_2CH{=}CH_2$ | H |
| 2 | $CH_2C{\equiv}CH$ | $CH_2C{\equiv}CH$ | H |
| 2 | $CH(CH_3)_2$ | $CH(CH_3)_2$ | H |
| 2 | $-(CH_2)_5-$ | | H |
| 2 | $-(CH_2)_4-$ | | H |
| 2 | $CH_2CH{=}CH_2$ | $C_2H_5$ | H |
| 2 | $CH_2C{\equiv}CH$ | $C_2H_5$ | H |
| 2 | $OC_2H_5$ | $CH_3$ | H |
| 2 | $OC_2H_5$ | $C_2H_5$ | H |
| 2 | H | 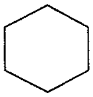 | H |
| 2 | 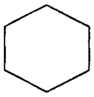 | 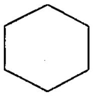 | H |
| 2 | H | $CH_2CH{=}CH_2$ | H |
| 2 | $CH_2CH_2CH_3$ | $CH_3$ | H |
| 2 | $CH_2CH{=}CH_2$ | $CH_3$ | $CH_3$ |
| 2 | $CH_2CH{=}CH_2$ | $C_2H_5$ | $CH_3$ |
| 2 | $CH_2CH{=}CH_2$ | $CH_2CH{=}CH_2$ | $CH_3$ |
| 2 | $CH_2CH_2CH_3$ | $CH_2CH_2CH_3$ | $CH_3$ |
| 2 | $CH_2CH_2CH_3$ | $C_2H_5$ | $CH_3$ |
| 2 | $-(CH_2)_5-$ | | $CH_3$ |
| 0 | $CH_3$ | $CH_3$ | H |
| 1 | $CH_3$ | $CH_3$ | H |

A = A-1; X = $NCH_2CH_2CH_3$; $R^1 = C_2H_5$; $R^2 = C_2H_5$

| n | $R^3$ | $R^4$ | $R^5$ |
|---|---|---|---|
| 2 | H | H | H |
| 2 | H | H | $CH_3$ |
| 2 | H | H | $C_2H_5$ |
| 2 | H | H | $CH_2CH_2CH_3$ |
| 2 | H | Cl | H |
| 2 | H | Cl | $CH_3$ |
| 2 | H | Cl | $C_2H_5$ |
| 2 | H | Cl | $CH_2CH_2CH_3$ |
| 2 | H | $OCH_3$ | H |
| 2 | H | $OCH_3$ | $CH_3$ |
| 2 | H | $OCH_3$ | $C_2H_5$ |
| 2 | H | $OCH_3$ | $CH_2CH_2CH_3$ |
| 2 | H | $CH_3$ | H |
| 2 | H | $CH_3$ | $CH_3$ |
| 2 | H | $CH_3$ | $C_2H_5$ |
| 2 | H | $CH_3$ | $CH_2CH_2CH_3$ |
| 2 | H | $C_2H_5$ | H |
| 2 | H | $C_2H_5$ | $CH_3$ |
| 2 | H | $C_2H_5$ | $C_2H_5$ |
| 2 | H | $C_2H_5$ | $CH_2CH_2CH_3$ |
| 2 | H | $CH(CH_3)_2$ | H |
| 2 | H | $CH(CH_3)_2$ | $CH_3$ |
| 2 | H | $CH(CH_3)_2$ | $C_2H_5$ |
| 2 | H | $CH(CH_3)_2$ | $CH_2CH_2CH_3$ |
| 2 | H | $CH_2CH_2CH_3$ | H |

TABLE 1-continued

| | | | |
|---|---|---|---|
| 2 | H | $CH_2CH_2CH_3$ | $CH_3$ |
| 2 | H | $CH_2CH_2CH_3$ | $C_2H_5$ |
| 2 | H | $CH_2CH_2CH_3$ | $CH_2CH_2CH_3$ |
| 0 | $CH_3$ | $CH_3$ | H |
| 2 | Cl | H | H |
| 2 | Cl | H | $CH_3$ |
| 2 | Cl | H | $C_2H_5$ |
| 2 | Cl | H | $CH_2CH_2CH_3$ |
| 2 | Cl | Cl | H |
| 2 | Cl | Cl | $CH_3$ |
| 2 | Cl | Cl | $C_2H_5$ |
| 2 | Cl | Cl | $CH_2CH_2CH_3$ |
| 2 | Cl | $OCH_3$ | H |
| 2 | Cl | $OCH_3$ | $CH_3$ |
| 2 | Cl | $OCH_3$ | $C_2H_5$ |
| 2 | Cl | $OCH_3$ | $CH_2CH_2CH_3$ |
| 2 | Cl | $CH_3$ | H |
| 2 | Cl | $CH_3$ | $CH_3$ |
| 2 | Cl | $CH_3$ | $C_2H_5$ |
| 2 | Cl | $CH_3$ | $CH_2CH_2CH_3$ |
| 2 | Cl | $C_2H_5$ | H |
| 2 | Cl | $C_2H_5$ | $CH_3$ |
| 2 | Cl | $C_2H_5$ | $C_2H_5$ |
| 2 | Cl | $C_2H_5$ | $CH_2CH_2CH_3$ |
| 1 | $CH_3$ | $CH_3$ | H |
| 2 | $OCH_3$ | H | H |
| 2 | $OCH_3$ | H | $CH_3$ |
| 2 | $OCH_3$ | H | $C_2H_5$ |
| 2 | $OCH_3$ | H | $CH_2CH_2CH_3$ |
| 2 | $OCH_3$ | Cl | H |
| 2 | $OCH_3$ | Cl | $CH_3$ |
| 2 | $OCH_3$ | Cl | $C_2H_5$ |
| 2 | $OCH_3$ | Cl | $CH_2CH_2CH_3$ |
| 2 | $OCH_3$ | $OCH_3$ | H |
| 2 | $OCH_3$ | $OCH_3$ | $CH_3$ |
| 2 | $OCH_3$ | $OCH_3$ | $C_2H_5$ |
| 2 | $OCH_3$ | $OCH_3$ | $CH_2CH_2CH_3$ |
| 2 | $OCH_3$ | $CH_3$ | H |
| 2 | $OCH_3$ | $CH_3$ | $CH_3$ |
| 2 | $OCH_3$ | $CH_3$ | $C_2H_5$ |
| 2 | $OCH_3$ | $CH_3$ | $CH_2CH_2CH_3$ |
| 2 | $OCH_3$ | $C_2H_5$ | H |
| 2 | $OCH_3$ | $C_2H_5$ | $CH_3$ |
| 2 | $OCH_3$ | $C_2H_5$ | $C_2H_5$ |
| 2 | $OCH_3$ | $C_2H_5$ | $CH_2CH_2CH_3$ |
| 2 | $CH_3$ | H | H |
| 2 | $CH_3$ | H | $CH_3$ |
| 2 | $CH_3$ | H | $C_2H_5$ |
| 2 | $CH_3$ | H | $CH_2CH_2CH_3$ |
| 2 | $CH_3$ | Cl | H |
| 2 | $CH_3$ | Cl | $CH_3$ |
| 2 | $CH_3$ | Cl | $C_2H_5$ |
| 2 | $CH_3$ | Cl | $CH_2CH_2CH_3$ |
| 2 | $CH_3$ | $OCH_3$ | H |
| 2 | $CH_3$ | $OCH_3$ | $CH_3$ |
| 2 | $CH_3$ | $OCH_3$ | $C_2H_5$ |
| 2 | $CH_3$ | $OCH_3$ | $CH_2CH_2CH_3$ |
| 2 | $CH_3$ | $CH_3$ | H |
| 2 | $CH_3$ | $CH_3$ | $CH_3$ |
| 2 | $CH_3$ | $CH_3$ | $C_2H_5$ |
| 2 | $CH_3$ | $CH_3$ | $CH_2CH_2CH_3$ |
| 2 | $CH_3$ | $C_2H_5$ | H |
| 2 | $CH_3$ | $C_2H_5$ | $CH_3$ |
| 2 | $CH_3$ | $C_2H_5$ | $C_2H_5$ |
| 2 | $CH_3$ | $C_2H_5$ | $CH_2CH_2CH_3$ |
| 2 | $C_2H_5$ | H | H |
| 2 | $C_2H_5$ | H | $CH_3$ |
| 2 | $C_2H_5$ | H | $C_2H_5$ |
| 2 | $C_2H_5$ | H | $CH_2CH_2CH_3$ |
| 2 | $C_2H_5$ | Cl | H |
| 2 | $C_2H_5$ | Cl | $CH_3$ |
| 2 | $C_2H_5$ | Cl | $C_2H_5$ |
| 2 | $C_2H_5$ | Cl | $CH_2CH_2CH_3$ |
| 2 | $C_2H_5$ | $OCH_3$ | H |
| 2 | $C_2H_5$ | $OCH_3$ | $CH_3$ |
| 2 | $C_2H_5$ | $OCH_3$ | $C_2H_5$ |
| 2 | $C_2H_5$ | $OCH_3$ | $CH_2CH_2CH_3$ |
| 2 | $C_2H_5$ | $CH_3$ | H |

TABLE 1-continued

| | | | |
|---|---|---|---|
| 2 | $C_2H_5$ | $CH_3$ | $CH_3$ |
| 2 | $C_2H_5$ | $CH_3$ | $C_2H_5$ |
| 2 | $C_2H_5$ | $CH_3$ | $CH_2CH_2CH_3$ |
| 2 | $C_2H_5$ | $C_2H_5$ | H |
| 2 | $C_2H_5$ | $C_2H_5$ | $CH_3$ |
| 2 | $C_2H_5$ | $C_2H_5$ | $C_2H_5$ |
| 2 | $C_2H_5$ | $C_2H_5$ | $CH_2CH_2CH_3$ |
| 2 | $CH_2CH_2CH_3$ | $CH_2CH_2CH_3$ | H |
| 2 | $CH_2CH_2CH_3$ | $CH_2CH_2CH_3$ | $CH_3$ |
| 2 | $CH_2CH_2CH_3$ | $CH_2CH_2CH_3$ | $C_2H_5$ |
| 2 | $CH_2CH_2CH_3$ | $CH_2CH_2CH_3$ | $CH_2CH_2CH_3$ |
| 2 | $CH_3$ | $CH_3$ | Cl |
| 2 | $CH_3$ | $CH_3$ | $OCH_3$ |
| 2 | $CH_3$ | $CH_3$ | F |
| 2 | $CH_3$ | $CH_3$ | Br |
| 2 | $CH_3$ | $CH_3$ | $CO_2CH_3$ |
| 2 | $CH_3$ | $CH_3$ | $CO_2C_2H_5$ |
| 2 | $CH_3$ | $CH_3$ | $CH_2OCH_3$ |
| 2 | $CH_3$ | $CH_3$ | $CON(CH_3)_2$ |
| 2 | $CH_3$ | $CH_3$ | $SCH_3$ |
| 2 | $CH_3$ | $CH_3$ | $SO_2CH_3$ |
| 2 | $CH_3$ | $CH_3$ | $NO_2$ |
| 2 | $CH_3$ | $CH_3$ | $N(CH_3)_2$ |
| 2 | $CH_3$ | $CH_3$ | $NH_2$ |
| 2 | $CH_3$ | $CH_3$ | $C_6H_5$ |
| 2 | $CH_3$ | $C_6H_5$ | H |
| 2 | $C_6H_5$ | $CH_3$ | H |
| 2 | $CH_3$ | $CF_3$ | H |
| 2 | $CF_3$ | $CH_3$ | H |
| 2 | $COCH_3$ | H | H |
| 2 | $CH{=}CH_2$ | $CH_3$ | H |
| 2 | $CH_3$ | $CH{=}CH_2$ | H |
| 2 | $SCH_3$ | $CH_3$ | H |
| 2 | $CH_3$ | $SCH_3$ | H |
| 2 | $NO_2$ | $CH_3$ | H |
| 2 | $NH_2$ | $CH_3$ | H |
| 2 | CHO | $CH_3$ | H |
| 2 | $CO_2CH_3$ | H | H |
| 2 | $CH(OCH_3)_2$ | H | H |
| 2 | $COCH_3$ | H | Cl |
| 2 | $C_2H_5$ | H | Cl |
| 2 | $CO_2CH_3$ | H | Cl |

A = A-1; X = $NCH_2CH_2CH_3$; $R^3$ = $CH_3$; $R^4$ = $CH_3$

| n | $R^1$ | $R^2$ | $R^5$ |
|---|---|---|---|
| 2 | $CH_3$ | $CH_3$ | H |
| 2 | $C_2H_5$ | $CH_3$ | H |
| 2 | H | $CH_3$ | H |
| 2 | H | $C_2H_5$ | H |
| 2 | H | $CH_2CH_2CH_3$ | H |
| 2 | $OCH_3$ | $CH_3$ | H |
| 2 | $OCH_3$ | $C_2H_5$ | H |
| 2 | $CH_2CH_2CH_3$ | $CH_2CH_2CH_3$ | H |
| 2 | $CH_2CH{=}CH_2$ | $CH_2CH{=}CH_2$ | H |
| 2 | $CH_2C{\equiv}CH$ | $CH_2C{\equiv}CH$ | H |
| 2 | $CH(CH_3)_2$ | $CH(CH_3)_2$ | H |
| 2 | $-(CH_2)_5-$ | | H |
| 2 | $-(CH_2)_4-$ | | H |
| 2 | $CH_2CH{=}CH_2$ | $C_2H_5$ | H |
| 2 | $CH_2C{\equiv}CH$ | $C_2H_5$ | H |
| 2 | $OC_2H_5$ | $CH_3$ | H |
| 2 | $OC_2H_5$ | $C_2H_5$ | H |
| 2 | H | 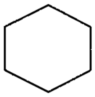 | H |
| 2 | 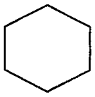 | 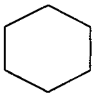 | H |

TABLE 1-continued

| | | | |
|---|---|---|---|
| 2 | H | $CH_2CH{=}CH_2$ | H |
| 2 | $CH_2CH_2CH_3$ | $CH_3$ | H |
| 2 | $CH_2CH{=}CH_2$ | $CH_3$ | $CH_3$ |
| 2 | $CH_2CH{=}CH_2$ | $C_2H_5$ | $CH_3$ |
| 2 | $CH_2CH{=}CH_2$ | $CH_2CH{=}CH_2$ | $CH_3$ |
| 2 | $CH_2CH_2CH_3$ | $CH_2CH_2CH_3$ | $CH_3$ |
| 2 | $CH_2CH_2CH_3$ | $C_2H_5$ | $CH_3$ |
| 2 | $-(CH_2)_5-$ | | $CH_3$ |
| 0 | $CH_3$ | $CH_3$ | H |
| 1 | $CH_3$ | $CH_3$ | H |

TABLE 2

A = A-2; X = O; $R^1$ = $C_2H_5$; $R^2$ = $C_2H_5$

| n | $R^3$ | $R^4$ | $R^5$ |
|---|---|---|---|
| 2 | H | H | H |
| 2 | H | H | $CH_3$ |
| 2 | H | H | $C_2H_5$ |
| 2 | H | H | $CH_2CH_2CH_3$ |
| 2 | H | Cl | H |
| 2 | H | Cl | $CH_3$ |
| 2 | H | Cl | $C_2H_5$ |
| 2 | H | Cl | $CH_2CH_2CH_3$ |
| 2 | H | $OCH_3$ | H |
| 2 | H | $OCH_3$ | $CH_3$ |
| 2 | H | $OCH_3$ | $C_2H_5$ |
| 2 | H | $OCH_3$ | $CH_2CH_2CH_3$ |
| 2 | H | $CH_3$ | H |
| 2 | H | $CH_3$ | $CH_3$ |
| 2 | H | $CH_3$ | $C_2H_5$ |
| 2 | H | $CH_3$ | $CH_2CH_2CH_3$ |
| 2 | H | $C_2H_5$ | H |
| 2 | H | $C_2H_5$ | $CH_3$ |
| 2 | H | $C_2H_5$ | $C_2H_5$ |
| 2 | H | $C_2H_5$ | $CH_2CH_2CH_3$ |
| 0 | $CH_3$ | $CH_3$ | H |
| 2 | Cl | H | H |
| 2 | Cl | H | $CH_3$ |
| 2 | Cl | H | $C_2H_5$ |
| 2 | Cl | H | $CH_2CH_2CH_3$ |
| 2 | Cl | Cl | H |
| 2 | Cl | Cl | $CH_3$ |
| 2 | Cl | Cl | $C_2H_5$ |
| 2 | Cl | Cl | $CH_2CH_2CH_3$ |
| 2 | Cl | $OCH_3$ | H |
| 2 | Cl | $OCH_3$ | $CH_3$ |
| 2 | Cl | $OCH_3$ | $C_2H_5$ |
| 2 | Cl | $OCH_3$ | $CH_2CH_2CH_3$ |
| 2 | Cl | $CH_3$ | H |
| 2 | Cl | $CH_3$ | $CH_3$ |
| 2 | Cl | $CH_3$ | $C_2H_5$ |
| 2 | Cl | $CH_3$ | $CH_2CH_2CH_3$ |
| 2 | Cl | $C_2H_5$ | H |
| 2 | Cl | $C_2H_5$ | $CH_3$ |
| 2 | Cl | $C_2H_5$ | $C_2H_5$ |
| 2 | Cl | $C_2H_5$ | $CH_2CH_2CH_3$ |
| 1 | $CH_3$ | $CH_3$ | H |
| 2 | $OCH_3$ | H | H |
| 2 | $OCH_3$ | H | $CH_3$ |
| 2 | $OCH_3$ | H | $C_2H_5$ |
| 2 | $OCH_3$ | H | $CH_2CH_2CH_3$ |
| 2 | $OCH_3$ | Cl | H |
| 2 | $OCH_3$ | Cl | $CH_3$ |
| 2 | $OCH_3$ | Cl | $C_2H_5$ |
| 2 | $OCH_3$ | Cl | $CH_2CH_2CH_3$ |
| 2 | $OCH_3$ | $OCH_3$ | H |
| 2 | $OCH_3$ | $OCH_3$ | $CH_3$ |
| 2 | $OCH_3$ | $OCH_3$ | $C_2H_5$ |
| 2 | $OCH_3$ | $OCH_3$ | $CH_2CH_2CH_3$ |
| 2 | $OCH_3$ | $CH_3$ | H |
| 2 | $OCH_3$ | $CH_3$ | $CH_3$ |
| 2 | $OCH_3$ | $CH_3$ | $C_2H_5$ |

TABLE 2-continued

| | | | |
|---|---|---|---|
| 2 | $OCH_3$ | $CH_3$ | $CH_2CH_2CH_3$ |
| 2 | $OCH_3$ | $C_2H_5$ | H |
| 2 | $OCH_3$ | $C_2H_5$ | $CH_3$ |
| 2 | $OCH_3$ | $C_2H_5$ | $C_2H_5$ |
| 2 | $OCH_3$ | $C_2H_5$ | $CH_2CH_2CH_3$ |
| 2 | $CH_3$ | H | H |
| 2 | $CH_3$ | H | $CH_3$ |
| 2 | $CH_3$ | H | $C_2H_5$ |
| 2 | $CH_3$ | H | $CH_2CH_2CH_3$ |
| 2 | $CH_3$ | Cl | H |
| 2 | $CH_3$ | Cl | $CH_3$ |
| 2 | $CH_3$ | Cl | $C_2H_5$ |
| 2 | $CH_3$ | Cl | $CH_2CH_2CH_3$ |
| 2 | $CH_3$ | $OCH_3$ | H |
| 2 | $CH_3$ | $OCH_3$ | $CH_3$ |
| 2 | $CH_3$ | $OCH_3$ | $C_2H_5$ |
| 2 | $CH_3$ | $OCH_3$ | $CH_2CH_2CH_3$ |
| 2 | $CH_3$ | $CH_3$ | H |
| 2 | $CH_3$ | $CH_3$ | $CH_3$ |
| 2 | $CH_3$ | $CH_3$ | $C_2H_5$ |
| 2 | $CH_3$ | $CH_3$ | $CH_2CH_2CH_3$ |
| 2 | $CH_3$ | $C_2H_5$ | H |
| 2 | $CH_3$ | $C_2H_5$ | $CH_3$ |
| 2 | $CH_3$ | $C_2H_5$ | $C_2H_5$ |
| 2 | $CH_3$ | $C_2H_5$ | $CH_2CH_2CH_3$ |
| 2 | $C_2H_5$ | H | H |
| 2 | $C_2H_5$ | H | $CH_3$ |
| 2 | $C_2H_5$ | H | $C_2H_5$ |
| 2 | $C_2H_5$ | H | $CH_2CH_2CH_3$ |
| 2 | $C_2H_5$ | Cl | H |
| 2 | $C_2H_5$ | Cl | $CH_3$ |
| 2 | $C_2H_5$ | Cl | $C_2H_5$ |
| 2 | $C_2H_5$ | Cl | $CH_2CH_2CH_3$ |
| 2 | $C_2H_5$ | $OCH_3$ | H |
| 2 | $C_2H_5$ | $OCH_3$ | $CH_3$ |
| 2 | $C_2H_5$ | $OCH_3$ | $C_2H_5$ |
| 2 | $C_2H_5$ | $OCH_3$ | $CH_2CH_2CH_3$ |
| 2 | $C_2H_5$ | $CH_3$ | H |
| 2 | $C_2H_5$ | $CH_3$ | $CH_3$ |
| 2 | $C_2H_5$ | $CH_3$ | $C_2H_5$ |
| 2 | $C_2H_5$ | $CH_3$ | $CH_2CH_2CH_3$ |
| 2 | $C_2H_5$ | $C_2H_5$ | H |
| 2 | $C_2H_5$ | $C_2H_5$ | $CH_3$ |
| 2 | $C_2H_5$ | $C_2H_5$ | $C_2H_5$ |
| 2 | $C_2H_5$ | $C_2H_5$ | $CH_2CH_2CH_3$ |
| 2 | $CH_3$ | $CH_3$ | Cl |
| 2 | $CH_3$ | $CH_3$ | $OCH_3$ |
| 2 | $CH_3$ | $CH_3$ | F |
| 2 | $CH_3$ | $CH_3$ | Br |
| 2 | $CH_3$ | $CH_3$ | $CO_2CH_3$ |
| 2 | $CH_3$ | $CH_3$ | $CO_2C_2H_5$ |
| 2 | $CH_3$ | $CH_3$ | $CH_2OCH_3$ |
| 2 | $CH_3$ | $CH_3$ | $CON(CH_3)_2$ |
| 2 | $CH_3$ | $CH_3$ | $SCH_3$ |
| 2 | $CH_3$ | $CH_3$ | $SO_2CH_3$ |
| 2 | $CH_3$ | $CH_3$ | $NO_2$ |
| 2 | $CH_3$ | $CH_3$ | $N(CH_3)_2$ |
| 2 | $CH_3$ | $CH_3$ | $NH_2$ |
| 2 | $CH_3$ | $CH_3$ | $C_6H_5$ |
| 2 | $CH_3$ | $C_6H_5$ | H |
| 2 | $C_6H_5$ | $CH_3$ | H |
| 2 | $CH_3$ | $CF_3$ | H |
| 2 | $CF_3$ | $CH_3$ | H |
| 2 | $COCH_3$ | H | H |
| 2 | $CH=CH_2$ | $CH_3$ | H |
| 2 | $CH_3$ | $CH=CH_2$ | H |
| 2 | $SCH_3$ | $CH_3$ | H |
| 2 | $CH_3$ | $SCH_3$ | H |
| 2 | $NO_2$ | $CH_3$ | H |
| 2 | $NH_2$ | $CH_3$ | H |
| 2 | CHO | $CH_3$ | H |
| 2 | $CO_2CH_3$ | H | H |
| 2 | $CH(OCH_3)_2$ | H | H |
| 2 | $COCH_3$ | H | Cl |
| 2 | $C_2H_5$ | H | Cl |
| 2 | $CO_2CH_3$ | H | Cl |

TABLE 2-continued

| A = A-2; X = O; $R^3 = CH_3$; $R^4 = CH_3$ | | | |
|---|---|---|---|
| n | $R^1$ | $R^2$ | $R^5$ |
| 2 | $CH_3$ | $CH_3$ | H |
| 2 | $C_2H_5$ | $CH_3$ | H |
| 2 | H | $CH_3$ | H |
| 2 | H | $C_2H_5$ | H |
| 2 | H | $CH_2CH_2CH_3$ | H |
| 2 | $OCH_3$ | $CH_3$ | H |
| 2 | $OCH_3$ | $C_2H_5$ | H |
| 2 | $CH_2CH=CH_2$ | $CH_2CH=CH_2$ | H |
| 2 | $CH_2C\equiv CH$ | $CH_2C\equiv CH$ | H |
| 2 | $CH(CH_3)_2$ | $CH(CH_3)_2$ | H |
| 2 | | $-(CH_2)_5-$ | H |
| 2 | | $-(CH_2)_4-$ | H |
| 2 | $CH_2CH=CH_2$ | $C_2H_5$ | H |
| 2 | $CH_2C\equiv CH$ | $C_2H_5$ | H |
| 2 | $OC_2H_5$ | $CH_3$ | H |
| 2 | $OC_2H_5$ | $C_2H_5$ | H |
| 2 | H | 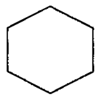 | H |
| 2 | 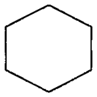 | 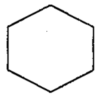 | H |
| 2 | H | $CH_2CH=CH_2$ | H |
| 2 | $CH_2CH_2CH_3$ | $CH_3$ | H |
| 2 | $CH_2CH=CH_2$ | $CH_3$ | $CH_3$ |
| 2 | $CH_2CH=CH_2$ | $C_2H_5$ | $CH_3$ |
| 2 | $CH_2CH=CH_2$ | $CH_2CH=CH_2$ | $CH_3$ |
| 2 | $CH_2CH_2CH_3$ | $CH_2CH_2CH_3$ | $CH_3$ |
| 2 | $CH_2CH_2CH_3$ | $C_2H_5$ | $CH_3$ |
| 2 | | $-(CH_2)_5-$ | H |
| 0 | $CH_3$ | $CH_3$ | H |
| 1 | $CH_3$ | $CH_3$ | H |
| A = A-2; X = S; $R^1 = C_2H_5$; $R^2 = C_2H_5$ | | | |
| n | $R^3$ | $R^4$ | $R^5$ |
| 2 | H | H | H |
| 2 | H | H | $CH_3$ |
| 2 | H | H | $C_2H_5$ |
| 2 | H | H | $CH_2CH_2CH_3$ |
| 2 | H | Cl | H |
| 2 | H | Cl | $CH_3$ |
| 2 | H | Cl | $C_2H_5$ |
| 2 | H | Cl | $CH_2CH_2CH_3$ |
| 2 | H | $OCH_3$ | H |
| 2 | H | $OCH_3$ | $CH_3$ |
| 2 | H | $OCH_3$ | $C_2H_5$ |
| 2 | H | $OCH_3$ | $CH_2CH_2CH_3$ |
| 2 | H | $CH_3$ | H |
| 2 | H | $CH_3$ | $CH_3$ |
| 2 | H | $CH_3$ | $C_2H_5$ |
| 2 | H | $CH_3$ | $CH_2CH_2CH_3$ |
| 2 | H | $C_2H_5$ | H |
| 2 | H | $C_2H_5$ | $CH_3$ |
| 2 | H | $C_2H_5$ | $C_2H_5$ |
| 2 | H | $C_2H_5$ | $CH_2CH_2CH_3$ |
| 0 | $CH_3$ | $CH_3$ | H |
| 2 | Cl | H | H |
| 2 | Cl | H | $CH_3$ |
| 2 | Cl | H | $C_2H_5$ |
| 2 | Cl | H | $CH_2CH_2CH_3$ |

TABLE 2-continued

| | | | |
|---|---|---|---|
| 2 | Cl | Cl | H |
| 2 | Cl | Cl | $CH_3$ |
| 2 | Cl | Cl | $C_2H_5$ |
| 2 | Cl | Cl | $CH_2CH_2CH_3$ |
| 2 | Cl | $OCH_3$ | H |
| 2 | Cl | $OCH_3$ | $CH_3$ |
| 2 | Cl | $OCH_3$ | $C_2H_5$ |
| 2 | Cl | $OCH_3$ | $CH_2CH_2CH_3$ |
| 2 | Cl | $CH_3$ | H |
| 2 | Cl | $CH_3$ | $CH_3$ |
| 2 | Cl | $CH_3$ | $C_2H_5$ |
| 2 | Cl | $CH_3$ | $CH_2CH_2CH_3$ |
| 2 | Cl | $C_2H_5$ | H |
| 2 | Cl | $C_2H_5$ | $CH_3$ |
| 2 | Cl | $C_2H_5$ | $C_2H_5$ |
| 2 | Cl | $C_2H_5$ | $CH_2CH_2CH_3$ |
| 2 | Cl | $CH(CH_3)_2$ | H |
| 2 | Cl | $CH(CH_3)_2$ | $CH_3$ |
| 2 | Cl | $CH(CH_3)_2$ | $C_2H_5$ |
| 2 | Cl | $CH(CH_3)_2$ | $CH_2CH_2CH_3$ |
| 2 | Cl | $CH_2CH_2CH_3$ | H |
| 2 | Cl | $CH_2CH_2CH_3$ | $CH_3$ |
| 2 | Cl | $CH_2CH_2CH_3$ | $C_2H_5$ |
| 2 | Cl | $CH_2CH_2CH_3$ | $CH_2CH_2CH_3$ |
| 1 | $CH_3$ | $CH_3$ | H |
| 2 | $OCH_3$ | H | H |
| 2 | $OCH_3$ | H | $CH_3$ |
| 2 | $OCH_3$ | H | $C_2H_5$ |
| 2 | $OCH_3$ | H | $CH_2CH_2CH_3$ |
| 2 | $OCH_3$ | Cl | H |
| 2 | $OCH_3$ | Cl | $CH_3$ |
| 2 | $OCH_3$ | Cl | $C_2H_5$ |
| 2 | $OCH_3$ | Cl | $CH_2CH_2CH_3$ |
| 2 | $OCH_3$ | $OCH_3$ | H |
| 2 | $OCH_3$ | $OCH_3$ | $CH_3$ |
| 2 | $OCH_3$ | $OCH_3$ | $C_2H_5$ |
| 2 | $OCH_3$ | $OCH_3$ | $CH_2CH_2CH_3$ |
| 2 | $OCH_3$ | $CH_3$ | H |
| 2 | $OCH_3$ | $CH_3$ | $CH_3$ |
| 2 | $OCH_3$ | $CH_3$ | $C_2H_5$ |
| 2 | $OCH_3$ | $CH_3$ | $CH_2CH_2CH_3$ |
| 2 | $OCH_3$ | $C_2H_5$ | H |
| 2 | $OCH_3$ | $C_2H_5$ | $CH_3$ |
| 2 | $OCH_3$ | $C_2H_5$ | $C_2H_5$ |
| 2 | $OCH_3$ | $C_2H_5$ | $CH_2CH_2CH_3$ |
| 2 | $OCH_3$ | $CH(CH_3)_2$ | H |
| 2 | $OCH_3$ | $CH(CH_3)_2$ | $CH_3$ |
| 2 | $OCH_3$ | $CH(CH_3)_2$ | $C_2H_5$ |
| 2 | $OCH_3$ | $CH(CH_3)_2$ | $CH_2CH_2CH_3$ |
| 2 | $OCH_3$ | $CH_2CH_2CH_3$ | H |
| 2 | $OCH_3$ | $CH_2CH_2CH_3$ | $CH_3$ |
| 2 | $OCH_3$ | $CH_2CH_2CH_3$ | $C_2H_5$ |
| 2 | $OCH_3$ | $CH_2CH_2CH_3$ | $CH_2CH_2CH_3$ |
| 2 | $CH_3$ | H | H |
| 2 | $CH_3$ | H | $CH_3$ |
| 2 | $CH_3$ | H | $C_2H_5$ |
| 2 | $CH_3$ | H | $CH_2CH_2CH_3$ |
| 2 | $CH_3$ | Cl | H |
| 2 | $CH_3$ | Cl | $CH_3$ |
| 2 | $CH_3$ | Cl | $C_2H_5$ |
| 2 | $CH_3$ | Cl | $CH_2CH_2CH_3$ |
| 2 | $CH_3$ | $OCH_3$ | H |
| 2 | $CH_3$ | $OCH_3$ | $CH_3$ |
| 2 | $CH_3$ | $OCH_3$ | $C_2H_5$ |
| 2 | $CH_3$ | $OCH_3$ | $CH_2CH_2CH_3$ |
| 2 | $CH_3$ | $CH_3$ | H |
| 2 | $CH_3$ | $CH_3$ | $CH_3$ |
| 2 | $CH_3$ | $CH_3$ | $C_2H_5$ |
| 2 | $CH_3$ | $CH_3$ | $CH_2CH_2CH_3$ |
| 2 | $CH_3$ | $C_2H_5$ | H |
| 2 | $CH_3$ | $C_2H_5$ | $CH_3$ |
| 2 | $CH_3$ | $C_2H_5$ | $C_2H_5$ |
| 2 | $CH_3$ | $C_2H_5$ | $CH_2CH_2CH_3$ |
| 2 | $CH_3$ | $CH(CH_3)_2$ | H |
| 2 | $CH_3$ | $CH(CH_3)_2$ | $CH_3$ |
| 2 | $CH_3$ | $CH(CH_3)_2$ | $C_2H_5$ |
| 2 | $CH_3$ | $CH(CH_3)_2$ | $CH_2CH_2CH_3$ |

TABLE 2-continued

| | | | |
|---|---|---|---|
| 2 | $CH_3$ | $CH_2CH_2CH_3$ | H |
| 2 | $CH_3$ | $CH_2CH_2CH_3$ | $CH_3$ |
| 2 | $CH_3$ | $CH_2CH_2CH_3$ | $C_2H_5$ |
| 2 | $CH_3$ | $CH_2CH_2CH_3$ | $CH_2CH_2CH_3$ |
| 2 | $C_2H_5$ | H | H |
| 2 | $C_2H_5$ | H | $CH_3$ |
| 2 | $C_2H_5$ | H | $C_2H_5$ |
| 2 | $C_2H_5$ | H | $CH_2CH_2CH_3$ |
| 2 | $C_2H_5$ | Cl | H |
| 2 | $C_2H_5$ | Cl | $CH_3$ |
| 2 | $C_2H_5$ | Cl | $C_2H_5$ |
| 2 | $C_2H_5$ | Cl | $CH_2CH_2CH_3$ |
| 2 | $C_2H_5$ | $OCH_3$ | H |
| 2 | $C_2H_5$ | $OCH_3$ | $CH_3$ |
| 2 | $C_2H_5$ | $OCH_3$ | $C_2H_5$ |
| 2 | $C_2H_5$ | $OCH_3$ | $CH_2CH_2CH_3$ |
| 2 | $C_2H_5$ | $CH_3$ | H |
| 2 | $C_2H_5$ | $CH_3$ | $CH_3$ |
| 2 | $C_2H_5$ | $CH_3$ | $C_2H_5$ |
| 2 | $C_2H_5$ | $CH_3$ | $CH_2CH_2CH_3$ |
| 2 | $C_2H_5$ | $C_2H_5$ | H |
| 2 | $CH_3$ | $CH_3$ | Cl |
| 2 | $CH_3$ | $CH_3$ | $OCH_3$ |
| 2 | $CH_3$ | $CH_3$ | F |
| 2 | $CH_3$ | $CH_3$ | Br |
| 2 | $CH_3$ | $CH_3$ | $CO_2CH_3$ |
| 2 | $CH_3$ | $CH_3$ | $CO_2C_2H_5$ |
| 2 | $CH_3$ | $CH_3$ | $CH_2OCH_3$ |
| 2 | $CH_3$ | $CH_3$ | $CON(CH_3)_2$ |
| 2 | $CH_3$ | $CH_3$ | $SCH_3$ |
| 2 | $CH_3$ | $CH_3$ | $SO_2CH_3$ |
| 2 | $CH_3$ | $CH_3$ | $NO_2$ |
| 2 | $CH_3$ | $CH_3$ | $N(CH_3)_2$ |
| 2 | $CH_3$ | $CH_3$ | $NH_2$ |
| 2 | $CH_3$ | $CH_3$ | $C_6H_5$ |
| 2 | $CH_3$ | $C_6H_5$ | H |
| 2 | $C_6H_5$ | $CH_3$ | H |
| 2 | $CH_3$ | $CF_3$ | H |
| 2 | $CF_3$ | $CH_3$ | H |
| 2 | $COCH_3$ | H | H |
| 2 | $CH=CH_2$ | $CH_3$ | H |
| 2 | $CH_3$ | $CH=CH_2$ | H |
| 2 | $SCH_3$ | $CH_3$ | H |
| 2 | $CH_3$ | $SCH_3$ | H |
| 2 | $NO_2$ | $CH_3$ | H |
| 2 | $NH_2$ | $CH_3$ | H |
| 2 | CHO | $CH_3$ | H |
| 2 | $CO_2CH_3$ | H | H |
| 2 | $CH(OCH_3)_2$ | H | H |
| 2 | $COCH_3$ | H | Cl |
| 2 | $C_2H_5$ | H | Cl |
| 2 | $CO_2CH_3$ | H | Cl |

A = A-2; X = S; $R^3 = CH_3$; $R^4 = CH_3$

| n | $R^1$ | $R^2$ | $R^5$ |
|---|---|---|---|
| 2 | $CH_3$ | $CH_3$ | H |
| 2 | $C_2H_5$ | $CH_3$ | H |
| 2 | H | $CH_3$ | H |
| 2 | H | $C_2H_5$ | H |
| 2 | H | $CH_2CH_2CH_3$ | H |
| 2 | $OCH_3$ | $CH_3$ | H |
| 2 | $OCH_3$ | $C_2H_5$ | H |
| 2 | $CH_2CH_2CH_3$ | $CH_2CH_2CH_3$ | H |
| 2 | $CH_2CH=CH_2$ | $CH_2CH=CH_2$ | H |
| 2 | $CH_2C\equiv CH$ | $CH_2C\equiv CH$ | H |
| 2 | $CH(CH_3)_2$ | $CH(CH_3)_2$ | H |
| 2 | $-(CH_2)_5-$ | | H |
| 2 | $-(CH_2)_4-$ | | H |
| 2 | $CH_2CH=CH_2$ | $C_2H_5$ | H |
| 2 | $CH_2C\equiv CH$ | $C_2H_5$ | H |

TABLE 2-continued

| | | | |
|---|---|---|---|
| 2 | $OC_2H_5$ | $CH_3$ | H |
| 2 | $OC_2H_5$ | $C_2H_5$ | H |
| 2 | H | 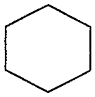 | H |
| 2 | 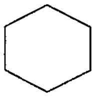 | 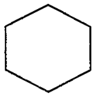 | H |
| 2 | H | $CH_2CH{=}CH_2$ | H |
| 2 | $CH_2CH_2CH_3$ | $CH_3$ | H |
| 2 | $CH_2CH{=}CH_2$ | $CH_3$ | $CH_3$ |
| 2 | $CH_2CH{=}CH_2$ | $C_2H_5$ | $CH_3$ |
| 2 | $CH_2CH{=}CH_2$ | $CH_2CH{=}CH_2$ | $CH_3$ |
| 2 | $CH_2CH_2CH_3$ | $CH_2CH_2CH_3$ | $CH_3$ |
| 2 | $CH_2CH_2CH_3$ | $C_2H_5$ | $CH_3$ |
| 2 | $-(CH_2)_5-$ | | $CH_3$ |
| 0 | $CH_3$ | $CH_3$ | H |
| 1 | $CH_3$ | $CH_3$ | H |

A = A-2; X = $NCH_3$; $R^1 = C_2H_5$; $R^2 = C_2H_5$

| n | $R^3$ | $R^4$ | $R^5$ |
|---|---|---|---|
| 2 | H | H | H |
| 2 | H | H | $CH_3$ |
| 2 | H | H | $C_2H_5$ |
| 2 | H | H | $CH_2CH_2CH_3$ |
| 2 | H | Cl | H |
| 2 | H | Cl | $CH_3$ |
| 2 | H | Cl | $C_2H_5$ |
| 2 | H | Cl | $CH_2CH_2CH_3$ |
| 2 | H | $OCH_3$ | H |
| 2 | H | $OCH_3$ | $CH_3$ |
| 2 | H | $OCH_3$ | $C_2H_5$ |
| 2 | H | $OCH_3$ | $CH_2CH_2CH_3$ |
| 2 | H | $CH_3$ | H |
| 2 | H | $CH_3$ | $CH_3$ |
| 2 | H | $CH_3$ | $C_2H_5$ |
| 2 | H | $CH_3$ | $CH_2CH_2CH_3$ |
| 2 | H | $C_2H_5$ | H |
| 2 | H | $C_2H_5$ | $CH_3$ |
| 2 | H | $C_2H_5$ | $C_2H_5$ |
| 2 | H | $C_2H_5$ | $CH_2CH_2CH_3$ |
| 0 | $CH_3$ | $CH_3$ | H |
| 2 | Cl | H | H |
| 2 | Cl | H | $CH_3$ |
| 2 | Cl | H | $C_2H_5$ |
| 2 | Cl | H | $CH_2CH_2CH_3$ |
| 2 | Cl | Cl | H |
| 2 | Cl | Cl | $CH_3$ |
| 2 | Cl | Cl | $C_2H_5$ |
| 2 | Cl | Cl | $CH_2CH_2CH_3$ |
| 2 | Cl | $OCH_3$ | H |
| 2 | Cl | $OCH_3$ | $CH_3$ |
| 2 | Cl | $OCH_3$ | $C_2H_5$ |
| 2 | Cl | $OCH_3$ | $CH_2CH_2CH_3$ |
| 2 | Cl | $CH_3$ | H |
| 2 | Cl | $CH_3$ | $CH_3$ |
| 2 | Cl | $CH_3$ | $C_2H_5$ |
| 2 | Cl | $CH_3$ | $CH_2CH_2CH_3$ |
| 2 | Cl | $C_2H_5$ | H |
| 2 | Cl | $C_2H_5$ | $CH_3$ |
| 2 | Cl | $C_2H_5$ | $C_2H_5$ |
| 2 | Cl | $C_2H_5$ | $CH_2CH_2CH_3$ |
| 1 | $CH_3$ | $CH_3$ | H |
| 2 | $OCH_3$ | H | H |
| 2 | $OCH_3$ | H | $CH_3$ |
| 2 | $OCH_3$ | H | $C_2H_5$ |
| 2 | $OCH_3$ | H | $CH_2CH_2CH_3$ |
| 2 | $OCH_3$ | Cl | H |
| 2 | $OCH_3$ | Cl | $CH_3$ |
| 2 | $OCH_3$ | Cl | $C_2H_5$ |
| 2 | $OCH_3$ | Cl | $CH_2CH_2CH_3$ |
| 2 | $OCH_3$ | $OCH_3$ | H |
| 2 | $OCH_3$ | $OCH_3$ | $CH_3$ |
| 2 | $OCH_3$ | $OCH_3$ | $C_2H_5$ |
| 2 | $OCH_3$ | $OCH_3$ | $CH_2CH_2CH_3$ |
| 2 | $OCH_3$ | $CH_3$ | H |
| 2 | $OCH_3$ | $CH_3$ | $CH_3$ |
| 2 | $OCH_3$ | $CH_3$ | $C_2H_5$ |
| 2 | $OCH_3$ | $CH_3$ | $CH_2CH_2CH_3$ |
| 2 | $OCH_3$ | $C_2H_5$ | H |
| 2 | $OCH_3$ | $C_2H_5$ | $CH_3$ |
| 2 | $OCH_3$ | $C_2H_5$ | $C_2H_5$ |
| 2 | $OCH_3$ | $C_2H_5$ | $CH_2CH_2CH_3$ |
| 2 | $CH_3$ | H | H |
| 2 | $CH_3$ | H | $CH_3$ |
| 2 | $CH_3$ | H | $C_2H_5$ |
| 2 | $CH_3$ | H | $CH_2CH_2CH_3$ |
| 2 | $CH_3$ | Cl | H |
| 2 | $CH_3$ | Cl | $CH_3$ |
| 2 | $CH_3$ | Cl | $C_2H_5$ |
| 2 | $CH_3$ | Cl | $CH_2CH_2CH_3$ |
| 2 | $CH_3$ | $OCH_3$ | H |
| 2 | $CH_3$ | $OCH_3$ | $CH_3$ |
| 2 | $CH_3$ | $OCH_3$ | $C_2H_5$ |
| 2 | $CH_3$ | $OCH_3$ | $CH_2CH_2CH_3$ |
| 2 | $CH_3$ | $CH_3$ | H |
| 2 | $CH_3$ | $CH_3$ | $CH_3$ |
| 2 | $CH_3$ | $CH_3$ | $C_2H_5$ |
| 2 | $CH_3$ | $CH_3$ | $CH_2CH_2CH_3$ |
| 2 | $CH_3$ | $C_2H_5$ | H |
| 2 | $CH_3$ | $C_2H_5$ | $CH_3$ |
| 2 | $CH_3$ | $C_2H_5$ | $C_2H_5$ |
| 2 | $CH_3$ | $C_2H_5$ | $CH_2CH_2CH_3$ |
| 2 | $C_2H_5$ | H | H |
| 2 | $C_2H_5$ | H | $CH_3$ |
| 2 | $C_2H_5$ | H | $C_2H_5$ |
| 2 | $C_2H_5$ | H | $CH_2CH_2CH_3$ |
| 2 | $C_2H_5$ | Cl | H |
| 2 | $C_2H_5$ | Cl | $CH_3$ |
| 2 | $C_2H_5$ | Cl | $C_2H_5$ |
| 2 | $C_2H_5$ | Cl | $CH_2CH_2CH_3$ |
| 2 | $C_2H_5$ | $OCH_3$ | H |
| 2 | $C_2H_5$ | $OCH_3$ | $CH_3$ |
| 2 | $C_2H_5$ | $OCH_3$ | $C_2H_5$ |
| 2 | $C_2H_5$ | $OCH_3$ | $CH_2CH_2CH_3$ |
| 2 | $C_2H_5$ | $CH_3$ | H |
| 2 | $C_2H_5$ | $CH_3$ | $CH_3$ |
| 2 | $C_2H_5$ | $CH_3$ | $C_2H_5$ |
| 2 | $C_2H_5$ | $CH_3$ | $CH_2CH_2CH_3$ |
| 2 | $C_2H_5$ | $C_2H_5$ | H |
| 2 | $C_2H_5$ | $C_2H_5$ | $CH_3$ |
| 2 | $C_2H_5$ | $C_2H_5$ | $C_2H_5$ |
| 2 | $C_2H_5$ | $C_2H_5$ | $CH_2CH_2CH_3$ |
| 2 | $CH_3$ | $CH_3$ | Cl |
| 2 | $CH_3$ | $CH_3$ | $OCH_3$ |
| 2 | $CH_3$ | $CH_3$ | F |
| 2 | $CH_3$ | $CH_3$ | Br |
| 2 | $CH_3$ | $CH_3$ | $CO_2CH_3$ |
| 2 | $CH_3$ | $CH_3$ | $CO_2C_2H_5$ |
| 2 | $CH_3$ | $CH_3$ | $CH_2OCH_3$ |
| 2 | $CH_3$ | $CH_3$ | $CON(CH_3)_2$ |
| 2 | $CH_3$ | $CH_3$ | $SCH_3$ |
| 2 | $CH_3$ | $CH_3$ | $SO_2CH_3$ |
| 2 | $CH_3$ | $CH_3$ | $NO_2$ |
| 2 | $CH_3$ | $CH_3$ | $N(CH_3)_2$ |
| 2 | $CH_3$ | $CH_3$ | $NH_2$ |
| 2 | $CH_3$ | $CH_3$ | $C_6H_5$ |
| 2 | $CH_3$ | $C_6H_5$ | H |
| 2 | $C_6H_5$ | $CH_3$ | H |
| 2 | $CH_3$ | $CF_3$ | H |
| 2 | $CF_3$ | $CH_3$ | H |
| 2 | $COCH_3$ | H | H |
| 2 | $CH{=}CH_2$ | $CH_3$ | H |
| 2 | $CH_3$ | $CH{=}CH_2$ | H |
| 2 | $SCH_3$ | $CH_3$ | H |
| 2 | $CH_3$ | $SCH_3$ | H |

TABLE 2-continued

| | | | |
|---|---|---|---|
| 2 | $NO_2$ | $CH_3$ | H |
| 2 | $NH_2$ | $CH_3$ | H |
| 2 | CHO | $CH_3$ | H |
| 2 | $CO_2CH_3$ | H | H |
| 2 | $CH(CH_3)_2$ | H | H |
| 2 | $COCH_3$ | H | Cl |
| 2 | $C_2H_5$ | H | Cl |
| 2 | $CO_2CH_3$ | H | Cl |

A = A-2; X = $NCH_3$; $R^3$ = $CH_3$; $R^4$ = $CH_3$

| n | $R^1$ | $R^2$ | $R^5$ |
|---|---|---|---|
| 2 | $CH_3$ | $CH_3$ | H |
| 2 | $C_2H_5$ | $CH_3$ | H |
| 2 | H | $CH_3$ | H |
| 2 | H | $C_2H_5$ | H |
| 2 | H | $CH_2CH_2CH_3$ | H |
| 2 | $OCH_3$ | $CH_3$ | H |
| 2 | $OCH_3$ | $C_2H_5$ | H |
| 2 | $CH_2CH_2CH_3$ | $CH_2CH_2CH_3$ | H |
| 2 | $CH_2CH{=}CH_2$ | $CH_2CH{=}CH_2$ | H |
| 2 | $CH_2C{\equiv}CH$ | $CH_2C{\equiv}CH$ | H |
| 2 | $CH(CH_3)_2$ | $CH(CH_3)_2$ | H |
| 2 | $-(CH_2)_5-$ | | H |
| 2 | $-(CH_2)_4-$ | | H |
| 2 | $CH_2CH-CH_2$ | $C_2H_5$ | H |
| 2 | $CH_2C{\equiv}CH$ | $C_2H_5$ | H |
| 2 | $OC_2H_5$ | $CH_3$ | H |
| 2 | $OC_2H_5$ | $C_2H_5$ | H |
| 2 | H | 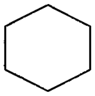 | H |
| 2 | 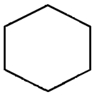 | 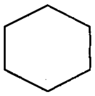 | H |
| 2 | H | $CH_2CH{=}CH_2$ | H |
| 2 | $CH_2CH_2CH_3$ | $CH_3$ | H |
| 2 | $CH_2CH{=}CH_2$ | $CH_3$ | $CH_3$ |
| 2 | $CH_2CH{=}CH_2$ | $C_2H_5$ | $CH_3$ |
| 2 | $CH_2CH{=}CH_2$ | $CH_2CH{=}CH_2$ | $CH_3$ |
| 2 | $CH_2CH_2CH_3$ | $CH_2CH_2CH_3$ | $CH_3$ |
| 2 | $CH_2CH_2CH_3$ | $C_2H_5$ | $CH_3$ |
| 2 | $-(CH_2)_5-$ | | $CH_3$ |
| 0 | $CH_3$ | $CH_3$ | H |

A = A-2; X = $NC_2H_5$; $R^1$ = $C_2H_5$; $R^2$ = $C_2H_5$

| n | $R^3$ | $R^4$ | $R^5$ |
|---|---|---|---|
| 2 | H | H | H |
| 2 | H | H | $CH_3$ |
| 2 | H | H | $C_2H_5$ |
| 2 | H | H | $CH_2CH_2CH_3$ |
| 2 | H | Cl | H |
| 2 | H | Cl | $CH_3$ |
| 2 | H | Cl | $C_2H_5$ |
| 2 | H | Cl | $CH_2CH_2CH_3$ |
| 2 | H | $OCH_3$ | H |
| 2 | H | $OCH_3$ | $CH_3$ |
| 2 | H | $OCH_3$ | $C_2H_5$ |
| 2 | H | $OCH_3$ | $CH_2CH_2CH_3$ |
| 2 | H | $CH_3$ | H |
| 2 | H | $CH_3$ | $CH_3$ |
| 2 | H | $CH_3$ | $C_2H_5$ |
| 2 | H | $CH_3$ | $CH_2CH_2CH_3$ |

TABLE 2-continued

| | | | |
|---|---|---|---|
| 2 | H | $C_2H_5$ | H |
| 2 | H | $C_2H_5$ | $CH_3$ |
| 2 | H | $C_2H_5$ | $C_2H_5$ |
| 2 | H | $C_2H_5$ | $CH_2CH_2CH_3$ |
| 2 | H | $CH(CH_3)_2$ | H |
| 2 | H | $CH(CH_3)_2$ | $CH_3$ |
| 2 | H | $CH(CH_3)_2$ | $C_2H_5$ |
| 2 | H | $CH(CH_3)_2$ | $CH_2CH_2CH_3$ |
| 2 | H | $CH_2CH_2CH_3$ | H |
| 2 | H | $CH_2CH_2CH_3$ | $CH_3$ |
| 2 | H | $CH_2CH_2CH_3$ | $C_2H_5$ |
| 2 | H | $CH_2CH_2CH_3$ | $CH_2CH_2CH_3$ |
| 0 | $CH_3$ | $CH_3$ | H |
| 2 | Cl | H | H |
| 2 | Cl | H | $CH_3$ |
| 2 | Cl | H | $C_2H_5$ |
| 2 | Cl | H | $CH_2CH_2CH_3$ |
| 2 | Cl | Cl | H |
| 2 | Cl | Cl | $CH_3$ |
| 2 | Cl | Cl | $C_2H_5$ |
| 2 | Cl | Cl | $CH_2CH_2CH_3$ |
| 2 | Cl | $OCH_3$ | H |
| 2 | Cl | $OCH_3$ | $CH_3$ |
| 2 | Cl | $OCH_3$ | $C_2H_5$ |
| 2 | Cl | $OCH_3$ | $CH_2CH_2CH_3$ |
| 2 | Cl | $CH_3$ | H |
| 2 | Cl | $CH_3$ | $CH_3$ |
| 2 | Cl | $CH_3$ | $C_2H_5$ |
| 2 | Cl | $CH_3$ | $CH_2CH_2CH_3$ |
| 2 | Cl | $C_2H_5$ | H |
| 2 | Cl | $C_2H_5$ | $CH_3$ |
| 2 | Cl | $C_2H_5$ | $C_2H_5$ |
| 2 | Cl | $C_2H_5$ | $CH_2CH_2CH_3$ |
| 2 | Cl | $CH(CH_3)_2$ | H |
| 2 | Cl | $CH(CH_3)_2$ | $CH_3$ |
| 2 | Cl | $CH(CH_3)_2$ | $C_2H_5$ |
| 2 | Cl | $CH(CH_3)_2$ | $CH_2CH_2CH_3$ |
| 2 | Cl | $CH_2CH_2CH_3$ | H |
| 2 | Cl | $CH_2CH_2CH_3$ | $CH_3$ |
| 2 | Cl | $CH_2CH_2CH_3$ | $C_2H_5$ |
| 2 | Cl | $CH_2CH_2CH_3$ | $CH_2CH_2CH_3$ |
| 1 | $CH_3$ | $CH_3$ | H |
| 2 | $OCH_3$ | H | H |
| 2 | $OCH_3$ | H | $CH_3$ |
| 2 | $OCH_3$ | H | $C_2H_5$ |
| 2 | $OCH_3$ | H | $CH_2CH_2CH_3$ |
| 2 | $OCH_3$ | Cl | H |
| 2 | $OCH_3$ | Cl | $CH_3$ |
| 2 | $OCH_3$ | Cl | $C_2H_5$ |
| 2 | $OCH_3$ | Cl | $CH_2CH_2CH_3$ |
| 2 | $OCH_3$ | $OCH_3$ | H |
| 2 | $OCH_3$ | $OCH_3$ | $CH_3$ |
| 2 | $OCH_3$ | $OCH_3$ | $C_2H_5$ |
| 2 | $OCH_3$ | $OCH_3$ | $CH_2CH_2CH_3$ |
| 2 | $OCH_3$ | $CH_3$ | H |
| 2 | $OCH_3$ | $CH_3$ | $CH_3$ |
| 2 | $OCH_3$ | $CH_3$ | $C_2H_5$ |
| 2 | $OCH_3$ | $CH_3$ | $CH_2CH_2CH_3$ |
| 2 | $OCH_3$ | $C_2H_5$ | H |
| 2 | $OCH_3$ | $C_2H_5$ | $CH_3$ |
| 2 | $OCH_3$ | $C_2H_5$ | $C_2H_5$ |
| 2 | $OCH_3$ | $C_2H_5$ | $CH_2CH_2CH_3$ |
| 2 | $OCH_3$ | $CH(CH_3)_2$ | H |
| 2 | $OCH_3$ | $CH(CH_3)_2$ | $CH_3$ |
| 2 | $OCH_3$ | $CH(CH_3)_2$ | $C_2H_5$ |
| 2 | $OCH_3$ | $CH(CH_3)_2$ | $CH_2CH_2CH_3$ |
| 2 | $OCH_3$ | $CH_2CH_2CH_3$ | H |
| 2 | $OCH_3$ | $CH_2CH_2CH_3$ | $CH_3$ |
| 2 | $OCH_3$ | $CH_2CH_2CH_3$ | $C_2H_5$ |
| 2 | $OCH_3$ | $CH_2CH_2CH_3$ | $CH_2CH_2CH_3$ |
| 2 | $CH_3$ | H | H |
| 2 | $CH_3$ | H | $CH_3$ |
| 2 | $CH_3$ | H | $C_2H_5$ |
| 2 | $CH_3$ | H | $CH_2CH_2CH_3$ |
| 2 | $CH_3$ | Cl | H |
| 2 | $CH_3$ | Cl | $CH_3$ |
| 2 | $CH_3$ | Cl | $C_2H_5$ |

TABLE 2-continued

| | | | |
|---|---|---|---|
| 2 | $CH_3$ | Cl | $CH_2CH_2CH_3$ |
| 2 | $CH_3$ | $OCH_3$ | H |
| 2 | $CH_3$ | $OCH_3$ | $CH_3$ |
| 2 | $CH_3$ | $OCH_3$ | $C_2H_5$ |
| 2 | $CH_3$ | $OCH_3$ | $CH_2CH_2CH_3$ |
| 2 | $CH_3$ | $CH_3$ | H |
| 2 | $CH_3$ | $CH_3$ | $CH_3$ |
| 2 | $CH_3$ | $CH_3$ | $C_2H_5$ |
| 2 | $CH_3$ | $CH_3$ | $CH_2CH_2CH_3$ |
| 2 | $CH_3$ | $C_2H_5$ | H |
| 2 | $CH_3$ | $C_2H_5$ | $CH_3$ |
| 2 | $CH_3$ | $C_2H_5$ | $C_2H_5$ |
| 2 | $CH_3$ | $C_2H_5$ | $CH_2CH_2CH_3$ |
| 2 | $C_2H_5$ | H | H |
| 2 | $C_2H_5$ | H | $CH_3$ |
| 2 | $C_2H_5$ | H | $C_2H_5$ |
| 2 | $C_2H_5$ | H | $CH_2CH_2CH_3$ |
| 2 | $C_2H_5$ | Cl | H |
| 2 | $C_2H_5$ | Cl | $CH_3$ |
| 2 | $C_2H_5$ | Cl | $C_2H_5$ |
| 2 | $C_2H_5$ | Cl | $CH_2CH_2CH_3$ |
| 2 | $C_2H_5$ | $OCH_3$ | H |
| 2 | $C_2H_5$ | $OCH_3$ | $CH_3$ |
| 2 | $C_2H_5$ | $OCH_3$ | $C_2H_5$ |
| 2 | $C_2H_5$ | $OCH_3$ | $CH_2CH_2CH_3$ |
| 2 | $C_2H_5$ | $CH_3$ | H |
| 2 | $C_2H_5$ | $CH_3$ | $CH_3$ |
| 2 | $C_2H_5$ | $CH_3$ | $C_2H_5$ |
| 2 | $C_2H_5$ | $CH_3$ | $CH_2CH_2CH_3$ |
| 2 | $C_2H_5$ | $C_2H_5$ | H |
| 2 | $C_2H_5$ | $C_2H_5$ | $CH_3$ |
| 2 | $C_2H_5$ | $C_2H_5$ | $C_2H_5$ |
| 2 | $C_2H_5$ | $C_2H_5$ | $CH_2CH_2CH_3$ |
| 2 | $CH_3$ | $CH_3$ | Cl |
| 2 | $CH_3$ | $CH_3$ | $OCH_3$ |
| 2 | $CH_3$ | $CH_3$ | F |
| 2 | $CH_3$ | $CH_3$ | Br |
| 2 | $CH_3$ | $CH_3$ | $CO_2CH_3$ |
| 2 | $CH_3$ | $CH_3$ | $CO_2C_2H_5$ |
| 2 | $CH_3$ | $CH_3$ | $CH_2OCH_3$ |
| 2 | $CH_3$ | $CH_3$ | $CON(CH_3)_2$ |
| 2 | $CH_3$ | $CH_3$ | $SCH_3$ |
| 2 | $CH_3$ | $CH_3$ | $SO_2CH_3$ |
| 2 | $CH_3$ | $CH_3$ | $NO_2$ |
| 2 | $CH_3$ | $CH_3$ | $N(CH_3)_2$ |
| 2 | $CH_3$ | $CH_3$ | $NH_2$ |
| 2 | $CH_3$ | $CH_3$ | $C_6H_5$ |
| 2 | $CH_3$ | $C_6H_5$ | H |
| 2 | $C_6H_5$ | $CH_3$ | H |
| 2 | $CH_3$ | $CF_3$ | H |
| 2 | $CF_3$ | $CH_3$ | H |
| 2 | $COCH_3$ | H | H |
| 2 | $CH{=}CH_2$ | $CH_3$ | H |
| 2 | $CH_3$ | $CH{=}CH_2$ | H |
| 2 | $SCH_3$ | $CH_3$ | H |
| 2 | $CH_3$ | $SCH_3$ | H |
| 2 | $NO_2$ | $CH_3$ | H |
| 2 | $NH_2$ | $CH_3$ | H |
| 2 | CHO | $CH_3$ | H |
| 2 | $CO_2CH_3$ | H | H |
| 2 | $CH(OCH_3)_2$ | H | H |
| 2 | $COCH_3$ | H | Cl |
| 2 | $C_2H_5$ | H | Cl |
| 2 | $CO_2CH_3$ | H | Cl |

A = A-2; X = $NC_2H_5$; $R^3$ = $CH_3$; $R^4$ = $CH_3$

| n | $R^1$ | $R^2$ | $R^5$ |
|---|---|---|---|
| 2 | $CH_3$ | $CH_3$ | H |
| 2 | $C_2H_5$ | $CH_3$ | H |
| 2 | H | $CH_3$ | H |
| 2 | H | $C_2H_5$ | H |
| 2 | H | $CH_2CH_2CH_3$ | H |
| 2 | $OCH_3$ | $CH_3$ | H |
| 2 | $OCH_3$ | $C_2H_5$ | H |
| 2 | $CH_2CH_2CH_3$ | $CH_2CH_2CH_3$ | H |
| 2 | $CH_2CH{=}CH_2$ | $CH_2CH{=}CH_2$ | H |
| 2 | $CH_2C{\equiv}CH$ | $CH_2C{\equiv}CH$ | H |
| 2 | $CH(CH_3)_2$ | $CH(CH_3)_2$ | H |
| 2 | $-(CH_2)_5-$ | | H |
| 2 | $-(CH_2)_4-$ | | H |
| 2 | $CH_2CH{=}CH_2$ | $C_2H_5$ | H |
| 2 | $CH_2C{\equiv}CH$ | $C_2H_5$ | H |
| 2 | $OC_2H_5$ | $CH_3$ | H |
| 2 | $OC_2H_5$ | $C_2H_5$ | H |
| 2 | H | 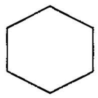 | H |
| 2 | 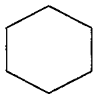 | 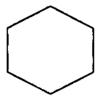 | H |
| 2 | H | $CH_2CH{=}CH_2$ | H |
| 2 | $CH_2CH_2CH_3$ | $CH_3$ | H |
| 2 | $CH_2CH{=}CH_2$ | $CH_3$ | $CH_3$ |
| 2 | $CH_2CH{=}CH_2$ | $C_2H_5$ | $CH_3$ |
| 2 | $CH_2CH{=}CH_2$ | $CH_2CH{=}CH_2$ | $CH_3$ |
| 2 | $CH_2CH_2CH_3$ | $CH_2CH_2CH_3$ | $CH_3$ |
| 2 | $CH_2CH_2CH_3$ | $C_2H_5$ | $CH_3$ |
| 2 | $-(CH_2)_5-$ | | H |
| 0 | $CH_3$ | $CH_3$ | H |
| 1 | $CH_3$ | $CH_3$ | H |

A = A-2; X = $NCH_2CH_2CH_3$; $R^1$ = $C_2H_5$; $R^2$ = $C_2H_5$

| n | $R^3$ | $R^4$ | $R^5$ |
|---|---|---|---|
| 2 | H | H | H |
| 2 | H | H | $CH_3$ |
| 2 | H | H | $C_2H_5$ |
| 2 | H | H | $CH_2CH_2CH_3$ |
| 2 | H | Cl | H |
| 2 | H | Cl | $CH_3$ |
| 2 | H | Cl | $C_2H_5$ |
| 2 | H | Cl | $CH_2CH_2CH_3$ |
| 2 | H | $OCH_3$ | H |
| 2 | H | $OCH_3$ | $CH_3$ |
| 2 | H | $OCH_3$ | $C_2H_5$ |
| 2 | H | $OCH_3$ | $CH_2CH_2CH_3$ |
| 2 | H | $CH_3$ | H |
| 2 | H | $CH_3$ | $CH_3$ |
| 2 | H | $CH_3$ | $C_2H_5$ |
| 2 | H | $CH_3$ | $CH_2CH_2CH_3$ |
| 2 | H | $C_2H_5$ | H |
| 2 | H | $C_2H_5$ | $CH_3$ |
| 2 | H | $C_2H_5$ | $C_2H_5$ |
| 2 | H | $C_2H_5$ | $CH_2CH_2CH_3$ |
| 2 | H | $CH(CH_3)_2$ | H |
| 2 | H | $CH(CH_3)_2$ | $CH_3$ |
| 2 | H | $CH(CH_3)_2$ | $C_2H_5$ |
| 2 | H | $CH(CH_3)_2$ | $CH_2CH_2CH_3$ |
| 2 | H | $CH_2CH_2CH_3$ | H |
| 2 | H | $CH_2CH_2CH_3$ | $CH_3$ |
| 2 | H | $CH_2CH_2CH_3$ | $C_2H_5$ |
| 2 | H | $CH_2CH_2CH_3$ | $CH_2CH_2CH_3$ |
| 0 | $CH_3$ | $CH_3$ | H |
| 2 | Cl | H | H |
| 2 | Cl | H | $CH_3$ |
| 2 | Cl | H | $C_2H_5$ |
| 2 | Cl | H | $CH_2CH_2CH_3$ |
| 2 | Cl | Cl | H |
| 2 | Cl | Cl | $CH_3$ |

TABLE 2-continued

| | | | |
|---|---|---|---|
| 2 | Cl | Cl | $C_2H_5$ |
| 2 | Cl | Cl | $CH_2CH_2CH_3$ |
| 2 | Cl | $OCH_3$ | H |
| 2 | Cl | $OCH_3$ | $CH_3$ |
| 2 | Cl | $OCH_3$ | $C_2H_5$ |
| 2 | Cl | $OCH_3$ | $CH_2CH_2CH_3$ |
| 2 | Cl | $CH_3$ | H |
| 2 | Cl | $CH_3$ | $CH_3$ |
| 2 | Cl | $CH_3$ | $C_2H_5$ |
| 2 | Cl | $CH_3$ | $CH_2CH_2CH_3$ |
| 2 | Cl | $C_2H_5$ | H |
| 2 | Cl | $C_2H_5$ | $CH_3$ |
| 2 | Cl | $C_2H_5$ | $C_2H_5$ |
| 2 | Cl | $C_2H_5$ | $CH_2CH_2CH_3$ |
| 1 | $CH_3$ | $CH_3$ | H |
| 2 | $OCH_3$ | H | H |
| 2 | $OCH_3$ | H | $CH_3$ |
| 2 | $OCH_3$ | H | $C_2H_5$ |
| 2 | $OCH_3$ | H | $CH_2CH_2CH_3$ |
| 2 | $OCH_3$ | Cl | H |
| 2 | $OCH_3$ | Cl | $CH_3$ |
| 2 | $OCH_3$ | Cl | $C_2H_5$ |
| 2 | $OCH_3$ | Cl | $CH_2CH_2CH_3$ |
| 2 | $OCH_3$ | $OCH_3$ | H |
| 2 | $OCH_3$ | $OCH_3$ | $CH_3$ |
| 2 | $OCH_3$ | $OCH_3$ | $C_2H_5$ |
| 2 | $OCH_3$ | $OCH_3$ | $CH_2CH_2CH_3$ |
| 2 | $OCH_3$ | $CH_3$ | H |
| 2 | $OCH_3$ | $CH_3$ | $CH_3$ |
| 2 | $OCH_3$ | $CH_3$ | $C_2H_5$ |
| 2 | $OCH_3$ | $CH_3$ | $CH_2CH_2CH_3$ |
| 2 | $OCH_3$ | $C_2H_5$ | H |
| 2 | $OCH_3$ | $C_2H_5$ | $CH_3$ |
| 2 | $OCH_3$ | $C_2H_5$ | $C_2H_5$ |
| 2 | $OCH_3$ | $C_2H_5$ | $CH_2CH_2CH_3$ |
| 2 | $CH_3$ | H | H |
| 2 | $CH_3$ | H | $CH_3$ |
| 2 | $CH_3$ | H | $C_2H_5$ |
| 2 | $CH_3$ | H | $CH_2CH_2CH_3$ |
| 2 | $CH_3$ | Cl | H |
| 2 | $CH_3$ | Cl | $CH_3$ |
| 2 | $CH_3$ | Cl | $C_2H_5$ |
| 2 | $CH_3$ | Cl | $CH_2CH_2CH_3$ |
| 2 | $CH_3$ | $OCH_3$ | H |
| 2 | $CH_3$ | $OCH_3$ | $CH_3$ |
| 2 | $CH_3$ | $OCH_3$ | $C_2H_5$ |
| 2 | $CH_3$ | $OCH_3$ | $CH_2CH_2CH_3$ |
| 2 | $CH_3$ | $CH_3$ | H |
| 2 | $CH_3$ | $CH_3$ | $CH_3$ |
| 2 | $CH_3$ | $CH_3$ | $C_2H_5$ |
| 2 | $CH_3$ | $CH_3$ | $CH_2CH_2CH_3$ |
| 2 | $CH_3$ | $C_2H_5$ | H |
| 2 | $CH_3$ | $C_2H_5$ | $CH_3$ |
| 2 | $CH_3$ | $C_2H_5$ | $C_2H_5$ |
| 2 | $CH_3$ | $C_2H_5$ | $CH_2CH_2CH_3$ |
| 2 | $C_2H_5$ | H | H |
| 2 | $C_2H_5$ | H | $CH_3$ |
| 2 | $C_2H_5$ | H | $C_2H_5$ |
| 2 | $C_2H_5$ | H | $CH_2CH_2CH_3$ |
| 2 | $C_2H_5$ | Cl | H |
| 2 | $C_2H_5$ | Cl | $CH_3$ |
| 2 | $C_2H_5$ | Cl | $C_2H_5$ |
| 2 | $C_2H_5$ | Cl | $CH_2CH_2CH_3$ |
| 2 | $C_2H_5$ | $OCH_3$ | H |
| 2 | $C_2H_5$ | $OCH_3$ | $CH_3$ |
| 2 | $C_2H_5$ | $OCH_3$ | $C_2H_5$ |
| 2 | $C_2H_5$ | $OCH_3$ | $CH_2CH_2CH_3$ |
| 2 | $C_2H_5$ | $CH_3$ | H |
| 2 | $C_2H_5$ | $CH_3$ | $CH_3$ |
| 2 | $C_2H_5$ | $CH_3$ | $C_2H_5$ |
| 2 | $C_2H_5$ | $CH_3$ | $CH_2CH_2CH_3$ |
| 2 | $C_2H_5$ | $C_2H_5$ | H |
| 2 | $C_2H_5$ | $C_2H_5$ | $CH_3$ |
| 2 | $C_2H_5$ | $C_2H_5$ | $C_2H_5$ |
| 2 | $C_2H_5$ | $C_2H_5$ | $CH_2CH_2CH_3$ |
| 2 | $CH(CH_3)_2$ | H | H |
| 2 | $CH(CH_3)_2$ | H | $CH_3$ |

TABLE 2-continued

| | | | |
|---|---|---|---|
| 2 | $CH(CH_3)_2$ | H | $C_2H_5$ |
| 2 | $CH(CH_3)_2$ | H | $CH_2CH_2CH_3$ |
| 2 | $CH_2CH_2CH_3$ | $CH_2CH_2CH_3$ | H |
| 2 | $CH_2CH_2CH_3$ | $CH_2CH_2CH_3$ | $CH_3$ |
| 2 | $CH_2CH_2CH_3$ | $CH_2CH_2CH_3$ | $C_2H_5$ |
| 2 | $CH_2CH_2CH_3$ | $CH_2CH_2CH_3$ | $CH_2CH_2CH_3$ |
| 2 | $CH_3$ | $CH_3$ | Cl |
| 2 | $CH_3$ | $CH_3$ | $OCH_3$ |
| 2 | $CH_3$ | $CH_3$ | F |
| 2 | $CH_3$ | $CH_3$ | Br |
| 2 | $CH_3$ | $CH_3$ | $CO_2CH_3$ |
| 2 | $CH_3$ | $CH_3$ | $CO_2C_2H_5$ |
| 2 | $CH_3$ | $CH_3$ | $CH_2OCH_3$ |
| 2 | $CH_3$ | $CH_3$ | $CON(CH_3)_2$ |
| 2 | $CH_3$ | $CH_3$ | $SCH_3$ |
| 2 | $CH_3$ | $CH_3$ | $SO_2CH_3$ |
| 2 | $CH_3$ | $CH_3$ | $NO_2$ |
| 2 | $CH_3$ | $CH_3$ | $N(CH_3)_2$ |
| 2 | $CH_3$ | $CH_3$ | $NH_2$ |
| 2 | $CH_3$ | $CH_3$ | $C_6H_5$ |
| 2 | $CH_3$ | $C_6H_5$ | H |
| 2 | $C_6H_5$ | $CH_3$ | H |
| 2 | $CH_3$ | $CF_3$ | H |
| 2 | $CF_3$ | $CH_3$ | H |
| 2 | $COCH_3$ | H | H |
| 2 | $CH{=}CH_2$ | $CH_3$ | H |
| 2 | $CH_3$ | $CH{=}CH_2$ | H |
| 2 | $SCH_3$ | $CH_3$ | H |
| 2 | $CH_3$ | $SCH_3$ | H |
| 2 | $NO_2$ | $CH_3$ | H |
| 2 | $NH_2$ | $CH_3$ | H |
| 2 | CHO | $CH_3$ | H |
| 2 | $CO_2CH_3$ | H | H |
| 2 | $CH(OCH_3)_2$ | H | H |
| 2 | $COCH_3$ | H | Cl |
| 2 | $C_2H_5$ | H | Cl |
| 2 | $CO_2CH_3$ | H | Cl |
| A = A-2; X = $NCH_2CH_2CH_3$; $R^3$ = $CH_3$; $R^4$ = $CH_3$ | | | |
| n | $R^1$ | $R^2$ | $R^5$ |
| 2 | $CH_3$ | $CH_3$ | H |
| 2 | $C_2H_5$ | $CH_3$ | H |
| 2 | H | $CH_3$ | H |
| 2 | H | $C_2H_5$ | H |
| 2 | H | $CH_2CH_2CH_3$ | H |
| 2 | $OCH_3$ | $CH_3$ | H |
| 2 | $OCH_3$ | $C_2H_5$ | H |
| 2 | $CH_2CH_2CH_3$ | $CH_2CH_2CH_3$ | H |
| 2 | $CH_2CH{=}CH_2$ | $CH_2CH{=}CH_2$ | H |
| 2 | $CH_2C{\equiv}CH$ | $CH_2C{\equiv}CH$ | H |
| 2 | $CH(CH_3)_2$ | $CH(CH_3)_2$ | H |
| 2 | $-(CH_2)_5-$ | | H |
| 2 | $-(CH_2)_4-$ | | H |
| 2 | $CH_2CH{=}CH_2$ | $C_2H_5$ | H |
| 2 | $CH_2C{\equiv}CH$ | $C_2H_5$ | H |
| 2 | $OC_2H_5$ | $CH_3$ | H |
| 2 | $OC_2H_5$ | $C_2H_5$ | H |
| 2 | H | 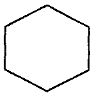 | H |
| 2 | 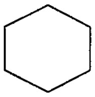 | 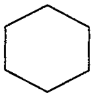 | H |

TABLE 2-continued

| | | | |
|---|---|---|---|
| 2 | H | $CH_2CH{=}CH_2$ | H |
| 2 | $CH_2CH_2CH_3$ | $CH_3$ | H |
| 2 | $CH_2CH{=}CH_2$ | $CH_3$ | $CH_3$ |
| 2 | $CH_2CH{=}CH_2$ | $C_2H_5$ | $CH_3$ |
| 2 | $CH_2CH{=}CH_2$ | $CH_2CH{=}CH_2$ | $CH_3$ |
| 2 | $CH_2CH_2CH_3$ | $CH_2CH_2CH_3$ | $CH_3$ |
| 2 | $CH_2CH_2CH_3$ | $C_2H_5$ | $CH_3$ |
| 2 | $-(CH_2)_5-$ | | H |
| 0 | $CH_3$ | $CH_3$ | H |
| 1 | $CH_3$ | $CH_3$ | H |

TABLE 3

A = A-3; X = O; $R^1 = C_2H_5$; $R^2 = C_2H_5$

| n | $R^3$ | $R^4$ |
|---|---|---|
| 2 | H | H |
| 2 | H | Cl |
| 2 | H | $OCH_3$ |
| 2 | H | $CH_3$ |
| 2 | H | $C_2H_5$ |
| 2 | H | $CH(CH_3)_2$ |
| 2 | H | $CH_2CH_2CH_3$ |
| 2 | Cl | H |
| 2 | Cl | Cl |
| 2 | Cl | $OCH_3$ |
| 2 | Cl | $CH_3$ |
| 2 | Cl | $C_2H_5$ |
| 2 | Cl | $CH(CH_3)_2$ |
| 2 | Cl | $CH_2CH_2CH_3$ |
| 2 | $OCH_3$ | H |
| 2 | $OCH_3$ | Cl |
| 2 | $OCH_3$ | $OCH_3$ |
| 2 | $OCH_3$ | $CH_3$ |
| 2 | $OCH_3$ | $C_2H_5$ |
| 2 | $OCH_3$ | $CH(CH_3)_2$ |
| 2 | $OCH_3$ | $CH_2CH_2CH_3$ |
| 2 | $CH_3$ | H |
| 2 | $CH_3$ | Cl |
| 2 | $CH_3$ | $OCH_3$ |
| 2 | $CH_3$ | $CH_3$ |
| 0 | $CH_3$ | H |
| 2 | $CH_3$ | $C_2H_5$ |
| 2 | $CH_3$ | $CH(CH_3)_2$ |
| 2 | $CH_3$ | $CH_2CH_2CH_3$ |
| 2 | $C_2H_5$ | H |
| 2 | $C_2H_5$ | Cl |
| 2 | $C_2H_5$ | $OCH_3$ |
| 2 | $C_2H_5$ | $CH_3$ |
| 2 | $C_2H_5$ | $C_2H_5$ |
| 2 | $C_2H_5$ | $CH(CH_3)_2$ |
| 2 | $C_2H_5$ | $CH_2CH_2CH_3$ |
| 2 | $CH(CH_3)_2$ | H |
| 2 | $CH(CH_3)_2$ | Cl |
| 2 | $CH(CH_3)_2$ | $OCH_3$ |
| 2 | $CH(CH_3)_2$ | $CH_3$ |
| 2 | $CH(CH_3)_2$ | $C_2H_5$ |
| 2 | $CH(CH_3)_2$ | $CH(CH_3)_2$ |
| 2 | $CH(CH_3)_2$ | $CH_2CH_2CH_3$ |
| 2 | $CH_2CH_2CH_3$ | H |
| 2 | $CH_2CH_2CH_3$ | Cl |
| 2 | $CH_2CH_2CH_3$ | $OCH_3$ |
| 2 | $CH_2CH_2CH_3$ | $CH_3$ |
| 2 | $CH_2CH_2CH_3$ | $C_2H_5$ |
| 2 | $CH_2CH_2CH_3$ | $CH(CH_3)_2$ |
| 2 | $CH_2CH_2CH_3$ | $CH_2CH_2CH_3$ |
| 1 | $CH_3$ | H |
| 2 | $CH_3$ | $C_6H_5$ |
| 2 | $C_6H_5$ | $CH_3$ |
| 2 | $CH_3$ | $CF_3$ |
| 2 | $CF_3$ | $CH_3$ |
| 2 | $COCH_3$ | H |
| 2 | $CH{=}CH_2$ | $CH_3$ |

TABLE 3-continued

| | | |
|---|---|---|
| 2 | $CH_3$ | $CH{=}CH_2$ |
| 2 | $SCH_3$ | $CH_3$ |
| 2 | $CH_3$ | $SCH_3$ |
| 2 | $NO_2$ | $CH_3$ |
| 2 | $NH_2$ | $CH_3$ |
| 2 | CHO | $CH_3$ |
| 2 | $CO_2CH_3$ | H |
| 2 | $CH(OCH_3)_2$ | H |

A = A-3; X = O; $R^3 = CH_3$; $R^4 = CH_3$

| n | $R^1$ | $R^2$ |
|---|---|---|
| 2 | $CH_3$ | $CH_3$ |
| 2 | $C_2H_5$ | $CH_3$ |
| 2 | H | $CH_3$ |
| 2 | H | $C_2H_5$ |
| 2 | H | $CH_2CH_2CH_3$ |
| 2 | $OCH_3$ | $CH_3$ |
| 2 | $OCH_3$ | $C_2H_5$ |
| 2 | $CH_2CH_2CH_3$ | $CH_2CH_2CH_3$ |
| 2 | $CH_2CH{=}CH_2$ | $CH_2CH{=}CH_2$ |
| 2 | $CH_2C{\equiv}CH$ | $CH_2C{\equiv}CH$ |
| 2 | $CH(CH_3)_2$ | $CH(CH_3)_2$ |
| 2 | $-(CH_2)_5-$ | |
| 2 | $-(CH_2)_4-$ | |
| 2 | $CH_2CH{=}CH_2$ | $C_2H_5$ |
| 2 | $CH_2C{\equiv}CH$ | $C_2H_5$ |
| 2 | $OC_2H_5$ | $CH_3$ |
| 2 | $OC_2H_5$ | $C_2H_5$ |
| 2 | H | 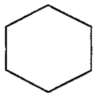 |
| 2 | 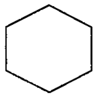 | 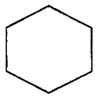 |
| 2 | H | $CH_2CH{=}CH_2$ |
| 2 | $CH_2CH_2CH_3$ | $CH_3$ |
| 0 | H | $CH_3$ |
| 1 | H | $CH_3$ |

A = A-3; X = S; $R^1 = C_2H_5$; $R^2 = C_2H_5$

| n | $R^3$ | $R^4$ |
|---|---|---|
| 2 | H | H |
| 2 | H | Cl |
| 2 | H | $OCH_3$ |
| 2 | H | $CH_3$ |
| 2 | H | $C_2H_5$ |
| 2 | H | $CH(CH_3)_2$ |
| 2 | H | $CH_2CH_2CH_3$ |
| 2 | Cl | H |
| 2 | Cl | Cl |
| 2 | Cl | $OCH_3$ |
| 2 | Cl | $CH_3$ |
| 2 | Cl | $C_2H_5$ |
| 2 | Cl | $CH(CH_3)_2$ |
| 2 | Cl | $CH_2CH_2CH_3$ |
| 2 | $OCH_3$ | H |
| 2 | $OCH_3$ | Cl |
| 2 | $OCH_3$ | $OCH_3$ |
| 2 | $OCH_3$ | $CH_3$ |
| 2 | $OCH_3$ | $C_2H_5$ |
| 2 | $OCH_3$ | $CH(CH_3)_2$ |
| 2 | $OCH_3$ | $CH_2CH_2CH_3$ |

TABLE 3-continued

| | | |
|---|---|---|
| 2 | $CH_3$ | H |
| 2 | $CH_3$ | Cl |
| 2 | $CH_3$ | $OCH_3$ |
| 2 | $CH_3$ | $CH_3$ |
| 0 | $CH_3$ | H |
| 2 | $CH_3$ | $C_2H_5$ |
| 2 | $CH_3$ | $CH(CH_3)_2$ |
| 2 | $CH_3$ | $CH_2CH_2CH_3$ |
| 2 | $C_2H_5$ | H |
| 2 | $C_2H_5$ | Cl |
| 2 | $C_2H_5$ | $OCH_3$ |
| 2 | $C_2H_5$ | $CH_3$ |
| 2 | $C_2H_5$ | $C_2H_5$ |
| 2 | $C_2H_5$ | $CH(CH_3)_2$ |
| 2 | $C_2H_5$ | $CH_2CH_2CH_3$ |
| 2 | $CH(CH_3)_2$ | H |
| 2 | $CH(CH_3)_2$ | Cl |
| 2 | $CH(CH_3)_2$ | $OCH_3$ |
| 2 | $CH(CH_3)_2$ | $CH_3$ |
| 2 | $CH(CH_3)_2$ | $C_2H_5$ |
| 2 | $CH(CH_3)_2$ | $CH(CH_3)_2$ |
| 2 | $CH(CH_3)_2$ | $CH_2CH_2CH_3$ |
| 2 | $CH_2CH_2CH_3$ | H |
| 2 | $CH_2CH_2CH_3$ | Cl |
| 2 | $CH_2CH_2CH_3$ | $OCH_3$ |
| 2 | $CH_2CH_2CH_3$ | $CH_3$ |
| 2 | $CH_2CH_2CH_3$ | $C_2H_5$ |
| 2 | $CH_2CH_2CH_3$ | $CH(CH_3)_2$ |
| 2 | $CH_2CH_2CH_3$ | $CH_2CH_2CH_3$ |
| 1 | $CH_3$ | H |
| 2 | $CH_3$ | $C_6H_5$ |
| 2 | $C_6H_5$ | $CH_3$ |
| 2 | $CH_3$ | $CF_3$ |
| 2 | $CF_3$ | $CH_3$ |
| 2 | $COCH_3$ | H |
| 2 | $CH=CH_2$ | $CH_3$ |
| 2 | $CH_3$ | $CH=CH_2$ |
| 2 | $SCH_3$ | $CH_3$ |
| 2 | $CH_3$ | $SCH_3$ |
| 2 | $NO_2$ | $CH_3$ |
| 2 | $NH_2$ | $CH_3$ |
| 2 | CHO | $CH_3$ |
| 2 | $CO_2CH_3$ | H |
| 2 | $CH(OCH_3)_2$ | H |
| A = A-3; X = S; $R^3 = CH_3$; $R^4 = CH_3$ | | |
| n | $R^1$ | $R^2$ |
| 2 | $CH_3$ | $CH_3$ |
| 2 | $C_2H_5$ | $CH_3$ |
| 2 | H | $CH_3$ |
| 2 | H | $C_2H_5$ |
| 2 | H | $CH_2CH_2CH_3$ |
| 2 | $OCH_3$ | $CH_3$ |
| 2 | $OCH_3$ | $C_2H_5$ |
| 2 | $CH_2CH_2CH_3$ | $CH_2CH_2CH_3$ |
| 2 | $CH_2CH=CH_2$ | $CH_2CH=CH_2$ |
| 2 | $CH_2C{\equiv}CH$ | $CH_2C{\equiv}CH$ |
| 2 | $CH(CH_3)_2$. | $CH(CH_3)_2$ |
| 2 | | $-(CH_2)_5-$ |
| 2 | | $-(CH_2)_4-$ |
| 2 | $CH_2CH=CH_2$ | $C_2H_5$ |
| 2 | $CH_2C{\equiv}CH$ | $C_2H_5$ |
| 2 | $OC_2H_5$ | $CH_3$ |
| 2 | $OC_2H_5$ | $C_2H_5$ |
| 2 | H | 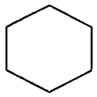 |

TABLE 3-continued

| | | |
|---|---|---|
| 2 | 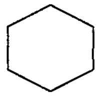 | 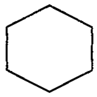 |
| 2 | H | $CH_2CH=CH_2$ |
| 2 | $CH_2CH_2CH_3$ | $CH_3$ |
| 0 | H | $CH_3$ |
| 1 | H | $CH_3$ |
| A = A-3; X = $NCH_3$; $R^1 = C_2H_5$; $R^2 = C_2H_5$ | | |
| n | $R^3$ | $R^4$ |
| 2 | H | H |
| 2 | H | Cl |
| 2 | H | $OCH_3$ |
| 2 | H | $CH_3$ |
| 2 | H | $C_2H_5$ |
| 2 | H | $CH(CH_3)_2$ |
| 2 | H | $CH_2CH_2CH_3$ |
| 2 | Cl | H |
| 2 | Cl | Cl |
| 2 | Cl | $OCH_3$ |
| 2 | Cl | $CH_3$ |
| 2 | Cl | $C_2H_5$ |
| 2 | Cl | $CH(CH_3)_2$ |
| 2 | Cl | $CH_2CH_2CH_3$ |
| 2 | $OCH_3$ | H |
| 2 | $OCH_3$ | Cl |
| 2 | $OCH_3$ | $OCH_3$ |
| 2 | $OCH_3$ | $CH_3$ |
| 2 | $OCH_3$ | $C_2H_5$ |
| 2 | $OCH_3$ | $CH(CH_3)_2$ |
| 2 | $OCH_3$ | $CH_2CH_2CH_3$ |
| 2 | $CH_3$ | H |
| 2 | $CH_3$ | Cl |
| 2 | $CH_3$ | $OCH_3$ |
| 2 | $CH_3$ | $CH_3$ |
| 0 | $CH_3$ | H |
| 2 | $CH_3$ | $C_2H_5$ |
| 2 | $CH_3$ | $CH(CH_3)_2$ |
| 2 | $CH_3$ | $CH_2CH_2CH_3$ |
| 2 | $C_2H_5$ | H |
| 2 | $C_2H_5$ | Cl |
| 2 | $C_2H_5$ | $OCH_3$ |
| 2 | $C_2H_5$ | $CH_3$ |
| 2 | $C_2H_5$ | $C_2H_5$ |
| 2 | $C_2H_5$ | $CH(CH_3)_2$ |
| 2 | $C_2H_5$ | $CH_2CH_2CH_3$ |
| 2 | $CH(CH_3)_2$ | H |
| 2 | $CH(CH_3)_2$ | Cl |
| 2 | $CH(CH_3)_2$ | $OCH_3$ |
| 2 | $CH(CH_3)_2$ | $CH_3$ |
| 2 | $CH(CH_3)_2$ | $C_2H_5$ |
| 2 | $CH(CH_3)_2$ | $CH(CH_3)_2$ |
| 2 | $CH(CH_3)_2$ | $CH_2CH_2CH_3$ |
| 2 | $CH_2CH_2CH_3$ | H |
| 2 | $CH_2CH_2CH_3$ | Cl |
| 2 | $CH_2CH_2CH_3$ | $OCH_3$ |
| 2 | $CH_2CH_2CH_3$ | $CH_3$ |
| 2 | $CH_2CH_2CH_3$ | $C_2H_5$ |
| 2 | $CH_2CH_2CH_3$ | $CH(CH_3)_2$ |
| 2 | $CH_2CH_2CH_3$ | $CH_2CH_2CH_3$ |
| 1 | $CH_3$ | H |
| 2 | $CH_3$ | $C_6H_5$ |
| 2 | $C_6H_5$ | $CH_3$ |
| 2 | $CH_3$ | $CF_3$ |
| 2 | $CF_3$ | $CH_3$ |
| 2 | $COCH_3$ | H |
| 2 | $CH=CH_2$ | $CH_3$ |
| 2 | $CH_3$ | $CH=CH_2$ |
| 2 | $SCH_3$ | $CH_3$ |
| 2 | $CH_3$ | $SCH_3$ |
| 2 | $NO_2$ | $CH_3$ |
| 2 | $CHF_2$ | $CH_3$ |

TABLE 3-continued

| | | |
|---|---|---|
| 2 | $CHF_2$ | $C_2H_5$ |
| 2 | $CHF_2$ | $CH_2CH_2CH_3$ |
| 2 | $CH_2Br$ | $CH_3$ |
| 2 | $CH_2OCH_3$ | $CH_3$ |
| 2 | $NH_2$ | $CH_3$ |
| 2 | CHO | $CH_3$ |
| 2 | $CO_2CH_3$ | H |
| 2 | $CH(OCH_3)_2$ | H |
| A = A-3; X = $NCH_3$; $R^3$ = $CH_3$; $R^4$ = $CH_3$ | | |
| n | $R^1$ | $R^2$ |
| 2 | $CH_3$ | $CH_3$ |
| 2 | $C_2H_5$ | $CH_3$ |
| 2 | H | $CH_3$ |
| 2 | H | $C_2H_5$ |
| 2 | H | $CH_2CH_2CH_3$ |
| 2 | $OCH_3$ | $CH_3$ |
| 2 | $OCH_3$ | $C_2H_5$ |
| 2 | $CH_2CH_2CH_3$ | $CH_2CH_2CH_3$ |
| 2 | $CH_2CH=CH_2$ | $CH_2CH=CH_2$ |
| 2 | $CH_2C{\equiv}CH$ | $CH_2C{\equiv}CH$ |
| 2 | $CH(CH_3)_2$ | $CH(CH_3)_2$ |
| 2 | $-(CH_2)_5-$ | |
| 2 | $-(CH_2)_4-$ | |
| 2 | $CH_2CH=CH_2$ | $C_2H_5$ |
| 2 | $CH_2C{\equiv}CH$ | $C_2H_5$ |
| 2 | $OC_2H_5$ | $CH_3$ |
| 2 | $OC_2H_5$ | $C_2H_5$ |
| 2 | H | 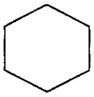 |
| 2 | 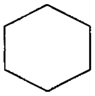 | 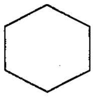 |
| 2 | H | $CH_2CH=CH_2$ |
| 2 | $CH_2CH_2CH_3$ | $CH_3$ |
| 0 | H | $CH_3$ |
| 1 | H | $CH_3$ |
| A = A-3; X = $NC_2H_5$; $R^1$ = $C_2H_5$; $R^2$ = $C_2H_5$ | | |
| 2 | $R^3$ | $R^4$ |
| 2 | H | H |
| 2 | H | Cl |
| 2 | H | $OCH_3$ |
| 2 | H | $CH_3$ |
| 2 | H | $C_2H_5$ |
| 2 | H | $CH(CH_3)_2$ |
| 2 | H | $CH_2CH_2CH_3$ |
| 2 | Cl | H |
| 2 | Cl | Cl |
| 2 | Cl | $OCH_3$ |
| 2 | Cl | $CH_3$ |
| 2 | Cl | $C_2H_5$ |
| 2 | Cl | $CH(CH_3)_2$ |
| 2 | Cl | $CH_2CH_2CH_3$ |
| 2 | $OCH_3$ | H |
| 2 | $OCH_3$ | Cl |
| 2 | $OCH_3$ | $OCH_3$ |
| 2 | $OCH_3$ | $CH_3$ |
| 2 | $OCH_3$ | $C_2H_5$ |
| 2 | $OCH_3$ | $CH(CH_3)_2$ |
| 2 | $OCH_3$ | $CH_2CH_2CH_3$ |

TABLE 3-continued

| | | |
|---|---|---|
| 2 | $CH_3$ | H |
| 2 | $CH_3$ | Cl |
| 2 | $CH_3$ | $OCH_3$ |
| 2 | $CH_3$ | $CH_3$ |
| 0 | $CH_3$ | H |
| 2 | $CH_3$ | $C_2H_5$ |
| 2 | $CH_3$ | $CH(CH_3)_2$ |
| 2 | $CH_3$ | $CH_2CH_2CH_3$ |
| 2 | $C_2H_5$ | H |
| 2 | $C_2H_5$ | Cl |
| 2 | $C_2H_5$ | $OCH_3$ |
| 2 | $C_2H_5$ | $CH_3$ |
| 2 | $C_2H_5$ | $C_2H_5$ |
| 2 | $C_2H_5$ | $CH(CH_3)_2$ |
| 2 | $C_2H_5$ | $CH_2CH_2CH_3$ |
| 2 | $CH(CH_3)_2$ | H |
| 2 | $CH(CH_3)_2$ | Cl |
| 2 | $CH(CH_3)_2$ | $OCH_3$ |
| 2 | $CH(CH_3)_2$ | $CH_3$ |
| 2 | $CH(CH_3)_2$ | $C_2H_5$ |
| 2 | $CH(CH_3)_2$ | $CH(CH_3)_2$ |
| 2 | $CH(CH_3)_2$ | $CH_2CH_2CH_3$ |
| 2 | $CH_2CH_2CH_3$ | H |
| 2 | $CH_2CH_2CH_3$ | Cl |
| 2 | $CH_2CH_2CH_3$ | $OCH_3$ |
| 2 | $CH_2CH_2CH_3$ | $CH_3$ |
| 2 | $CH_2CH_2CH_3$ | $C_2H_5$ |
| 2 | $CH_2CH_2CH_3$ | $CH(CH_3)_2$ |
| 2 | $CH_2CH_2CH_3$ | $CH_2CH_2CH_3$ |
| 1 | $CH_3$ | H |
| 2 | $CH_3$ | $C_6H_5$ |
| 2 | $C_6H_5$ | $CH_3$ |
| 2 | $CH_3$ | $CF_3$ |
| 2 | $CF_3$ | $CH_3$ |
| 2 | $COCH_3$ | H |
| 2 | $CH=CH_2$ | $CH_3$ |
| 2 | $CH_3$ | $CH=CH_2$ |
| 2 | $SCH_3$ | $CH_3$ |
| 2 | $CH_3$ | $SCH_3$ |
| 2 | $NO_2$ | $CH_3$ |
| 2 | $NH_2$ | $CH_3$ |
| 2 | CHO | $CH_3$ |
| 2 | $CO_2CH_3$ | H |
| 2 | $CH(OCH_3)_2$ | H |
| 2 | $CHF_2$ | $CH_3$ |
| 2 | $CHF_2$ | $C_2H_5$ |
| 2 | $CHF_2$ | $CH_2CH_2CH_3$ |
| A = A-3; X = $NC_2H_5$; $R^3$ = $CH_3$; $R^4$ = $CH_3$ | | |
| 2 | $R^1$ | $R^2$ |
| 2 | $CH_3$ | $CH_3$ |
| 2 | $C_2H_5$ | $CH_3$ |
| 2 | H | $CH_3$ |
| 2 | H | $C_2H_5$ |
| 2 | H | $CH_2CH_2CH_3$ |
| 2 | $OCH_3$ | $CH_3$ |
| 2 | $OCH_3$ | $C_2H_5$ |
| 2 | $CH_2CH_2CH_3$ | $CH_2CH_2CH_3$ |
| 2 | $CH_2CH=CH_2$ | $CH_2CH=CH_2$ |
| 2 | $CH_2C{\equiv}CH$ | $CH_2C{\equiv}CH$ |
| 2 | $CH(CH_3)_2$ | $CH(CH_3)_2$ |
| 2 | $-(CH_2)_5-$ | |
| 2 | $-(CH_2)_4-$ | |
| 2 | $CH_2CH=CH_2$ | $C_2H_5$ |
| 2 | $OC_2H_5$ | $CH_3$ |
| 2 | $OC_2H_5$ | $C_2H_5$ |
| 2 | H | 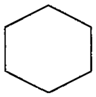 |

TABLE 3-continued

| | | |
|---|---|---|
| | 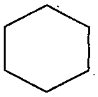 | 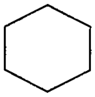 |
| 2 | H | $CH_2CH{=}CH_2$ |
| 2 | $CH_2CH_2CH_3$ | $CH_3$ |
| 0 | H | $CH_3$ |
| 1 | H | $CH_3$ |

A = A-3; X = $NCH_2CH_2CH_3$; $R^1$ = $C_2H_5$; $R^2$ = $C_2H_5$

| n | $R^3$ | $R^4$ |
|---|---|---|
| 2 | H | H |
| 2 | H | Cl |
| 2 | H | $OCH_3$ |
| 2 | H | $CH_3$ |
| 2 | H | $C_2H_5$ |
| 2 | H | $CH(CH_3)_2$ |
| 2 | H | $CH_2CH_2CH_3$ |
| 2 | Cl | H |
| 2 | Cl | Cl |
| 2 | Cl | $OCH_3$ |
| 2 | Cl | $CH_3$ |
| 2 | Cl | $C_2H_5$ |
| 2 | Cl | $CH(CH_3)_2$ |
| 2 | Cl | $CH_2CH_2CH_3$ |
| 2 | $OCH_3$ | H |
| 2 | $OCH_3$ | Cl |
| 2 | $OCH_3$ | $OCH_3$ |
| 2 | $OCH_3$ | $CH_3$ |
| 2 | $OCH_3$ | $C_2H_5$ |
| 2 | $OCH_3$ | $CH(CH_3)_2$ |
| 2 | $OCH_3$ | $CH_2CH_2CH_3$ |
| 2 | $CH_3$ | H |
| 2 | $CH_3$ | Cl |
| 2 | $CH_3$ | $OCH_3$ |
| 2 | $CH_3$ | $CH_3$ |
| 0 | $CH_3$ | H |
| 1 | $CH_3$ | H |
| 2 | $CH_3$ | $C_2H_5$ |
| 2 | $CH_3$ | $CH(CH_3)_2$ |
| 2 | $CH_3$ | $CH_2CH_2CH_3$ |
| 2 | $C_2H_5$ | H |
| 2 | $C_2H_5$ | Cl |
| 2 | $C_2H_5$ | $OCH_3$ |
| 2 | $C_2H_5$ | $CH_3$ |
| 2 | $C_2H_5$ | $C_2H_5$ |
| 2 | $C_2H_5$ | $CH(CH_3)_2$ |
| 2 | $C_2H_5$ | $CH_2CH_2CH_3$ |
| 2 | $CH(CH_3)_2$ | H |
| 2 | $CH(CH_3)_2$ | Cl |
| 2 | $CH(CH_3)_2$ | $OCH_3$ |
| 2 | $CH(CH_3)_2$ | $CH_3$ |
| 2 | $CH(CH_3)_2$ | $C_2H_5$ |
| 2 | $CH(CH_3)_2$ | $CH(CH_3)_2$ |
| 2 | $CH(CH_3)_2$ | $CH_2CH_2CH_3$ |
| 2 | $CH_2CH_2CH_3$ | H |
| 2 | $CH_2CH_2CH_3$ | Cl |
| 2 | $CH_2CH_2CH_3$ | $OCH_3$ |
| 2 | $CH_2CH_2CH_3$ | $CH_3$ |
| 2 | $CH_2CH_2CH_3$ | $C_2H_5$ |
| 2 | $CH_2CH_2CH_3$ | $CH(CH_3)_2$ |
| 2 | $CH_2CH_2CH_3$ | $CH_2CH_2CH_3$ |
| 2 | $CH_3$ | $C_6H_5$ |
| 2 | $C_6H_5$ | $CH_3$ |
| 2 | $CH_3$ | $CF_3$ |
| 2 | $CF_3$ | $CH_3$ |
| 2 | $COCH_3$ | H |
| 2 | $CH{=}CH_2$ | $CH_3$ |
| 2 | $CH_3$ | $CH{=}CH_2$ |
| 2 | $SCH_3$ | $CH_3$ |
| 2 | $CH_3$ | $SCH_3$ |
| 2 | $NO_2$ | $CH_3$ |
| 2 | $NH_2$ | $CH_3$ |
| 2 | CHO | $CH_3$ |

TABLE 3-continued

| | | |
|---|---|---|
| 2 | $CO_2CH_3$ | H |
| 2 | $CHF_2$ | $CH_3$ |
| 2 | $CHF_2$ | $C_2H_5$ |
| 2 | $CHF_2$ | $CH_2CH_2CH_3$ |
| 2 | $CH(OCH_3)_2$ | H |

A = A-3; X = $NCH_2CH_2CH_3$; $R^3$ = $CH_3$; $R^4$ = $CH_3$

| n | $R^1$ | $R^2$ |
|---|---|---|
| 2 | $CH_3$ | $CH_3$ |
| 2 | $C_2H_5$ | $CH_3$ |
| 2 | H | $CH_3$ |
| 2 | H | $C_2H_5$ |
| 2 | H | $CH_2CH_2CH_3$ |
| 2 | $OCH_3$ | $CH_3$ |
| 2 | $OCH_3$ | $C_2H_5$ |
| 2 | $CH_2CH_2CH_3$ | $CH_2CH_2CH_3$ |
| 2 | $CH_2CH{=}CH_2$ | $CH_2CH{=}CH_2$ |
| 2 | $CH_2C{\equiv}CH$ | $CH_2C{\equiv}CH$ |
| 2 | $CH(CH_3)_2$ | $CH(CH_3)_2$ |
| 2 | $-(CH_2)_5-$ | |
| 2 | $-(CH_2)_4-$ | |
| 2 | $CH_2CH{=}CH_2$ | $C_2H_5$ |
| 2 | $CH_2C{\equiv}CH$ | $C_2H_5$ |
| 2 | $OC_2H_5$ | $CH_3$ |
| 2 | $OC_2H_5$ | $C_2H_5$ |
| 2 | H | 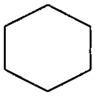 |
| 2 | 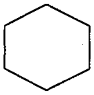 | 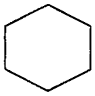 |
| 2 | H | $CH_2CH{=}CH_2$ |
| 2 | $CH_2CH_2CH_3$ | $CH_3$ |
| 0 | H | $CH_3$ |
| 1 | H | $CH_3$ |

TABLE 4

A = A-4; X = O; $R^1$ = $C_2H_5$; $R^2$ = $C_2H_5$

| n | $R^3$ | $R^4$ |
|---|---|---|
| 2 | H | H |
| 2 | H | Cl |
| 2 | H | $OCH_3$ |
| 2 | H | $CH_3$ |
| 2 | H | $C_2H_5$ |
| 2 | H | $CH(CH_3)_2$ |
| 2 | H | $CH_2CH_2CH_3$ |
| 2 | Cl | H |
| 2 | Cl | Cl |
| 2 | Cl | $OCH_3$ |
| 2 | Cl | $CH_3$ |
| 2 | Cl | $C_2H_5$ |
| 2 | Cl | $CH(CH_3)_2$ |
| 2 | Cl | $CH_2CH_2CH_3$ |
| 2 | $OCH_3$ | H |
| 2 | $OCH_3$ | Cl |
| 2 | $OCH_3$ | $OCH_3$ |
| 2 | $OCH_3$ | $CH_3$ |

TABLE 4-continued

| | | |
|---|---|---|
| 2 | $OCH_3$ | $C_2H_5$ |
| 2 | $OCH_3$ | $CH(CH_3)_2$ |
| 2 | $OCH_3$ | $CH_2CH_2CH_3$ |
| 2 | $CH_3$ | H |
| 2 | $CH_3$ | Cl |
| 2 | $CH_3$ | $OCH_3$ |
| 2 | $CH_3$ | $CH_3$ |
| 0 | $CH_3$ | H |
| 2 | $CH_3$ | $C_2H_5$ |
| 2 | $CH_3$ | $CH(CH_3)_2$ |
| 2 | $CH_3$ | $CH_2CH_2CH_3$ |
| 2 | $C_2H_5$ | H |
| 2 | $C_2H_5$ | Cl |
| 2 | $C_2H_5$ | $OCH_3$ |
| 2 | $C_2H_5$ | $CH_3$ |
| 2 | $C_2H_5$ | $C_2H_5$ |
| 2 | $C_2H_5$ | $CH(CH_3)_2$ |
| 2 | $C_2H_5$ | $CH_2CH_2CH_3$ |
| 2 | $CH(CH_3)_2$ | H |
| 2 | $CH(CH_3)_2$ | Cl |
| 2 | $CH(CH_3)_2$ | $OCH_3$ |
| 2 | $CH(CH_3)_2$ | $CH_3$ |
| 2 | $CH(CH_3)_2$ | $C_2H_5$ |
| 2 | $CH(CH_3)_2$ | $CH(CH_3)_2$ |
| 2 | $CH(CH_3)_2$ | $CH_2CH_2CH_3$ |
| 2 | $CH_2CH_2CH_3$ | H |
| 2 | $CH_2CH_2CH_3$ | Cl |
| 2 | $CH_2CH_2CH_3$ | $OCH_3$ |
| 2 | $CH_2CH_2CH_3$ | $CH_3$ |
| 2 | $CH_2CH_2CH_3$ | $C_2H_5$ |
| 2 | $CH_2CH_2CH_3$ | $CH(CH_3)_2$ |
| 2 | $CH_2CH_2CH_3$ | $CH_2CH_2CH_3$ |
| 1 | $CH_3$ | H |
| 0 | $CH_3$ | $CH_3$ |
| 2 | $CH_3$ | $C_6H_5$ |
| 2 | $C_6H_5$ | $CH_3$ |
| 2 | $CH_3$ | $CF_3$ |
| 2 | $CF_3$ | $CH_3$ |
| 2 | $COCH_3$ | H |
| 2 | $CH=CH_2$ | $CH_3$ |
| 2 | $CH_3$ | $CH=CH_2$ |
| 2 | $SCH_3$ | $CH_3$ |
| 2 | $CH_3$ | $SCH_3$ |
| 2 | $NO_2$ | $CH_3$ |
| 2 | $NH_2$ | $CH_3$ |
| 2 | CHO | $CH_3$ |
| 2 | $CO_2CH_3$ | H |
| 2 | $CH(OCH_3)_2$ | H |

A = A-4; X = O; $R^3 = CH_3$; $R^4 = CH_3$

| n | $R^1$ | $R^2$ |
|---|---|---|
| 2 | $CH_3$ | $CH_3$ |
| 2 | $C_2H_5$ | $CH_3$ |
| 2 | H | $CH_3$ |
| 2 | H | $C_2H_5$ |
| 2 | H | $CH_2CH_2CH_3$ |
| 2 | $OCH_3$ | $CH_3$ |
| 2 | $OCH_3$ | $C_2H_5$ |
| 2 | $CH_2CH_2CH_3$ | $CH_2CH_2CH_3$ |
| 2 | $CH_2CH=CH_2$ | $CH_2CH=CH_2$ |
| 2 | $CH_2C\equiv CH$ | $CH_2C\equiv CH$ |
| 2 | $CH(CH_3)_2$ | $CH(CH_3)_2$ |
| 2 | $-(CH_2)_5-$ | |
| 2 | $-(CH_2)_4-$ | |
| 2 | $CH_2CH=CH_2$ | $C_2H_5$ |
| 2 | $CH_2C\equiv CH$ | $C_2H_5$ |
| 2 | $OC_2H_5$ | $CH_3$ |
| 2 | $OC_2H_5$ | $C_2H_5$ |

TABLE 4-continued

| | | |
|---|---|---|
| 2 | H | 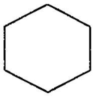 |
| 2 | 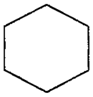 | 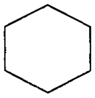 |
| 2 | H | $CH_2CH=CH_2$ |
| 2 | $CH_2CH_2CH_3$ | $CH_3$ |
| 0 | H | $CH_3$ |
| 1 | H | $CH_3$ |

A = A-4; X = S; $R^1 = C_2H_5$; $R^2 = C_2H_5$

| n | $R^3$ | $R^4$ |
|---|---|---|
| 2 | H | H |
| 2 | H | Cl |
| 2 | H | $OCH_3$ |
| 2 | H | $CH_3$ |
| 2 | H | $C_2H_5$ |
| 2 | H | $CH(CH_3)_2$ |
| 2 | H | $CH_2CH_2CH_3$ |
| 2 | Cl | H |
| 2 | Cl | Cl |
| 2 | Cl | $OCH_3$ |
| 2 | Cl | $CH_3$ |
| 2 | Cl | $C_2H_5$ |
| 2 | Cl | $CH(CH_3)_2$ |
| 2 | Cl | $CH_2CH_2CH_3$ |
| 2 | $OCH_3$ | H |
| 2 | $OCH_3$ | Cl |
| 2 | $OCH_3$ | $OCH_3$ |
| 2 | $OCH_3$ | $CH_3$ |
| 2 | $OCH_3$ | $C_2H_5$ |
| 2 | $OCH_3$ | $CH(CH_3)_2$ |
| 2 | $OCH_3$ | $CH_2CH_2CH_3$ |
| 2 | $CH_3$ | H |
| 2 | $CH_3$ | Cl |
| 2 | $CH_3$ | $OCH_3$ |
| 2 | $CH_3$ | $CH_3$ |
| 0 | $CH_3$ | H |
| 2 | $CH_3$ | $C_2H_5$ |
| 2 | $CH_3$ | $CH(CH_3)_2$ |
| 2 | $CH_3$ | $CH_2CH_2CH_3$ |
| 2 | $C_2H_5$ | H |
| 2 | $C_2H_5$ | Cl |
| 2 | $C_2H_5$ | $OCH_3$ |
| 2 | $C_2H_5$ | $CH_3$ |
| 2 | $C_2H_5$ | $C_2H_5$ |
| 2 | $C_2H_5$ | $CH(CH_3)_2$ |
| 2 | $C_2H_5$ | $CH_2CH_2CH_3$ |
| 2 | $CH(CH_3)_2$ | H |
| 2 | $CH(CH_3)_2$ | Cl |
| 2 | $CH(CH_3)_2$ | $OCH_3$ |
| 2 | $CH(CH_3)_2$ | $CH_3$ |
| 2 | $CH(CH_3)_2$ | $C_2H_5$ |
| 2 | $CH(CH_3)_2$ | $CH(CH_3)_2$ |
| 2 | $CH(CH_3)_2$ | $CH_2CH_2CH_3$ |
| 2 | $CH_2CH_2CH_3$ | H |
| 2 | $CH_2CH_2CH_3$ | Cl |
| 2 | $CH_2CH_2CH_3$ | $OCH_3$ |
| 2 | $CH_2CH_2CH_3$ | $CH_3$ |
| 2 | $CH_2CH_2CH_3$ | $C_2H_5$ |
| 2 | $CH_2CH_2CH_3$ | $CH(CH_3)_2$ |
| 2 | $CH_2CH_2CH_3$ | $CH_2CH_2CH_3$ |
| 1 | $CH_3$ | H |
| 2 | $CH_3$ | $C_6H_5$ |
| 2 | $C_6H_5$ | $CH_3$ |
| 2 | $CH_3$ | $CF_3$ |
| 2 | $CF_3$ | $CH_3$ |
| 2 | $COCH_3$ | H |
| 2 | $CH=CH_2$ | $CH_3$ |
| 2 | $CH_3$ | $CH=CH_2$ |

TABLE 4-continued

| | | |
|---|---|---|
| 2 | $SCH_3$ | $CH_3$ |
| 2 | $CH_3$ | $SCH_3$ |
| 2 | $NO_2$ | $CH_3$ |
| 2 | $NH_2$ | $CH_3$ |
| 2 | CHO | $CH_3$ |
| 2 | $CO_2CH_3$ | H |
| 2 | $CH(OCH_3)_2$ | H |

A = A-4; X = S; $R^3 = CH_3$; $R^4 = CH_3$

| n | $R^1$ | $R^2$ |
|---|---|---|
| 2 | $CH_3$ | $CH_3$ |
| 2 | $C_2H_5$ | $CH_3$ |
| 2 | H | $CH_3$ |
| 2 | H | $C_2H_5$ |
| 2 | H | $CH_2CH_2CH_3$ |
| 2 | $OCH_3$ | $CH_3$ |
| 2 | $OCH_3$ | $C_2H_5$ |
| 2 | $CH_2CH_2CH_3$ | $CH_2CH_2CH_3$ |
| 2 | $CH_2CH=CH_2$ | $CH_2CH=CH_2$ |
| 2 | $CH_2C\equiv CH$ | $CH_2C\equiv CH$ |
| 2 | $CH(CH_3)_2$ | $CH(CH_3)_2$ |
| 2 | $-(CH_2)_5-$ | |
| 2 | $-(CH_2)_4-$ | |
| 2 | $CH_2CH=CH_2$ | $C_2H_5$ |
| 2 | $CH_2C\equiv CH$ | $C_2H_5$ |
| 2 | $OC_2H_5$ | $CH_3$ |
| 2 | $OC_2H_5$ | $C_2H_5$ |
| 2 | H | 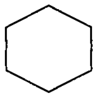 |
| 2 | 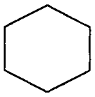 | 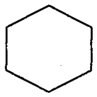 |
| 2 | H | $CH_2CH=CH_2$ |
| 2 | $CH_2CH_2CH_3$ | $CH_3$ |
| 0 | H | $CH_3$ |
| 1 | H | $CH_3$ |

A = A-4; X = $NCH_3$; $R^1 = C_2H_5$; $R^2 = C_2H_5$

| n | $R^3$ | $R^4$ |
|---|---|---|
| 2 | H | H |
| 2 | H | Cl |
| 2 | H | $OCH_3$ |
| 2 | H | $CH_3$ |
| 2 | H | $C_2H_5$ |
| 2 | H | $CH(CH_3)_2$ |
| 2 | H | $CH_2CH_2CH_3$ |
| 2 | Cl | H |
| 2 | Cl | Cl |
| 2 | Cl | $OCH_3$ |
| 2 | Cl | $CH_3$ |
| 2 | Cl | $C_2H_5$ |
| 2 | Cl | $CH(CH_3)_2$ |
| 2 | Cl | $CH_2CH_2CH_3$ |
| 2 | $OCH_3$ | H |
| 2 | $OCH_3$ | Cl |
| 2 | $OCH_3$ | $OCH_3$ |
| 2 | $OCH_3$ | $CH_3$ |
| 2 | $OCH_3$ | $C_2H_5$ |
| 2 | $OCH_3$ | $CH(CH_3)_2$ |
| 2 | $OCH_3$ | $CH_2CH_2CH_3$ |
| 2 | $CH_3$ | H |

TABLE 4-continued

| | | |
|---|---|---|
| 2 | $CH_3$ | Cl |
| 2 | $CH_3$ | $OCH_3$ |
| 2 | $CH_3$ | $CH_3$ |
| 0 | $CH_3$ | $CH_3$ |
| 1 | $CH_3$ | H |
| 2 | $CH_3$ | $C_2H_5$ |
| 2 | $CH_3$ | $CH(CH_3)_2$ |
| 2 | $CH_3$ | $CH_2CH_2CH_3$ |
| 2 | $C_2H_5$ | H |
| 2 | $C_2H_5$ | Cl |
| 2 | $C_2H_5$ | $OCH_3$ |
| 2 | $C_2H_5$ | $CH_3$ |
| 2 | $C_2H_5$ | $C_2H_5$ |
| 2 | $C_2H_5$ | $CH(CH_3)_2$ |
| 2 | $C_2H_5$ | $CH_2CH_2CH_3$ |
| 2 | $CH(CH_3)_2$ | H |
| 2 | $CH(CH_3)_2$ | Cl |
| 2 | $CH(CH_3)_2$ | $OCH_3$ |
| 2 | $CH(CH_3)_2$ | $CH_3$ |
| 2 | $CH(CH_3)_2$ | $C_2H_5$ |
| 2 | $CH(CH_3)_2$ | $CH(CH_3)_2$ |
| 2 | $CH(CH_3)_2$ | $CH_2CH_2CH_3$ |
| 2 | $CH_2CH_2CH_3$ | H |
| 2 | $CH_2CH_2CH_3$ | Cl |
| 2 | $CH_2CH_2CH_3$ | $OCH_3$ |
| 2 | $CH_2CH_2CH_3$ | $CH_3$ |
| 2 | $CH_2CH_2CH_3$ | $C_2H_5$ |
| 2 | $CH_2CH_2CH_3$ | $CH(CH_3)_2$ |
| 2 | $CH_2CH_2CH_3$ | $CH_2CH_2CH_3$ |
| 0 | $CH_3$ | H |
| 2 | $CH_3$ | $C_6H_5$ |
| 2 | $C_6H_5$ | $CH_3$ |
| 2 | $CH_3$ | $CF_3$ |
| 2 | $CF_3$ | $CH_3$ |
| 2 | $COCH_3$ | H |
| 2 | $CH=CH_2$ | $CH_3$ |
| 2 | $CH_3$ | $CH=CH_2$ |
| 2 | $SCH_3$ | $CH_3$ |
| 2 | $CH_3$ | $SCH_3$ |
| 2 | $NO_2$ | $CH_3$ |
| 2 | $NH_2$ | $CH_3$ |
| 2 | CHO | $CH_3$ |
| 2 | $CO_2CH_3$ | H |
| 2 | $CH(OCH_3)_2$ | H |

A = A-4; X = $NCH_3$; $R^3 = CH_3$; $R^4 = CH_3$

| n | $R^1$ | $R^2$ |
|---|---|---|
| 2 | $CH_3$ | $CH_3$ |
| 2 | $C_2H_5$ | $CH_3$ |
| 2 | H | $CH_3$ |
| 2 | H | $C_2H_5$ |
| 2 | H | $CH_2CH_2CH_3$ |
| 2 | $OCH_3$ | $CH_3$ |
| 2 | $OCH_3$ | $C_2H_5$ |
| 2 | $CH_2CH_2CH_3$ | $CH_2CH_2CH_3$ |
| 2 | $CH_2CH=CH_2$ | $CH_2CH=CH_2$ |
| 2 | $CH_2C\equiv CH$ | $CH_2C\equiv CH$ |
| 2 | $CH(CH_3)_2$ | $CH(CH_3)_2$ |
| 2 | $-(CH_2)_5-$ | |
| 2 | $-(CH_2)_4-$ | |
| 2 | $CH_2CH=CH_2$ | $C_2H_5$ |
| 2 | $CH_2C\equiv CH$ | $C_2H_5$ |
| 2 | $OC_2H_5$ | $CH_3$ |
| 2 | $OC_2H_5$ | $C_2H_5$ |
| 2 | H | 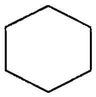 |

TABLE 4-continued

| | | |
|---|---|---|
| 2 | 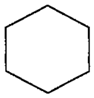 | 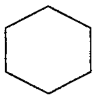 |
| 2 | H | $CH_2CH{=}CH_2$ |
| 2 | $CH_2CH_2CH_3$ | $CH_3$ |
| 0 | H | $CH_3$ |
| 1 | H | $CH_3$ |

$A = A\text{-}4$; $X = NC_2H_5$; $R^1 = C_2H_5$; $R^2 = C_2H_5$

| n | $R^3$ | $R^4$ |
|---|---|---|
| 2 | H | H |
| 2 | H | Cl |
| 2 | H | $OCH_3$ |
| 2 | H | $CH_3$ |
| 2 | H | $C_2H_5$ |
| 2 | H | $CH(CH_3)_2$ |
| 2 | H | $CH_2CH_2CH_3$ |
| 2 | Cl | H |
| 2 | Cl | Cl |
| 2 | Cl | $OCH_3$ |
| 2 | Cl | $CH_3$ |
| 2 | Cl | $C_2H_5$ |
| 2 | Cl | $CH(CH_3)_2$ |
| 2 | Cl | $CH_2CH_2CH_3$ |
| 2 | $OCH_3$ | H |
| 2 | $OCH_3$ | Cl |
| 2 | $OCH_3$ | $OCH_3$ |
| 2 | $OCH_3$ | $CH_3$ |
| 2 | $OCH_3$ | $C_2H_5$ |
| 2 | $OCH_3$ | $CH(CH_3)_2$ |
| 2 | $OCH_3$ | $CH_2CH_2CH_3$ |
| 2 | $CH_3$ | H |
| 2 | $CH_3$ | Cl |
| 2 | $CH_3$ | $OCH_3$ |
| 2 | $CH_3$ | $CH_3$ |
| 0 | $CH_3$ | $CH_3$ |
| 1 | $CH_3$ | H |
| 2 | $CH_3$ | $C_2H_5$ |
| 2 | $CH_3$ | $CH(CH_3)_2$ |
| 2 | $CH_3$ | $CH_2CH_2CH_3$ |
| 2 | $C_2H_5$ | H |
| 2 | $C_2H_5$ | Cl |
| 2 | $C_2H_5$ | $OCH_3$ |
| 2 | $C_2H_5$ | $CH_3$ |
| 2 | $C_2H_5$ | $C_2H_5$ |
| 2 | $C_2H_5$ | $CH(CH_3)_2$ |
| 2 | $C_2H_5$ | $CH_2CH_2CH_3$ |
| 2 | $CH(CH_3)_2$ | H |
| 2 | $CH(CH_3)_2$ | Cl |
| 2 | $CH(CH_3)_2$ | $OCH_3$ |
| 2 | $CH(CH_3)_2$ | $CH_3$ |
| 2 | $CH(CH_3)_2$ | $C_2H_5$ |
| 2 | $CH(CH_3)_2$ | $CH(CH_3)_2$ |
| 2 | $CH(CH_3)_2$ | $CH_2CH_2CH_3$ |
| 2 | $CH_2CH_2CH_3$ | H |
| 2 | $CH_2CH_2CH_3$ | Cl |
| 2 | $CH_2CH_2CH_3$ | $OCH_3$ |
| 2 | $CH_2CH_2CH_3$ | $CH_3$ |
| 2 | $CH_2CH_2CH_3$ | $C_2H_5$ |
| 2 | $CH_2CH_2CH_3$ | $CH(CH_3)_2$ |
| 2 | $CH_2CH_2CH_3$ | $CH_2CH_2CH_3$ |
| 0 | $CH_3$ | H |
| 1 | Cl | H |
| 1 | Cl | $CH_3$ |
| 2 | $CH_3$ | $C_6H_5$ |
| 2 | $C_6H_5$ | $CH_3$ |
| 2 | $CH_3$ | $CF_3$ |
| 2 | $CF_3$ | $CH_3$ |
| 2 | $COCH_3$ | H |
| 2 | $CH{=}CH_2$ | $CH_3$ |
| 2 | $CH_3$ | $CH{=}CH_2$ |
| 2 | $SCH_3$ | $CH_3$ |
| 2 | $CH_3$ | $SCH_3$ |
| 2 | $NO_2$ | $CH_3$ |
| 2 | $NH_2$ | $CH_3$ |
| 2 | CHO | $CH_3$ |
| 2 | $CO_2CH_3$ | H |
| 2 | $CH(OCH_3)_2$ | H |

$A = A\text{-}4$; $X = NC_2H_5$; $R^3 = CH_3$; $R^4 = CH_3$

| n | $R^1$ | $R^2$ |
|---|---|---|
| 2 | $CH_3$ | $CH_3$ |
| 2 | $C_2H_5$ | $CH_3$ |
| 2 | H | $CH_3$ |
| 2 | H | $C_2H_5$ |
| 2 | H | $CH_2CH_2CH_3$ |
| 2 | $OCH_3$ | $CH_3$ |
| 2 | $OCH_3$ | $C_2H_5$ |
| 2 | $CH_2CH_2CH_3$ | $CH_2CH_2CH_3$ |
| 2 | $CH_2CH{=}CH_2$ | $CH_2CH{=}CH_2$ |
| 2 | $CH_2C{\equiv}CH$ | $CH_2C{\equiv}CH$ |
| 2 | $CH(CH_3)_2$ | $CH(CH_3)_2$ |
| 2 | $-(CH_2)_5-$ | |
| 2 | $-(CH_2)_4-$ | |
| 2 | $CH_2CH{=}CH_2$ | $C_2H_5$ |
| 2 | $OC_2H_5$ | $CH_3$ |
| 2 | $OC_2H_5$ | $C_2H_5$ |
| 2 | H | 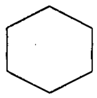 |
| 2 | 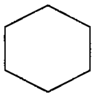 | 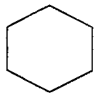 |
| 2 | H | $CH_2CH{=}CH_2$ |
| 2 | $CH_2CH_2CH_3$ | $CH_3$ |
| 0 | H | $CH_3$ |
| 1 | H | $CH_3$ |
| 0 | $CH_3$ | $CH_3$ |

$A = A\text{-}4$; $X = NCH_2CH_2CH_3$; $R^1 = C_2H_5$; $R^2 = C_2H_5$

| n | $R^3$ | $R^4$ |
|---|---|---|
| 2 | H | H |
| 2 | H | Cl |
| 2 | H | $OCH_3$ |
| 2 | H | $CH_3$ |
| 2 | H | $C_2H_5$ |
| 2 | H | $CH(CH_3)_2$ |
| 2 | H | $CH_2CH_2CH_3$ |
| 2 | Cl | H |
| 2 | Cl | Cl |
| 2 | Cl | $OCH_3$ |
| 2 | Cl | $CH_3$ |
| 2 | Cl | $C_2H_5$ |
| 2 | Cl | $CH(CH_3)_2$ |
| 2 | Cl | $CH_2CH_2CH_3$ |
| 2 | $OCH_3$ | H |
| 2 | $OCH_3$ | Cl |
| 2 | $OCH_3$ | $OCH_3$ |
| 2 | $OCH_3$ | $CH_3$ |
| 2 | $OCH_3$ | $C_2H_5$ |
| 2 | $OCH_3$ | $CH(CH_3)_2$ |
| 2 | $OCH_3$ | $CH_2CH_2CH_3$ |
| 2 | $CH_3$ | H |
| 2 | $CH_3$ | Cl |
| 2 | $CH_3$ | $OCH_3$ |
| 2 | $CH_3$ | $CH_3$ |

TABLE 4-continued

| | | |
|---|---|---|
| 0 | $CH_3$ | H |
| 1 | $CH_3$ | H |
| 2 | $CH_3$ | $C_2H_5$ |
| 2 | $CH_3$ | $CH(CH_3)_2$ |
| 2 | $CH_3$ | $CH_2CH_2CH_3$ |
| 2 | $C_2H_5$ | H |
| 2 | $C_2H_5$ | Cl |
| 2 | $C_2H_5$ | $OCH_3$ |
| 2 | $C_2H_5$ | $CH_3$ |
| 2 | $C_2H_5$ | $C_2H_5$ |
| 2 | $C_2H_5$ | $CH(CH_3)_2$ |
| 2 | $C_2H_5$ | $CH_2CH_2CH_3$ |
| 2 | $CH(CH_3)_2$ | H |
| 2 | $CH(CH_3)_2$ | Cl |
| 2 | $CH(CH_3)_2$ | $OCH_3$ |
| 2 | $CH(CH_3)_2$ | $CH_3$ |
| 2 | $CH(CH_3)_2$ | $C_2H_5$ |
| 2 | $CH(CH_3)_2$ | $CH(CH_3)_2$ |
| 2 | $CH(CH_3)_2$ | $CH_2CH_2CH_3$ |
| 2 | $CH_2CH_2CH_3$ | H |
| 2 | $CH_2CH_2CH_3$ | Cl |
| 2 | $CH_2CH_2CH_3$ | $OCH_3$ |
| 2 | $CH_2CH_2CH_3$ | $CH_3$ |
| 2 | $CH_2CH_2CH_3$ | $C_2H_5$ |
| 2 | $CH_2CH_2CH_3$ | $CH(CH_3)_2$ |
| 2 | $CH_2CH_2CH_3$ | $CH_2CH_2CH_3$ |
| 0 | $CH_3$ | $CH_3$ |
| 0 | Cl | $CH_3$ |
| 2 | $CH_3$ | $C_6H_5$ |
| 2 | $C_6H_5$ | $CH_3$ |
| 2 | $CH_3$ | $CF_3$ |
| 2 | $CF_3$ | $CH_3$ |
| 2 | $COCH_3$ | H |
| 2 | $CH{=}CH_2$ | $CH_3$ |
| 2 | $CH_3$ | $CH{=}CH_2$ |
| 2 | $SCH_3$ | $CH_3$ |
| 2 | $CH_3$ | $SCH_3$ |
| 2 | $NO_2$ | $CH_3$ |
| 2 | $NH_2$ | $CH_3$ |
| 2 | CHO | $CH_3$ |
| 2 | $CO_2CH_3$ | H |
| 2 | $CH(OCH_3)_2$ | H |

A = A-4; X = $NCH_2H_2CH_3$; $R^3$ = $CH_3$; $R^4$ = $CH_3$

| n | $R^1$ | $R^2$ |
|---|---|---|
| 2 | $CH_3$ | $CH_3$ |
| 2 | $C_2H_5$ | $CH_3$ |
| 2 | H | $CH_3$ |
| 2 | H | $C_2H_5$ |
| 2 | H | $CH_2CH_2CH_3$ |
| 2 | $OCH_3$ | $CH_3$ |
| 2 | $OCH_3$ | $C_2H_5$ |
| 2 | $CH_2CH_2CH_3$ | $CH_2CH_2CH_3$ |
| 2 | $CH_2CH{=}CH_2$ | $CH_2CH{=}CH_2$ |
| 2 | $CH_2C{\equiv}CH$ | $CH_2C{\equiv}CH$ |
| 2 | $CH(CH_3)_2$ | $CH(CH_3)_2$ |
| 2 | $-(CH_2)_5-$ | |
| 2 | $-(CH_2)_4-$ | |
| 2 | $CH_2CH{=}CH_2$ | $C_2H_5$ |
| 2 | $CH_2C{\equiv}CH$ | $C_2H_5$ |
| 2 | $OC_2H_5$ | $CH_3$ |
| 2 | $OC_2H_5$ | $C_2H_5$ |
| 2 | H | 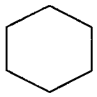 |

TABLE 4-continued

| | | |
|---|---|---|
| 2 | 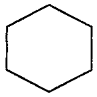 | 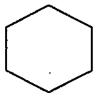 |
| 2 | H | $CH_2CH{=}CH_2$ |
| 2 | $CH_2CH_2CH_3$ | $CH_3$ |
| 0 | H | $CH_3$ |
| 1 | H | $CH_3$ |

A = A-4; X = $NC_6H_5$; $R^1$ = $C_2H_5$; $R^2$ = $C_2H_5$

| n | $R^3$ | $R^4$ |
|---|---|---|
| 2 | H | H |
| 2 | H | Cl |
| 2 | H | $OCH_3$ |
| 2 | H | $CH_3$ |
| 2 | H | $C_2H_5$ |
| 2 | H | $CH(CH_3)_2$ |
| 2 | H | $CH_2CH_2CH_3$ |
| 2 | Cl | H |
| 2 | Cl | Cl |
| 2 | Cl | $OCH_3$ |
| 2 | Cl | $CH_3$ |
| 2 | Cl | $C_2H_5$ |
| 2 | Cl | $CH(CH_3)_2$ |
| 2 | Cl | $CH_2CH_2CH_3$ |
| 2 | $OCH_3$ | H |
| 2 | $OCH_3$ | Cl |
| 2 | $OCH_3$ | $OCH_3$ |
| 2 | $OCH_3$ | $CH_3$ |
| 2 | $OCH_3$ | $C_2H_5$ |
| 2 | $OCH_3$ | $CH(CH_3)_2$ |
| 2 | $OCH_3$ | $CH_2CH_2CH_3$ |
| 2 | $CH_3$ | H |
| 2 | $CH_3$ | Cl |
| 2 | $CH_3$ | $OCH_3$ |
| 2 | $CH_3$ | $CH_3$ |
| 0 | $CH_3$ | H |
| 1 | $CH_3$ | H |
| 2 | $CH_3$ | $C_2H_5$ |
| 2 | $CH_3$ | $CH(CH_3)_2$ |
| 2 | $CH_3$ | $CH_2CH_2CH_3$ |
| 2 | $C_2H_5$ | H |
| 2 | $C_2H_5$ | Cl |
| 2 | $C_2H_5$ | $OCH_3$ |
| 2 | $C_2H_5$ | $CH_3$ |
| 2 | $C_2H_5$ | $C_2H_5$ |
| 2 | $C_2H_5$ | $CH(CH_3)_2$ |
| 2 | $C_2H_5$ | $CH_2CH_2CH_3$ |
| 2 | $CH(CH_3)_2$ | H |
| 2 | $CH(CH_3)_2$ | Cl |
| 2 | $CH(CH_3)_2$ | $OCH_3$ |
| 2 | $CH(CH_3)_2$ | $CH_3$ |
| 2 | $CH(CH_3)_2$ | $C_2H_5$ |
| 2 | $CH(CH_3)_2$ | $CH(CH_3)_2$ |
| 2 | $CH(CH_3)_2$ | $CH_2CH_2CH_3$ |
| 2 | $CH_2CH_2CH_3$ | H |
| 2 | $CH_2CH_2CH_3$ | Cl |
| 2 | $CH_2CH_2CH_3$ | $OCH_3$ |
| 2 | $CH_2CH_2CH_3$ | $CH_3$ |
| 2 | $CH_2CH_2CH_3$ | $C_2H_5$ |
| 2 | $CH_2CH_2CH_3$ | $CH(CH_3)_2$ |
| 2 | $CH_2CH_2CH_3$ | $CH_2CH_2CH_3$ |
| 0 | $CH_3$ | $CH_3$ |
| 2 | $CH_3$ | $C_6H_5$ |
| 2 | $C_6H_5$ | $CH_3$ |
| 2 | $CH_3$ | $CF_3$ |
| 2 | $CF_3$ | $CH_3$ |
| 2 | $COCH_3$ | H |
| 2 | $CH{=}CH_2$ | $CH_3$ |
| 2 | $CH_3$ | $CH{=}CH_2$ |
| 2 | $SCH_3$ | $CH_3$ |
| 2 | $CH_3$ | $SCH_3$ |
| 2 | $NO_2$ | $CH_3$ |
| 2 | $NH_2$ | $CH_3$ |

TABLE 4-continued

| | | |
|---|---|---|
| 2 | CHO | $CH_3$ |
| 2 | $CO_2CH_3$ | H |
| 2 | $CH(OCH_3)_2$ | H |

A = A-4; X = $NC_6H_5$; $R^3 = CH_3$; $R^4 = CH_3$

| n | $R^1$ | $R^2$ |
|---|---|---|
| 2 | $CH_3$ | $CH_3$ |
| 2 | $C_2H_5$ | $CH_3$ |
| 2 | H | $CH_3$ |
| 2 | H | $C_2H_5$ |
| 2 | H | $CH_2CH_2CH_3$ |
| 2 | $OCH_3$ | $CH_3$ |
| 2 | $OCH_3$ | $C_2H_5$ |
| 2 | $CH_2CH_2CH_3$ | $CH_2CH_2CH_3$ |
| 2 | $CH_2CH{=}CH_2$ | $CH_2CH{=}CH_2$ |
| 2 | $CH_2C{\equiv}CH$ | $CH_2C{\equiv}CH$ |
| 2 | $CH(CH_3)_2$ | $CH(CH_3)_2$ |
| 2 | $-(CH_2)_5-$ | |
| 2 | $-(CH_2)_4-$ | |
| 2 | $CH_2CH{=}CH_2$ | $C_2H_5$ |
| 2 | $CH_2C{\equiv}CH$ | $C_2H_5$ |
| 2 | $OC_2H_5$ | $CH_3$ |
| 2 | $OC_2H_5$ | $C_2H_5$ |
| 2 | H | 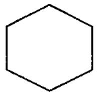 |
| 2 | 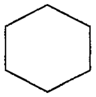 | 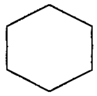 |
| 2 | H | $CH_2CH{=}CH_2$ |
| 2 | $CH_2CH_2CH_3$ | $CH_3$ |
| 0 | H | $CH_3$ |
| 1 | H | $CH_3$ |

A = A-4; X = $NCH_2CF_3$; $R^1 = C_2H_5$; $R^2 = C_2H_5$

| n | $R^3$ | $R^4$ |
|---|---|---|
| 2 | H | H |
| 2 | H | Cl |
| 2 | H | $OCH_3$ |
| 2 | H | $CH_3$ |
| 2 | H | $C_2H_5$ |
| 2 | H | $CH(CH_3)_2$ |
| 2 | H | $CH_2CH_2CH_3$ |
| 2 | Cl | H |
| 2 | Cl | Cl |
| 2 | Cl | $OCH_3$ |
| 2 | Cl | $CH_3$ |
| 2 | Cl | $C_2H_5$ |
| 2 | Cl | $CH(CH_3)_2$ |
| 2 | Cl | $CH_2CH_2CH_3$ |
| 2 | $OCH_3$ | H |
| 2 | $OCH_3$ | Cl |
| 2 | $OCH_3$ | $OCH_3$ |
| 2 | $OCH_3$ | $CH_3$ |
| 2 | $OCH_3$ | $C_2H_5$ |
| 2 | $OCH_3$ | $CH(CH_3)_2$ |
| 2 | $OCH_3$ | $CH_2CH_2CH_3$ |
| 2 | $CH_3$ | H |
| 2 | $CH_3$ | Cl |
| 2 | $CH_3$ | $OCH_3$ |
| 2 | $CH_3$ | $CH_3$ |
| 0 | $CH_3$ | H |
| 1 | $CH_3$ | H |
| 2 | $CH_3$ | $C_2H_5$ |
| 2 | $CH_3$ | $CH(CH_3)_2$ |
| 2 | $CH_3$ | $CH_2CH_2CH_3$ |
| 2 | $C_2H_5$ | H |
| 2 | $C_2H_5$ | Cl |
| 2 | $C_2H_5$ | $OCH_3$ |
| 2 | $C_2H_5$ | $CH_3$ |
| 2 | $C_2H_5$ | $C_2H_5$ |
| 2 | $C_2H_5$ | $CH(CH_3)_2$ |
| 2 | $C_2H_5$ | $CH_2CH_2CH_3$ |
| 2 | $CH(CH_3)_2$ | H |
| 2 | $CH(CH_3)_2$ | Cl |
| 2 | $CH(CH_3)_2$ | $OCH_3$ |
| 2 | $CH(CH_3)_2$ | $CH_3$ |
| 2 | $CH(CH_3)_2$ | $C_2H_5$ |
| 2 | $CH(CH_3)_2$ | $CH(CH_3)_2$ |
| 2 | $CH(CH_3)_2$ | $CH_2CH_2CH_3$ |
| 2 | $CH_2CH_2CH_3$ | H |
| 2 | $CH_2CH_2CH_3$ | Cl |
| 2 | $CH_2CH_2CH_3$ | $OCH_3$ |
| 2 | $CH_2CH_2CH_3$ | $CH_3$ |
| 2 | $CH_2CH_2CH_3$ | $C_2H_5$ |
| 2 | $CH_2CH_2CH_3$ | $CH(CH_3)_2$ |
| 2 | $CH_2CH_2CH_3$ | $CH_2CH_2CH_3$ |
| 0 | $CH_3$ | $CH_3$ |
| 0 | Cl | $CH_3$ |
| 2 | $CH_3$ | $C_6H_5$ |
| 2 | $C_6H_5$ | $CH_3$ |
| 2 | $CH_3$ | $CF_3$ |
| 2 | $CF_3$ | $CH_3$ |
| 2 | $COCH_3$ | H |
| 2 | $CH{=}CH_2$ | $CH_3$ |
| 2 | $CH_3$ | $CH{=}CH_2$ |
| 2 | $SCH_3$ | $CH_3$ |
| 2 | $CH_3$ | $SCH_3$ |
| 2 | $NO_2$ | $CH_3$ |
| 2 | $NH_2$ | $CH_3$ |
| 2 | CHO | $CH_3$ |
| 2 | $CO_2CH_3$ | H |
| 2 | $CH(OCH_3)_2$ | H |

A = A-4; X = $NCH_2CF_3$; $R^3 = CH_3$; $R^4 = CH_3$

| n | $R^1$ | $R^2$ |
|---|---|---|
| 2 | $CH_3$ | $CH_3$ |
| 2 | $C_2H_5$ | $CH_3$ |
| 2 | H | $CH_3$ |
| 2 | H | $C_2H_5$ |
| 2 | H | $CH_2CH_2CH_3$ |
| 2 | $OCH_3$ | $CH_3$ |
| 2 | $OCH_3$ | $C_2H_5$ |
| 2 | $CH_2CH_2CH_3$ | $CH_2CH_2CH_3$ |
| 2 | $CH_2CH{=}CH_2$ | $CH_2CH{=}CH_2$ |
| 2 | $CH_2C{\equiv}CH$ | $CH_2C{\equiv}CH$ |
| 2 | $CH(CH_3)_2$ | $CH(CH_3)_2$ |
| 2 | $-(CH_2)_5-$ | |
| 2 | $-(CH_2)_4-$ | |
| 2 | $CH_2CH{=}CH_2$ | $C_2H_5$ |
| 2 | $CH_2C{\equiv}CH$ | $C_2H_5$ |
| 2 | $OC_2H_5$ | $CH_3$ |
| 2 | $OC_2H_5$ | $C_2H_5$ |
| 2 | H | 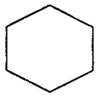 |

TABLE 4-continued

| | | |
|---|---|---|
| 2 | 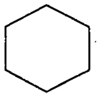 | 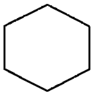 |
| 2 | H | $CH_2CH{=}CH_2$ |
| 2 | $CH_2CH_2CH_3$ | $CH_3$ |
| 0 | H | $CH_3$ |
| 1 | H | $CH_3$ |

A = A-4; X = $NCH_2CO_2C_2H_5$; $R^1$ = $C_2H_5$; $R^2$ = $C_2H_5$

| n | $R^3$ | $R^4$ |
|---|---|---|
| 2 | H | H |
| 2 | H | Cl |
| 2 | H | $OCH_3$ |
| 2 | H | $CH_3$ |
| 2 | H | $C_2H_5$ |
| 2 | H | $CH(CH_3)_2$ |
| 2 | H | $CH_2CH_2CH_3$ |
| 2 | Cl | H |
| 2 | Cl | Cl |
| 2 | Cl | $OCH_3$ |
| 2 | Cl | $CH_3$ |
| 2 | Cl | $C_2H_5$ |
| 2 | Cl | $CH(CH_3)_2$ |
| 2 | Cl | $CH_2CH_2CH_3$ |
| 2 | $OCH_3$ | H |
| 2 | $OCH_3$ | Cl |
| 2 | $OCH_3$ | $OCH_3$ |
| 2 | $OCH_3$ | $CH_3$ |
| 2 | $OCH_3$ | $C_2H_5$ |
| 2 | $OCH_3$ | $CH(CH_3)_2$ |
| 2 | $OCH_3$ | $CH_2CH_2CH_3$ |
| 2 | $CH_3$ | H |
| 2 | $CH_3$ | Cl |
| 2 | $CH_3$ | $OCH_3$ |
| 2 | $CH_3$ | $CH_3$ |
| 0 | $CH_3$ | H |
| 1 | $CH_3$ | H |
| 2 | $CH_3$ | $C_2H_5$ |
| 2 | $CH_3$ | $CH(CH_3)_2$ |
| 2 | $CH_3$ | $CH_2CH_2CH_3$ |
| 2 | $C_2H_5$ | H |
| 2 | $C_2H_5$ | Cl |
| 2 | $C_2H_5$ | $OCH_3$ |
| 2 | $C_2H_5$ | $CH_3$ |
| 2 | $C_2H_5$ | $C_2H_5$ |
| 2 | $C_2H_5$ | $CH(CH_3)_2$ |
| 2 | $C_2H_5$ | $CH_2CH_2CH_3$ |
| 2 | $CH(CH_3)_2$ | H |
| 2 | $CH(CH_3)_2$ | Cl |
| 2 | $CH(CH_3)_2$ | $OCH_3$ |
| 2 | $CH(CH_3)_2$ | $CH_3$ |
| 2 | $CH(CH_3)_2$ | $C_2H_5$ |
| 2 | $CH(CH_3)_2$ | $CH(CH_3)_2$ |
| 2 | $CH(CH_3)_2$ | $CH_2CH_2CH_3$ |
| 2 | $CH_2CH_2CH_3$ | H |
| 2 | $CH_2CH_2CH_3$ | Cl |
| 2 | $CH_2CH_2CH_3$ | $OCH_3$ |
| 2 | $CH_2CH_2CH_3$ | $CH_3$ |
| 2 | $CH_2CH_2CH_3$ | $C_2H_5$ |
| 2 | $CH_2CH_2CH_3$ | $CH(CH_3)_2$ |
| 2 | $CH_2CH_2CH_3$ | $CH_2CH_2CH_3$ |
| 0 | $CH_3$ | $CH_3$ |
| 2 | $CH_3$ | $C_6H_5$ |
| 2 | $C_6H_5$ | $CH_3$ |
| 2 | $CH_3$ | $CF_3$ |
| 2 | $CF_3$ | $CH_3$ |
| 2 | $COCH_3$ | H |
| 2 | $CH{=}CH_2$ | $CH_3$ |
| 2 | $CH_3$ | $CH{=}CH_2$ |
| 2 | $SCH_3$ | $CH_3$ |
| 2 | $CH_3$ | $SCH_3$ |
| 2 | $NO_2$ | $CH_3$ |
| 2 | $NH_2$ | $CH_3$ |
| 2 | CHO | $CH_3$ |
| 2 | $CO_2CH_3$ | H |
| 2 | $CH(OCH_3)_2$ | H |

A = A-4; X = $NCH_2CO_2C_2H_5$; $R^3$ = $CH_3$; $R^4$ = $CH_3$

| n | $R^1$ | $R^2$ |
|---|---|---|
| 2 | $CH_3$ | $CH_3$ |
| 2 | $C_2H_5$ | $CH_3$ |
| 2 | H | $CH_3$ |
| 2 | H | $C_2H_5$ |
| 2 | H | $CH_2CH_2CH_3$ |
| 2 | $OCH_3$ | $CH_3$ |
| 2 | $OCH_3$ | $C_2H_5$ |
| 2 | $CH_2CH_2CH_3$ | $CH_2CH_2CH_3$ |
| 2 | $CH_2CH{=}CH_2$ | $CH_2CH{=}CH_2$ |
| 2 | $CH_2C{\equiv}CH$ | $CH_2C{\equiv}CH$ |
| 2 | $CH(CH_3)_2$ | $CH(CH_3)_2$ |
| 2 | $-(CH_2)_5-$ | |
| 2 | $-(CH_2)_4-$ | |
| 2 | $CH_2CH{=}CH_2$ | $C_2H_5$ |
| 2 | $CH_2C{\equiv}CH$ | $C_2H_5$ |
| 2 | $OC_2H_5$ | $CH_3$ |
| 2 | $OC_2H_5$ | $C_2H_5$ |
| 2 | H | 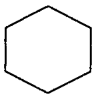 |
| 2 | 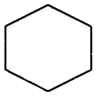 | 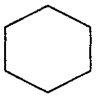 |
| 2 | H | $CH_2CH{=}CH_2$ |
| 2 | $CH_2CH_2CH_3$ | $CH_3$ |
| 0 | H | $CH_3$ |
| 1 | H | $CH_3$ |

A = A-4; X = $NCH_2CH_2CN$; $R^1$ = $C_2H_5$; $R^2$ = $C_2H_5$

| n | $R^3$ | $R^4$ |
|---|---|---|
| 2 | H | H |
| 2 | H | Cl |
| 2 | H | $OCH_3$ |
| 2 | H | $CH_3$ |
| 2 | H | $C_2H_5$ |
| 2 | H | $CH(CH_3)_2$ |
| 2 | H | $CH_2CH_2CH_3$ |
| 2 | Cl | H |
| 2 | Cl | Cl |
| 2 | Cl | $OCH_3$ |
| 2 | Cl | $CH_3$ |
| 2 | Cl | $C_2H_5$ |
| 2 | Cl | $CH(CH_3)_2$ |
| 2 | Cl | $CH_2CH_2CH_3$ |
| 2 | $OCH_3$ | H |
| 2 | $OCH_3$ | Cl |
| 2 | $OCH_3$ | $OCH_3$ |
| 2 | $OCH_3$ | $CH_3$ |
| 2 | $OCH_3$ | $C_2H_5$ |
| 2 | $OCH_3$ | $CH(CH_3)_2$ |
| 2 | $OCH_3$ | $CH_2CH_2CH_3$ |
| 2 | $CH_3$ | H |
| 2 | $CH_3$ | Cl |

TABLE 4-continued

| | | |
|---|---|---|
| 2 | $CH_3$ | $OCH_3$ |
| 2 | $CH_3$ | $CH_3$ |
| 0 | $CH_3$ | H |
| 1 | $CH_3$ | H |
| 2 | $CH_3$ | $C_2H_5$ |
| 2 | $CH_3$ | $CH(CH_3)_2$ |
| 2 | $CH_3$ | $CH_2CH_2CH_3$ |
| 2 | $C_2H_5$ | H |
| 2 | $C_2H_5$ | Cl |
| 2 | $C_2H_5$ | $OCH_3$ |
| 2 | $C_2H_5$ | $CH_3$ |
| 2 | $C_2H_5$ | $C_2H_5$ |
| 2 | $C_2H_5$ | $CH(CH_3)_2$ |
| 2 | $C_2H_5$ | $CH_2CH_2CH_3$ |
| 2 | $CH(CH_3)_2$ | H |
| 2 | $CH(CH_3)_2$ | Cl |
| 2 | $CH(CH_3)_2$ | $OCH_3$ |
| 2 | $CH(CH_3)_2$ | $CH_3$ |
| 2 | $CH(CH_3)_2$ | $C_2H_5$ |
| 2 | $CH(CH_3)_2$ | $CH(CH_3)_2$ |
| 2 | $CH(CH_3)_2$ | $CH_2CH_2CH_3$ |
| 2 | $CH_2CH_2CH_3$ | H |
| 2 | $CH_2CH_2CH_3$ | Cl |
| 2 | $CH_2CH_2CH_3$ | $OCH_3$ |
| 2 | $CH_2CH_2CH_3$ | $CH_3$ |
| 2 | $CH_2CH_2CH_3$ | $C_2H_5$ |
| 2 | $CH_2CH_2CH_3$ | $CH(CH_3)_2$ |
| 2 | $CH_2CH_2CH_3$ | $CH_2CH_2CH_3$ |
| 0 | $CH_3$ | $CH_3$ |
| 2 | $CH_3$ | $C_6H_5$ |
| 2 | $C_6H_5$ | $CH_3$ |
| 2 | $CH_3$ | $CF_3$ |
| 2 | $CF_3$ | $CH_3$ |
| 2 | $COCH_3$ | H |
| 2 | $CH=CH_2$ | $CH_3$ |
| 2 | $CH_3$ | $CH=CH_2$ |
| 2 | $SCH_3$ | $CH_3$ |
| 2 | $CH_3$ | $SCH_3$ |
| 2 | $NO_2$ | $CH_3$ |
| 2 | $NH_2$ | $CH_3$ |
| 2 | CHO | $CH_3$ |
| 2 | $CO_2CH_3$ | H |
| 2 | $CH(OCH_3)_2$ | H |

A = A-4; X = $NCH_2CH_2CN$; $R^3 = CH_3$; $R^4 = CH_3$

| n | $R^1$ | $R^2$ |
|---|---|---|
| 2 | $CH_3$ | $CH_3$ |
| 2 | $C_2H_5$ | $CH_3$ |
| 2 | H | $CH_3$ |
| 2 | H | $C_2H_5$ |
| 2 | H | $CH_2CH_2CH_3$ |
| 2 | $OCH_3$ | $CH_3$ |
| 2 | $OCH_3$ | $C_2H_5$ |
| 2 | $CH_2CH_2CH_3$ | $CH_2CH_2CH_3$ |
| 2 | $CH_2CH=CH_2$ | $CH_2CH=CH_2$ |
| 2 | $CH_2C\equiv CH$ | $CH_2C\equiv CH$ |
| 2 | $CH(CH_3)_2$ | $CH(CH_3)_2$ |
| 2 | $-(CH_2)_5-$ | |
| 2 | $-(CH_2)_4-$ | |
| 2 | $CH_2CH=CH_2$ | $C_2H_5$ |
| 2 | $CH_2C\equiv CH$ | $C_2H_5$ |
| 2 | $OC_2H_5$ | $CH_3$ |
| 2 | $OC_2H_5$ | $C_2H_5$ |
| 2 | H | 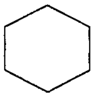 |

TABLE 4-continued

| n | $R^1$ | $R^2$ |
|---|---|---|
| 2 | 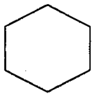 | 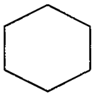 |
| 2 | H | $CH_2CH=CH_2$ |
| 2 | $CH_2CH_2CH_3$ | $CH_3$ |
| 0 | H | $CH_3$ |
| 1 | H | $CH_3$ |

A = A-4; X = $NC(O)N(C_2H_5)_2$; $R^1 = C_2H_5$; $R^2 = C_2H_5$

| n | $R^3$ | $R^4$ |
|---|---|---|
| 2 | H | H |
| 2 | H | Cl |
| 0 | $CH_3$ | $CH_3$ |
| 2 | H | $OCH_3$ |
| 2 | H | $CH_3$ |
| 2 | H | $C_2H_5$ |
| 2 | H | $CH(CH_3)_2$ |
| 2 | H | $CH_2CH_2CH_3$ |
| 2 | Cl | H |
| 2 | Cl | Cl |
| 2 | Cl | $OCH_3$ |
| 2 | Cl | $CH_3$ |
| 2 | Cl | $C_2H_5$ |
| 2 | Cl | $CH(CH_3)_2$ |
| 2 | Cl | $CH_2CH_2CH_3$ |
| 2 | $OCH_3$ | H |
| 2 | $OCH_3$ | Cl |
| 2 | $OCH_3$ | $OCH_3$ |
| 2 | $OCH_3$ | $CH_3$ |
| 2 | $OCH_3$ | $C_2H_5$ |
| 2 | $OCH_3$ | $CH(CH_3)_2$ |
| 2 | $OCH_3$ | $CH_2CH_2CH_3$ |
| 2 | $CH_3$ | H |
| 2 | $CH_3$ | Cl |
| 2 | $CH_3$ | $OCH_3$ |
| 2 | $CH_3$ | $CH_3$ |
| 0 | $CH_3$ | H |
| 1 | $CH_3$ | H |
| 2 | $CH_3$ | $C_2H_5$ |
| 2 | $CH_3$ | $CH(CH_3)_2$ |
| 2 | $CH_3$ | $CH_2CH_2CH_3$ |
| 2 | $C_2H_5$ | H |
| 2 | $C_2H_5$ | Cl |
| 2 | $C_2H_5$ | $OCH_3$ |
| 2 | $C_2H_5$ | $CH_3$ |
| 2 | $C_2H_5$ | $C_2H_5$ |
| 2 | $C_2H_5$ | $CH(CH_3)_2$ |
| 2 | $C_2H_5$ | $CH_2CH_2CH_3$ |
| 2 | $CH(CH_3)_2$ | H |
| 2 | $CH(CH_3)_2$ | Cl |
| 2 | $CH(CH_3)_2$ | $OCH_3$ |
| 2 | $CH(CH_3)_2$ | $CH_3$ |
| 2 | $CH(CH_3)_2$ | $C_2H_5$ |
| 2 | $CH(CH_3)_2$ | $CH(CH_3)_2$ |
| 2 | $CH(CH_3)_2$ | $CH_2CH_2CH_3$ |
| 2 | $CH_2CH_2CH_3$ | H |
| 2 | $CH_2CH_2CH_3$ | Cl |
| 2 | $CH_2CH_2CH_3$ | $OCH_3$ |
| 2 | $CH_2CH_2CH_3$ | $CH_3$ |
| 2 | $CH_2CH_2CH_3$ | $C_2H_5$ |
| 2 | $CH_2CH_2CH_3$ | $CH(CH_3)_2$ |
| 2 | $CH_2CH_2CH_3$ | $CH_2CH_2CH_3$ |
| 2 | $CH_3$ | $C_6H_5$ |
| 2 | $C_6H_5$ | $CH_3$ |
| 2 | $CH_3$ | $CF_3$ |
| 2 | $CF_3$ | $CH_3$ |
| 2 | $COCH_3$ | H |
| 2 | $CH=CH_2$ | $CH_3$ |
| 2 | $CH_3$ | $CH=CH_2$ |
| 0 | $CH_3$ | $CH_3$ |
| 2 | $SCH_3$ | $CH_3$ |

TABLE 4-continued

| | | |
|---|---|---|
| 2 | $CH_3$ | $SCH_3$ |
| 2 | $NO_2$ | $CH_3$ |
| 2 | $NH_2$ | $CH_3$ |
| 2 | CHO | $CH_3$ |
| 2 | $CO_2CH_3$ | H |
| 2 | $CH(OCH_3)_2$ | H |

A = A-4; X = $NC(O)N(C_2H_5)_2$; $R^3 = CH_3$; $R^4 = CH_3$

| n | $R^1$ | $R^2$ |
|---|---|---|
| 2 | $CH_3$ | $CH_3$ |
| 2 | $C_2H_5$ | $CH_3$ |
| 2 | H | $CH_3$ |
| 2 | H | $C_2H_5$ |
| 2 | H | $CH_2CH_2CH_3$ |
| 2 | $OCH_3$ | $CH_3$ |
| 2 | $OCH_3$ | $C_2H_5$ |
| 2 | $CH_2CH_2CH_3$ | $CH_2CH_2CH_3$ |
| 2 | $CH_2CH=CH_2$ | $CH_2CH=CH_2$ |
| 2 | $CH_2C\equiv CH$ | $CH_2C\equiv CH$ |
| 2 | $CH(CH_3)_2$ | $CH(CH_3)_2$ |
| 2 | $-(CH_2)_5-$ | |
| 2 | $-(CH_2)_4-$ | |
| 2 | $CH_2CH=CH_2$ | $C_2H_5$ |
| 2 | $CH_2C\equiv CH$ | $C_2H_5$ |
| 2 | $OC_2H_5$ | $CH_3$ |
| 2 | $OC_2H_5$ | $C_2H_5$ |
| 2 | H | 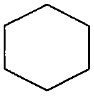 |
| 2 | 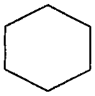 | 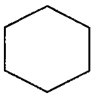 |
| 2 | H | $CH_2CH=CH_2$ |
| 2 | $CH_2CH_2CH_3$ | $CH_3$ |
| 0 | H | $CH_3$ |
| 1 | H | $CH_3$ |

A = A-4; X = $NCH_2CH_2CH_2CH_3$; $R^1 = C_2H_5$; $R^2 = C_2H_5$

| n | $R^3$ | $R^4$ |
|---|---|---|
| 2 | H | H |
| 2 | H | Cl |
| 2 | H | $OCH_3$ |
| 2 | H | $CH_3$ |
| 2 | H | $C_2H_5$ |
| 2 | H | $CH(CH_3)_2$ |
| 2 | H | $CH_2CH_2CH_3$ |
| 2 | Cl | H |
| 2 | Cl | Cl |
| 2 | Cl | $OCH_3$ |
| 2 | Cl | $CH_3$ |
| 2 | Cl | $C_2H_5$ |
| 2 | Cl | $CH(CH_3)_2$ |
| 2 | Cl | $CH_2CH_2CH_3$ |
| 2 | $OCH_3$ | H |
| 2 | $OCH_3$ | Cl |
| 2 | $OCH_3$ | $OCH_3$ |
| 2 | $OCH_3$ | $CH_3$ |
| 2 | $OCH_3$ | $C_2H_5$ |
| 2 | $OCH_3$ | $CH(CH_3)_2$ |

TABLE 4-continued

| | | |
|---|---|---|
| 2 | $OCH_3$ | $CH_2CH_2CH_3$ |
| 2 | $CH_3$ | H |
| 2 | $CH_3$ | Cl |
| 2 | $CH_3$ | $OCH_3$ |
| 2 | $CH_3$ | $CH_3$ |
| 0 | $CH_3$ | H |
| 1 | $CH_3$ | H |
| 2 | $CH_3$ | $C_2H_5$ |
| 2 | $CH_3$ | $CH(CH_3)_2$ |
| 2 | $CH_3$ | $CH_2CH_2CH_3$ |
| 2 | $C_2H_5$ | H |
| 2 | $C_2H_5$ | Cl |
| 2 | $C_2H_5$ | $OCH_3$ |
| 2 | $C_2H_5$ | $CH_3$ |
| 2 | $C_2H_5$ | $C_2H_5$ |
| 2 | $C_2H_5$ | $CH(CH_3)_2$ |
| 2 | $C_2H_5$ | $CH;CH_2CH_3$ |
| 2 | $CH(CH_3)_2$ | H |
| 2 | $CH(CH_3)_2$ | Cl |
| 2 | $CH(CH_3)_2$ | $OCH_3$ |
| 2 | $CH(CH_3)_2$ | $CH_3$ |
| 2 | $CH(CH_3)_2$ | $C_2H_5$ |
| 2 | $CH(CH_3)_2$ | $CH(CH_3)_2$ |
| 2 | $CH(CH_3)_2$ | $CH_2CH_2CH_3$ |
| 2 | $CH_2CH_2CH_3$ | H |
| 2 | $CH_2CH_2CH_3$ | Cl |
| 2 | $CH_2CH_2CH_3$ | $OCH_3$ |
| 2 | $CH_2CH_2CH_3$ | $CH_3$ |
| 2 | $CH_2CH_2CH_3$ | $C_2H_5$ |
| 2 | $CH_2CH_2CH_3$ | $CH(CH_3)_2$ |
| 2 | $CH_2CH_2CH_3$ | $CH_2CH_2CH_3$ |
| 0 | $CH_3$ | $CH_3$ |
| 0 | Cl | $CH_3$ |
| 2 | $CH_3$ | $C_6H_5$ |
| 2 | $C_6H_5$ | $CH_3$ |
| 2 | $CH_3$ | $CF_3$ |
| 2 | $CF_3$ | $CH_3$ |
| 2 | $COCH_3$ | H |
| 2 | $CH=CH_2$ | $CH_3$ |
| 2 | $CH_3$ | $CH=CH_2$ |
| 2 | $SCH_3$ | $CH_3$ |
| 2 | $CH_3$ | $SCH_3$ |
| 2 | $NO_2$ | $CH_3$ |
| 2 | $NH_2$ | $CH_3$ |
| 2 | CHO | $CH_3$ |
| 2 | $CO_2CH_3$ | H |
| 2 | $CH(OCH_3)_2$ | H |

A = A-4; X = $NCH_2CH_2CH_2CH_3$; $R^3 = CH_3$; $R^4 = CH_3$

| n | $R^1$ | $R^2$ |
|---|---|---|
| 2 | $CH_3$ | $CH_3$ |
| 2 | $C_2H_5$ | $CH_3$ |
| 2 | H | $CH_3$ |
| 2 | H | $C_2H_5$ |
| 2 | H | $CH_2CH_2CH_3$ |
| 2 | $OCH_3$ | $CH_3$ |
| 2 | $OCH_3$ | $C_2H_5$ |
| 2 | $CH_2CH_2CH_3$ | $CH_2CH_2CH_3$ |
| 2 | $CH_2CH=CH_2$ | $CH_2CH=CH_2$ |
| 2 | $CH_2C\equiv CH$ | $CH_2C\equiv CH$ |
| 2 | $CH(CH_3)_2$ | $CH(CH_3)_2$ |
| 2 | $-(CH_2)_5-$ | |
| 2 | $-(CH_2)_4-$ | |
| 2 | $CH_2CH=CH_2$ | $C_2H_5$ |
| 2 | $CH_2C\equiv CH$ | $C_2H_5$ |
| 2 | $OC_2H_5$ | $CH_3$ |
| 2 | $OC_2H_4$ | $C_2H_5$ |

TABLE 4-continued

| | | |
|---|---|---|
| 2 | H | 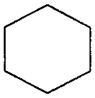 |
| 2 | 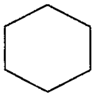 | 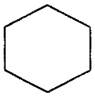 |
| 2 | H | $CH_2CH{=}CH_2$ |
| 2 | $CH_2CH_2CH_3$ | $CH_3$ |
| 0 | H | $CH_3$ |
| 1 | H | $CH_3$ |

A = A-4; X = $NCH_2CH(CH_3)_2$; $R^1$ = $C_2H_5$; $R^2$ = $C_2H_5$

| n | $R^3$ | $R^4$ |
|---|---|---|
| 2 | H | H |
| 2 | H | Cl |
| 2 | H | $OCH_3$ |
| 2 | H | $CH_3$ |
| 2 | H | $C_2H_5$ |
| 2 | H | $CH(CH_3)_2$ |
| 2 | H | $CH_2CH_2CH_3$ |
| 2 | Cl | H |
| 2 | Cl | Cl |
| 2 | Cl | $OCH_3$ |
| 2 | Cl | $CH_3$ |
| 2 | Cl | $C_2H_5$ |
| 2 | Cl | $CH(CH_3)_2$ |
| 2 | Cl | $CH_2CH_2CH_3$ |
| 2 | $OCH_3$ | H |
| 2 | $OCH_3$ | Cl |
| 2 | $OCH_3$ | $OCH_3$ |
| 2 | $OCH_3$ | $CH_3$ |
| 2 | $OCH_3$ | $C_2H_5$ |
| 2 | $OCH_3$ | $CH(CH_3)_2$ |
| 2 | $OCH_3$ | $CH_2CH_2CH_3$ |
| 2 | $CH_3$ | H |
| 2 | $CH_3$ | Cl |
| 2 | $CH_3$ | $OCH_3$ |
| 2 | $CH_3$ | $CH_3$ |
| 0 | $CH_3$ | H |
| 1 | $CH_3$ | H |
| 2 | $CH_3$ | $C_2H_5$ |
| 2 | $CH_3$ | $CH(CH_3)_2$ |
| 2 | $CH_3$ | $CH_2CH_2CH_3$ |
| 2 | $C_2H_5$ | H |
| 2 | $C_2H_5$ | Cl |
| 2 | $C_2H_5$ | $OCH_3$ |
| 2 | $C_2H_5$ | $CH_3$ |
| 2 | $C_2H_5$ | $C_2H_5$ |
| 2 | $C_2H_5$ | $CH(CH_3)_2$ |
| 2 | $C_2H_5$ | $CH_2CH_2CH_3$ |
| 2 | $CH(CH_3)_2$ | H |
| 2 | $CH(CH_3)_2$ | Cl |
| 2 | $CH(CH_3)_2$ | $OCH_3$ |
| 2 | $CH(CH_3)_2$ | $CH_3$ |
| 2 | $CH(CH_3)_2$ | $C_2H_5$ |
| 2 | $CH(CH_3)_2$ | $CH(CH_3)_2$ |
| 2 | $CH(CH_3)_2$ | $CH_2CH_2CH_3$ |
| 2 | $CH_2CH_2CH_3$ | H |
| 2 | $CH_2CH_2CH_3$ | Cl |
| 2 | $CH_2CH_2CH_3$ | $OCH_3$ |
| 2 | $CH_2CH_2CH_3$ | $CH_3$ |
| 2 | $CH_2CH_2CH_3$ | $C_2H_5$ |
| 2 | $CH_2CH_2CH_3$ | $CH(CH_3)_2$ |
| 2 | $CH_2CH_2CH_3$ | $CH_2CH_2CH_3$ |
| 0 | $CH_3$ | $CH_3$ |
| 2 | $CH_3$ | $C_6H_5$ |
| 2 | $C_6H_5$ | $CH_3$ |
| 2 | $CH_3$ | $CF_3$ |
| 2 | $CF_3$ | $CH_3$ |
| 2 | $COCH_3$ | H |

TABLE 4-continued

| | | |
|---|---|---|
| 2 | $CH{=}CH_2$ | $CH_3$ |
| 2 | $CH_3$ | $CH{=}CH_2$ |
| 2 | $SCH_3$ | $CH_3$ |
| 2 | $CH_3$ | $SCH_3$ |
| 2 | $NO_2$ | $CH_3$ |
| 2 | $NH_2$ | $CH_3$ |
| 2 | CHO | $CH_3$ |
| 2 | $CO_2CH_3$ | H |
| 2 | $CH(OCH_3)_2$ | H |

A = A-4; X = $NCH_2CH(CH_3)_2$; $R^3$ = $CH_3$; $R^4$ = $CH_3$

| n | $R^1$ | $R^2$ |
|---|---|---|
| 2 | $CH_3$ | $CH_3$ |
| 2 | $C_2H_5$ | $CH_3$ |
| 2 | H | $CH_3$ |
| 2 | H | $C_2H_5$ |
| 2 | H | $CH_2CH_2CH_3$ |
| 2 | $OCH_3$ | $CH_3$ |
| 2 | $OCH_3$ | $C_2H_5$ |
| 2 | $CH_2CH_2CH_3$ | $CH_2CH_2CH_3$ |
| 2 | $CH_2CH{=}CH_2$ | $CH_2CH{=}CH_2$ |
| 2 | $CH_2C{\equiv}CH$ | $CH_2C{\equiv}CH$ |
| 2 | $CH(CH_3)_2$ | $CH(CH_3)_2$ |
| 2 | $-(CH_2)_5-$ | |
| 2 | $-(CH_2)_4-$ | |
| 2 | $CH_2CH{=}CH_2$ | $C_2H_5$ |
| 2 | $CH_2C{\equiv}CH$ | $C_2H_5$ |
| 2 | $OC_2H_5$ | $CH_3$ |
| 2 | $OC_2H_5$ | $C_2H_5$ |
| 2 | H | 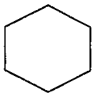 |
| 2 | 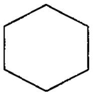 | 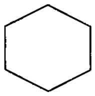 |
| 2 | H | $CH_2CH{=}CH_2$ |
| 2 | $CH_2CH_2CH_3$ | $CH_3$ |
| 0 | H | $CH_3$ |
| 1 | H | $CH_3$ |

A = A-4; X = $NCH_2C_6H_5$; $R^1$ = $C_2H_5$; $R^2$ = $C_2H_5$

| n | $R^3$ | $R^4$ |
|---|---|---|
| 2 | H | H |
| 2 | H | Cl |
| 2 | H | $OCH_3$ |
| 2 | H | $CH_3$ |
| 2 | H | $C_2H_5$ |
| 2 | H | $CH(CH_3)_2$ |
| 2 | H | $CH_2CH_2CH_3$ |
| 2 | Cl | H |
| 2 | Cl | Cl |
| 2 | Cl | $OCH_3$ |
| 2 | Cl | $CH_3$ |
| 2 | Cl | $C_2H_5$ |
| 2 | Cl | $CH(CH_3)_2$ |
| 2 | Cl | $CH_2CH_2CH_3$ |
| 2 | $OCH_3$ | H |
| 2 | $OCH_3$ | Cl |
| 2 | $OCH_3$ | $OCH_3$ |
| 2 | $OCH_3$ | $CH_3$ |

TABLE 4-continued

| | | |
|---|---|---|
| 2 | $OCH_3$ | $C_2H_5$ |
| 2 | $OCH_3$ | $CH(CH_3)_2$ |
| 2 | $OCH_3$ | $CH_2CH_2CH_3$ |
| 2 | $CH_3$ | H |
| 2 | $CH_3$ | Cl |
| 2 | $CH_3$ | $OCH_3$ |
| 2 | $CH_3$ | $CH_3$ |
| 0 | $CH_3$ | H |
| 1 | $CH_3$ | H |
| 2 | $CH_3$ | $C_2H_5$ |
| 2 | $CH_3$ | $CH(CH_3)_2$ |
| 2 | $CH_3$ | $CH_2CH_2CH_3$ |
| 2 | $C_2H_5$ | H |
| 2 | $C_2H_5$ | Cl |
| 2 | $C_2H_5$ | $OCH_3$ |
| 2 | $C_2H_5$ | $CH_3$ |
| 2 | $C_2H_5$ | $C_2H_5$ |
| 2 | $C_2H_5$ | $CH(CH_3)_2$ |
| 2 | $C_2H_5$ | $CH_2CH_2CH_3$ |
| 2 | $CH(CH_3)_2$ | H |
| 2 | $CH(CH_3)_2$ | Cl |
| 2 | $CH(CH_3)_2$ | $OCH_3$ |
| 2 | $CH(CH_3)_2$ | $CH_3$ |
| 2 | $CH(CH_3)_2$ | $C_2H_5$ |
| 2 | $CH(CH_3)_2$ | $CH(CH_3)_2$ |
| 2 | $CH(CH_3)_2$ | $CH_2CH_2CH_3$ |
| 2 | $CH_2CH_2CH_3$ | H |
| 2 | $CH_2CH_2CH_3$ | Cl |
| 2 | $CH_2CH_2CH_3$ | $OCH_3$ |
| 2 | $CH_2CH_2CH_3$ | $CH_3$ |
| 2 | $CH_2CH_2CH_3$ | $C_2H_5$ |
| 2 | $CH_2CH_2CH_3$ | $CH(CH_3)_2$ |
| 2 | $CH_2CH_2CH_3$ | $CH_2CH_2CH_3$ |
| 0 | $CH_3$ | $CH_3$ |
| 2 | $CH_3$ | $C_6H_5$ |
| 2 | $C_6H_5$ | $CH_3$ |
| 2 | $CH_3$ | $CF_3$ |
| 2 | $CF_3$ | $CH_3$ |
| 2 | $COCH_3$ | H |
| 2 | $CH=CH_2$ | $CH_3$ |
| 2 | $CH_3$ | $CH=CH_2$ |
| 2 | $SCH_3$ | $CH_3$ |
| 2 | $CH_3$ | $SCH_3$ |
| 2 | $NO_2$ | $CH_3$ |
| 2 | $NH_2$ | $CH_3$ |
| 2 | CHO | $CH_3$ |
| 2 | $CO_2CH_3$ | H |
| 2 | $CH(OCH_3)_2$ | H |

A = A-4; X = $NCH_2C_6H_5$; $R^3$ = $CH_3$; $R^4$ = $CH_3$

| n | $R^1$ | $R^2$ |
|---|---|---|
| 2 | $CH_3$ | $CH_3$ |
| 2 | $C_2H_5$ | $CH_3$ |
| 2 | H | $CH_3$ |
| 2 | H | $C_2H_5$ |
| 2 | H | $CH_2CH_2CH_3$ |
| 2 | $OCH_3$ | $CH_3$ |
| 2 | $OCH_3$ | $C_2H_5$ |
| 2 | $CH_2CH_2CH_3$ | $CH_2CH_2CH_3$ |
| 2 | $CH_2CH=CH_2$ | $CH_2CH=CH_2$ |
| 2 | $CH_2C\equiv CH$ | $CH_2C\equiv CH$ |
| 2 | $CH(CH_3)_2$ | $CH(CH_3)_2$ |
| 2 | $-(CH_2)_5-$ | |
| 2 | $-(CH_2)_4-$ | |
| 2 | $CH_2CH=CH_2$ | $C_2H_5$ |
| 2 | $CH_2C\equiv CH$ | $C_2H_5$ |
| 2 | $OC_2H_5$ | $CH_3$ |
| 2 | $OC_2H_4$ | $C_2H_5$ |

TABLE 4-continued

| | | |
|---|---|---|
| 2 | H | 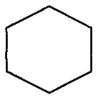 |
| 2 | 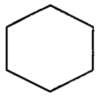 | 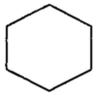 |
| 2 | H | $CH_2CH=CH_2$ |
| 2 | $CH_2CH_2CH_3$ | $CH_3$ |
| 0 | H | $CH_3$ |
| 1 | H | $CH_3$ |

A = A-4; X = NH; $R^1$ = $C_2H_5$; $R^2$ = $C_2H_5$

| n | $R^3$ | $R^4$ |
|---|---|---|
| 2 | H | H |
| 2 | H | Cl |
| 2 | H | $OCH_3$ |
| 2 | H | $CH_3$ |
| 2 | H | $C_2H_5$ |
| 2 | H | $CH(CH_3)_2$ |
| 2 | H | $CH_2CH_2CH_3$ |
| 2 | Cl | H |
| 2 | Cl | Cl |
| 2 | Cl | $OCH_3$ |
| 2 | Cl | $CH_3$ |
| 2 | Cl | $C_2H_5$ |
| 2 | Cl | $CH(CH_3)_2$ |
| 2 | Cl | $CH_2CH_2CH_3$ |
| 2 | $OCH_3$ | H |
| 2 | $OCH_3$ | Cl |
| 2 | $OCH_3$ | $OCH_3$ |
| 2 | $OCH_3$ | $CH_3$ |
| 2 | $OCH_3$ | $C_2H_5$ |
| 2 | $OCH_3$ | $CH(CH_3)_2$ |
| 2 | $OCH_3$ | $CH_2CH_2CH_3$ |
| 2 | $CH_3$ | H |
| 2 | $CH_3$ | Cl |
| 2 | $CH_3$ | $OCH_3$ |
| 2 | $CH_3$ | $CH_3$ |
| 0 | $CH_3$ | H |
| 1 | $CH_3$ | H |
| 2 | $CH_3$ | $C_2H_5$ |
| 2 | $CH_3$ | $CH(CH_3)_2$ |
| 2 | $CH_3$ | $CH_2CH_2CH_3$ |
| 2 | $C_2H_5$ | H |
| 2 | $C_2H_5$ | Cl |
| 2 | $C_2H_5$ | $OCH_3$ |
| 2 | $C_2H_5$ | $CH_3$ |
| 2 | $C_2H_5$ | $C_2H_5$ |
| 2 | $C_2H_5$ | $CH(CH_3)_2$ |
| 2 | $C_2H_5$ | $CH_2CH_2CH_3$ |
| 2 | $CH(CH_3)_2$ | H |
| 2 | $CH(CH_3)_2$ | Cl |
| 2 | $CH(CH_3)_2$ | $OCH_3$ |
| 2 | $CH(CH_3)_2$ | $CH_3$ |
| 2 | $CH(CH_3)_2$ | $C_2H_5$ |
| 2 | $CH(CH_3)_2$ | $CH(CH_3)_2$ |
| 2 | $CH(CH_3)_2$ | $CH_2CH_2CH_3$ |
| 2 | $CH_2CH_2CH_3$ | H |
| 2 | $CH_2CH_2CH_3$ | Cl |
| 2 | $CH_2CH_2CH_3$ | $OCH_3$ |
| 2 | $CH_2CH_2CH_3$ | $CH_3$ |
| 2 | $CH_2CH_2CH_3$ | $C_2H_5$ |
| 2 | $CH_2CH_2CH_3$ | $CH(CH_3)_2$ |
| 2 | $CH_2CH_2CH_3$ | $CH_2CH_2CH_3$ |
| 0 | $CH_3$ | $CH_3$ |
| 1 | Cl | $CH_3$ |
| 2 | $CH_3$ | $C_6H_5$ |
| 2 | $C_6H_5$ | $CH_3$ |
| 2 | $CH_3$ | $CF_3$ |
| 2 | $CF_3$ | $CH_3$ |

TABLE 4-continued

| | | |
|---|---|---|
| 2 | $COCH_3$ | H |
| 2 | $CH=CH_2$ | $CH_3$ |
| 2 | $CH_3$ | $CH=CH_2$ |
| 2 | $SCH_3$ | $CH_3$ |
| 2 | $CH_3$ | $SCH_3$ |
| 2 | $NO_2$ | $CH_3$ |
| 2 | $NH_2$ | $CH_3$ |
| 2 | CHO | $CH_3$ |
| 2 | $CO_2CH_3$ | H |
| 2 | $CH(OCH_3)_2$ | H |

A = A-4; X = NH; $R^3 = CH_3$; $R^4 = CH_3$

| n | $R^1$ | $R^2$ |
|---|---|---|
| 2 | $CH_3$ | $CH_3$ |
| 2 | $C_2H_5$ | $CH_3$ |
| 2 | H | $CH_3$ |
| 2 | H | $C_2H_5$ |
| 2 | H | $CH_2CH_2CH_3$ |
| 2 | $OCH_3$ | $CH_3$ |
| 2 | $OCH_3$ | $C_2H_5$ |
| 2 | $CH_2CH_2CH_3$ | $CH_2CH_2CH_3$ |
| 2 | $CH_2CH=CH_2$ | $CH_2CH=CH_2$ |
| 2 | $CH_2C\equiv CH$ | $CH_2C\equiv CH$ |
| 2 | $CH(CH_3)_2$ | $CH(CH_3)_2$ |
| 2 | $-(CH_2)_5-$ | |
| 2 | $-(CH_2)_4-$ | |
| 2 | $CH_2CH=CH_2$ | $C_2H_5$ |
| 2 | $CH_2C\equiv CH$ | $C_2H_5$ |
| 2 | $OC_2H_5$ | $CH_3$ |
| 2 | $OC_2H_5$ | $C_2H_5$ |
| 2 | H | 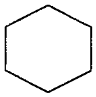 |
| 2 | 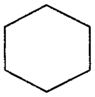 | 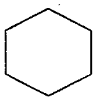 |
| 2 | H | $CH_2CH=CH_2$ |
| 2 | $CH_2CH_2CH_3$ | $CH_3$ |
| 0 | H | $CH_3$ |
| 1 | H | $CH_3$ |

A = A-4; X = $NCH_2CH(CH_3)_2$; $R^1 = C_2H_5$; $R^2 = C_2H_5$

| n | $R^3$ | $R^4$ |
|---|---|---|
| 2 | H | H |
| 2 | H | Cl |
| 2 | H | $OCH_3$ |
| 2 | H | $CH_3$ |
| 2 | H | $C_2H_5$ |
| 2 | H | $CH(CH_3)_2$ |
| 2 | H | $CH_2CH_2CH_3$ |
| 2 | Cl | H |
| 2 | Cl | Cl |
| 2 | Cl | $OCH_3$ |
| 2 | Cl | $CH_3$ |
| 2 | Cl | $C_2H_5$ |
| 2 | Cl | $CH(CH_3)_2$ |
| 2 | Cl | $CH_2CH_2CH_3$ |
| 2 | $OCH_3$ | H |
| 2 | $OCH_3$ | Cl |
| 2 | $OCH_3$ | $OCH_3$ |
| 2 | $OCH_3$ | $CH_3$ |

TABLE 4-continued

| | | |
|---|---|---|
| 2 | $OCH_3$ | $C_2H_5$ |
| 2 | $OCH_3$ | $CH(CH_3)_2$ |
| 2 | $OCH_3$ | $CH_2CH_2CH_3$ |
| 2 | $CH_3$ | H |
| 2 | $CH_3$ | Cl |
| 2 | $CH_3$ | $OCH_3$ |
| 2 | $CH_3$ | $CH_3$ |
| 0 | $CH_3$ | H |
| 1 | $CH_3$ | H |
| 2 | $CH_3$ | $C_2H_5$ |
| 2 | $CH_3$ | $CH(CH_3)_2$ |
| 2 | $CH_3$ | $CH_2CH_2CH_3$ |
| 2 | $C_2H_5$ | H |
| 2 | $C_2H_5$ | Cl |
| 2 | $C_2H_5$ | $OCH_3$ |
| 2 | $C_2H_5$ | $CH_3$ |
| 2 | $C_2H_5$ | $C_2H_5$ |
| 2 | $C_2H_5$ | $CH(CH_3)_2$ |
| 2 | $C_2H_5$ | $CH_2CH_2CH_3$ |
| 2 | $CH(CH_3)_2$ | H |
| 2 | $CH(CH_3)_2$ | Cl |
| 2 | $CH(CH_3)_2$ | $OCH_3$ |
| 2 | $CH(CH_3)_2$ | $CH_3$ |
| 2 | $CH(CH_3)_2$ | $C_2H_5$ |
| 2 | $CH(CH_3)_2$ | $CH(CH_3)_2$ |
| 2 | $CH(CH_3)_2$ | $CH_2CH_2CH_3$ |
| 2 | $CH_2CH_2CH_3$ | H |
| 2 | $CH_2CH_2CH_3$ | Cl |
| 2 | $CH_2CH_2CH_3$ | $OCH_3$ |
| 2 | $CH_2CH_2CH_3$ | $CH_3$ |
| 2 | $CH_2CH_2CH_3$ | $C_2H_5$ |
| 2 | $CH_2CH_2CH_3$ | $CH(CH_3)_2$ |
| 2 | $CH_2CH_2CH_3$ | $CH_2CH_2CH_3$ |

A = A-4; X = $NCH(CH_3)_2$;

$R^1 = C_2H_5$ ; $R^2 = C_2H_5$

| n | $R^3$ | $R^4$ |
|---|---|---|
| 0 | $CH_3$ | H |
| 0 | Cl | H |
| 2 | $CH_3$ | $C_6H_5$ |
| 2 | $C_6H_5$ | $CH_3$ |
| 2 | $CH_3$ | $CF_3$ |
| 2 | $CF_3$ | $CH_3$ |
| 2 | $COCH_3$ | H |
| 2 | $CH=CH_2$ | $CH_3$ |
| 2 | $CH_3$ | $CH=CH_2$ |
| 2 | $SCH_3$ | $CH_3$ |
| 2 | $CH_3$ | $SCH_3$ |
| 2 | $NO_2$ | $CH_3$ |
| 2 | $NH_2$ | $CH_3$ |
| 2 | CHO | $CH_3$ |
| 2 | $CO_2CH_3$ | H |
| 2 | $CH(OCH_3)_2$ | H |

A = A-4; X = $NC_2H_5$; $R^3 = CH_3$; $R^4 = CH_3$

| n | $R^1$ | $R^2$ |
|---|---|---|
| 2 | $CH_3$ | $CH_3$ |
| 2 | $C_2H_5$ | $CH_3$ |
| 2 | H | $CH_3$ |
| 2 | H | $C_2H_5$ |
| 2 | H | $CH_2CH_2CH_3$ |
| 2 | $OCH_3$ | $CH_3$ |
| 2 | $OCH_3$ | $C_2H_5$ |
| 2 | $CH_2CH_2CH_3$ | $CH_2CH_2CH_3$ |
| 2 | $CH_2CH=CH_2$ | $CH_2CH=CH_2$ |
| 2 | $CH_2C\equiv CH$ | $CH_2C\equiv CH$ |

TABLE 4-continued

| | | |
|---|---|---|
| 2 | $CH(CH_3)_2$ | $CH(CH_3)_2$ |
| 2 | $-(CH_2)_5-$ | |
| 2 | $-(CH_2)_4-$ | |
| 2 | $CH_2CH{=}CH_2$ | $C_2H_5$ |
| 2 | $CH_2C{\equiv}CH$ | $C_2H_5$ |
| 2 | $OC_2H_5$ | $CH_3$ |
| 2 | $OC_2H_5$ | $C_2H_5$ |
| 2 | H | 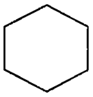 |
| 2 | 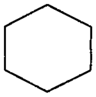 | 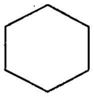 |
| 2 | H | $CH_2CH{=}CH_2$ |
| 2 | $CH_2CH_2CH_3$ | $CH_3$ |
| 1 | H | $CH_3$ |
| 0 | $CH_3$ | $CH_3$ |

A = A-4; X = $NR^6$; $R^1 = C_2H_5$; $R^2 = C_2H_5$; $R^3 = CH_3$; $R^4 = CH_3$

| n | $R^6$ |
|---|---|
| 2 | 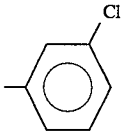 |
| 2 | 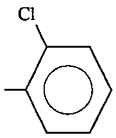 |
| 2 | 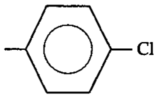 |
| 2 | 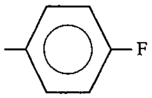 |
| 2 | 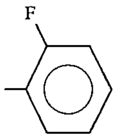 |
| 2 | 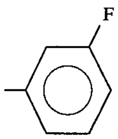 |
| 2 | $-CH_2CH_2Cl$ |
| 2 | $-CH_2CH_2Br$ |
| 2 | $-CH_2CH{=}CH_2$ |
| 2 | $-CH{=}CH_2$ |
| 2 | $-CH_2CH_2OCH_3$ |

TABLE 4-continued

A = A-4; X = $NR^6$; $R^1 = C_2H_5$; $R^2 = C_2H_5$; $R^3 = C_2H_5$; $R^4 = C_2H_5$

| n | $R^6$ |
|---|---|
| 2 | 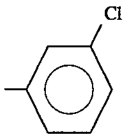 |
| 2 | 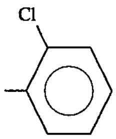 |
| 2 | 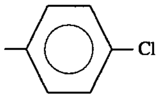 |
| 2 | 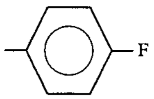 |
| 2 | 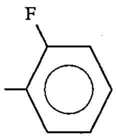 |
| 2 | 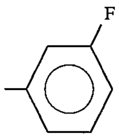 |
| 2 | $-CH_2CH_2Cl$ |
| 2 | $-CH_2CH_2Br$ |
| 2 | $-CH_2CH{=}CH_2$ |
| 2 | $-CH{=}CH_2$ |
| 2 | $-CH_2CH_2OCH_3$ |

A = A-4; X = $NR^6$; $R^1 = C_2H_5$; $R^2 = C_2H_5$; $R^3 = C_2H_5$; $R^4 = CH_3$

| n | $R^6$ |
|---|---|
| 2 | 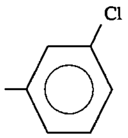 |
| 2 | 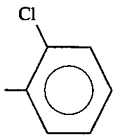 |
| 2 | 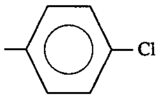 |

TABLE 4-continued
| n | $R^6$ |
|---|---|
| 2 | 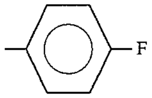 |
| 2 | 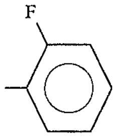 |
| 2 | 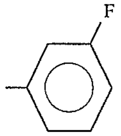 |
| 2 | $-CH_2CH_2Cl$ |
| 2 | $-CH_2CH_2Br$ |
| 2 | $-CH_2CH=CH_2$ |
| 2 | $-CH=CH_2$ |
| 2 | $-CH_2CH_2OCH_3$ |
A = A-4; X = $NR^6$; $R^1 = C_2H_5$; $R^2 = C_2H_5$; $R^3 = CH_3$; $R^4 = C_2H_5$
| n | $R^6$ |
|---|---|
| 2 | 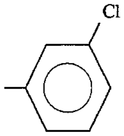 |
| 2 | 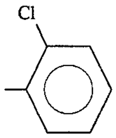 |
| 2 | 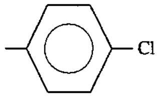 |
| 2 | 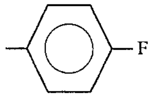 |
| 2 | 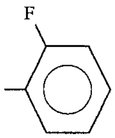 |
| 2 | 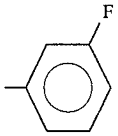 |
| 2 | $-CH_2CH_2Cl$ |
| 2 | $-CH_2CH_2Br$ |
| 2 | $-CH_2CH=CH_2$ |
| 2 | $-CH=CH_2$ |
| 2 | $-CH_2CH_2OCH_3$ |
TABLE 4-continued
A = A-4; X = $NR^6$; $R^1 = C_2H_5$, $R^2 = C_2H_5$; $R^3 = Cl$; $R^4 = CH_3$
| n | $R^6$ |
|---|---|
| 2 | 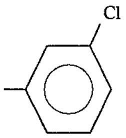 |
| 2 | 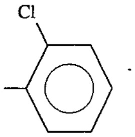 |
| 2 | 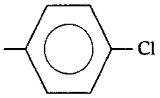 |
| 2 | 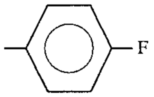 |
| 2 | 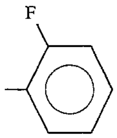 |
| 2 | 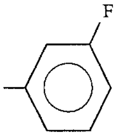 |
| 2 | $-CH_2CH_2Cl$ |
| 2 | $-CH_2CH_2Br$ |
| 2 | $-CH_2CH=CH_2$ |
| 2 | $-CH=CH_2$ |
| 2 | $-CH_2CH_2OCH_3$ |
A = A-4; X = $NR^6$; $R^1 = C_2H_5$; $R^2 = C_2H_5$; $R^3 = Cl$; $R^4 = Cl$
| n | $R^6$ |
|---|---|
| 2 | 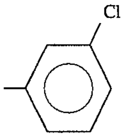 |
| 2 | 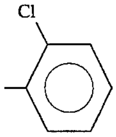 |
| 2 | 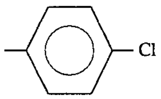 |

TABLE 4-continued

| | |
|---|---|
| 2 | 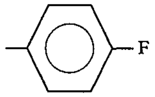 |
| 2 | 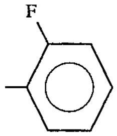 |
| 2 | 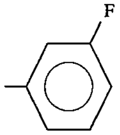 |
| 2 | $-CH_2CH_2Cl$ |
| 2 | $-CH_2CH_2Br$ |
| 2 | $-CH_2CH=CH_2$ |
| 2 | $-CH=CH_2$ |
| 2 | $-CH_2CH_2OCH_3$ |

A = A-4; X = $NCH_3$; $R^1$ and $R^2$ = $CH(CH_3)CH_2CH_2CH_2CH_2-$

| n | $R^3$ | $R^4$ |
|---|---|---|
| 2 | Cl | H |
| 2 | Cl | Cl |
| 2 | Cl | $OCH_3$ |
| 2 | Cl | $CH_3$ |
| 2 | Cl | $C_2H_5$ |
| 2 | $OCH_3$ | Cl |
| 2 | $OCH_3$ | $CH_3$ |
| 2 | $OCH_3$ | $C_2H_5$ |
| 2 | $CH_3$ | Cl |
| 2 | $CH_3$ | $OCH_3$ |
| 2 | $CH_3$ | $CH_3$ |
| 2 | $CH_3$ | $C_2H_5$ |
| 2 | $C_2H_5$ | Cl |
| 2 | $C_2H_5$ | $OCH_3$ |
| 2 | $C_2H_5$ | $CH_3$ |
| 2 | $C_2H_5$ | $C_2H_5$ |
| 2 | $CH_2CH_2CH_3$ | Cl |
| 2 | $CH_2CH_2CH_3$ | $OCH_3$ |
| 2 | $CH_2CH_2CH_3$ | $CH_3$ |
| 1 | $CH_3$ | H |
| 2 | $CH_3$ | $CF_3$ |
| 2 | $CF_3$ | $CH_3$ |
| 2 | $COCH_3$ | H |
| 2 | $CH=CH_2$ | $CH_3$ |

A = A-4; X = $NC_2H_5$; $R^1$ and $R^2$ = $CH(CH_3)CH_2CH_2CH_2CH_2-$

| n | $R^3$ | $R^4$ |
|---|---|---|
| 2 | $CH_3$ | $CH_3$ |
| 2 | $CH_3$ | Cl |
| 2 | $CH_3$ | $OCH_3$ |
| 2 | $OCH_3$ | $CH_3$ |
| 2 | $C_2H_5$ | $C_2H_5$ |
| 2 | Cl | Cl |
| 2 | Cl | $OCH_3$ |
| 2 | Cl | $CH_3$ |
| 2 | Cl | $C_2H_5$ |
| 2 | $C_2H_5$ | $CH_3$ |
| 2 | $CH_3$ | $C_2H_5$ |

TABLE 4-continued

A = A-4; X = $NCH_2CH_2CH_3$; $R^1$ and $R^2$ = $CH(CH_3)CH_2CH_2CH_2CH_2-$

| n | $R^3$ | $R^4$ |
|---|---|---|
| 2 | $OCH_3$ | $OCH_3$ |
| 2 | $OCH_3$ | $CH_3$ |
| 2 | $OCH_3$ | $C_2H_5$ |
| 2 | $CH_3$ | H |
| 2 | $CH_3$ | Cl |
| 2 | $CH_3$ | $OCH_3$ |
| 2 | $CH_3$ | $CH_3$ |
| 2 | $CH_3$ | $C_2H_5$ |
| 2 | $C_2H_5$ | Cl |
| 2 | $C_2H_5$ | $OCH_3$ |
| 2 | $C_2H_5$ | $CH_3$ |
| 2 | $C_2H_5$ | $C_2H_5$ |

A = A-4; X = $NCH_2CF_3$; $R^1$ and $R^2$ = $CH(CH_3)CH_2CH_2CH_2CH_2-$

| n | $R^3$ | $R^4$ |
|---|---|---|
| 2 | $CH_3$ | $CH_3$ |
| 2 | $CH_3$ | $C_2H_5$ |
| 2 | $C_2H_5$ | $CH_3$ |
| 2 | $CH_3$ | $CF_3$ |
| 2 | $CF_3$ | $CH_3$ |
| 2 | $C_2H_5$ | $C_2H_5$ |

A = A-4; X = N— 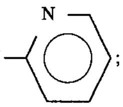 ;

$R^1$ = $C_2H_5$; $R^2$ = $C_2H_5$

| n | $R^3$ | $R^4$ |
|---|---|---|
| 2 | H | H |
| 2 | H | Cl |
| 2 | H | $OCH_3$ |
| 2 | H | $CH_3$ |
| 2 | H | $C_2H_5$ |
| 2 | H | $CH(CH_3)_2$ |
| 2 | H | $CH_2CH_2CH_3$ |
| 2 | Cl | H |
| 2 | Cl | Cl |
| 2 | Cl | $OCH_3$ |
| 2 | Cl | $CH_3$ |
| 2 | Cl | $C_2H_5$ |
| 2 | Cl | $CH(CH_3)_2$ |
| 2 | Cl | $CH_2CH_2CH_3$ |
| 2 | $OCH_3$ | H |
| 2 | $OCH_3$ | Cl |
| 2 | $OCH_3$ | $OCH_3$ |
| 2 | $OCH_3$ | $CH_3$ |
| 2 | $OCH_3$ | $C_2H_5$ |
| 2 | $OCH_3$ | $CH(CH_3)_2$ |
| 2 | $OCH_3$ | $CH_2CH_2CH_3$ |
| 2 | $CH_3$ | H |
| 2 | $CH_3$ | Cl |
| 2 | $CH_3$ | $OCH_3$ |
| 2 | $CH_3$ | $CH_3$ |
| 0 | $CH_3$ | $CH_3$ |
| 1 | $CH_3$ | $CH_3$ |
| 2 | $CH_3$ | $C_2H_5$ |
| 2 | $CH_3$ | $CH(CH_3)_2$ |
| 2 | $CH_3$ | $CH_2CH_2CH_3$ |
| 2 | $C_2H_5$ | H |
| 2 | $C_2H_5$ | Cl |
| 2 | $C_2H_5$ | $OCH_3$ |
| 2 | $C_2H_5$ | $CH_3$ |
| 2 | $C_2H_5$ | $C_2H_5$ |
| 2 | $C_2H_5$ | $CH(CH_3)_2$ |
| 2 | $C_2H_5$ | $CH_2CH_2CH_3$ |
| 2 | $CH(CH_3)_2$ | H |

TABLE 4-continued

| | | |
|---|---|---|
| 2 | $CH(CH_3)_2$ | Cl |
| 2 | $CH(CH_3)_2$ | $OCH_3$ |
| 2 | $CH(CH_3)_2$ | $CH_3$ |
| 2 | $CH(CH_3)_2$ | $C_2H_5$ |
| 2 | $CH(CH_3)_2$ | $CH(CH_3)_2$ |
| 2 | $CH(CH_3)_2$ | $CH_2CH_2CH_3$ |
| 2 | $CH_2CH_2CH_3$ | H |
| 2 | $CH_2CH_2CH_3$ | Cl |
| 2 | $CH_2CH_2CH_3$ | $OCH_3$ |
| 2 | $CH_2CH_2CH_3$ | $CH_3$ |
| 2 | $CH_2CH_2CH_3$ | $C_2H_5$ |
| 2 | $CH_2CH_2CH_3$ | $CH(CH_3)_2$ |
| 2 | $CH_2CH_2CH_3$ | $CH_2CH_2CH_3$ |
| 0 | $CH_3$ | H |
| 2 | $CH_3$ | $C_6H_5$ |
| 2 | $C_6H_5$ | $CH_3$ |
| 2 | $CH_3$ | $CF_3$ |
| 2 | $CF_3$ | $CH_3$ |
| 2 | $COCH_3$ | H |
| 2 | $CH{=}CH_2$ | $CH_3$ |
| 2 | $CH_3$ | $CH{=}CH_2$ |
| 2 | $SCH_3$ | $CH_3$ |
| 2 | $CH_3$ | $SCH_3$ |
| 2 | $NO_2$ | $CH_3$ |

A = A-4; X = N 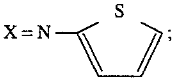 ;

$R^1 = C_2H_5$; $R^2 = C_2H_5$

| n | $R^3$ | $R^4$ |
|---|---|---|
| 2 | Cl | Cl |
| 2 | $CH_3$ | $CH_3$ |
| 2 | $C_2H_5$ | $CH_3$ |
| 2 | $CH_3$ | $C_2H_5$ |
| 2 | $C_2H_5$ | $C_2H_5$ |
| 2 | $CH_3$ | Cl |
| 2 | Cl | $CH_3$ |

A = A-4; X = N 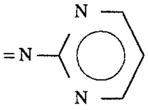 ;

$R^1 = C_2H_5$; $R^2 = C_2H_5$

| n | $R^3$ | $R^4$ |
|---|---|---|
| 2 | Cl | H |
| 2 | Cl | Cl |
| 2 | Cl | $OCH_3$ |
| 2 | Cl | $CH_3$ |
| 2 | Cl | $C_2H_5$ |
| 2 | $OCH_3$ | H |
| 2 | $OCH_3$ | Cl |
| 2 | $OCH_3$ | $OCH_3$ |
| 2 | $OCH_3$ | $CH_3$ |
| 2 | $OCH_3$ | $C_2H_5$ |
| 2 | $CH_3$ | H |
| 2 | $CH_3$ | Cl |
| 2 | $CH_3$ | $OCH_3$ |
| 2 | $CH_3$ | $CH_3$ |
| 0 | $CH_3$ | $CH_3$ |
| 1 | $CH_3$ | H |
| 2 | $CH_3$ | $C_2H_5$ |
| 2 | $C_2H_5$ | H |
| 2 | $C_2H_5$ | Cl |
| 2 | $C_2H_5$ | $OCH_3$ |
| 2 | $C_2H_5$ | $CH_3$ |
| 2 | $C_2H_5$ | $C_2H_5$ |
| 1 | $CH_3$ | H |
| 1 | Cl | H |
| 2 | $CH_3$ | $C_6H_5$ |
| 2 | $C_6H_5$ | $CH_3$ |
| 2 | $CH_3$ | $CF_3$ |

TABLE 4-continued

| | | |
|---|---|---|
| 2 | $CF_3$ | $CH_3$ |
| 2 | $COCH_3$ | H |
| 2 | $CH{=}CH_2$ | $CH_3$ |
| 2 | $CH_3$ | $CH{=}CH_2$ |
| 2 | $SCH_3$ | $CH_3$ |
| 2 | $CH_3$ | $SCH_3$ |

A = A-4; X = N 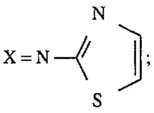 ;

$R^1 = C_2H_5$; $R^2 = C_2H_5$

| n | $R^3$ | $R^4$ |
|---|---|---|
| 2 | Cl | H |
| 2 | Cl | Cl |
| 2 | Cl | $OCH_3$ |
| 2 | Cl | $CH_3$ |
| 2 | Cl | $C_2H_5$ |
| 2 | $OCH_3$ | H |
| 2 | $OCH_3$ | Cl |
| 2 | $OCH_3$ | $CH_3$ |
| 2 | $OCH_3$ | $C_2H_5$ |
| 2 | $CH_3$ | H |
| 2 | $CH_3$ | Cl |
| 2 | $CH_3$ | $OCH_3$ |
| 2 | $CH_3$ | $CH_3$ |
| 1 | $CH_3$ | $CH_3$ |
| 1 | $CH_3$ | $CH_3$ |
| 2 | $CH_3$ | $C_2H_5$ |
| 2 | $CH_3$ | $CH(CH_3)_2$ |
| 2 | $CH_3$ | $CH_2CH_2CH_3$ |
| 2 | $C_2H_5$ | H |
| 2 | $C_2H_5$ | Cl |
| 2 | $C_2H_5$ | $OCH_3$ |
| 2 | $C_2H_5$ | $CH_3$ |
| 2 | $C_2H_5$ | $C_2H_5$ |
| 2 | $CH(CH_3)_2$ | Cl |
| 2 | $CH(CH_3)_2$ | $CH_3$ |
| 2 | $CH_2CH_2CH_3$ | Cl |
| 2 | $CH_2CH_2CH_3$ | $CH_3$ |
| 1 | $CH_3$ | H |
| 1 | Cl | H |
| 2 | $CH_3$ | $C_6H_5$ |
| 2 | $C_6H_5$ | $CH_3$ |
| 2 | $CH_3$ | $CF_3$ |
| 2 | $CF_3$ | $CH_3$ |
| 2 | $COCH_3$ | H |
| 2 | $CH{=}CH_2$ | $CH_3$ |
| 2 | $CH_3$ | $CH{=}CH_2$ |
| 2 | $SCH_3$ | $CH_3$ |
| 2 | $CH_3$ | $SCH_3$ |
| 2 | $NO_2$ | $CH_3$ |
| 2 | $NH_2$ | $CH_3$ |

A = A-4; X = N 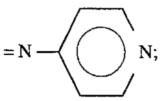 ;

$R^1 = C_2H_5$; $R^2 = C_2H_5$

| n | $R^3$ | $R^4$ |
|---|---|---|
| 2 | H | Cl |
| 2 | H | $CH_3$ |
| 2 | H | $C_2H_5$ |
| 2 | Cl | H |
| 2 | Cl | Cl |
| 2 | Cl | $OCH_3$ |
| 2 | Cl | $CH_3$ |
| 2 | Cl | $C_2H_5$ |
| 2 | $OCH_3$ | Cl |
| 2 | $OCH_3$ | $CH_3$ |

TABLE 4-continued

| | | |
|---|---|---|
| 2 | $OCH_3$ | $C_2H_5$ |
| 2 | $CH_3$ | H |
| 2 | $CH_3$ | Cl |
| 2 | $CH_3$ | $OCH_3$ |
| 2 | $CH_3$ | $CH_3$ |
| 1 | $CH_3$ | H |
| 2 | $CH_3$ | $C_2H_5$ |
| 2 | $C_2H_5$ | H |
| 2 | $C_2H_5$ | Cl |
| 2 | $C_2H_5$ | $OCH_3$ |
| 2 | $C_2H_5$ | $CH_3$ |
| 2 | $C_2H_5$ | $C_2H_5$ |
| 2 | $CH(CH_3)_2$ | H |
| 2 | $CH(CH_3)_2$ | Cl |
| 2 | $CH(CH_3)_2$ | $OCH_3$ |
| 2 | $CH(CH_3)_2$ | $CH_3$ |
| 2 | $CH(CH_3)_2$ | $C_2H_5$ |
| 2 | $CH_2CH_2CH_3$ | Cl |
| 2 | $CH_2CH_2CH_3$ | $OCH_3$ |
| 2 | $CH_2CH_2CH_3$ | $CH_3$ |
| 1 | $CH_3$ | $CH_3$ |
| 2 | $CH_3$ | $CF_3$ |
| 2 | $CF_3$ | $CH_3$ |
| 2 | $COCH_3$ | H |
| 2 | $CH{=}CH_2$ | $CH_3$ |
| 2 | $CH_3$ | $CH{=}CH_2$ |
| 2 | $SCH_3$ | $CH_3$ |
| 2 | $CH_3$ | $SCH_3$ |
| 2 | $NO_2$ | $CH_3$ |
| 2 | $NH_2$ | $CH_3$ |
| 2 | CHO | $CH_3$ |
| 2 | $CO_2CH_3$ | H |
| 2 | $CH(OCH_3)_2$ | H |

A = A-4; X = N— 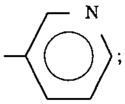 ;

$R^1 = C_2H_5$; $R^2 = C_2H_5$

| n | $R^3$ | $R^4$ |
|---|---|---|
| 2 | Cl | H |
| 2 | Cl | Cl |
| 2 | Cl | $OCH_3$ |
| 2 | Cl | $CH_3$ |
| 2 | Cl | $C_2H_5$ |
| 2 | $OCH_3$ | H |
| 2 | $OCH_3$ | Cl |
| 2 | $OCH_3$ | $OCH_3$ |
| 2 | $OCH_3$ | $CH_3$ |
| 2 | $OCH_3$ | $C_2H_5$ |
| 2 | $CH_3$ | H |
| 2 | $CH_3$ | Cl |
| 2 | $CH_3$ | $OCH_3$ |
| 2 | $CH_3$ | $CH_3$ |
| 0 | $CH_3$ | H |
| 1 | $CH_3$ | H |
| 2 | $CH_3$ | $C_2H_5$ |
| 2 | $C_2H_5$ | H |
| 2 | $C_2H_5$ | Cl |
| 2 | $C_2H_5$ | $OCH_3$ |
| 2 | $C_2H_5$ | $CH_3$ |
| 2 | $C_2H_5$ | $C_2H_5$ |
| 2 | $CH(CH_3)_2$ | H |
| 2 | $CH(CH_3)_2$ | Cl |
| 2 | $CH(CH_3)_2$ | $CH_3$ |
| 2 | $CH_2CH_2CH_3$ | H |
| 2 | $CH_2CH_2CH_3$ | Cl |
| 2 | $CH_2CH_2CH_3$ | $CH_3$ |
| 1 | $CH_3$ | $CH_3$ |
| 1 | Cl | $CH_3$ |
| 2 | $CH_3$ | $C_6H_5$ |
| 2 | $C_6H_5$ | $CH_3$ |
| 2 | $CH_3$ | $CF_3$ |
| 2 | $CF_3$ | $CH_3$ |

TABLE 4-continued

| | | |
|---|---|---|
| 2 | $COCH_3$ | H |
| 2 | $CH{=}CH_2$ | $CH_3$ |
| 2 | $CH_3$ | $CH{=}CH_2$ |
| 2 | $SCH_3$ | $CH_3$ |
| 2 | $CH_3$ | $SCH_3$ |

A = A-4; X = N— 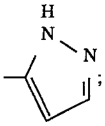 ;

$R^1 = C_2H_5$; $R^2 = C_2H_5$

| n | $R^3$ | $R^4$ |
|---|---|---|
| 2 | $CH_3$ | $CH_3$ |
| 2 | $CH_3$ | Cl |
| 2 | $CH_3$ | $OCH_3$ |
| 2 | $C_2H_5$ | $CH_3$ |
| 2 | $CH_3$ | $C_2H_5$ |
| 2 | $C_2H_5$ | $C_2H_5$ |
| 2 | $CH_3$ | Cl |
| 2 | Cl | $CH_3$ |
| 2 | Cl | Cl |
| 2 | Cl | $OCH_3$ |
| 2 | Cl | $CH_3$ |
| 2 | Cl | $C_2H_5$ |
| 2 | $OCH_3$ | H |
| 2 | $OCH_3$ | Cl |
| 2 | $OCH_3$ | $OCH_3$ |
| 2 | $OCH_3$ | $CH_3$ |
| 2 | $OCH_3$ | $C_2H_5$ |
| 2 | $CH_3$ | H |
| 2 | $CH_3$ | Cl |
| 2 | $CH_3$ | $OCH_3$ |
| 2 | $CH_3$ | $CH_3$ |
| 1 | $CH_3$ | H |
| 2 | $CH_3$ | $C_2H_5$ |
| 2 | $C_2H_5$ | H |
| 2 | $C_2H_5$ | Cl |
| 2 | $C_2H_5$ | $OCH_3$ |
| 2 | $C_2H_5$ | $CH_3$ |
| 2 | $C_2H_5$ | $C_2H_5$ |
| 2 | $CH(CH_3)_2$ | Cl |
| 2 | $CH(CH_3)_2$ | $CH_3$ |
| 2 | $CH_2CH_2CH_3$ | Cl |
| 2 | $CH_2CH_2CH_3$ | $CH_3$ |
| 1 | $CH_3$ | $CH_3$ |
| 2 | $CH_3$ | $CF_3$ |
| 2 | $CF_3$ | $CH_3$ |
| 2 | $COCH_3$ | H |
| 2 | $CH{=}CH_2$ | $CH_3$ |
| 2 | $CH_3$ | $CH{=}CH_2$ |
| 2 | $SCH_3$ | $CH_3$ |
| 2 | $CH_3$ | $SCH_3$ |
| 2 | $NO_2$ | $CH_3$ |

TABLE 5

A = A-5; X = O; $R^1 = C_2H_5$; $R^2 = C_2H_5$

| n | $R^3$ | $R^4$ |
|---|---|---|
| 2 | H | H |
| 2 | H | Cl |
| 2 | H | $OCH_3$ |
| 2 | H | $CH_3$ |
| 2 | H | $C_2H_5$ |
| 2 | H | $CH(CH_3)_2$ |
| 2 | H | $CH_2CH_2CH_3$ |
| 2 | Cl | H |
| 2 | Cl | Cl |

TABLE 5-continued

| | | |
|---|---|---|
| 2 | Cl | $OCH_3$ |
| 2 | Cl | $CH_3$ |
| 2 | Cl | $C_2H_5$ |
| 2 | Cl | $CH(CH_3)_2$ |
| 2 | Cl | $CH_2CH_2CH_3$ |
| 2 | $OCH_3$ | H |
| 2 | $OCH_3$ | Cl |
| 2 | $OCH_3$ | $OCH_3$ |
| 2 | $OCH_3$ | $CH_3$ |
| 2 | $OCH_3$ | $C_2H_5$ |
| 2 | $OCH_3$ | $CH(CH_3)_2$ |
| 2 | $OCH_3$ | $CH_2CH_2CH_3$ |
| 2 | $CH_3$ | H |
| 2 | $CH_3$ | Cl |
| 2 | $CH_3$ | $OCH_3$ |
| 2 | $CH_3$ | $CH_3$ |
| 0 | $CH_3$ | H |
| 1 | $CH_3$ | H |
| 2 | $CH_3$ | $C_2H_5$ |
| 2 | $CH_3$ | $CH(CH_3)_2$ |
| 2 | $CH_3$ | $CH_2CH_2CH_3$ |
| 2 | $C_2H_5$ | H |
| 2 | $C_2H_5$ | Cl |
| 2 | $C_2H_5$ | $OCH_3$ |
| 2 | $C_2H_5$ | $CH_3$ |
| 2 | $C_2H_5$ | $C_2H_5$ |
| 2 | $C_2H_5$ | $CH(CH_3)_2$ |
| 2 | $C_2H_5$ | $CH_2CH_2CH_3$ |
| 2 | $CH(CH_3)_2$ | H |
| 2 | $CH(CH_3)_2$ | Cl |
| 2 | $CH(CH_3)_2$ | $OCH_3$ |
| 2 | $CH(CH_3)_2$ | $CH_3$ |
| 2 | $CH(CH_3)_2$ | $C_2H_5$ |
| 2 | $CH(CH_3)_2$ | $CH(CH_3)_2$ |
| 2 | $CH(CH_3)_2$ | $CH_2CH_2CH_3$ |
| 2 | $CH_2CH_2CH_3$ | H |
| 2 | $CH_2CH_2CH_3$ | Cl |
| 2 | $CH_2CH_2CH_3$ | $OCH_3$ |
| 2 | $CH_2CH_2CH_3$ | $CH_3$ |
| 2 | $CH_2CH_2CH_3$ | $C_2H_5$ |
| 2 | $CH_2CH_2CH_3$ | $CH(CH_3)_2$ |
| 2 | $CH_2CH_2CH_3$ | $CH_2CH_2CH_3$ |
| 2 | $CH_3$ | $C_6H_5$ |
| 2 | $C_6H_5$ | $CH_3$ |
| 2 | $CH_3$ | $CF_3$ |
| 2 | $CF_3$ | $CH_3$ |
| 2 | $COCH_3$ | H |
| 2 | $CH=CH_2$ | $CH_3$ |
| 2 | $CH_3$ | $CH=CH_2$ |
| 2 | $SCH_3$ | $CH_3$ |
| 2 | $CH_3$ | $SCH_3$ |
| 2 | $NO_2$ | $CH_3$ |
| 2 | $NH_2$ | $CH_3$ |
| 2 | CHO | $CH_3$ |
| 2 | $CO_2CH_3$ | H |
| 2 | $CH(OCH_3)_2$ | H |

A = A-5; X = O; $R^3$ = $CH_3$; $R^4$ = $CH_3$

| n | $R^1$ | $R^2$ |
|---|---|---|
| 2 | $CH_3$ | $CH_3$ |
| 2 | $C_2H_5$ | $CH_3$ |
| 2 | H | $CH_3$ |
| 2 | H | $C_2H_5$ |
| 2 | H | $CH_2CH_2CH_3$ |
| 2 | $OCH_3$ | $CH_3$ |
| 2 | $OCH_3$ | $C_2H_5$ |
| 2 | $CH_2CH_2CH_3$ | $CH_2CH_2CH_3$ |
| 2 | $CH_2CH=CH_2$ | $CH_2CH=CH_2$ |
| 2 | $CH_2C\equiv CH$ | $CH_2C\equiv CH$ |
| 2 | $CH(CH_3)_2$ | $CH(CH_3)_2$ |
| 2 | $-(CH_2)_5-$ | |
| 2 | $-(CH_2)_4-$ | |
| 2 | $CH_2CH=CH_2$ | $C_2H_5$ |
| 2 | $CH_2C\equiv CH$ | $C_2H_5$ |
| 2 | $OC_2H_5$ | $CH_3$ |
| 2 | $OC_2H_5$ | $C_2H_5$ |
| 2 | H | 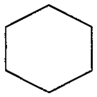 |
| 2 | 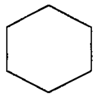 | 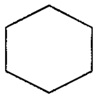 |
| 2 | H | $CH_2CH=CH_2$ |
| 2 | $CH_2CH_2CH_3$ | $CH_3$ |
| 0 | H | $CH_3$ |
| 1 | H | $CH_3$ |

A = A-5; X = S; $R^1$ = $C_2H_5$; $R^2$ = $C_2H_5$

| n | $R^3$ | $R^4$ |
|---|---|---|
| 2 | H | H |
| 2 | H | Cl |
| 2 | H | $OCH_3$ |
| 2 | H | $CH_3$ |
| 2 | H | $C_2H_5$ |
| 2 | H | $CH(CH_3)_2$ |
| 2 | H | $CH_2CH_2CH_3$ |
| 2 | Cl | H |
| 2 | Cl | Cl |
| 2 | Cl | $OCH_3$ |
| 2 | Cl | $CH_3$ |
| 2 | Cl | $C_2H_5$ |
| 2 | Cl | $CH(CH_3)_2$ |
| 2 | Cl | $CH_2CH_2CH_3$ |
| 2 | $OCH_3$ | H |
| 2 | $OCH_3$ | Cl |
| 2 | $OCH_3$ | $OCH_3$ |
| 2 | $OCH_3$ | $CH_3$ |
| 2 | $OCH_3$ | $C_2H_5$ |
| 2 | $OCH_3$ | $CH(CH_3)_2$ |
| 2 | $OCH_3$ | $CH_2CH_2CH_3$ |
| 2 | $CH_3$ | H |
| 2 | $CH_3$ | Cl |
| 2 | $CH_3$ | $OCH_3$ |
| 2 | $CH_3$ | $CH_3$ |
| 0 | $CH_3$ | H |
| 1 | $CH_3$ | H |
| 2 | $CH_3$ | $C_2H_5$ |
| 2 | $CH_3$ | $CH(CH_3)_2$ |
| 2 | $CH_3$ | $CH_2CH_2CH_3$ |
| 2 | $C_2H_5$ | H |
| 2 | $C_2H_5$ | Cl |
| 2 | $C_2H_5$ | $OCH_3$ |
| 2 | $C_2H_5$ | $CH_3$ |
| 2 | $C_2H_5$ | $C_2H_5$ |
| 2 | $C_2H_5$ | $CH(CH_3)_2$ |
| 2 | $C_2H_5$ | $CH_2CH_2CH_3$ |
| 2 | $CH(CH_3)_2$ | H |
| 2 | $CH(CH_3)_2$ | Cl |
| 2 | $CH(CH_3)_2$ | $OCH_3$ |
| 2 | $CH(CH_3)_2$ | $CH_3$ |
| 2 | $CH(CH_3)_2$ | $C_2H_5$ |
| 2 | $CH(CH_3)_2$ | $CH(CH_3)_2$ |
| 2 | $CH(CH_3)_2$ | $CH_2CH_2CH_3$ |
| 2 | $CH_2CH_2CH_3$ | H |
| 2 | $CH_2CH_2CH_3$ | Cl |
| 2 | $CH_2CH_2CH_3$ | $OCH_3$ |
| 2 | $CH_2CH_2CH_3$ | $CH_3$ |
| 2 | $CH_2CH_2CH_3$ | $C_2H_5$ |
| 2 | $CH_2CH_2CH_3$ | $CH(CH_3)_2$ |

TABLE 5-continued

| n | | |
|---|---|---|
| 2 | $CH_2CH_2CH_3$ | $CH_2CH_2CH_3$ |
| 2 | $CH_3$ | $C_6H_5$ |
| 2 | $C_6H_5$ | $CH_3$ |
| 2 | $CH_3$ | $CF_3$ |
| 2 | $CF_3$ | $CH_3$ |
| 2 | $COCH_3$ | H |
| 2 | $CH{=}CH_2$ | $CH_3$ |
| 2 | $CH_3$ | $CH{=}CH_2$ |
| 2 | $SCH_3$ | $CH_3$ |
| 2 | $CH_3$ | $SCH_3$ |
| 2 | $NO_2$ | $CH_3$ |
| 2 | $NH_2$ | $CH_3$ |
| 2 | CHO | $CH_3$ |
| 2 | $CO_2CH_3$ | H |
| 2 | $CH(OCH_3)_2$ | H |

A = A-5; X = S; $R^3 = CH_3$; $R^4 = CH_3$

| n | $R^1$ | $R^2$ |
|---|---|---|
| 2 | $CH_3$ | $CH_3$ |
| 2 | $C_2H_5$ | $CH_3$ |
| 2 | H | $CH_3$ |
| 2 | H | $C_2H_5$ |
| 2 | H | $CH_2CH_2CH_3$ |
| 2 | $OCH_3$ | $CH_3$ |
| 2 | $OCH_3$ | $C_2H_5$ |
| 2 | $CH_2CH_2CH_3$ | $CH_2CH_2CH_3$ |
| 2 | $CH_2CH{=}CH_2$ | $CH_2CH{=}CH_2$ |
| 2 | $CH_2C{\equiv}CH$ | $CH_2C{\equiv}CH$ |
| 2 | $CH(CH_3)_2$ | $CH(CH_3)_2$ |
| 2 | $-(CH_2)_5-$ | |
| 2 | $-(CH_2)_4-$ | |
| 2 | $CH_2CH{=}CH_2$ | $C_2H_5$ |
| 2 | $CH_2C{\equiv}CH$ | $C_2H_5$ |
| 2 | $OC_2H_5$ | $CH_3$ |
| 2 | $OC_2H_5$ | $C_2H_5$ |
| 2 | H | 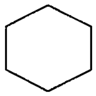 |
| 2 | 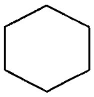 | 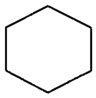 |
| 2 | H | $CH_2CH{=}CH_2$ |
| 2 | $CH_2CH_2CH_3$ | $CH_3$ |
| 0 | H | $CH_3$ |
| 1 | H | $CH_3$ |

A = A-5; X = $NCH_3$; $R^1 = C_2H_5$; $R^2 = C_2H_5$

| n | $R^3$ | $R^4$ |
|---|---|---|
| 2 | H | H |
| 2 | H | Cl |
| 2 | H | $OCH_3$ |
| 2 | H | $CH_3$ |
| 2 | H | $C_2H_5$ |
| 2 | H | $CH(CH_3)_2$ |
| 2 | H | $CH_2CH_2CH_3$ |
| 2 | Cl | H |
| 2 | Cl | Cl |
| 2 | Cl | $OCH_3$ |
| 2 | Cl | $CH_3$ |
| 2 | Cl | $C_2H_5$ |
| 2 | Cl | $CH(CH_3)_2$ |
| 2 | Cl | $CH_2CH_2CH_3$ |

TABLE 5-continued

| | | |
|---|---|---|
| 2 | $OCH_3$ | H |
| 2 | $OCH_3$ | Cl |
| 2 | $OCH_3$ | $OCH_3$ |
| 2 | $OCH_3$ | $CH_3$ |
| 2 | $OCH_3$ | $C_2H_5$ |
| 2 | $OCH_3$ | $CH(CH_3)_2$ |
| 2 | $OCH_3$ | $CH_2CH_2CH_3$ |
| 2 | $CH_3$ | H |
| 2 | $CH_3$ | Cl |
| 2 | $CH_3$ | $OCH_3$ |
| 2 | $CH_3$ | $CH_3$ |
| 0 | $CH_3$ | H |
| 1 | $CH_3$ | H |
| 2 | $CH_3$ | $C_2H_5$ |
| 2 | $CH_3$ | $CH(CH_3)_2$ |
| 2 | $CH_3$ | $CH_2CH_2CH_3$ |
| 2 | $C_2H_5$ | H |
| 2 | $C_2H_5$ | Cl |
| 2 | $C_2H_5$ | $OCH_3$ |
| 2 | $C_2H_5$ | $CH_3$ |
| 2 | $C_2H_5$ | $C_2H_5$ |
| 2 | $C_2H_5$ | $CH(CH_3)_2$ |
| 2 | $C_2H_5$ | $CH_2CH_2CH_3$ |
| 2 | $CH(CH_3)_2$ | H |
| 2 | $CH(CH_3)_2$ | Cl |
| 2 | $CH(CH_3)_2$ | $OCH_3$ |
| 2 | $CH(CH_3)_2$ | $CH_3$ |
| 2 | $CH(CH_3)_2$ | $C_2H_5$ |
| 2 | $CH(CH_3)_2$ | $CH(CH_3)_2$ |
| 2 | $CH(CH_3)_2$ | $CH_2CH_2CH_3$ |
| 2 | $CH_2CH_2CH_3$ | H |
| 2 | $CH_2CH_2CH_3$ | Cl |
| 2 | $CH_2CH_2CH_3$ | $OCH_3$ |
| 2 | $CH_2CH_2CH_3$ | $CH_3$ |
| 2 | $CH_2CH_2CH_3$ | $C_2H_5$ |
| 2 | $CH_2CH_2CH_3$ | $CH(CH_3)_2$ |
| 2 | $CH_2CH_2CH_3$ | $CH_2CH_2CH_3$ |
| 2 | $CH_3$ | $C_6H_5$ |
| 2 | $C_6H_5$ | $CH_3$ |
| 2 | $CH_3$ | $CF_3$ |
| 2 | $CF_3$ | $CH_3$ |
| 2 | $COCH_3$ | H |
| 2 | $CH{=}CH_2$ | $CH_3$ |
| 2 | $CH_3$ | $CH{=}CH_2$ |
| 2 | $SCH_3$ | $CH_3$ |
| 2 | $CH_3$ | $SCH_3$ |
| 2 | $NO_2$ | $CH_3$ |
| 2 | $NH_2$ | $CH_3$ |
| 2 | CHO | $CH_3$ |
| 2 | $CO_2CH_3$ | H |
| 2 | $CH(OCH_3)_2$ | H |

A = A-5; X = $NCH_3$; $R^3 = CH_3$; $R^4 = CH_3$

| n | $R^1$ | $R^2$ |
|---|---|---|
| 2 | $CH_3$ | $CH_3$ |
| 2 | $C_2H_5$ | $CH_3$ |
| 2 | H | $CH_3$ |
| 2 | H | $C_2H_5$ |
| 2 | H | $CH_2CH_2CH_3$ |
| 2 | $OCH_3$ | $CH_3$ |
| 2 | $OCH_3$ | $C_2H_5$ |
| 2 | $CH_2CH_2CH_3$ | $CH_2CH_2CH_3$ |
| 2 | $CH_2CH{=}CH_2$ | $CH_2CH{=}CH_2$ |
| 2 | $CH_2C{\equiv}CH$ | $CH_2C{\equiv}CH$ |
| 2 | $CH(CH_3)_2$ | $CH(CH_3)_2$ |
| 2 | $-(CH_2)_5-$ | |
| 2 | $-(CH_2)_4-$ | |
| 2 | $CH_2CH{=}CH_2$ | $C_2H_5$ |
| 2 | $CH_2C{\equiv}CH$ | $C_2H_5$ |

TABLE 5-continued

| | | |
|---|---|---|
| 2 | $OC_2H_5$ | $CH_3$ |
| 2 | $OC_2H_5$ | $C_2H_5$ |
| 2 | H | 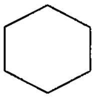 |
| 2 | 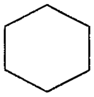 | 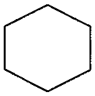 |
| 2 | H | $CH_2CH{=}CH_2$ |
| 2 | $CH_2CH_2CH_3$ | $CH_3$ |
| 0 | H | $CH_3$ |
| 1 | H | $CH_3$ |

$A = A\text{-}5;\ X = NC_2H_5;\ R^1 = C_2H_5;\ R^2 = C_2H_5$

| n | $R^3$ | $R^4$ |
|---|---|---|
| 2 | H | H |
| 2 | H | Cl |
| 2 | H | $OCH_3$ |
| 2 | H | $CH_3$ |
| 2 | H | $C_2H_5$ |
| 2 | H | $CH(CH_3)_2$ |
| 2 | H | $CH_2CH_2CH_3$ |
| 2 | Cl | H |
| 2 | Cl | Cl |
| 2 | Cl | $OCH_3$ |
| 2 | Cl | $CH_3$ |
| 2 | Cl | $C_2H_5$ |
| 2 | Cl | $CH(CH_3)_2$ |
| 2 | Cl | $CH_2CH_2CH_3$ |
| 2 | $OCH_3$ | H |
| 2 | $OCH_3$ | Cl |
| 2 | $OCH_3$ | $OCH_3$ |
| 2 | $OCH_3$ | $CH_3$ |
| 2 | $OCH_3$ | $C_2H_5$ |
| 2 | $OCH_3$ | $CH(CH_3)_2$ |
| 2 | $OCH_3$ | $CH_2CH_2CH_3$ |
| 2 | $CH_3$ | H |
| 2 | $CH_3$ | Cl |
| 2 | $CH_3$ | $OCH_3$ |
| 2 | $CH_3$ | $CH_3$ |
| 0 | $CH_3$ | H |
| 1 | $CH_3$ | H |
| 2 | $CH_3$ | $C_2H_5$ |
| 2 | $CH_3$ | $CH(CH_3)_2$ |
| 2 | $CH_3$ | $CH_2CH_2CH_3$ |
| 2 | $C_2H_5$ | H |
| 2 | $C_2H_5$ | Cl |
| 2 | $C_2H_5$ | $OCH_3$ |
| 2 | $C_2H_5$ | $CH_3$ |
| 2 | $C_2H_5$ | $C_2H_5$ |
| 2 | $C_2H_5$ | $CH(CH_3)_2$ |
| 2 | $C_2H_5$ | $CH_2CH_2CH_3$ |
| 2 | $CH(CH_3)_2$ | H |
| 2 | $CH(CH_3)_2$ | Cl |
| 2 | $CH(CH_3)_2$ | $OCH_3$ |
| 2 | $CH(CH_3)_2$ | $CH_3$ |
| 2 | $CH(CH_3)_2$ | $C_2H_5$ |
| 2 | $CH(CH_3)_2$ | $CH(CH_3)_2$ |
| 2 | $CH(CH_3)_2$ | $CH_2CH_2CH_3$ |
| 2 | $CH_2CH_2CH_3$ | H |
| 2 | $CH_2CH_2CH_3$ | Cl |
| 2 | $CH_2CH_2CH_3$ | $OCH_3$ |
| 2 | $CH_2CH_2CH_3$ | $CH_3$ |
| 2 | $CH_2CH_2CH_3$ | $C_2H_5$ |
| 2 | $CH_2CH_2CH_3$ | $CH(CH_3)_2$ |
| 2 | $CH_2CH_2CH_3$ | $CH_2CH_2CH_3$ |
| 2 | $CH_3$ | $C_6H_5$ |
| 2 | $C_6H_5$ | $CH_3$ |
| 2 | $CH_3$ | $CF_3$ |
| 2 | $CF_3$ | $CH_3$ |

TABLE 5-continued

| | | |
|---|---|---|
| 2 | $COCH_3$ | H |
| 2 | $CH{=}CH_2$ | $CH_3$ |
| 2 | $CH_3$ | $CH{=}CH_2$ |
| 2 | $SCH_3$ | $CH_3$ |
| 2 | $CH_3$ | $SCH_3$ |
| 2 | $NO_2$ | $CH_3$ |
| 2 | $NH_2$ | $CH_3$ |
| 2 | CHO | $CH_3$ |
| 2 | $CO_2CH_3$ | H |
| 2 | $CH(OCH_3)_2$ | H |

$A = A\text{-}5;\ X = NC_2H_5;\ R^3 = CH_3;\ R^4 = CH_3$

| n | $R^1$ | $R^2$ |
|---|---|---|
| 2 | $CH_3$ | $CH_3$ |
| 2 | $C_2H_5$ | $CH_3$ |
| 2 | H | $CH_3$ |
| 2 | H | $C_2H_5$ |
| 2 | H | $CH_2CH_2CH_3$ |
| 2 | $OCH_3$ | $CH_3$ |
| 2 | $OCH_3$ | $C_2H_5$ |
| 2 | $CH_2CH_2CH_3$ | $CH_2CH_2CH_3$ |
| 2 | $CH_2CH{=}CH_2$ | $CH_2CH{=}CH_2$ |
| 2 | $CH_2C{\equiv}CH$ | $CH_2C{\equiv}CH$ |
| 2 | $CH(CH_3)_2$ | $CH(CH_3)_2$ |
| 2 | $-(CH_2)_5-$ | |
| 2 | $-(CH_2)_4-$ | |
| 2 | $CH_2CH{=}CH_2$ | $C_2H_5$ |
| 2 | $OC_2H_5$ | $CH_3$ |
| 2 | $OC_2H_5$ | $C_2H_5$ |
| 2 | H | 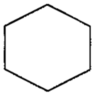 |
| 2 | 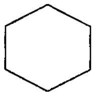 | 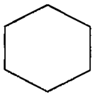 |
| 2 | H | $CH_2CH{=}CH_2$ |
| 2 | $CH_2CH_2CH_3$ | $CH_3$ |
| 0 | H | $CH_3$ |
| 1 | H | $CH_3$ |

$A = A\text{-}5;\ X = NCH_2CH_2CH_3;\ R^1 = C_2H_5;\ R^2 = C_2H_5$

| n | $R^3$ | $R^4$ |
|---|---|---|
| 2 | H | H |
| 2 | H | Cl |
| 2 | H | $OCH_3$ |
| 2 | H | $CH_3$ |
| 2 | H | $C_2H_5$ |
| 2 | H | $CH(CH_3)_2$ |
| 2 | H | $CH_2CH_2CH_3$ |
| 2 | Cl | H |
| 2 | Cl | Cl |
| 2 | Cl | $OCH_3$ |
| 2 | Cl | $CH_3$ |
| 2 | Cl | $C_2H_5$ |
| 2 | Cl | $CH(CH_3)_2$ |
| 2 | Cl | $CH_2CH_2CH_3$ |
| 2 | $OCH_3$ | H |
| 2 | $OCH_3$ | Cl |
| 2 | $OCH_3$ | $OCH_3$ |
| 2 | $OCH_3$ | $CH_3$ |
| 2 | $OCH_3$ | $C_2H_5$ |
| 2 | $OCH_3$ | $CH(CH_3)_2$ |
| 2 | $OCH_3$ | $CH_2CH_2CH_3$ |

TABLE 5-continued

| | | |
|---|---|---|
| 2 | $CH_3$ | H |
| 2 | $CH_3$ | Cl |
| 2 | $CH_3$ | $OCH_3$ |
| 2 | $CH_3$ | $CH_3$ |
| 0 | $CH_3$ | H |
| 1 | $CH_3$ | H |
| 2 | $CH_3$ | $C_2H_5$ |
| 2 | $CH_3$ | $CH(CH_3)_2$ |
| 2 | $CH_3$ | $CH_2CH_2CH_3$ |
| 2 | $C_2H_5$ | H |
| 2 | $C_2H_5$ | Cl |
| 2 | $C_2H_5$ | $OCH_3$ |
| 2 | $C_2H_5$ | $CH_3$ |
| 2 | $C_2H_5$ | $C_2H_5$ |
| 2 | $C_2H_5$ | $CH(CH_3)_2$ |
| 2 | $C_2H_5$ | $CH_2CH_2CH_3$ |
| 2 | $CH(CH_3)_2$ | H |
| 2 | $CH(CH_3)_2$ | Cl |
| 2 | $CH(CH_3)_2$ | $OCH_3$ |
| 2 | $CH(CH_3)_2$ | $CH_3$ |
| 2 | $CH(CH_3)_2$ | $C_2H_5$ |
| 2 | $CH(CH_3)_2$ | $CH(CH_3)_2$ |
| 2 | $CH(CH_3)_2$ | $CH_2CH_2CH_3$ |
| 2 | $CH_2CH_2CH_3$ | H |
| 2 | $CH_2CH_2CH_3$ | Cl |
| 2 | $CH_2CH_2CH_3$ | $OCH_3$ |
| 2 | $CH_2CH_2CH_3$ | $CH_3$ |
| 2 | $CH_2CH_2CH_3$ | $C_2H_5$ |
| 2 | $CH_2CH_2CH_3$ | $CH(CH_3)_2$ |
| 2 | $CH_2CH_2CH_3$ | $CH_2CH_2CH_3$ |
| 2 | $CH_3$ | $C_6H_5$ |
| 2 | $C_6H_5$ | $CH_3$ |
| 2 | $CH_3$ | $CF_3$ |
| 2 | $CF_3$ | $CH_3$ |
| 2 | $COCH_3$ | H |
| 2 | $CH=CH_2$ | $CH_3$ |
| 2 | $CH_3$ | $CH=CH_2$ |
| 2 | $SCH_3$ | $CH_3$ |
| 2 | $CH_3$ | $SCH_3$ |
| 2 | $NO_2$ | $CH_3$ |
| 2 | $NH_2$ | $CH_3$ |
| 2 | CHO | $CH_3$ |
| 2 | $CO_2CH_3$ | H |
| 2 | $CH(OCH_3)_2$ | H |

A = A-5; X = $NCH_2CH_2CH_3$; $R^3$ = $CH_3$; $R^4$ = $CH_3$

| n | $R^1$ | $R^2$ |
|---|---|---|
| 2 | $CH_3$ | $CH_3$ |
| 2 | $C_2H_5$ | $CH_3$ |
| 2 | H | $CH_3$ |
| 2 | H | $C_2H_5$ |
| 2 | H | $CH_2CH_2CH_3$ |
| 2 | $OCH_3$ | $CH_3$ |
| 2 | $OCH_3$ | $C_2H_5$ |
| 2 | $CH_2CH_2CH_3$ | $CH_2CH_2CH_3$ |
| 2 | $CH_2CH=CH_2$ | $CH_2CH=CH_2$ |
| 2 | $CH_2C\equiv CH$ | $CH_2C\equiv CH$ |
| 2 | $CH(CH_3)_2$ | $CH(CH_3)_2$ |
| 2 | $-(CH_2)_5-$ | |
| 2 | $-(CH_2)_4-$ | |
| 2 | $CH_2CH=CH_2$ | $C_2H_5$ |
| 2 | $CH_2C\equiv CH$ | $C_2H_5$ |
| 2 | $OC_2H_5$ | $CH_3$ |
| 2 | $OC_2H_5$ | $C_2H_5$ |

TABLE 5-continued

| | | |
|---|---|---|
| 2 | H | 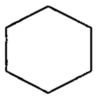 |
| 2 | 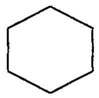 | 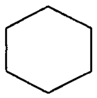 |
| 2 | H | $CH_2CH=CH_2$ |
| 2 | $CH_2CH_2CH_3$ | $CH_3$ |
| 0 | H | $CH_3$ |
| 1 | H | $CH_3$ |

TABLE 6

A = A-6; X = O; $R^1$ = $C_2H_5$; $R^2$ = $C_2H_5$

| n | $R^4$ | $R^5$ |
|---|---|---|
| 2 | H | H |
| 2 | H | Cl |
| 2 | H | $OCH_3$ |
| 2 | H | $CH_3$ |
| 2 | H | $C_2H_5$ |
| 2 | H | $CH(CH_3)_2$ |
| 2 | H | $CH_2CH_2CH_3$ |
| 2 | Cl | H |
| 2 | Cl | Cl |
| 2 | Cl | $OCH_3$ |
| 2 | Cl | $CH_3$ |
| 2 | Cl | $C_2H_5$ |
| 2 | Cl | $CH(CH_3)_2$ |
| 2 | Cl | $CH_2CH_2CH_3$ |
| 2 | $OCH_3$ | H |
| 2 | $OCH_3$ | Cl |
| 2 | $OCH_3$ | $OCH_3$ |
| 2 | $OCH_3$ | $CH_3$ |
| 2 | $OCH_3$ | $C_2H_5$ |
| 2 | $OCH_3$ | $CH(CH_3)_2$ |
| 2 | $OCH_3$ | $CH_2CH_2CH_3$ |
| 2 | $CH_3$ | H |
| 2 | $CH_3$ | Cl |
| 2 | $CH_3$ | $OCH_3$ |
| 2 | $CH_3$ | $CH_3$ |
| 0 | $CH_3$ | H |
| 1 | $CH_3$ | H |
| 2 | $CH_3$ | $C_2H_5$ |
| 2 | $CH_3$ | $CH(CH_3)_2$ |
| 2 | $CH_3$ | $CH_2CH_2CH_3$ |
| 2 | $C_2H_5$ | H |
| 2 | $C_2H_5$ | Cl |
| 2 | $C_2H_5$ | $OCH_3$ |
| 2 | $C_2H_5$ | $CH_3$ |
| 2 | $C_2H_5$ | $C_2H_5$ |
| 2 | $C_2H_5$ | $CH(CH_3)_2$ |
| 2 | $C_2H_5$ | $CH_2CH_2CH_3$ |
| 2 | $CH(CH_3)_2$ | H |
| 2 | $CH(CH_3)_2$ | Cl |
| 2 | $CH(CH_3)_2$ | $OCH_3$ |
| 2 | $CH(CH_3)_2$ | $CH_3$ |
| 2 | $CH(CH_3)_2$ | $C_2H_5$ |
| 2 | $CH(CH_3)_2$ | $CH(CH_3)_2$ |
| 2 | $CH(CH_3)_2$ | $CH_2CH_2CH_3$ |
| 2 | $CH_2CH_2CH_3$ | H |
| 2 | $CH_2CH_2CH_3$ | Cl |
| 2 | $CH_2CH_2CH_3$ | $OCH_3$ |
| 2 | $CH_2CH_2CH_3$ | $CH_3$ |
| 2 | $CH_2CH_2CH_3$ | $C_2H_5$ |
| 2 | $CH_2CH_2CH_3$ | $CH(CH_3)_2$ |
| 2 | $CH_2CH_2CH_3$ | $CH_2CH_2CH_3$ |
| 2 | $CH_3$ | $C_6H_5$ |

TABLE 6-continued

| | | |
|---|---|---|
| 2 | $C_6H_5$ | $CH_3$ |
| 2 | $CH_3$ | $CF_3$ |
| 2 | $CF_3$ | $CH_3$ |
| 2 | $COCH_3$ | H |
| 2 | $CH=CH_2$ | $CH_3$ |
| 2 | $CH_3$ | $CH=CH_2$ |
| 2 | $SCH_3$ | $CH_3$ |
| 2 | $CH_3$ | $SCH_3$ |
| 2 | $NO_2$ | $CH_3$ |
| 2 | $NH_2$ | $CH_3$ |
| 2 | CHO | $CH_3$ |
| 2 | $CO_2CH_3$ | H |
| 2 | $CH(OCH_3)_2$ | H |

A = A-6; X = O; $R^4 = CH_3$; $R^5 = CH_3$

| n | $R^1$ | $R^2$ |
|---|---|---|
| 2 | $CH_3$ | $CH_3$ |
| 2 | $C_2H_5$ | $CH_3$ |
| 2 | H | $CH_3$ |
| 2 | H | $C_2H_5$ |
| 2 | H | $CH_2CH_2CH_3$ |
| 2 | $OCH_3$ | $CH_3$ |
| 2 | $OCH_3$ | $C_2H_5$ |
| 2 | $CH_2CH_2CH_3$ | $CH_2CH_2CH_3$ |
| 2 | $CH_2CH=CH_2$ | $CH_2CH=CH_2$ |
| 2 | $CH_2C\equiv CH$ | $CH_2C\equiv CH$ |
| 2 | $CH(CH_3)_2$ | $CH(CH_3)_2$ |
| 2 | $-(CH_2)_5-$ | |
| 2 | $-(CH_2)_4-$ | |
| 2 | $CH_2CH=CH_2$ | $C_2H_5$ |
| 2 | $CH_2C\equiv CH$ | $C_2H_5$ |
| 2 | $OC_2H_5$ | $CH_3$ |
| 2 | $OC_2H_5$ | $C_2H_5$ |
| 2 | H | 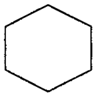 |
| 2 | 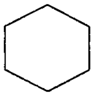 | 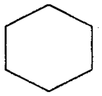 |
| 2 | H | $CH_2CH=CH_2$ |
| 2 | $CH_2CH_2CH_3$ | $CH_3$ |
| 0 | H | $CH_3$ |
| 1 | H | $CH_3$ |

A = A-6; X = S; $R^1 = C_2H_5$; $R^2 = C_2H_5$

| n | $R^4$ | $R^5$ |
|---|---|---|
| 2 | H | H |
| 2 | H | Cl |
| 2 | H | $OCH_3$ |
| 2 | H | $CH_3$ |
| 2 | H | $C_2H_5$ |
| 2 | H | $CH(CH_3)_2$ |
| 2 | H | $CH_2CH_2CH_3$ |
| 2 | Cl | H |
| 2 | Cl | Cl |
| 2 | Cl | $OCH_3$ |
| 2 | Cl | $CH_3$ |
| 2 | Cl | $C_2H_5$ |
| 2 | Cl | $CH(CH_3)_2$ |
| 2 | Cl | $CH_2CH_2CH_3$ |
| 2 | $OCH_3$ | H |
| 2 | $OCH_3$ | Cl |

TABLE 6-continued

| | | |
|---|---|---|
| 2 | $OCH_3$ | $OCH_3$ |
| 2 | $OCH_3$ | $CH_3$ |
| 2 | $OCH_3$ | $C_2H_5$ |
| 2 | $OCH_3$ | $CH(CH_3)_2$ |
| 2 | $OCH_3$ | $CH_2CH_2CH_3$ |
| 2 | $CH_3$ | H |
| 2 | $CH_3$ | Cl |
| 2 | $CH_3$ | $OCH_3$ |
| 2 | $CH_3$ | $CH_3$ |
| 0 | $CH_3$ | H |
| 1 | $CH_3$ | H |
| 2 | $CH_3$ | $C_2H_5$ |
| 2 | $CH_3$ | $CH(CH_3)_2$ |
| 2 | $CH_3$ | $CH_2CH_2CH_3$ |
| 2 | $C_2H_5$ | H |
| 2 | $C_2H_5$ | Cl |
| 2 | $C_2H_5$ | $OCH_3$ |
| 2 | $C_2H_5$ | $CH_3$ |
| 2 | $C_2H_5$ | $C_2H_5$ |
| 2 | $C_2H_5$ | $CH(CH_3)_2$ |
| 2 | $C_2H_5$ | $CH_2CH_2CH_3$ |
| 2 | $CH(CH_3)_2$ | H |
| 2 | $CH(CH_3)_2$ | Cl |
| 2 | $CH(CH_3)_2$ | $OCH_3$ |
| 2 | $CH(CH_3)_2$ | $CH_3$ |
| 2 | $CH(CH_3)_2$ | $C_2H_5$ |
| 2 | $CH(CH_3)_2$ | $CH(CH_3)_2$ |
| 2 | $CH(CH_3)_2$ | $CH_2CH_2CH_3$ |
| 2 | $CH_2CH_2CH_3$ | H |
| 2 | $CH_2CH_2CH_3$ | Cl |
| 2 | $CH_2CH_2CH_3$ | $OCH_3$ |
| 2 | $CH_2CH_2CH_3$ | $CH_3$ |
| 2 | $CH_2CH_2CH_3$ | $C_2H_5$ |
| 2 | $CH_2CH_2CH_3$ | $CH(CH_3)_2$ |
| 2 | $CH_2CH_2CH_3$ | $CH_2CH_2CH_3$ |
| 2 | $CH_3$ | $C_6H_5$ |
| 2 | $C_6H_5$ | $CH_3$ |
| 2 | $CH_3$ | $CF_3$ |
| 2 | $CF_3$ | $CH_3$ |
| 2 | $COCH_3$ | H |
| 2 | $CH=CH_2$ | $CH_3$ |
| 2 | $CH_3$ | $CH=CH_2$ |
| 2 | $SCH_3$ | $CH_3$ |
| 2 | $CH_3$ | $SCH_3$ |
| 2 | $NO_2$ | $CH_3$ |
| 2 | $NH_2$ | $CH_3$ |
| 2 | CHO | $CH_3$ |
| 2 | $CO_2CH_3$ | H |
| 2 | $CH(OCH_3)_2$ | H |

A = A-6; X = S; $R^4 = CH_5$; $R^4 = CH_3$

| n | $R^1$ | $R^2$ |
|---|---|---|
| 2 | $CH_3$ | $CH_3$ |
| 2 | $C_2H_5$ | $CH_3$ |
| 2 | H | $CH_3$ |
| 2 | H | $C_2H_5$ |
| 2 | H | $CH_2CH_2CH_3$ |
| 2 | $OCH_3$ | $CH_3$ |
| 2 | $OCH_3$ | $C_2H_5$ |
| 2 | $CH_2CH_2CH_3$ | $CH_2CH_2CH_3$ |
| 2 | $CH_2CH=CH_2$ | $CH_2CH=CH_2$ |
| 2 | $CH_2C\equiv CH$ | $CH_2C\equiv CH$ |
| 2 | $CH(CH_3)_2$ | $CH(CH_3)_2$ |
| 2 | $-(CH_2)_5-$ | |
| 2 | $-(CH_2)_4-$ | |
| 2 | $CH_2CH=CH_2$ | $C_2H_5$ |
| 2 | $CH_2C\equiv CH$ | $C_2H_5$ |
| 2 | $OC_2H_5$ | $CH_3$ |
| 2 | $OC_2H_5$ | $C_2H_5$ |

TABLE 6-continued

| | | |
|---|---|---|
| 2 | H | 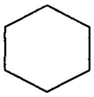 |
| 2 | 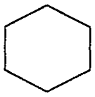 | 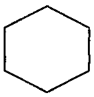 |
| 2 | H | $CH_2CH=CH_2$ |
| 2 | $CH_2CH_2CH_3$ | $CH_3$ |
| 0 | H | $CH_3$ |
| 1 | H | $CH_3$ |

A = A-6; X = $NCH_3$; $R^1$ = $C_2H_5$; $R^2$ = $C_2H_5$

| n | $R^4$ | $R^5$ |
|---|---|---|
| 2 | H | H |
| 2 | H | Cl |
| 2 | H | $OCH_3$ |
| 2 | H | $CH_3$ |
| 2 | H | $C_2H_5$ |
| 2 | H | $CH(CH_3)_2$ |
| 2 | H | $CH_2CH_2CH_3$ |
| 2 | Cl | H |
| 2 | Cl | Cl |
| 2 | Cl | $OCH_3$ |
| 2 | Cl | $CH_3$ |
| 2 | Cl | $C_2H_5$ |
| 2 | Cl | $CH(CH_3)_2$ |
| 2 | Cl | $CH_2CH_2CH_3$ |
| 2 | $OCH_3$ | H |
| 2 | $OCH_3$ | Cl |
| 2 | $OCH_3$ | $OCH_3$ |
| 2 | $OCH_3$ | $CH_3$ |
| 2 | $OCH_3$ | $C_2H_5$ |
| 2 | $OCH_3$ | $CH(CH_3)_2$ |
| 2 | $OCH_3$ | $CH_2CH_2CH_3$ |
| 2 | $CH_3$ | H |
| 2 | $CH_3$ | Cl |
| 2 | $CH_3$ | $OCH_3$ |
| 2 | $CH_3$ | $CH_3$ |
| 0 | $CH_3$ | H |
| 1 | $CH_3$ | H |
| 2 | $CH_3$ | $C_2H_5$ |
| 2 | $CH_3$ | $CH(CH_3)_2$ |
| 2 | $CH_3$ | $CH_2CH_2CH_3$ |
| 2 | $C_2H_5$ | H |
| 2 | $C_2H_5$ | Cl |
| 2 | $C_2H_5$ | $OCH_3$ |
| 2 | $C_2H_5$ | $CH_3$ |
| 2 | $C_2H_5$ | $C_2H_5$ |
| 2 | $C_2H_5$ | $CH(CH_3)_2$ |
| 2 | $C_2H_5$ | $CH_2CH_2CH_3$ |
| 2 | $CH(CH_3)_2$ | H |
| 2 | $CH(CH_3)_2$ | Cl |
| 2 | $CH(CH_3)_2$ | $OCH_3$ |
| 2 | $CH(CH_3)_2$ | $CH_3$ |
| 2 | $CH(CH_3)_2$ | $C_2H_5$ |
| 2 | $CH(CH_3)_2$ | $CH(CH_3)_2$ |
| 2 | $CH(CH_3)_2$ | $CH_2CH_2CH_3$ |
| 2 | $CH_2CH_2CH_3$ | H |
| 2 | $CH_2CH_2CH_3$ | Cl |
| 2 | $CH_2CH_2CH_3$ | $OCH_3$ |
| 2 | $CH_2CH_2CH_3$ | $CH_3$ |
| 2 | $CH_2CH_2CH_3$ | $C_2H_5$ |
| 2 | $CH_2CH_2CH_3$ | $CH(CH_3)_2$ |
| 2 | $CH_2CH_2CH_3$ | $CH_2CH_2CH_3$ |
| 2 | $CH_3$ | $C_6H_5$ |
| 2 | $C_6H_5$ | $CH_3$ |
| 2 | $CH_3$ | $CF_3$ |
| 2 | $CF_3$ | $CH_3$ |
| 2 | $COCH_3$ | H |
| 2 | $CH=CH_2$ | $CH_3$ |
| 2 | $CH_3$ | $CH=CH_2$ |
| 2 | $SCH_3$ | $CH_3$ |
| 2 | $CH_3$ | $SCH_3$ |
| 2 | $NO_2$ | $CH_3$ |
| 2 | $NH_2$ | $CH_3$ |
| 2 | CHO | $CH_3$ |
| 2 | $CO_2CH_3$ | H |
| 2 | $CH(OCH_3)_2$ | H |

A = A-6; X = $NCH_3$; $R^4$ = $CH_3$; $R^5$ = $CH_3$

| n | $R^1$ | $R^2$ |
|---|---|---|
| 2 | $CH_3$ | $CH_3$ |
| 2 | $C_2H_5$ | $CH_3$ |
| 2 | H | $CH_3$ |
| 2 | H | $C_2H_5$ |
| 2 | H | $CH_2CH_2CH_3$ |
| 2 | $OCH_3$ | $CH_3$ |
| 2 | $OCH_3$ | $C_2H_5$ |
| 2 | $CH_2CH_2CH_3$ | $CH_2CH_2CH_3$ |
| 2 | $CH_2CH=CH_2$ | $CH_2CH=CH_2$ |
| 2 | $CH_2C\equiv CH$ | $CH_2C\equiv CH$ |
| 2 | $CH(CH_3)_2$ | $CH(CH_3)_2$ |
| 2 | $-(CH_2)_5-$ | |
| 2 | $-(CH_2)_4-$ | |
| 2 | $CH_2CH=CH_2$ | $C_2H_5$ |
| 2 | $CH_2C\equiv CH$ | $C_2H_5$ |
| 2 | $OC_2H_5$ | $CH_3$ |
| 2 | $OC_2H_5$ | $C_2H_5$ |
| 2 | H | 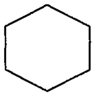 |
| 2 | 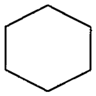 | 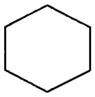 |
| 2 | H | $CH_2CH=CH_2$ |
| 2 | $CH_2CH_2CH_3$ | $CH_3$ |
| 0 | H | $CH_3$ |
| 1 | H | $CH_3$ |

A = A-6; X = $NC_2H_5$; $R^1$ = $C_2H_5$; $R^2$ = $C_2H_5$

| n | $R^4$ | $R^5$ |
|---|---|---|
| 2 | H | H |
| 2 | H | Cl |
| 2 | H | $OCH_3$ |
| 2 | H | $CH_3$ |
| 2 | H | $C_2H_5$ |
| 2 | H | $CH(CH_3)_2$ |
| 2 | H | $CH_2CH_2CH_3$ |
| 2 | Cl | H |
| 2 | Cl | Cl |
| 2 | Cl | $OCH_3$ |
| 2 | Cl | $CH_3$ |
| 2 | Cl | $C_2H_5$ |
| 2 | Cl | $CH(CH_3)_2$ |
| 2 | Cl | $CH_2CH_2CH_3$ |
| 2 | $OCH_3$ | H |
| 2 | $OCH_3$ | Cl |
| 2 | $OCH_3$ | $OCH_3$ |
| 2 | $OCH_3$ | $CH_3$ |
| 2 | $OCH_3$ | $C_2H_5$ |
| 2 | $OCH_3$ | $CH(CH_3)_2$ |
| 2 | $OCH_3$ | $CH_2CH_2CH_3$ |

TABLE 6-continued

| | | |
|---|---|---|
| 2 | $CH_3$ | H |
| 2 | $CH_3$ | Cl |
| 2 | $CH_3$ | $OCH_3$ |
| 2 | $CH_3$ | $CH_3$ |
| 0 | $CH_3$ | H |
| 1 | $CH_3$ | H |
| 2 | $CH_3$ | $C_2H_5$ |
| 2 | $CH_3$ | $CH(CH_3)_2$ |
| 2 | $CH_3$ | $CH_2CH_2CH_3$ |
| 2 | $C_2H_5$ | H |
| 2 | $C_2H_5$ | Cl |
| 2 | $C_2H_5$ | $OCH_3$ |
| 2 | $C_2H_5$ | $CH_3$ |
| 2 | $C_2H_5$ | $C_2H_5$ |
| 2 | $C_2H_5$ | $CH(CH_3)_2$ |
| 2 | $C_2H_5$ | $CH_2CH_2CH_3$ |
| 2 | $CH(CH_3)_2$ | H |
| 2 | $CH(CH_3)_2$ | Cl |
| 2 | $CH(CH_3)_2$ | $OCH_3$ |
| 2 | $CH(CH_3)_2$ | $CH_3$ |
| 2 | $CH(CH_3)_2$ | $C_2H_5$ |
| 2 | $CH(CH_3)_2$ | $CH(CH_3)_2$ |
| 2 | $CH(CH_3)_2$ | $CH_2CH_2CH_3$ |
| 2 | $CH_2CH_2CH_3$ | H |
| 2 | $CH_2CH_2CH_3$ | Cl |
| 2 | $CH_2CH_2CH_3$ | $OCH_3$ |
| 2 | $CH_2CH_2CH_3$ | $CH_3$ |
| 2 | $CH_2CH_2CH_3$ | $C_2H_5$ |
| 2 | $CH_2CH_2CH_3$ | $CH(CH_3)_2$ |
| 2 | $CH_2CH_2CH_3$ | $CH_2CH_2CH_3$ |
| 2 | $CH_3$ | $C_6H_5$ |
| 2 | $C_6H_5$ | $CH_3$ |
| 2 | $CH_3$ | $CF_3$ |
| 2 | $CF_3$ | $CH_3$ |
| 2 | $COCH_3$ | H |
| 2 | $CH{=}CH_2$ | $CH_3$ |
| 2 | $CH_3$ | $CH{=}CH_2$ |
| 2 | $SCH_3$ | $CH_3$ |
| 2 | $CH_3$ | $SCH_3$ |
| 2 | $NO_2$ | $CH_3$ |
| 2 | $NH_2$ | $CH_3$ |
| 2 | CHO | $CH_3$ |
| 2 | $CO_2CH_3$ | H |
| 2 | $CH(OCH_3)_2$ | H |

A = A-6; X = $NC_2H_5$; $R^4$ = $CH_3$; $R^5$ = $CH_3$

| n | $R^1$ | $R^2$ |
|---|---|---|
| 2 | $CH_3$ | $CH_3$ |
| 2 | $C_2H_5$ | $CH_3$ |
| 2 | H | $CH_3$ |
| 2 | H | $C_2H_5$ |
| 2 | H | $CH_2CH_2CH_3$ |
| 2 | $OCH_3$ | $CH_3$ |
| 2 | $OCH_3$ | $C_2H_5$ |
| 2 | $CH_2CH_2CH_3$ | $CH_2CH_2CH_3$ |
| 2 | $CH_2CH{=}CH_2$ | $CH_2CH{=}CH_2$ |
| 2 | $CH_2C{\equiv}CH$ | $CH_2C{\equiv}CH$ |
| 2 | $CH(CH_3)_2$ | $CH(CH_3)_2$ |
| 2 | $-(CH_2)_5-$ | |
| 2 | $-(CH_2)_4-$ | |
| 2 | $CH_2CH{=}CH_2$ | $C_2H_5$ |
| 2 | $CH_2C{\equiv}CH$ | $C_2H_5$ |
| 2 | $OC_2H_5$ | $CH_3$ |
| 2 | $OC_2H_5$ | $C_2H_5$ |
| 2 | H | 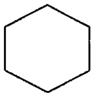 |
| 2 | 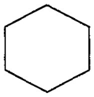 | 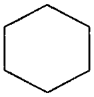 |
| 2 | H | $CH_2CH{=}CH_2$ |
| 2 | $CH_2CH_2CH_3$ | $CH_3$ |
| 0 | H | $CH_3$ |
| 1 | H | $CH_3$ |

A = A-6; X = $NCH_2CH_2CH_3$; $R^1$ = $C_2H_5$; $R^2$ = $C_2H_5$

| n | $R^4$ | $R^5$ |
|---|---|---|
| 2 | H | H |
| 2 | H | Cl |
| 2 | H | $OCH_3$ |
| 2 | H | $CH_3$ |
| 2 | H | $C_2H_5$ |
| 2 | H | $CH(CH_3)_2$ |
| 2 | H | $CH_2CH_2CH_3$ |
| 2 | Cl | H |
| 2 | Cl | Cl |
| 2 | Cl | $OCH_3$ |
| 2 | Cl | $CH_3$ |
| 2 | Cl | $C_2H_5$ |
| 2 | Cl | $CH(CH_3)_2$ |
| 2 | Cl | $CH_2CH_2CH_3$ |
| 2 | $OCH_3$ | H |
| 2 | $OCH_3$ | Cl |
| 2 | $OCH_3$ | $OCH_3$ |
| 2 | $OCH_3$ | $CH_3$ |
| 2 | $OCH_3$ | $C_2H_5$ |
| 2 | $OCH_3$ | $CH(CH_3)_2$ |
| 2 | $OCH_3$ | $CH_2CH_2CH_3$ |
| 2 | $CH_3$ | H |
| 2 | $CH_3$ | Cl |
| 2 | $CH_3$ | $OCH_3$ |
| 2 | $CH_3$ | $CH_3$ |
| 0 | $CH_3$ | H |
| 1 | $CH_3$ | H |
| 2 | $CH_3$ | $C_2H_5$ |
| 2 | $CH_3$ | $CH(CH_3)_2$ |
| 2 | $CH_3$ | $CH_2CH_2CH_3$ |
| 2 | $C_2H_5$ | H |
| 2 | $C_2H_5$ | Cl |
| 2 | $C_2H_5$ | $OCH_3$ |
| 2 | $C_2H_5$ | $CH_3$ |
| 2 | $C_2H_5$ | $C_2H_5$ |
| 2 | $C_2H_5$ | $CH(CH_3)_2$ |
| 2 | $C_2H_5$ | $CH_2CH_2CH_3$ |
| 2 | $CH(CH_3)_2$ | H |
| 2 | $CH(CH_3)_2$ | Cl |
| 2 | $CH(CH_3)_2$ | $OCH_3$ |
| 2 | $CH(CH_3)_2$ | $CH_3$ |
| 2 | $CH(CH_3)_2$ | $C_2H_5$ |
| 2 | $CH(CH_3)_2$ | $CH(CH_3)_2$ |
| 2 | $CH(CH_3)_2$ | $CH_2CH_2CH_3$ |
| 2 | $CH_2CH_2CH_3$ | H |
| 2 | $CH_2CH_2CH_3$ | Cl |
| 2 | $CH_2CH_2CH_3$ | $OCH_3$ |
| 2 | $CH_2CH_2CH_3$ | $CH_3$ |
| 2 | $CH_2CH_2CH_3$ | $C_2H_5$ |
| 2 | $CH_2CH_2CH_3$ | $CH(CH_3)_2$ |
| 2 | $CH_2CH_2CH_3$ | $CH_2CH_2CH_3$ |
| 2 | $CH_3$ | $C_6H_5$ |
| 2 | $C_6H_5$ | $CH_3$ |
| 2 | $CH_3$ | $CF_3$ |
| 2 | $CF_3$ | $CH_3$ |
| 2 | $COCH_3$ | H |
| 2 | $CH{=}CH_2$ | $CH_3$ |
| 2 | $CH_3$ | $CH{=}CH_2$ |
| 2 | $SCH_3$ | $CH_3$ |
| 2 | $CH_3$ | $SCH_3$ |
| 2 | $NO_2$ | $CH_3$ |

TABLE 6-continued

| n | $R^1$ | $R^2$ |
|---|---|---|
| 2 | $NH_2$ | $CH_3$ |
| 2 | CHO | $CH_3$ |
| 2 | $CO_2CH_3$ | H |
| 2 | $CH(OCH_3)_2$ | H |
| A = A-6; X = $NCH_2CH_2CH_3$; $R^4$ = $CH_3$; $R^5$ = $CH_3$ | | |
| n | $R^1$ | $R^2$ |
| 2 | $CH_3$ | $CH_3$ |
| 2 | $C_2H_5$ | $CH_3$ |
| 2 | H | $CH_3$ |
| 2 | H | $C_2H_5$ |
| 2 | H | $CH_2CH_2CH_3$ |
| 2 | $OCH_3$ | $CH_3$ |
| 2 | $OCH_3$ | $C_2H_5$ |
| 2 | $CH_2CH_2CH_3$ | $CH_2CH_2CH_3$ |
| 2 | $CH_2CH{=}CH_2$ | $CH_2CH{=}CH_2$ |
| 2 | $CH_2C{\equiv}CH$ | $CH_2C{\equiv}CH$ |
| 2 | $CH(CH_3)_2$ | $CH(CH_3)_2$ |
| 2 | $-(CH_2)_5-$ | |
| 2 | $-(CH_2)_4-$ | |
| 2 | $CH_2CH{=}CH_2$ | $C_2H_5$ |
| 2 | $CH_2C{\equiv}CH$ | $C_2H_5$ |
| 2 | $OC_2H_5$ | $CH_3$ |
| 2 | $OC_2H_5$ | $C_2H_5$ |
| 2 | H | 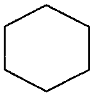 |
| 2 | 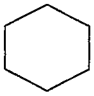 | 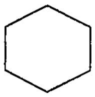 |
| 2 | H | $CH_2CH{=}CH_2$ |
| 2 | $CH_2CH_2CH_3$ | $CH_3$ |
| 0 | H | $CH_3$ |
| 1 | H | $CH_3$ |

TABLE 7

| n | $R^3$ | $R^5$ |
|---|---|---|
| A = A-7; X = O; $R^1$ = $C_2H_5$; $R^2$ = $C_2H_5$ | | |
| 2 | H | H |
| 2 | H | Cl |
| 2 | H | $OCH_3$ |
| 2 | H | $CH_3$ |
| 2 | H | $C_2H_5$ |
| 2 | H | $CH(CH_3)_2$ |
| 2 | H | $CH_2CH_2CH_3$ |
| 2 | Cl | H |
| 2 | Cl | Cl |
| 2 | Cl | $OCH_3$ |
| 2 | Cl | $CH_3$ |
| 2 | Cl | $C_2H_5$ |
| 2 | Cl | $CH(CH_3)_2$ |
| 2 | Cl | $CH_2CH_2CH_3$ |
| 2 | $OCH_3$ | H |
| 2 | $OCH_3$ | Cl |
| 2 | $OCH_3$ | $OCH_3$ |
| 2 | $OCH_3$ | $CH_3$ |

TABLE 7-continued

| n | $R^3$ | $R^5$ |
|---|---|---|
| 2 | $OCH_3$ | $C_2H_5$ |
| 2 | $OCH_3$ | $CH(CH_3)_2$ |
| 2 | $OCH_3$ | $CH_2CH_2CH_3$ |
| 2 | $CH_3$ | H |
| 2 | $CH_3$ | Cl |
| 2 | $CH_3$ | $OCH_3$ |
| 2 | $CH_3$ | $CH_3$ |
| 0 | $CH_3$ | H |
| 1 | $CH_3$ | H |
| 2 | $CH_3$ | $C_2H_5$ |
| 2 | $CH_3$ | $CH(CH_3)_2$ |
| 2 | $CH_3$ | $CH_2CH_2CH_3$ |
| 2 | $C_2H_5$ | H |
| 2 | $C_2H_5$ | Cl |
| 2 | $C_2H_5$ | $OCH_3$ |
| 2 | $C_2H_5$ | $CH_3$ |
| 2 | $C_2H_5$ | $C_2H_5$ |
| 2 | $C_2H_5$ | $CH(CH_3)_2$ |
| 2 | $C_2H_5$ | $CH_2CH_2CH_3$ |
| 2 | $CH(CH_3)_2$ | H |
| 2 | $CH(CH_3)_2$ | Cl |
| 2 | $CH(CH_3)_2$ | $OCH_3$ |
| 2 | $CH(CH_3)_2$ | $CH_3$ |
| 2 | $CH(CH_3)_2$ | $C_2H_5$ |
| 2 | $CH(CH_3)_2$ | $CH(CH_3)_2$ |
| 2 | $CH(CH_3)_2$ | $CH_2CH_2CH_3$ |
| 2 | $CH_2CH_2CH_3$ | H |
| 2 | $CH_2CH_2CH_3$ | Cl |
| 2 | $CH_2CH_2CH_3$ | $OCH_3$ |
| 2 | $CH_2CH_2CH_3$ | $CH_3$ |
| 2 | $CH_2CH_2CH_3$ | $C_2H_5$ |
| 2 | $CH_2CH_2CH_3$ | $CH(CH_3)_2$ |
| 2 | $CH_2CH_2CH_3$ | $CH_2CH_2CH_3$ |
| 2 | $CH_3$ | $C_6H_5$ |
| 2 | $C_6H_5$ | $CH_3$ |
| 2 | $CH_3$ | $CF_3$ |
| 2 | $CF_3$ | $CH_3$ |
| 2 | $COCH_3$ | H |
| 2 | $CH{=}CH_2$ | $CH_3$ |
| 2 | $CH_3$ | $CH{=}CH_2$ |
| 2 | $SCH_3$ | $CH_3$ |
| 2 | $CH_3$ | $SCH_3$ |
| 2 | $NO_2$ | $CH_3$ |
| 2 | $NH_2$ | $CH_3$ |
| 2 | CHO | $CH_3$ |
| 2 | $CO_2CH_3$ | H |
| 2 | $CH(OCH_3)_2$ | H |
| A = A-7; X = O; $R^3$ = $CH_3$; $R^5$ = $CH_3$ | | |
| n | $R^1$ | $R^2$ |
| 2 | $CH_3$ | $CH_3$ |
| 2 | $C_2H_5$ | $CH_3$ |
| 2 | H | $CH_3$ |
| 2 | H | $C_2H_5$ |
| 2 | H | $CH_2CH_2CH_3$ |
| 2 | $OCH_3$ | $CH_3$ |
| 2 | $OCH_3$ | $C_2H_5$ |
| 2 | $CH_2CH_2CH_3$ | $CH_2CH_2CH_3$ |
| 2 | $CH_2CH{=}CH$ | $CH_2CH{=}CH_2$ |
| 2 | $CH_2C{\equiv}CH$ | $CH_2C{\equiv}CH$ |
| 2 | $CH(CH_3)_2$ | $CH(CH_3)_2$ |
| 2 | $-(CH_2)_5-$ | |
| | $-(CH_2)_4-$ | |
| 2 | $CH_2CH{=}CH_2$ | $C_2H_5$ |
| 2 | $CH_2C{\equiv}CH$ | $C_2H_5$ |
| 2 | $OC_2H_5$ | $CH_3$ |
| 2 | $OC_2H_5$ | $C_2H_5$ |

TABLE 7-continued

| | | |
|---|---|---|
| 2 | H | 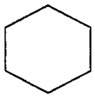 |
| 2 | 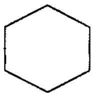 | 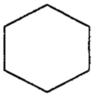 |
| 2 | H | $CH_2CH{=}CH_2$ |
| 2 | $CH_2CH_2CH_3$ | $CH_3$ |
| 0 | H | $CH_3$ |
| 1 | H | $CH_3$ |

A = A-7; X = S; $R^1 = C_2H_5$; $R^2 = C_2H_5$

| n | $R^3$ | $R^5$ |
|---|---|---|
| 2 | H | H |
| 2 | H | Cl |
| 2 | H | $OCH_3$ |
| 2 | H | $CH_3$ |
| 2 | H | $C_2H_5$ |
| 2 | H | $CH(CH_3)_2$ |
| 2 | H | $CH_2CH_2CH_3$ |
| 2 | Cl | H |
| 2 | Cl | Cl |
| 2 | Cl | $OCH_3$ |
| 2 | Cl | $CH_3$ |
| 2 | Cl | $C_2H_5$ |
| 2 | Cl | $CH(CH_3)_2$ |
| 2 | Cl | $CH_2CH_2CH_3$ |
| 2 | $OCH_3$ | H |
| 2 | $OCH_3$ | Cl |
| 2 | $OCH_3$ | $OCH_3$ |
| 2 | $OCH_3$ | $CH_3$ |
| 2 | $OCH_3$ | $C_2H_5$ |
| 2 | $OCH_3$ | $CH(CH_3)_2$ |
| 2 | $OCH_3$ | $CH_2CH_2CH_3$ |
| 2 | $CH_3$ | H |
| 2 | $CH_3$ | Cl |
| 2 | $CH_3$ | $OCH_3$ |
| 2 | $CH_3$ | $CH_3$ |
| 0 | $CH_3$ | H |
| 1 | $CH_3$ | H |
| 2 | $CH_3$ | $C_2H_5$ |
| 2 | $CH_3$ | $CH(CH_3)_2$ |
| 2 | $CH_3$ | $CH_2CH_2CH_3$ |
| 2 | $C_2H_5$ | H |
| 2 | $C_2H_5$ | Cl |
| 2 | $C_2H_5$ | $OCH_3$ |
| 2 | $C_2H_5$ | $CH_3$ |
| 2 | $C_2H_5$ | $C_2H_5$ |
| 2 | $C_2H_5$ | $CH(CH_3)_2$ |
| 2 | $C_2H_5$ | $CH_2CH_2CH_3$ |
| 2 | $CH(CH_3)_2$ | H |
| 2 | $CH(CH_3)_2$ | Cl |
| 2 | $CH(CH_3)_2$ | $OCH_3$ |
| 2 | $CH(CH_3)_2$ | $CH_3$ |
| 2 | $CH(CH_3)_2$ | $C_2H_5$ |
| 2 | $CH(CH_3)_2$ | $CH(CH_3)_2$ |
| 2 | $CH(CH_3)_2$ | $CH_2CH_2CH_3$ |
| 2 | $CH_2CH_2CH_3$ | H |
| 2 | $CH_2CH_2CH_3$ | Cl |
| 2 | $CH_2CH_2CH_3$ | $OCH_3$ |
| 2 | $CH_2CH_2CH_3$ | $CH_3$ |
| 2 | $CH_2CH_2CH_3$ | $C_2H_5$ |
| 2 | $CH_2CH_2CH_3$ | $CH(CH_3)_2$ |
| 2 | $CH_2CH_2CH_3$ | $CH_2CH_2CH_3$ |
| 2 | $CH_3$ | $C_6H_5$ |
| 2 | $C_6H_5$ | $CH_3$ |
| 2 | $CH_3$ | $CF_3$ |
| 2 | $CF_3$ | $CH_3$ |
| 2 | $COCH_3$ | H |
| 2 | $CH{=}CH_2$ | $CH_3$ |
| 2 | $CH_3$ | $CH{=}CH_2$ |

TABLE 7-continued

| | | |
|---|---|---|
| 2 | $SCH_3$ | $CH_3$ |
| 2 | $CH_3$ | $SCH_3$ |
| 2 | $NO_2$ | $CH_3$ |
| 2 | $NH_2$ | $CH_3$ |
| 2 | CHO | $CH_3$ |
| 2 | $CO_2CH_3$ | H |
| 2 | $CH(OCH_3)_2$ | H |

A = A-7; X = S; $R^3 = CH_3$; $R^5 = CH_3$

| n | $R^1$ | $R^2$ |
|---|---|---|
| 2 | $CH_3$ | $CH_3$ |
| 2 | $C_2H_5$ | $CH_3$ |
| 2 | H | $CH_3$ |
| 2 | H | $C_2H_5$ |
| 2 | H | $CH_2CH_2CH_3$ |
| 2 | $OCH_3$ | $CH_3$ |
| 2 | $OCH_3$ | $C_2H_5$ |
| 2 | $CH_2CH_2CH_3$ | $CH_2CH_2CH_3$ |
| 2 | $CH_2CH{=}CH_2$ | $CH_2CH{=}CH_2$ |
| 2 | $CH_2C{\equiv}CH$ | $CH_2C{\equiv}CH$ |
| 2 | $CH(CH_3)_2$ | $CH(CH_3)_2$ |
| 2 | $-(CH_2)_5-$ | |
| | $-(CH_2)_4-$ | |
| 2 | $CH_2CH{=}CH_2$ | $C_2H_5$ |
| 2 | $CH_2C{\equiv}CH$ | $C_2H_5$ |
| 2 | $OC_2H_5$ | $CH_3$ |
| 2 | $OC_2H_5$ | $C_2H_5$ |
| 2 | H | 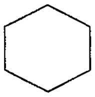 |
| 2 | 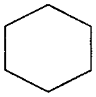 | 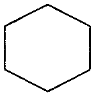 |
| 2 | H | $CH_2CH{=}CH_2$ |
| 2 | $CH_2CH_2CH_3$ | $CH_3$ |
| 0 | H | $CH_3$ |
| 1 | H | $CH_3$ |

A = A-7; X = $NCH_3$; $R^1 = C_2H_5$; $R^2 = C_2H_5$

| n | $R^3$ | $R^5$ |
|---|---|---|
| 2 | H | H |
| 2 | H | Cl |
| 2 | H | $OCH_3$ |
| 2 | H | $CH_3$ |
| 2 | H | $C_2H_5$ |
| 2 | H | $CH(CH_3)_2$ |
| 2 | H | $CH_2CH_2CH_3$ |
| 2 | Cl | H |
| 2 | Cl | Cl |
| 2 | Cl | $OCH_3$ |
| 2 | Cl | $CH_3$ |
| 2 | Cl | $C_2H_5$ |
| 2 | Cl | $CHF_2$ |
| 1 | Cl | $CHF_2$ |
| 2 | $CHF_2$ | $CH_2CH_2CH_3$ |
| 2 | Cl | $CH(CH_3)_2$ |
| 2 | Cl | $CH_2CH_2CH_3$ |
| 2 | $OCH_3$ | H |
| 2 | $OCH_3$ | Cl |
| 2 | $OCH_3$ | $OCH_3$ |
| 2 | $OCH_3$ | $CH_3$ |
| 2 | $OCH_3$ | $C_2H_5$ |

TABLE 7-continued

| | | |
|---|---|---|
| 2 | $OCH_3$ | $CH(CH_3)_2$ |
| 2 | $OCH_3$ | $CH_2CH_2CH_3$ |
| 2 | $CH_3$ | H |
| 2 | $CH_3$ | Cl |
| 2 | $CH_3$ | $OCH_3$ |
| 2 | $CH_3$ | $CH_3$ |
| 0 | $CH_3$ | H |
| 1 | $CH_3$ | H |
| 2 | $CH_3$ | $C_2H_5$ |
| 2 | $CH_3$ | $CH(CH_3)_2$ |
| 2 | $CH_3$ | $CH_2CH_2CH_3$ |
| 2 | $C_2H_5$ | H |
| 2 | $C_2H_5$ | Cl |
| 2 | $C_2H_5$ | $OCH_3$ |
| 2 | $C_2H_5$ | $CH_3$ |
| 2 | $C_2H_5$ | $C_2H_5$ |
| 2 | $C_2H_5$ | $CH(CH_3)_2$ |
| 2 | $C_2H_5$ | $CH_2CH_2CH_3$ |
| 2 | $CH(CH_3)_2$ | H |
| 2 | $CH(CH_3)_2$ | Cl |
| 2 | $CH(CH_3)_2$ | $OCH_3$ |
| 2 | $CH(CH_3)_2$ | $CH_3$ |
| 2 | $CH(CH_3)_2$ | $C_2H_5$ |
| 2 | $CH(CH_3)_2$ | $CH(CH_3)_2$ |
| 2 | $CH(CH_3)_2$ | $CH_2CH_2CH_3$ |
| 2 | $CH_2CH_2CH_3$ | H |
| 2 | $CH_2CH_2CH_3$ | Cl |
| 2 | $CH_2CH_2CH_3$ | $OCH_3$ |
| 2 | $CH_2CH_2CH_3$ | $CH_3$ |
| 2 | $CH_2CH_2CH_3$ | $C_2H_5$ |
| 2 | $CH_2CH_2CH_3$ | $CH(CH_3)_2$ |
| 2 | $CH_2CH_2CH_3$ | $CH_2CH_2CH_3$ |
| 2 | $CH_3$ | $C_6H_5$ |
| 2 | $C_6H_5$ | $CH_3$ |
| 2 | $CH_3$ | $CF_3$ |
| 2 | $CF_3$ | $CH_3$ |
| 2 | $COCH_3$ | H |
| 2 | $CH=CH_2$ | $CH_3$ |
| 2 | $CH_3$ | $CH=CH_2$ |
| 2 | $SCH_3$ | $CH_3$ |
| 2 | $CH_3$ | $SCH_3$ |
| 2 | $NO_2$ | $CH_3$ |
| 2 | $NH_2$ | $CH_3$ |
| 2 | CHO | $CH_3$ |
| 2 | $CO_2CH_3$ | H |
| 2 | $CH(OCH_3)_2$ | H |

A = A-7; X = $NCH_3$; $R^3$ = $CH_3$; $R^5$ = $CH_3$

| n | $R^1$ | $R^2$ |
|---|---|---|
| 2 | $CH_3$ | $CH_3$ |
| 2 | $C_2H_5$ | $CH_3$ |
| 2 | H | $CH_3$ |
| 2 | H | $C_2H_5$ |
| 2 | H | $CH_2CH_2CH_3$ |
| 2 | $OCH_3$ | $CH_3$ |
| 2 | $OCH_3$ | $C_2H_5$ |
| 2 | $CH_2CH_2CH_3$ | $CH_2CH_2CH_3$ |
| 2 | $CH_2CH=CH_2$ | $CH_2CH=CH_2$ |
| 2 | $CH_2C\equiv CH$ | $CH_2C\equiv CH$ |
| 2 | $CH(CH_3)_2$ | $CH(CH_3)_2$ |
| 2 | $-(CH_2)_5-$ | |
| | $-(CH_2)_4-$ | |
| 2 | $CH_2CH=CH_2$ | $C_2H_5$ |
| 2 | $CH_2C\equiv CH$ | $C_2H_5$ |
| 2 | $OC_2H_5$ | $CH_3$ |
| 2 | $OC_2H_5$ | $C_2H_5$ |

TABLE 7-continued

| | | |
|---|---|---|
| 2 | H | 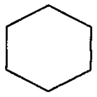 |
| 2 | 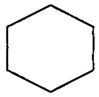 | 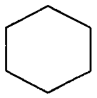 |
| 2 | H | $CH_2CH=CH_2$ |
| 2 | $CH_2CH_2CH_3$ | $CH_3$ |
| 0 | H | $CH_3$ |
| 1 | H | $CH_3$ |

A = A-7; X = $NC_2H_5$; $R^1$ = $C_2H_5$; $R^2$ = $C_2H_5$

| n | $R^3$ | $R^5$ |
|---|---|---|
| 2 | H | H |
| 2 | H | Cl |
| 2 | H | $OCH_3$ |
| 2 | H | $CH_3$ |
| 2 | H | $C_2H_5$ |
| 2 | H | $CH(CH_3)_2$ |
| 2 | H | $CH_2CH_2CH_3$ |
| 2 | Cl | H |
| 2 | Cl | Cl |
| 2 | Cl | $OCH_3$ |
| 2 | Cl | $CH_3$ |
| 2 | Cl | $C_2H_5$ |
| 2 | Cl | $CH(CH_3)_2$ |
| 2 | Cl | $CH_2CH_2CH_3$ |
| 2 | $OCH_3$ | H |
| 2 | $OCH_3$ | Cl |
| 2 | $OCH_3$ | $OCH_3$ |
| 2 | $OCH_3$ | $CH_3$ |
| 2 | $OCH_3$ | $C_2H_5$ |
| 2 | $OCH_3$ | $CH(CH_3)_2$ |
| 2 | $OCH_3$ | $CH_2CH_2CH_3$ |
| 2 | $CH_3$ | H |
| 2 | $CH_3$ | Cl |
| 2 | $CH_3$ | $OCH_3$ |
| 2 | $CH_3$ | $CH_3$ |
| 0 | $CH_3$ | H |
| 1 | $CH_3$ | H |
| 2 | $CH_3$ | $C_2H_5$ |
| 2 | $CH_3$ | $CH(CH_3)_2$ |
| 2 | $CH_3$ | $CH_2CH_2CH_3$ |
| 2 | $C_2H_5$ | H |
| 2 | $C_2H_5$ | Cl |
| 2 | $C_2H_5$ | $OCH_3$ |
| 2 | $C_2H_5$ | $CH_3$ |
| 2 | $C_2H_5$ | $C_2H_5$ |
| 2 | $C_2H_5$ | $CH(CH_3)_2$ |
| 2 | $C_2H_5$ | $CH_2CH_2CH_3$ |
| 2 | $CH(CH_3)_2$ | H |
| 2 | $CH(CH_3)_2$ | Cl |
| 2 | $CH(CH_3)_2$ | $OCH_3$ |
| 2 | $CH(CH_3)_2$ | $CH_3$ |
| 2 | $CH(CH_3)_2$ | $C_2H_5$ |
| 2 | $CH(CH_3)_2$ | $CH(CH_3)_2$ |
| 2 | $CH(CH_3)_2$ | $CH_2CH_2CH_3$ |
| 2 | $CH_2CH_2CH_3$ | H |
| 2 | $CH_2CH_2CH_3$ | Cl |
| 2 | $CH_2CH_2CH_3$ | $OCH_3$ |
| 2 | $CH_2CH_2CH_3$ | $CH_3$ |
| 2 | $CH_2CH_2CH_3$ | $C_2H_5$ |
| 2 | $CH_2CH_2CH_3$ | $CH(CH_3)_2$ |
| 2 | $CH_2CH_2CH_3$ | $CH_2CH_2CH_3$ |
| 2 | $CH_3$ | $C_6H_5$ |
| 2 | $C_6H_5$ | $CH_3$ |
| 2 | $CH_3$ | $CF_3$ |
| 2 | $CF_3$ | $CH_3$ |
| 2 | $COCH_3$ | H |
| 2 | $CH=CH_2$ | $CH_3$ |
| 2 | $CH_3$ | $CH=CH_2$ |

TABLE 7-continued

| n | R^1 | R^2 |
|---|---|---|
| 2 | $SCH_3$ | $CH_3$ |
| 2 | $CH_3$ | $SCH_3$ |
| 2 | $NO_2$ | $CH_3$ |
| 2 | $NH_2$ | $CH_3$ |
| 2 | CHO | $CH_3$ |
| 2 | $CO_2CH_3$ | H |
| 2 | $CH(OCH_3)_2$ | H |

$A = A\text{-}7;\ X = NC_2H_5;\ R^3 = CH_3;\ R^5 = CH_3$

| n | $R^1$ | $R^2$ |
|---|---|---|
| 2 | $CH_3$ | $CH_3$ |
| 2 | $C_2H_5$ | $CH_3$ |
| 2 | H | $CH_3$ |
| 2 | H | $C_2H_5$ |
| 2 | H | $CH_2CH_2CH_3$ |
| 2 | $OCH_3$ | $CH_3$ |
| 2 | $OCH_3$ | $C_2H_5$ |
| 2 | $CH_2CH_2CH_3$ | $CH_2CH_2CH_3$ |
| 2 | $CH_2CH{=}CH_2$ | $CH_2CH{=}CH_2$ |
| 2 | $CH_2C{\equiv}CH$ | $CH_2C{\equiv}CH$ |
| 2 | $CH(CH_3)_2$ | $CH(CH_3)_2$ |
| 2 | $-(CH_2)_5-$ | |
| | $-(CH_2)_4-$ | |
| 2 | $CH_2CH{=}CH_2$ | $C_2H_5$ |
| 2 | $CH_2C{\equiv}CH$ | $C_2H_5$ |
| 2 | $OC_2H_5$ | $CH_3$ |
| 2 | $OC_2H_5$ | $C_2H_5$ |
| 2 | H | 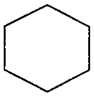 |
| 2 | 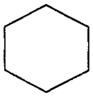 | 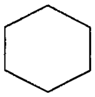 |
| 2 | H | $CH_2CH{=}CH_2$ |
| 2 | $CH_2CH_2CH_3$ | $CH_3$ |
| 0 | H | $CH_3$ |
| 1 | H | $CH_3$ |

$A = A\text{-}7;\ X = NCH_2CH_2CH_3;\ R^1 = C_2H_5;\ R^2 = C_2H_5$

| n | $R^3$ | $R^5$ |
|---|---|---|
| 2 | H | H |
| 2 | H | Cl |
| 2 | H | $OCH_3$ |
| 2 | H | $CH_3$ |
| 2 | H | $C_2H_5$ |
| 2 | H | $CH(CH_3)_2$ |
| 2 | H | $CH_2CH_2CH_3$ |
| 2 | Cl | H |
| 2 | Cl | Cl |
| 2 | Cl | $OCH_3$ |
| 2 | Cl | $CH_3$ |
| 2 | Cl | $C_2H_5$ |
| 2 | Cl | $CH(CH_3)_2$ |
| 2 | Cl | $CH_2CH_2CH_3$ |
| 2 | $OCH_3$ | H |
| 2 | $OCH_3$ | Cl |
| 2 | $OCH_3$ | $OCH_3$ |
| 2 | $OCH_3$ | $CH_3$ |
| 2 | $OCH_3$ | $C_2H_5$ |
| 2 | $OCH_3$ | $CH(CH_3)_2$ |
| 2 | $OCH_3$ | $CH_2CH_2CH_3$ |

TABLE 7-continued

| n | $R^3$ | $R^5$ |
|---|---|---|
| 2 | $CH_3$ | H |
| 2 | $CH_3$ | Cl |
| 2 | $CH_3$ | $OCH_3$ |
| 2 | $CH_3$ | $CH_3$ |
| 0 | $CH_3$ | H |
| 1 | $CH_3$ | H |
| 2 | $CH_3$ | $C_2H_5$ |
| 2 | $CH_3$ | $CH(CH_3)_2$ |
| 2 | $CH_3$ | $CH_2CH_2CH_3$ |
| 2 | $C_2H_5$ | H |
| 2 | $C_2H_5$ | Cl |
| 2 | $C_2H_5$ | $OCH_3$ |
| 2 | $C_2H_5$ | $CH_3$ |
| 2 | $C_2H_5$ | $C_2H_5$ |
| 2 | $C_2H_5$ | $CH(CH_3)_2$ |
| 2 | $C_2H_5$ | $CH_2CH_2CH_3$ |
| 2 | $CH(CH_3)_2$ | H |
| 2 | $CH(CH_3)_2$ | Cl |
| 2 | $CH(CH_3)_2$ | $OCH_3$ |
| 2 | $CH(CH_3)_2$ | $CH_3$ |
| 2 | $CH(CH_3)_2$ | $C_2H_5$ |
| 2 | $CH(CH_3)_2$ | $CH(CH_3)_2$ |
| 2 | $CH(CH_3)_2$ | $CH_2CH_2CH_3$ |
| 2 | $CH_2CH_2CH_3$ | H |
| 2 | $CH_2CH_2CH_3$ | Cl |
| 2 | $CH_2CH_2CH_3$ | $OCH_3$ |
| 2 | $CH_2CH_2CH_3$ | $CH_3$ |
| 2 | $CH_2CH_2CH_3$ | $C_2H_5$ |
| 2 | $CH_2CH_2CH_3$ | $CH(CH_3)_2$ |
| 2 | $CH_2CH_2CH_3$ | $CH_2CH_2CH_3$ |
| 2 | $CH_3$ | $C_6H_5$ |
| 2 | $C_6H_5$ | $CH_3$ |
| 2 | $CH_3$ | $CF_3$ |
| 2 | $CF_3$ | $CH_3$ |
| 2 | $COCH_3$ | H |
| 2 | $CH{=}CH_2$ | $CH_3$ |
| 2 | $CH_3$ | $CH{=}CH_3$ |
| 2 | $SCH_3$ | $CH_3$ |
| 2 | $CH_3$ | $SCH_3$ |
| 2 | $NO_2$ | $CH_3$ |
| 2 | $NH_2$ | $CH_3$ |
| 2 | CHO | $CH_3$ |
| 2 | $CO_2CH_3$ | H |
| 2 | $CH(OCH_3)_2$ | H |

$A = A\text{-}7;\ X = NCH_2CH_2CH_3;\ R^3 = CH_3;\ R^5 = CH_3$

| n | $R^1$ | $R^2$ |
|---|---|---|
| 2 | $CH_3$ | $CH_3$ |
| 2 | $C_2H_5$ | $CH_3$ |
| 2 | H | $CH_3$ |
| 2 | H | $C_2H_5$ |
| 2 | H | $CH_2CH_2CH_3$ |
| 2 | $OCH_3$ | $CH_3$ |
| 2 | $OCH_3$ | $C_2H_5$ |
| 2 | $CH_2CH_2CH_3$ | $CH_2CH_2CH_3$ |
| 2 | $CH_2CH{=}CH_2$ | $CH_2CH{=}CH_2$ |
| 2 | $CH_2C{\equiv}CH$ | $CH_2C{\equiv}CH$ |
| 2 | $CH(CH_3)_2$ | $CH(CH_3)_2$ |
| 2 | $-(CH_2)_5-$ | |
| | $-(CH_2)_4-$ | |
| 2 | $CH_2CH{=}CH_2$ | $C_2H_5$ |
| 2 | $CH_2C{\equiv}CH$ | $C_2H_5$ |
| 2 | $OC_2H_5$ | $CH_3$ |
| 2 | $OC_2H_5$ | $C_2H_5$ |

TABLE 7-continued

| | | |
|---|---|---|
| 2 | H | 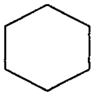 |
| 2 | 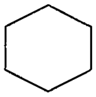 | 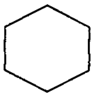 |
| 2 | H | $CH_2CH{=}CH_2$ |
| 2 | $CH_2CH_2CH_3$ | $CH_3$ |
| 0 | H | $CH_3$ |
| 1 | H | $CH_3$ |

TABLE 8

A = A-8; X = O; $R^1 = C_2H_5$; $R^2 = C_2H_5$

| n | $R^3$ | $R^5$ |
|---|---|---|
| 2 | H | H |
| 2 | H | Cl |
| 2 | H | $OCH_3$ |
| 2 | H | $CH_3$ |
| 2 | H | $C_2H_5$ |
| 2 | H | $CH(CH_3)_2$ |
| 2 | H | $CH_2CH_2CH_3$ |
| 2 | Cl | H |
| 2 | Cl | Cl |
| 2 | Cl | $OCH_3$ |
| 2 | Cl | $CH_3$ |
| 2 | Cl | $C_2H_5$ |
| 2 | Cl | $CH(CH_3)_2$ |
| 2 | Cl | $CH_2CH_2CH_3$ |
| 2 | $OCH_3$ | H |
| 2 | $OCH_3$ | Cl |
| 2 | $OCH_3$ | $OCH_3$ |
| 2 | $OCH_3$ | $CH_3$ |
| 2 | $OCH_3$ | $C_2H_5$ |
| 2 | $OCH_3$ | $CH(CH_3)_2$ |
| 2 | $OCH_3$ | $CH_2CH_2CH_3$ |
| 2 | $CH_3$ | H |
| 2 | $CH_3$ | Cl |
| 2 | $CH_3$ | $OCH_3$ |
| 2 | $CH_3$ | $CH_3$ |
| 0 | $CH_3$ | H |
| 1 | $CH_3$ | H |
| 2 | $CH_3$ | $C_2H_5$ |
| 2 | $CH_3$ | $CH(CH_3)_2$ |
| 2 | $CH_3$ | $CH_2CH_2CH_3$ |
| 2 | $C_2H_5$ | H |
| 2 | $C_2H_5$ | Cl |
| 2 | $C_2H_5$ | $OCH_3$ |
| 2 | $C_2H_5$ | $CH_3$ |
| 2 | $C_2H_5$ | $C_2H_5$ |
| 2 | $C_2H_5$ | $CH(CH_3)_2$ |
| 2 | $C_2H_5$ | $CH_2CH_2CH_3$ |
| 2 | $CH(CH_3)_2$ | H |
| 2 | $CH(CH_3)_2$ | Cl |
| 2 | $CH(CH_3)_2$ | $OCH_3$ |
| 2 | $CH(CH_3)_2$ | $CH_3$ |
| 2 | $CH(CH_3)_2$ | $C_2H_5$ |
| 2 | $CH(CH_3)_2$ | $CH(CH_3)_2$ |
| 2 | $CH(CH_3)_2$ | $CH_2CH_2CH_3$ |
| 2 | $CH_2CH_2CH_3$ | H |
| 2 | $CH_2CH_2CH_3$ | Cl |
| 2 | $CH_2CH_2CH_3$ | $OCH_3$ |
| 2 | $CH_2CH_2CH_3$ | $CH_3$ |
| 2 | $CH_2CH_2CH_3$ | $C_2H_5$ |
| 2 | $CH_2CH_2CH_3$ | $CH(CH_3)_2$ |
| 2 | $CH_2CH_2CH_3$ | $CH_2CH_2CH_3$ |
| 2 | $CH_3$ | $C_6H_5$ |

TABLE 8-continued

| | | |
|---|---|---|
| 2 | $C_6H_5$ | $CH_3$ |
| 2 | $CH_3$ | $CF_3$ |
| 2 | $CF_3$ | $CH_3$ |
| 2 | $COCH_3$ | H |
| 2 | $CH{=}CH_2$ | $CH_3$ |
| 2 | $CH_3$ | $CH{=}CH_3$ |
| 2 | $SCH_3$ | $CH_3$ |
| 2 | $CH_3$ | $SCH_3$ |
| 2 | $NO_2$ | $CH_3$ |
| 2 | $NH_2$ | $CH_3$ |
| 2 | CHO | $CH_3$ |
| 2 | $CO_2CH_3$ | H |
| 2 | $CH(OCH_3)_2$ | H |

A = A-8; X = O; $R^3 = CH_3$; $R^5 = CH_3$

| n | $R^1$ | $R^2$ |
|---|---|---|
| 2 | $CH_3$ | $CH_3$ |
| 2 | $C_2H_5$ | $CH_3$ |
| 2 | H | $CH_3$ |
| 2 | H | $C_2H_5$ |
| 2 | H | $CH_2CH_2CH_3$ |
| 2 | $OCH_3$ | $CH_3$ |
| 2 | $OCH_3$ | $C_2H_5$ |
| 2 | $CH_2CH_2CH_3$ | $CH_2CH_2CH_3$ |
| 2 | $CH_2CH{=}CH_2$ | $CH_2CH{=}CH_2$ |
| 2 | $CH_2C{\equiv}CH$ | $CH_2C{\equiv}CH$ |
| 2 | $CH(CH_3)_2$ | $CH(CH_3)_2$ |
| 2 | $-(CH_2)_5-$ | |
| | $-(CH_2)_4-$ | |
| 2 | $CH_2CH{=}CH_2$ | $C_2H_5$ |
| 2 | $CH_2C{\equiv}CH$ | $C_2H_5$ |
| 2 | $OC_2H_5$ | $CH_3$ |
| 2 | $OC_2H_5$ | $C_2H_5$ |
| 2 | H | 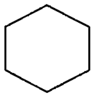 |
| 2 | 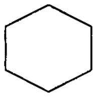 | 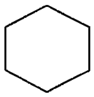 |
| 2 | H | $CH_2CH{=}CH_2$ |
| 2 | $CH_2CH_2CH_3$ | $CH_3$ |
| 0 | H | $CH_3$ |
| 1 | H | $CH_3$ |

A = A-8; X = S; $R^1 = C_2H_5$; $R^2 = C_2H_5$

| n | $R^3$ | $R^5$ |
|---|---|---|
| 2 | H | H |
| 2 | H | Cl |
| 2 | H | $OCH_3$ |
| 2 | H | $CH_3$ |
| 2 | H | $C_2H_5$ |
| 2 | H | $CH(CH_3)_2$ |
| 2 | H | $CH_2CH_2CH_3$ |
| 2 | Cl | H |
| 2 | Cl | Cl |
| 2 | Cl | $OCH_3$ |
| 2 | Cl | $CH_3$ |
| 2 | Cl | $C_2H_5$ |
| 2 | Cl | $CH(CH_3)_2$ |
| 2 | Cl | $CH_2CH_2CH_3$ |
| 2 | $OCH_3$ | H |
| 2 | $OCH_3$ | Cl |

TABLE 8-continued

| | | |
|---|---|---|
| 2 | $OCH_3$ | $OCH_3$ |
| 2 | $OCH_3$ | $CH_3$ |
| 2 | $OCH_3$ | $C_2H_5$ |
| 2 | $OCH_3$ | $CH(CH_3)_2$ |
| 2 | $OCH_3$ | $CH_2CH_2CH_3$ |
| 2 | $CH_3$ | H |
| 2 | $CH_3$ | Cl |
| 2 | $CH_3$ | $OCH_3$ |
| 2 | $CH_3$ | $CH_3$ |
| 0 | $CH_3$ | H |
| 1 | $CH_3$ | H |
| 2 | $CH_3$ | $C_2H_5$ |
| 2 | $CH_3$ | $CH(CH_3)_2$ |
| 2 | $CH_3$ | $CH_2CH_2CH_3$ |
| 2 | $C_2H_5$ | H |
| 2 | $C_2H_5$ | Cl |
| 2 | $C_2H_5$ | $OCH_3$ |
| 2 | $C_2H_5$ | $CH_3$ |
| 2 | $C_2H_5$ | $C_2H_5$ |
| 2 | $C_2H_5$ | $CH(CH_3)_2$ |
| 2 | $C_2H_5$ | $CH_2CH_2CH_3$ |
| 2 | $CH(CH_3)_2$ | H |
| 2 | $CH(CH_3)_2$ | Cl |
| 2 | $CH(CH_3)_2$ | $OCH_3$ |
| 2 | $CH(CH_3)_2$ | $CH_3$ |
| 2 | $CH(CH_3)_2$ | $C_2H_5$ |
| 2 | $CH(CH_3)_2$ | $CH(CH_3)_2$ |
| 2 | $CH(CH_3)_2$ | $CH_2CH_2CH_3$ |
| 2 | $CH_2CH_2CH_3$ | H |
| 2 | $CH_2CH_2CH_3$ | Cl |
| 2 | $CH_2CH_2CH_3$ | $OCH_3$ |
| 2 | $CH_2CH_2CH_3$ | $CH_3$ |
| 2 | $CH_2CH_2CH_3$ | $C_2H_5$ |
| 2 | $CH_2CH_2CH_3$ | $CH(CH_3)_2$ |
| 2 | $CH_2CH_2CH_3$ | $CH_2CH_2CH_3$ |
| 2 | $CH_3$ | $C_6H_5$ |
| 2 | $C_6H_5$ | $CH_3$ |
| 2 | $CH_3$ | $CF_3$ |
| 2 | $CF_3$ | $CH_3$ |
| 2 | $COCH_3$ | H |
| 2 | $CH{=}CH_2$ | $CH_3$ |
| 2 | $CH_3$ | $CH{=}CH_3$ |
| 2 | $SCH_3$ | $CH_3$ |
| 2 | $CH_3$ | $SCH_3$ |
| 2 | $NO_2$ | $CH_3$ |
| 2 | $NH_2$ | $CH_3$ |
| 2 | CHO | $CH_3$ |
| 2 | $CO_2CH_3$ | H |
| 2 | $CH(OCH_3)_2$ | H |

A = A-8; X = S; $R^3$ = $CH_3$; $R^5$ = $CH_3$

| n | $R^1$ | $R^2$ |
|---|---|---|
| 2 | $CH_3$ | $CH_3$ |
| 2 | $C_2H_5$ | $CH_3$ |
| 2 | H | $CH_3$ |
| 2 | H | $C_2H_5$ |
| 2 | H | $CH_2CH_2CH_3$ |
| 2 | $OCH_3$ | $CH_3$ |
| 2 | $OCH_3$ | $C_2H_5$ |
| 2 | $CH_2CH_2CH_3$ | $CH_2CH_2CH_3$ |
| 2 | $CH_2CH{=}CH_2$ | $CH_2CH{=}CH_2$ |
| 2 | $CH_2C{\equiv}CH$ | $CH_2C{\equiv}CH$ |
| 2 | $CH(CH_3)_2$ | $CH(CH_3)_2$ |
| 2 | $-(CH_2)_5-$ | |
| | $-(CH_2)_4-$ | |
| 2 | $CH_2CH{=}CH_2$ | $C_2H_5$ |
| 2 | $CH_2C{\equiv}CH$ | $C_2H_5$ |
| 2 | $OC_2H_5$ | $CH_3$ |
| 2 | $OC_2H_5$ | $C_2H_5$ |

TABLE 8-continued

| | | |
|---|---|---|
| 2 | H | 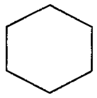 |
| 2 | 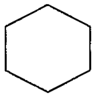 | 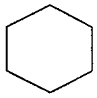 |
| 2 | H | $CH_2CH{=}CH_2$ |
| 2 | $CH_2CH_2CH_3$ | $CH_3$ |
| 0 | H | $CH_3$ |
| 1 | H | $CH_3$ |

A = A-8; X = $NCH_3$; $R^1$ = $C_2H_5$; $R^2$ = $C_2H_5$

| n | $R^3$ | $R^5$ |
|---|---|---|
| 2 | H | H |
| 2 | H | Cl |
| 2 | H | $OCH_3$ |
| 2 | H | $CH_3$ |
| 2 | H | $C_2H_5$ |
| 2 | H | $CH(CH_3)_2$ |
| 2 | H | $CH_2CH_2CH_3$ |
| 2 | Cl | H |
| 2 | Cl | Cl |
| 2 | Cl | $OCH_3$ |
| 2 | Cl | $CH_3$ |
| 2 | Cl | $C_2H_5$ |
| 2 | Cl | $CH(CH_3)_2$ |
| 2 | Cl | $CH_2CH_2CH_3$ |
| 2 | $OCH_3$ | H |
| 2 | $OCH_3$ | Cl |
| 2 | $OCH_3$ | $OCH_3$ |
| 2 | $OCH_3$ | $CH_3$ |
| 2 | $OCH_3$ | $C_2H_5$ |
| 2 | $OCH_3$ | $CH(CH_3)_2$ |
| 2 | $OCH_3$ | $CH_2CH_2CH_3$ |
| 2 | $CH_3$ | H |
| 2 | $CH_3$ | Cl |
| 2 | $CH_3$ | $OCH_3$ |
| 2 | $CH_3$ | $CH_3$ |
| 0 | $CH_3$ | H |
| 1 | $CH_3$ | H |
| 2 | $CH_3$ | $C_2H_5$ |
| 2 | $CH_3$ | $CH(CH_3)_2$ |
| 2 | $CH_3$ | $CH_2CH_2CH_3$ |
| 2 | $C_2H_5$ | H |
| 2 | $C_2H_5$ | Cl |
| 2 | $C_2H_5$ | $OCH_3$ |
| 2 | $C_2H_5$ | $CH_3$ |
| 2 | $C_2H_5$ | $C_2H_5$ |
| 2 | $C_2H_5$ | $CH(CH_3)_2$ |
| 2 | $C_2H_5$ | $CH_2CH_2CH_3$ |
| 2 | $CH(CH_3)_2$ | H |
| 2 | $CH(CH_3)_2$ | Cl |
| 2 | $CH(CH_3)_2$ | $OCH_3$ |
| 2 | $CH(CH_3)_2$ | $CH_3$ |
| 2 | $CH(CH_3)_2$ | $C_2H_5$ |
| 2 | $CH(CH_3)_2$ | $CH(CH_3)_2$ |
| 2 | $CH(CH_3)_2$ | $CH_2CH_2CH_3$ |
| 2 | $CH_2CH_2CH_3$ | H |
| 2 | $CH_2CH_2CH_3$ | Cl |
| 2 | $CH_2CH_2CH_3$ | $OCH_3$ |
| 2 | $CH_2CH_2CH_3$ | $CH_3$ |
| 2 | $CH_2CH_2CH_3$ | $C_2H_5$ |
| 2 | $CH_2CH_2CH_3$ | $CH(CH_3)_2$ |
| 2 | $CH_2CH_2CH_3$ | $CH_2CH_2CH_3$ |
| 2 | $CH_3$ | $C_6H_5$ |
| 2 | $C_6H_5$ | $CH_3$ |
| 2 | $CH_3$ | $CF_3$ |
| 2 | $CF_3$ | $CH_3$ |
| 2 | $COCH_3$ | H |
| 2 | $CH{=}CH_2$ | $CH_3$ |

TABLE 8-continued

| | | |
|---|---|---|
| 2 | $CH_3$ | $CH=CH_3$ |
| 2 | $SCH_3$ | $CH_3$ |
| 2 | $CH_3$ | $SCH_3$ |
| 2 | $NO_2$ | $CH_3$ |
| 2 | $NH_2$ | $CH_3$ |
| 2 | CHO | $CH_3$ |
| 2 | $CO_2CH_3$ | H |
| 2 | $CH(OCH_3)_2$ | H |

A = A-8; X = $NCH_3$; $R^3$ = $CH_3$; $R^5$ = $CH_3$

| n | $R^1$ | $R^2$ |
|---|---|---|
| 2 | $CH_3$ | $CH_3$ |
| 2 | $C_2H_5$ | $CH_3$ |
| 2 | H | $CH_3$ |
| 2 | H | $C_2H_5$ |
| 2 | H | $CH_2CH_2CH_3$ |
| 2 | $OCH_3$ | $CH_3$ |
| 2 | $OCH_3$ | $C_2H_5$ |
| 2 | $CH_2CH_2CH_3$ | $CH_2CH_2CH_3$ |
| 2 | $CH_2CH=CH_2$ | $CH_2CH=CH_2$ |
| 2 | $CH_2C\equiv CH$ | $CH_2C\equiv CH$ |
| 2 | $CH(CH_3)_2$ | $CH(CH_3)_2$ |
| 2 | $-(CH_2)_5-$ | |
| | $-(CH_2)_4-$ | |
| 2 | $CH_2CH=CH_2$ | $C_2H_5$ |
| 2 | $CH_2C\equiv CH$ | $C_2H_5$ |
| 2 | $OC_2H_5$ | $CH_3$ |
| 2 | $OC_2H_5$ | $C_2H_5$ |
| 2 | H | 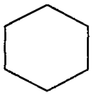 |
| 2 | 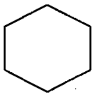 | 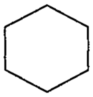 |
| 2 | H | $CH_2CH=CH_2$ |
| 2 | $CH_2CH_2CH_3$ | $CH_3$ |
| 0 | H | $CH_3$ |
| 1 | H | $CH_3$ |

A = A-8; X = $NC_2H_5$; $R^1$ = $C_2H_5$; $R^2$ = $C_2H_5$

| n | $R^3$ | $R^5$ |
|---|---|---|
| 2 | H | H |
| 2 | H | Cl |
| 2 | H | $OCH_3$ |
| 2 | H | $CH_3$ |
| 2 | H | $C_2H_5$ |
| 2 | H | $CH(CH_3)_2$ |
| 2 | H | $CH_2CH_2CH_3$ |
| 2 | Cl | H |
| 2 | Cl | Cl |
| 2 | Cl | $OCH_3$ |
| 2 | Cl | $CH_3$ |
| 2 | Cl | $C_2H_5$ |
| 2 | Cl | $CH(CH_3)_2$ |
| 2 | Cl | $CH_2CH_2CH_3$ |
| 2 | $OCH_3$ | H |
| 2 | $OCH_3$ | Cl |
| 2 | $OCH_3$ | $OCH_3$ |
| 2 | $OCH_3$ | $CH_3$ |
| 2 | $OCH_3$ | $C_2H_5$ |
| 2 | $OCH_3$ | $CH(CH_3)_2$ |
| 2 | $OCH_3$ | $CH_2CH_2CH_3$ |

TABLE 8-continued

| | | |
|---|---|---|
| 2 | $CH_3$ | H |
| 2 | $CH_3$ | Cl |
| 2 | $CH_3$ | $OCH_3$ |
| 2 | $CH_3$ | $CH_3$ |
| 0 | $CH_3$ | H |
| 1 | $CH_3$ | H |
| 2 | $CH_3$ | $C_2H_5$ |
| 2 | $CH_3$ | $CH(CH_3)_2$ |
| 2 | $CH_3$ | $CH_2CH_2CH_3$ |
| 2 | $C_2H_5$ | H |
| 2 | $C_2H_5$ | Cl |
| 2 | $C_2H_5$ | $OCH_3$ |
| 2 | $C_2H_5$ | $CH_3$ |
| 2 | $C_2H_5$ | $C_2H_5$ |
| 2 | $C_2H_5$ | $CH(CH_3)_2$ |
| 2 | $C_2H_5$ | $CH_2CH_2CH_3$ |
| 2 | $CH(CH_3)_2$ | H |
| 2 | $CH(CH_3)_2$ | Cl |
| 2 | $CH(CH_3)_2$ | $OCH_3$ |
| 2 | $CH(CH_3)_2$ | $CH_3$ |
| 2 | $CH(CH_3)_2$ | $C_2H_5$ |
| 2 | $CH(CH_3)_2$ | $CH(CH_3)_2$ |
| 2 | $CH(CH_3)_2$ | $CH_2CH_2CH_3$ |
| 2 | $CH_2CH_2CH_3$ | H |
| 2 | $CH_2CH_2CH_3$ | Cl |
| 2 | $CH_2CH_2CH_3$ | $OCH_3$ |
| 2 | $CH_2CH_2CH_3$ | $CH_3$ |
| 2 | $CH_2CH_2CH_3$ | $C_2H_5$ |
| 2 | $CH_2CH_2CH_3$ | $CH(CH_3)_2$ |
| 2 | $CH_2CH_2CH_3$ | $CH_2CH_2CH_3$ |
| 2 | $CH_3$ | $C_6H_5$ |
| 2 | $C_6H_5$ | $CH_3$ |
| 2 | $CH_3$ | $CF_3$ |
| 2 | $CF_3$ | $CH_3$ |
| 2 | $COCH_3$ | H |
| 2 | $CH=CH_2$ | $CH_3$ |
| 2 | $CH_3$ | $CH=CH_3$ |
| 2 | $SCH_3$ | $CH_3$ |
| 2 | $CH_3$ | $SCH_3$ |
| 2 | $NO_2$ | $CH_3$ |
| 2 | $NH_2$ | $CH_3$ |
| 2 | CHO | $CH_3$ |
| 2 | $CO_2CH_3$ | H |
| 2 | $CH(OCH_3)_2$ | H |

A = A-8; X = $NC_2H_5$; $R^3$ = $CH_3$; $R^5$ = $CH_3$

| n | $R^1$ | $R^2$ |
|---|---|---|
| 2 | $CH_3$ | $CH_3$ |
| 2 | $C_2H_5$ | $CH_3$ |
| 2 | H | $CH_3$ |
| 2 | H | $C_2H_5$ |
| 2 | H | $CH_2CH_2CH_3$ |
| 2 | $OCH_3$ | $CH_3$ |
| 2 | $OCH_3$ | $C_2H_5$ |
| 2 | $CH_2CH_2CH_3$ | $CH_2CH_2CH_3$ |
| 2 | $CH_2CH=CH_2$ | $CH_2CH=CH_2$ |
| 2 | $CH_2C\equiv CH$ | $CH_2C\equiv CH$ |
| 2 | $CH(CH_3)_2$ | $CH(CH_3)_2$ |
| 2 | $-(CH_2)_5-$ | |
| | $-(CH_2)_4-$ | |
| 2 | $CH_2CH=CH_2$ | $C_2H_5$ |
| 2 | $CH_2C\equiv CH$ | $C_2H_5$ |
| 2 | $OC_2H_5$ | $CH_3$ |
| 2 | $OC_2H_5$ | $C_2H_5$ |
| 2 | H | 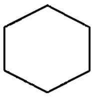 |

TABLE 8-continued

| | | |
|---|---|---|
| 2 | 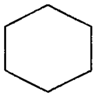 | 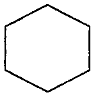 |
| 2 | H | $CH_2CH{=}CH_2$ |
| 2 | $CH_2CH_2CH_3$ | $CH_3$ |
| 0 | H | $CH_3$ |
| 1 | H | $CH_3$ |
| A = A-8; X = $NCH_2CH_2CH_3$; $R^1$ = $C_2H_5$; $R^2$ = $C_2H_5$ | | |
| n | $R^3$ | $R^5$ |
| 2 | H | H |
| 2 | H | Cl |
| 2 | H | $OCH_3$ |
| 2 | H | $CH_3$ |
| 2 | H | $C_2H_5$ |
| 2 | H | $CH(CH_3)_2$ |
| 2 | H | $CH_2CH_2CH_3$ |
| 2 | Cl | H |
| 2 | Cl | Cl |
| 2 | Cl | $OCH_3$ |
| 2 | Cl | $CH_3$ |
| 2 | Cl | $C_2H_5$ |
| 2 | Cl | $CH(CH_3)_2$ |
| 2 | Cl | $CH_2CH_2CH_3$ |
| 2 | $OCH_3$ | H |
| 2 | $OCH_3$ | Cl |
| 2 | $OCH_3$ | $OCH_3$ |
| 2 | $OCH_3$ | $CH_3$ |
| 2 | $OCH_3$ | $C_2H_5$ |
| 2 | $OCH_3$ | $CH(CH_3)_2$ |
| 2 | $OCH_3$ | $CH_2CH_2CH_3$ |
| 2 | $CH_3$ | H |
| 2 | $CH_3$ | Cl |
| 2 | $CH_3$ | $OCH_3$ |
| 2 | $CH_3$ | $CH_3$ |
| 0 | $CH_3$ | H |
| 1 | $CH_3$ | H |
| 2 | $CH_3$ | $C_2H_5$ |
| 2 | $CH_3$ | $CH(CH_3)_2$ |
| 2 | $CH_3$ | $CH_2CH_2CH_3$ |
| 2 | $C_2H_5$ | H |
| 2 | $C_2H_5$ | Cl |
| 2 | $C_2H_5$ | $OCH_3$ |
| 2 | $C_2H_5$ | $CH_3$ |
| 2 | $C_2H_5$ | $C_2H_5$ |
| 2 | $C_2H_5$ | $CH(CH_3)_2$ |
| 2 | $C_2H_5$ | $CH_2CH_2CH_3$ |
| 2 | $CH(CH_3)_2$ | H |
| 2 | $CH(CH_3)_2$ | Cl |
| 2 | $CH(CH_3)_2$ | $OCH_3$ |
| 2 | $CH(CH_3)_2$ | $CH_3$ |
| 2 | $CH(CH_3)_2$ | $C_2H_5$ |
| 2 | $CH(CH_3)_2$ | $CH(CH_3)_2$ |
| 2 | $CH(CH_3)_2$ | $CH_2CH_2CH_3$ |
| 2 | $CH_2CH_2CH_3$ | H |
| 2 | $CH_2CH_2CH_3$ | Cl |
| 2 | $CH_2CH_2CH_3$ | $OCH_3$ |
| 2 | $CH_2CH_2CH_3$ | $CH_3$ |
| 2 | $CH_2CH_2CH_3$ | $C_2H_5$ |
| 2 | $CH_2CH_2CH_3$ | $CH(CH_3)_2$ |
| 2 | $CH_2CH_2CH_3$ | $CH_2CH_2CH_3$ |
| 2 | $CH_3$ | $C_6H_5$ |
| 2 | $C_6H_5$ | $CH_3$ |
| 2 | $CH_3$ | $CF_3$ |
| 2 | $CF_3$ | $CH_3$ |
| 2 | $COCH_3$ | H |
| 2 | $CH{=}CH_2$ | $CH_3$ |
| 2 | $CH_3$ | $CH{=}CH_3$ |
| 2 | $SCH_3$ | $CH_3$ |
| 2 | $CH_3$ | $SCH_3$ |
| 2 | $NO_2$ | $CH_3$ |

TABLE 8-continued

| | | |
|---|---|---|
| 2 | $NH_2$ | $CH_3$ |
| 2 | CHO | $CH_3$ |
| 2 | $CO_2CH_3$ | H |
| 2 | $CH(OCH_3)_2$ | H |
| A = A-8; X = $NCH_2CH_2CH_3$; $R^3$ = $CH_3$; $R^5$ = $CH_3$ | | |
| n | $R^1$ | $R^2$ |
| 2 | $CH_3$ | $CH_3$ |
| 2 | $C_2H_5$ | $CH_3$ |
| 2 | H | $CH_3$ |
| 2 | H | $C_2H_5$ |
| 2 | H | $CH_2CH_2CH_3$ |
| 2 | $OCH_3$ | $CH_3$ |
| 2 | $OCH_3$ | $C_2H_5$ |
| 2 | $CH_2CH_2CH_3$ | $CH_2CH_2CH_3$ |
| 2 | $CH_2CH{=}CH_2$ | $CH_2CH{=}CH_2$ |
| 2 | $CH_2C{\equiv}CH$ | $CH_2C{\equiv}CH$ |
| 2 | $CH(CH_3)_2$ | $CH(CH_3)_2$ |
| 2 | $-(CH_2)_5-$ | |
| | $-(CH_2)_4-$ | |
| 2 | $CH_2CH{=}CH_2$ | $C_2H_5$ |
| 2 | $CH_2C{\equiv}CH$ | $C_2H_5$ |
| 2 | $OC_2H_5$ | $CH_3$ |
| 2 | $OC_2H_5$ | $C_2H_5$ |
| 2 | H | 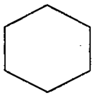 |
| 2 | 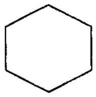 | 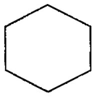 |
| 2 | H | $CH_2CH{=}CH_2$ |
| 2 | $CH_2CH_2CH_3$ | $CH_3$ |
| 0 | H | $CH_3$ |
| 1 | H | $CH_3$ |

TABLE 9

| | | |
|---|---|---|
| A = A-9; $R^1$ = $C_2H_5$; $R^2$ = $C_2H_5$ | | |
| n | $R^3$ | X |
| 2 | H | O |
| 2 | H | S |
| 2 | H | $NCH_3$ |
| 2 | H | $NC_2H_5$ |
| 2 | H | $NCH_2CH_2CH_3$ |
| 2 | Cl | O |
| 2 | Cl | S |
| 2 | Cl | $NCH_3$ |
| 2 | Cl | $NC_2H_5$ |
| 2 | Cl | $NCH_2CH_2CH_3$ |
| 2 | $OCH_3$ | O |
| 2 | $OCH_3$ | S |
| 2 | $OCH_3$ | $NCH_3$ |
| 2 | $OCH_3$ | $NC_2H_5$ |
| 2 | $OCH_3$ | $NCH_2CH_2CH_3$ |
| 2 | $CH_3$ | O |
| 2 | $CH_3$ | S |
| 2 | $CH_3$ | $NCH_3$ |
| 2 | $CH_3$ | $NC_2H_5$ |
| 2 | $CH_3$ | $NCH_2CH_2CH_3$ |

TABLE 9-continued

| A = A-9; $R^1 = C_2H_5$; $R^2 = C_2H_5$ | | |
|---|---|---|
| n | $R^3$ | X |
| 2 | $C_2H_5$ | O |
| 2 | $C_2H_5$ | S |
| 2 | $C_2H_5$ | $NCH_3$ |
| 2 | $C_2H_5$ | $NC_2H_5$ |
| 2 | $C_2H_5$ | $NCH_2CH_2CH_3$ |
| 2 | $CH(CH_3)_2$ | O |
| 2 | $CH(CH_3)_2$ | S |
| 2 | $CH(CH_3)_2$ | $NCH_3$ |
| 2 | $CH(CH_3)_2$ | $NC_2H_5$ |
| 2 | $CH(CH_3)_2$ | $NCH_2CH_2CH_3$ |
| 2 | $CH_2CH_2CH_3$ | O |
| 2 | $CH_2CH_2CH_3$ | S |
| 2 | $CH_2CH_2CH_3$ | $NCH_3$ |
| 2 | $CH_2CH_2CH_3$ | $NC_2H_5$ |
| 2 | $CH_2CH_2CH_3$ | $NCH_2CH_2CH_3$ |
| 0 | $CH_3$ | $NCH_3$ |
| 1 | $CH_3$ | $NCH_3$ |

TABLE 10

| A = A-10; $R^1 = C_2H_5$; $R^2 = C_2H_5$ | | |
|---|---|---|
| n | $R^3$ | X |
| 2 | H | O |
| 2 | H | S |
| 2 | H | $NCH_3$ |
| 2 | H | $NC_2H_5$ |
| 2 | H | $NCH_2CH_2CH_3$ |
| 2 | Cl | O |
| 2 | Cl | S |
| 2 | Cl | $NCH_3$ |
| 2 | Cl | $NC_2H_5$ |
| 2 | Cl | $NCH_2CH_2CH_3$ |
| 2 | $OCH_3$ | O |
| 2 | $OCH_3$ | S |
| 2 | $OCH_3$ | $NCH_3$ |
| 2 | $OCH_3$ | $NC_2H_5$ |
| 2 | $OCH_3$ | $NCH_2CH_2CH_3$ |
| 2 | $CH_3$ | O |
| 2 | $CH_3$ | S |
| 2 | $CH_3$ | $NCH_3$ |
| 2 | $CH_3$ | $NC_2H_5$ |
| 2 | $CH_3$ | $NCH_2CH_2CH_3$ |
| 2 | $C_2H_5$ | O |
| 2 | $C_2H_5$ | S |
| 2 | $C_2H_5$ | $NCH_3$ |
| 2 | $C_2H_5$ | $NC_2H_5$ |
| 2 | $C_2H_5$ | $NCH_2CH_2CH_3$ |
| 2 | $CH(CH_3)_2$ | O |
| 2 | $CH(CH_3)_2$ | S |
| 2 | $CH(CH_3)_2$ | $NCH_3$ |
| 2 | $CH(CH_3)_2$ | $NC_2H_5$ |
| 2 | $CH(CH_3)_2$ | $NCH_2CH_2CH_3$ |
| 2 | $CH_2CH_2CH_3$ | O |
| 2 | $CH_2CH_2CH_3$ | S |
| 2 | $CH_2CH_2CH_3$ | $NCH_3$ |
| 2 | $CH_2CH_2CH_3$ | $NC_2H_5$ |
| 2 | $CH_2CH_2CH_3$ | $NCH_2CH_2CH_3$ |
| 0 | $CH_3$ | $NCH_3$ |
| 1 | $CH_3$ | $NCH_3$ |

TABLE 11

| A = A-11; $R^1 = C_2H_5$; $R^2 = C_2H_5$ | | |
|---|---|---|
| n | $R^3$ | X |
| 2 | H | O |
| 2 | H | S |
| 2 | H | $NCH_3$ |
| 2 | H | $NC_2H_5$ |

TABLE 11-continued

| A = A-11; $R^1 = C_2H_5$; $R^2 = C_2H_5$ | | |
|---|---|---|
| n | $R^3$ | X |
| 2 | H | $NCH_2CH_2CH_3$ |
| 2 | Cl | O |
| 2 | Cl | S |
| 2 | Cl | $NCH_3$ |
| 2 | Cl | $NC_2H_5$ |
| 2 | Cl | $NCH_2CH_2CH_3$ |
| 2 | $OCH_3$ | O |
| 2 | $OCH_3$ | S |
| 2 | $OCH_3$ | $NCH_3$ |
| 2 | $OCH_3$ | $NC_2H_5$ |
| 2 | $OCH_3$ | $NCH_2CH_2CH_3$ |
| 2 | $CH_3$ | O |
| 2 | $CH_3$ | S |
| 2 | $CH_3$ | $NCH_3$ |
| 2 | $CH_3$ | $NC_2H_5$ |
| 2 | $CH_3$ | $NCH_2CH_2CH_3$ |
| 2 | $C_2H_5$ | O |
| 2 | $C_2H_5$ | S |
| 2 | $C_2H_5$ | $NCH_3$ |
| 2 | $C_2H_5$ | $NC_2H_5$ |
| 2 | $C_2H_5$ | $NCH_2CH_2CH_3$ |
| 2 | $CH(CH_3)_2$ | O |
| 2 | $CH(CH_3)_2$ | S |
| 2 | $CH(CH_3)_2$ | $NCH_3$ |
| 2 | $CH(CH_3)_2$ | $NC_2H_5$ |
| 2 | $CH(CH_3)_2$ | $NCH_2CH_2CH_3$ |
| 2 | $CH_2CH_2CH_3$ | O |
| 2 | $CH_2CH_2CH_3$ | S |
| 2 | $CH_2CH_2CH_3$ | $NCH_3$ |
| 2 | $CH_2CH_2CH_3$ | $NC_2H_5$ |
| 2 | $CH_2CH_2CH_3$ | $NCH_2CH_2CH_3$ |
| 0 | $CH_3$ | $NCH_3$ |
| 1 | $CH_3$ | $NCH_3$ |

TABLE 12

| A = A-12; $R^1 = C_2H_5$; $R^2 = C_2H_5$ | | |
|---|---|---|
| n | $R^5$ | X |
| 2 | H | O |
| 2 | H | S |
| 2 | H | $NCH_3$ |
| 2 | H | $NC_2H_5$ |
| 2 | H | $NCH_2CH_2CH_3$ |
| 2 | Cl | O |
| 2 | Cl | S |
| 2 | Cl | $NCH_3$ |
| 2 | Cl | $NC_2H_5$ |
| 2 | Cl | $NCH_2CH_2CH_3$ |
| 2 | $OCH_3$ | O |
| 2 | $OCH_3$ | S |
| 2 | $OCH_3$ | $NCH_3$ |
| 2 | $OCH_3$ | $NC_2H_5$ |
| 2 | $OCH_3$ | $NCH_2CH_2CH_3$ |
| 2 | $CH_3$ | O |
| 2 | $CH_3$ | S |
| 2 | $CH_3$ | $NCH_3$ |
| 2 | $CH_3$ | $NC_2H_5$ |
| 2 | $CH_3$ | $NCH_2CH_2CH_3$ |
| 2 | $C_2H_5$ | O |
| 2 | $C_2H_5$ | S |
| 2 | $C_2H_5$ | $NCH_3$ |
| 2 | $C_2H_5$ | $NC_2H_5$ |
| 2 | $C_2H_5$ | $NCH_2CH_2CH_3$ |
| 2 | $CH(CH_3)_2$ | O |
| 2 | $CH(CH_3)_2$ | S |
| 2 | $CH(CH_3)_2$ | $NCH_3$ |
| 2 | $CH(CH_3)_2$ | $NC_2H_5$ |
| 2 | $CH(CH_3)_2$ | $NCH_2CH_2CH_3$ |
| 2 | $CH_2CH_2CH_3$ | O |
| 2 | $CH_2CH_2CH_3$ | S |
| 2 | $CH_2CH_2CH_3$ | $NCH_3$ |

TABLE 12-continued

| A = A-12; $R^1 = C_2H_5$; $R^2 = C_2H_5$ | | |
|---|---|---|
| n | $R^5$ | X |
| 2 | $CH_2CH_2CH_3$ | $NC_2H_5$ |
| 2 | $CH_2CH_2CH_3$ | $NCH_2CH_2CH_3$ |
| 0 | $CH_3$ | $NCH_3$ |
| 1 | $CH_3$ | $NCH_3$ |

TABLE 13

| A = A-13; $R^1 = C_2H_5$; $R^2 = C_2H_5$ | | |
|---|---|---|
| n | $R^5$ | X |
| 2 | H | O |
| 2 | H | S |
| 2 | H | $NCH_3$ |
| 2 | H | $NC_2H_5$ |
| 2 | H | $NCH_2CH_2CH_3$ |
| 2 | Cl | O |
| 2 | Cl | S |
| 2 | Cl | $NCH_3$ |
| 2 | Cl | $NC_2H_5$ |
| 2 | Cl | $NCH_2CH_2CH_3$ |
| 2 | $OCH_3$ | O |
| 2 | $OCH_3$ | S |
| 2 | $OCH_3$ | $NCH_3$ |
| 2 | $OCH_3$ | $NC_2H_5$ |
| 2 | $OCH_3$ | $NCH_2CH_2CH_3$ |
| 2 | $CH_3$ | O |
| 2 | $CH_3$ | S |
| 2 | $CH_3$ | $NCH_3$ |
| 2 | $CH_3$ | $NC_2H_5$ |
| 2 | $CH_3$ | $NCH_2CH_2CH_3$ |
| 2 | $C_2H_5$ | O |
| 2 | $C_2H_5$ | S |
| 2 | $C_2H_5$ | $NCH_3$ |
| 2 | $C_2H_5$ | $NC_2H_5$ |
| 2 | $C_2H_5$ | $NCH_2CH_2CH_3$ |
| 2 | $CH(CH_3)_2$ | O |
| 2 | $CH(CH_3)_2$ | S |
| 2 | $CH(CH_3)_2$ | $NCH_3$ |
| 2 | $CH(CH_3)_2$ | $NC_2H_5$ |
| 2 | $CH(CH_3)_2$ | $NCH_2CH_2CH_3$ |
| 2 | $CH_2CH_2CH_3$ | O |
| 2 | $CH_2CH_2CH_3$ | S |
| 2 | $CH_2CH_2CH_3$ | $NCH_3$ |
| 2 | $CH_2CH_2CH_3$ | $NC_2H_5$ |
| 2 | $CH_2CH_2CH_3$ | $NCH_2CH_2CH_3$ |
| 0 | $CH_3$ | $NCH_3$ |
| 1 | $CH_3$ | $NCH_3$ |

TABLE 14

| A = A-14; $R^1 = C_2H_5$; $R^2 = C_2H_5$ | | |
|---|---|---|
| n | $R^5$ | X |
| 2 | H | O |
| 2 | H | S |
| 2 | H | $NCH_3$ |
| 2 | H | $NC_2H_5$ |
| 2 | H | $NCH_2CH_2CH_3$ |
| 2 | Cl | O |
| 2 | Cl | S |
| 2 | Cl | $NCH_3$ |
| 2 | Cl | $NC_2H_5$ |
| 2 | Cl | $NCH_2CH_2CH_3$ |
| 2 | $OCH_3$ | O |
| 2 | $OCH_3$ | S |
| 2 | $OCH_3$ | $NCH_3$ |
| 2 | $OCH_3$ | $NC_2H_5$ |
| 2 | $OCH_3$ | $NCH_2CH_2CH_3$ |
| 2 | $CH_3$ | O |
| 2 | $CH_3$ | S |

TABLE 14-continued

| A = A-14; $R^1 = C_2H_5$; $R^2 = C_2H_5$ | | |
|---|---|---|
| n | $R^5$ | X |
| 2 | $CH_3$ | $NCH_3$ |
| 2 | $CH_3$ | $NC_2H_5$ |
| 2 | $CH_3$ | $NCH_2CH_2CH_3$ |
| 2 | $C_2H_5$ | O |
| 2 | $C_2H_5$ | S |
| 2 | $C_2H_5$ | $NCH_3$ |
| 2 | $C_2H_5$ | $NC_2H_5$ |
| 2 | $C_2H_5$ | $NCH_2CH_2CH_3$ |
| 2 | $CH(CH_3)_2$ | O |
| 2 | $CH(CH_3)_2$ | S |
| 2 | $CH(CH_3)_2$ | $NCH_3$ |
| 2 | $CH(CH_3)_2$ | $NC_2H_5$ |
| 2 | $CH(CH_3)_2$ | $NCH_2CH_2CH_3$ |
| 2 | $CH_2CH_2CH_3$ | O |
| 2 | $CH_2CH_2CH_3$ | S |
| 2 | $CH_2CH_2CH_3$ | $NCH_3$ |
| 2 | $CH_2CH_2CH_3$ | $NC_2H_5$ |
| 2 | $CH_2CH_2CH_3$ | $NCH_2CH_2CH_3$ |
| 0 | $CH_3$ | $NCH_3$ |
| 1 | $CH_3$ | $NCH_3$ |

TABLE 15

| A = A-15; $R^1 = C_2H_5$; $R^2 = C_2H_5$ | | | |
|---|---|---|---|
| n | $R^3$ | $R^4$ | $R^5$ |
| 2 | H | H | H |
| 2 | H | H | $CH_3$ |
| 2 | H | H | $C_2H_5$ |
| 2 | H | H | $CH_2CH_2CH_3$ |
| 2 | H | Cl | H |
| 2 | H | Cl | $CH_3$ |
| 2 | H | Cl | $C_2H_5$ |
| 2 | H | Cl | $CH_2CH_2CH_3$ |
| 2 | H | $OCH_3$ | H |
| 2 | H | $OCH_3$ | $CH_3$ |
| 2 | H | $OCH_3$ | $C_2H_5$ |
| 2 | H | $OCH_3$ | $CH_2CH_2CH_3$ |
| 2 | H | $CH_3$ | H |
| 2 | H | $CH_3$ | $CH_3$ |
| 2 | H | $CH_3$ | $C_2H_5$ |
| 2 | H | $CH_3$ | $CH_2CH_2CH_3$ |
| 2 | H | $C_2H_5$ | H |
| 2 | H | $C_2H_5$ | $CH_3$ |
| 2 | H | $C_2H_5$ | $C_2H_5$ |
| 2 | H | $C_2H_5$ | $CH_2CH_2CH_3$ |
| 2 | H | $CH(CH_3)_2$ | H |
| 2 | H | $CH(CH_3)_2$ | $CH_3$ |
| 2 | H | $CH(CH_3)_2$ | $C_2H_5$ |
| 2 | H | $CH(CH_3)_2$ | $CH_2CH_2CH_3$ |
| 2 | H | $CH_2CH_2CH_3$ | H |
| 2 | H | $CH_2CH_2CH_3$ | $CH_3$ |
| 2 | H | $CH_2CH_2CH_3$ | $C_2H_5$ |
| 2 | H | $CH_2CH_2CH_3$ | $CH_2CH_2CH_3$ |
| 2 | Cl | H | $CH_3$ |
| 2 | Cl | H | $C_2H_5$ |
| 2 | Cl | H | $CH_2CH_2CH_3$ |
| 2 | Cl | Cl | H |
| 2 | Cl | Cl | $CH_3$ |
| 2 | Cl | Cl | $C_2H_5$ |
| 2 | Cl | Cl | $CH_2CH_2CH_3$ |
| 2 | Cl | $OCH_3$ | H |
| 2 | Cl | $OCH_3$ | $CH_3$ |
| 2 | Cl | $OCH_3$ | $C_2H_5$ |
| 2 | Cl | $OCH_3$ | $CH_2CH_2CH_3$ |
| 2 | Cl | $CH_3$ | H |
| 2 | Cl | $CH_3$ | $CH_3$ |
| 2 | Cl | $CH_3$ | $C_2H_5$ |
| 2 | Cl | $CH_3$ | $CH_2CH_2CH_3$ |
| 2 | Cl | $C_2H_5$ | H |
| 2 | Cl | $C_2H_5$ | $CH_3$ |
| 2 | Cl | $C_2H_5$ | $C_2H_5$ |

TABLE 15-continued

| | | | |
|---|---|---|---|
| 2 | Cl | $C_2H_5$ | $CH_2CH_2CH_3$ |
| 2 | Cl | $CH(CH_3)_2$ | H |
| 2 | Cl | $CH(CH_3)_2$ | $CH_3$ |
| 2 | Cl | $CH(CH_3)_2$ | $C_2H_5$ |
| 2 | Cl | $CH(CH_3)_2$ | $CH_2CH_2CH_3$ |
| 2 | Cl | $CH_2CH_2CH_3$ | H |
| 2 | Cl | $CH_2CH_2CH_3$ | $CH_3$ |
| 2 | Cl | $CH_2CH_2CH_3$ | $C_2H_5$ |
| 2 | Cl | $CH_2CH_2CH_3$ | $CH_2CH_2CH_3$ |
| 2 | $OCH_3$ | H | $CH_3$ |
| 2 | $OCH_3$ | H | $C_2H_5$ |
| 2 | $OCH_3$ | H | $CH_2CH_2CH_3$ |
| 2 | $OCH_3$ | Cl | $CH_3$ |
| 2 | $OCH_3$ | Cl | $C_2H_5$ |
| 2 | $OCH_3$ | Cl | $CH_2CH_2CH_3$ |
| 2 | $OCH_3$ | $OCH_3$ | H |
| 2 | $OCH_3$ | $OCH_3$ | $CH_3$ |
| 2 | $OCH_3$ | $OCH_3$ | $C_2H_5$ |
| 2 | $OCH_3$ | $OCH_3$ | $CH_2CH_2CH_3$ |
| 2 | $OCH_3$ | $CH_3$ | H |
| 2 | $OCH_3$ | $CH_3$ | $CH_3$ |
| 2 | $OCH_3$ | $CH_3$ | $C_2H_5$ |
| 2 | $OCH_3$ | $CH_3$ | $CH_2CH_2CH_3$ |
| 2 | $OCH_3$ | $C_2H_5$ | H |
| 2 | $OCH_3$ | $C_2H_5$ | $CH_3$ |
| 2 | $OCH_3$ | $C_2H_5$ | $C_2H_5$ |
| 2 | $OCH_3$ | $C_2H_5$ | $CH_2CH_2CH_3$ |
| 2 | $OCH_3$ | $CH(CH_3)_2$ | H |
| 2 | $OCH_3$ | $CH(CH_3)_2$ | $CH_3$ |
| 2 | $OCH_3$ | $CH(CH_3)_2$ | $C_2H_5$ |
| 2 | $OCH_3$ | $CH(CH_3)_2$ | $CH_2CH_2CH_3$ |
| 2 | $OCH_3$ | $CH_2CH_2CH_3$ | H |
| 2 | $OCH_3$ | $CH_2CH_2CH_3$ | $CH_3$ |
| 2 | $OCH_3$ | $CH_2CH_2CH_3$ | $C_2H_5$ |
| 2 | $OCH_3$ | $CH_2CH_2CH_3$ | $CH_2CH_2CH_3$ |
| 2 | $CH_3$ | H | $CH_3$ |
| 2 | $CH_3$ | H | $C_2H_5$ |
| 2 | $CH_3$ | H | $CH_2CH_2CH_3$ |
| 2 | $CH_3$ | Cl | $CH_3$ |
| 2 | $CH_3$ | Cl | $C_2H_5$ |
| 2 | $CH_3$ | Cl | $CH_2CH_2CH_3$ |
| 2 | $CH_3$ | $OCH_3$ | $CH_3$ |
| 2 | $CH_3$ | $OCH_3$ | $C_2H_5$ |
| 2 | $CH_3$ | $OCH_3$ | $CH_2CH_2CH_3$ |
| 2 | $CH_3$ | $CH_3$ | H |
| 2 | $CH_3$ | $CH_3$ | $CH_3$ |
| 2 | $CH_3$ | $CH_3$ | $C_2H_5$ |
| 2 | $CH_3$ | $CH_3$ | $CH_2CH_2CH_3$ |
| 2 | $CH_3$ | $C_2H_5$ | H |
| 2 | $CH_3$ | $C_2H_5$ | $CH_3$ |
| 2 | $CH_3$ | $C_2H_5$ | $C_2H_5$ |
| 2 | $CH_3$ | $C_2H_5$ | $CH_2CH_2CH_3$ |
| 2 | $CH_3$ | $CH(CH_3)_2$ | H |
| 2 | $CH_3$ | $CH(CH_3)_2$ | $CH_3$ |
| 2 | $CH_3$ | $CH(CH_3)_2$ | $C_2H_5$ |
| 2 | $CH_3$ | $CH(CH_3)_2$ | $CH_2CH_2CH_3$ |
| 2 | $CH_3$ | $CH_2CH_2CH_3$ | H |
| 2 | $CH_3$ | $CH_2CH_2CH_3$ | $CH_3$ |
| 2 | $CH_3$ | $CH_2CH_2CH_3$ | $C_2H_5$ |
| 2 | $CH_3$ | $CH_2CH_2CH_3$ | $CH_2CH_2CH_3$ |
| 2 | $C_2H_5$ | H | $CH_3$ |
| 2 | $C_2H_5$ | H | $C_2H_5$ |
| 2 | $C_2H_5$ | H | $CH_2CH_2CH_3$ |
| 2 | $C_2H_5$ | Cl | $CH_3$ |
| 2 | $C_2H_5$ | Cl | $C_2H_5$ |
| 2 | $C_2H_5$ | Cl | $CH_2CH_2CH_3$ |
| 2 | $C_2H_5$ | $OCH_3$ | $CH_3$ |
| 2 | $C_2H_5$ | $OCH_3$ | $C_2H_5$ |
| 2 | $C_2H_5$ | $OCH_3$ | $CH_2CH_2CH_3$ |
| 2 | $C_2H_5$ | $CH_3$ | $CH_3$ |
| 2 | $C_2H_5$ | $CH_3$ | $C_2H_5$ |
| 2 | $C_2H_5$ | $CH_3$ | $CH_2CH_2CH_3$ |
| 2 | $C_2H_5$ | $C_2H_5$ | H |
| 2 | $C_2H_5$ | $C_2H_5$ | $CH_3$ |
| 2 | $C_2H_5$ | $C_2H_5$ | $C_2H_5$ |
| 2 | $C_2H_5$ | $C_2H_5$ | $CH_2CH_2CH_3$ |
| 2 | $C_2H_5$ | $CH(CH_3)_2$ | H |
| 2 | $C_2H_5$ | $CH(CH_3)_2$ | $CH_3$ |
| 2 | $C_2H_5$ | $CH(CH_3)_2$ | $C_2H_5$ |

TABLE 15-continued

| | | | |
|---|---|---|---|
| 2 | $C_2H_5$ | $CH(CH_3)_2$ | $CH_2CH_2CH_3$ |
| 2 | $C_2H_5$ | $CH_2CH_2CH_3$ | H |
| 2 | $C_2H_5$ | $CH_2CH_2CH_3$ | $CH_3$ |
| 2 | $C_2H_5$ | $CH_2CH_2CH_3$ | $C_2H_5$ |
| 2 | $C_2H_5$ | $CH_2CH_2CH_3$ | $CH_2CH_2CH_3$ |
| 2 | $CH(CH_3)_2$ | H | $CH_3$ |
| 2 | $CH(CH_3)_2$ | H | $C_2H_5$ |
| 2 | $CH(CH_3)_2$ | H | $CH_2CH_2CH_3$ |
| 2 | $CH(CH_3)_2$ | Cl | $CH_3$ |
| 2 | $CH(CH_3)_2$ | Cl | $C_2H_5$ |
| 2 | $CH(CH_3)_2$ | Cl | $CH_2CH_2CH_3$ |
| 2 | $CH(CH_3)_2$ | $OCH_3$ | $CH_3$ |
| 2 | $CH(CH_3)_2$ | $OCH_3$ | $C_2H_5$ |
| 2 | $CH(CH_3)_2$ | $OCH_3$ | $CH_2CH_2CH_3$ |
| 2 | $CH(CH_3)_2$ | $CH_3$ | $CH_3$ |
| 2 | $CH(CH_3)_2$ | $CH_3$ | $C_2H_5$ |
| 2 | $CH(CH_3)_2$ | $CH_3$ | $CH_2CH_2CH_3$ |
| 2 | $CH(CH_3)_2$ | $C_2H_5$ | $CH_3$ |
| 2 | $CH(CH_3)_2$ | $C_2H_5$ | $C_2H_5$ |
| 2 | $CH(CH_3)_2$ | $C_2H_5$ | $CH_2CH_2CH_3$ |
| 2 | $CH(CH_3)_2$ | $CH(CH_3)_2$ | H |
| 2 | $CH(CH_3)_2$ | $CH(CH_3)_2$ | $CH_3$ |
| 2 | $CH(CH_3)_2$ | $CH(CH_3)_2$ | $C_2H_5$ |
| 2 | $CH(CH_3)_2$ | $CH(CH_3)_2$ | $CH_2CH_2CH_3$ |
| 2 | $CH(CH_3)_2$ | $CH_2CH_2CH_3$ | H |
| 2 | $CH(CH_3)_2$ | $CH_2CH_2CH_3$ | $CH_3$ |
| 2 | $CH(CH_3)_2$ | $CH_2CH_2CH_3$ | $C_2H_5$ |
| 2 | $CH(CH_3)_2$ | $CH_2CH_2CH_3$ | $CH_2CH_2CH_3$ |
| 2 | $CH_2CH_2CH_3$ | H | $CH_3$ |
| 2 | $CH_2CH_2CH_3$ | H | $C_2H_5$ |
| 2 | $CH_2CH_2CH_3$ | H | $CH_2CH_2CH_3$ |
| 2 | $CH_2CH_2CH_3$ | Cl | $CH_3$ |
| 2 | $CH_2CH_2CH_3$ | Cl | $C_2H_5$ |
| 2 | $CH_2CH_2CH_3$ | Cl | $CH_2CH_2CH_3$ |
| 2 | $CH_2CH_2CH_3$ | $OCH_3$ | $CH_3$ |
| 2 | $CH_2CH_2CH_3$ | $OCH_3$ | $C_2H_5$ |
| 2 | $CH_2CH_2CH_3$ | $OCH_3$ | $CH_2CH_2CH_3$ |
| 2 | $CH_2CH_2CH_3$ | $CH_3$ | $CH_3$ |
| 2 | $CH_2CH_2CH_3$ | $CH_3$ | $C_2H_5$ |
| 2 | $CH_2CH_2CH_3$ | $CH_3$ | $CH_2CH_2CH_3$ |
| 2 | $CH_2CH_2CH_3$ | $C_2H_5$ | $CH_3$ |
| 2 | $CH_2CH_2CH_3$ | $C_2H_5$ | $C_2H_5$ |
| 2 | $CH_2CH_2CH_3$ | $C_2H_5$ | $CH_2CH_2CH_3$ |
| 2 | $CH_2CH_2CH_3$ | $CH(CH_3)_2$ | $CH_3$ |
| 2 | $CH_2CH_2CH_3$ | $CH(CH_3)_2$ | $C_2H_5$ |
| 2 | $CH_2CH_2CH_3$ | $CH(CH_3)_2$ | $CH_2CH_2CH_3$ |
| 2 | $CH_2CH_2CH_3$ | $CH_2CH_2CH_3$ | H |
| 2 | $CH_2CH_2CH_3$ | $CH_2CH_2CH_3$ | $CH_3$ |
| 2 | $CH_2CH_2CH_3$ | $CH_2CH_2CH_3$ | $C_2H_5$ |
| 2 | $CH_2CH_2CH_3$ | $CH_2CH_2CH_3$ | $CH_2CH_2CH_3$ |
| 2 | $CH_3$ | $CH_3$ | Cl |
| 2 | $CH_3$ | $CH_3$ | $OCH_3$ |
| 2 | $CH_3$ | $CH_3$ | F |
| 2 | $CH_3$ | $CH_3$ | Br |
| 2 | $CH_3$ | $CH_3$ | $-COCH_3$ |
| 2 | $CH_3$ | $CH_3$ | $CO_2CH_3$ |
| 2 | $CH_3$ | $CH_3$ | $CO_2C_2H_5$ |
| 2 | $CH_3$ | $CH_3$ | $CH_2OCH_3$ |
| 2 | $CH_3$ | $CH_3$ | $CON(CH_3)_2$ |
| 2 | $CH_3$ | $CH_3$ | $SCH_3$ |
| 2 | $CH_3$ | $CH_3$ | $SO_2CH_3$ |
| 2 | $CH_3$ | $CH_3$ | $NO_2$ |
| 2 | $CH_3$ | $CH_3$ | $N(CH_3)_2$ |
| 2 | $CH_3$ | $CH_3$ | $NH_2$ |
| 2 | $CH_3$ | $CH_3$ | $C_6H_5$ |
| 2 | $CH_3$ | $C_6H_5$ | H |
| 2 | $CH_3$ | $CF_3$ | H |
| 2 | $COCH_3$ | H | H |
| 2 | $CH=CH_2$ | $CH_3$ | H |
| 2 | $SCH_3$ | $CH_3$ | H |
| 2 | $NO_2$ | $CH_3$ | H |
| 2 | $NH_2$ | $CH_3$ | H |
| 2 | CHO | $CH_3$ | H |
| 2 | $CO_2CH_3$ | H | H |
| 2 | $CH(OCH_3)_2$ | H | H |
| 2 | $COCH_3$ | H | Cl |
| 2 | $C_2H_5$ | H | Cl |
| 2 | $CO_2CH_3$ | H | Cl |

TABLE 15-continued

| A = A-15; $R^3 = CH_3$; $R^4 = CH_3$ | | | |
|---|---|---|---|
| n | $R^1$ | $R^2$ | $R^5$ |
| 2 | $CH_3$ | $CH_3$ | H |
| 2 | $C_2H_5$ | $CH_3$ | H |
| 2 | H | $CH_3$ | H |
| 2 | H | $C_2H_5$ | H |
| 2 | H | $CH_2CH_2CH_3$ | H |
| 2 | $OCH_3$ | $CH_3$ | H |
| 2 | $OCH_3$ | $C_2H_5$ | H |
| 2 | $CH_2CH_2CH_3$ | $CH_2CH_2CH_3$ | H |
| 2 | $CH_2CH{=}CH_2$ | $CH_2CH{=}CH_2$ | H |
| 2 | $CH_2C{\equiv}CH$ | $CH_2C{\equiv}CH$ | H |
| 2 | $CH(CH_3)_2$ | $CH(CH_3)_2$ | H |
| 2 | $-(CH_2)_5-$ | | H |
| 2 | $-(CH_2)_4-$ | | H |
| 2 | $CH_2CH{=}CH_2$ | $C_2H_5$ | H |
| 2 | $CH_2C{\equiv}CH$ | $C_2H_5$ | H |
| 2 | $OC_2H_5$ | $CH_3$ | H |
| 2 | $OC_2H_5$ | $C_2H_5$ | H |
| 2 | H | 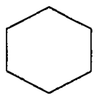 | H |
| 2 | 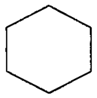 | 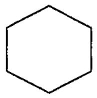 | H |
| 2 | H | $CH_2CH{=}CH_2$ | H |
| 2 | $CH_2CH_2CH_3$ | $CH_3$ | H |
| 2 | $CH_2CH{=}CH_2$ | $CH_3$ | $CH_3$ |
| 2 | $CH_2CH{=}CH_2$ | $C_2H_5$ | $CH_3$ |
| 2 | $CH_2CH{=}CH_2$ | $CH_2CH{=}CH_2$ | $CH_3$ |
| 2 | $CH_2CH_2CH_3$ | $CH_2CH_2CH_3$ | $CH_3$ |
| 2 | $CH_2CH_2CH_3$ | $C_2H_5$ | $CH_3$ |
| 2 | $-(CH_2)_5-$ | | $CH_3$ |

TABLE 16

| A = A-16; $R^1 = C_2H_5$; $R^2 = C_2H_5$ | | | |
|---|---|---|---|
| n | $R^3$ | $R^4$ | $R^5$ |
| 2 | H | H | H |
| 2 | H | H | $CH_3$ |
| 2 | H | H | $C_2H_5$ |
| 2 | H | H | $CH_2CH_2CH_3$ |
| 2 | H | Cl | H |
| 2 | H | Cl | $CH_3$ |
| 2 | H | Cl | $C_2H_5$ |
| 2 | H | Cl | $CH_2CH_2CH_3$ |
| 2 | H | $OCH_3$ | H |
| 2 | H | $OCH_3$ | $CH_3$ |
| 2 | H | $OCH_3$ | $C_2H_5$ |
| 2 | H | $OCH_3$ | $CH_2CH_2CH_3$ |
| 2 | H | $CH_3$ | H |
| 2 | H | $CH_3$ | $CH_3$ |
| 2 | H | $CH_3$ | $C_2H_5$ |
| 2 | H | $CH_3$ | $CH_2CH_2CH_3$ |
| 2 | H | $C_2H_5$ | H |
| 2 | H | $C_2H_5$ | $CH_3$ |
| 2 | H | $C_2H_5$ | $C_2H_5$ |
| 2 | H | $C_2H_5$ | $CH_2CH_2CH_3$ |
| 2 | H | $CH(CH_3)_2$ | H |
| 2 | H | $CH(CH_3)_2$ | $CH_3$ |

TABLE 16-continued

| | | | |
|---|---|---|---|
| 2 | H | $CH(CH_3)_2$ | $C_2H_5$ |
| 2 | H | $CH(CH_3)_2$ | $CH_2CH_2CH_3$ |
| 2 | H | $CH_2CH_2CH_3$ | H |
| 2 | H | $CH_2CH_2CH_3$ | $CH_3$ |
| 2 | H | $CH_2CH_2CH_3$ | $C_2H_5$ |
| 2 | H | $CH_2CH_2CH_3$ | $CH_2CH_2CH_3$ |
| 2 | Cl | H | H |
| 2 | Cl | H | $CH_3$ |
| 2 | Cl | H | $C_2H_5$ |
| 2 | Cl | H | $CH_2CH_2CH_3$ |
| 2 | Cl | Cl | H |
| 2 | Cl | Cl | $CH_3$ |
| 2 | Cl | Cl | $C_2H_5$ |
| 2 | Cl | Cl | $CH_2CH_2CH_3$ |
| 2 | Cl | $OCH_3$ | H |
| 2 | Cl | $OCH_3$ | $CH_3$ |
| 2 | Cl | $OCH_3$ | $C_2H_5$ |
| 2 | Cl | $OCH_3$ | $CH_2CH_2CH_3$ |
| 2 | Cl | $CH_3$ | H |
| 2 | Cl | $CH_3$ | $CH_3$ |
| 2 | Cl | $CH_3$ | $C_2H_5$ |
| 2 | Cl | $CH_3$ | $CH_2CH_2CH_3$ |
| 2 | Cl | $C_2H_5$ | H |
| 2 | Cl | $C_2H_5$ | $CH_3$ |
| 2 | Cl | $C_2H_5$ | $C_2H_5$ |
| 2 | Cl | $C_2H_5$ | $CH_2CH_2CH_3$ |
| 2 | Cl | $CH(CH_3)_2$ | H |
| 2 | Cl | $CH(CH_3)_2$ | $CH_3$ |
| 2 | Cl | $CH(CH_3)_2$ | $C_2H_5$ |
| 2 | Cl | $CH(CH_3)_2$ | $CH_2CH_2CH_3$ |
| 2 | Cl | $CH_2CH_2CH_3$ | H |
| 2 | Cl | $CH_2CH_2CH_3$ | $CH_3$ |
| 2 | Cl | $CH_2CH_2CH_3$ | $C_2H_5$ |
| 2 | Cl | $CH_2CH_2CH_3$ | $CH_2CH_2CH_3$ |
| 2 | $OCH_3$ | H | H |
| 2 | $OCH_3$ | H | $CH_3$ |
| 2 | $OCH_3$ | H | $C_2H_5$ |
| 2 | $OCH_3$ | H | $CH_2CH_2CH_3$ |
| 2 | $OCH_3$ | Cl | H |
| 2 | $OCH_3$ | Cl | $CH_3$ |
| 2 | $OCH_3$ | Cl | $C_2H_5$ |
| 2 | $OCH_3$ | Cl | $CH_2CH_2CH_3$ |
| 2 | $OCH_3$ | $OCH_3$ | H |
| 2 | $OCH_3$ | $OCH_3$ | $CH_3$ |
| 2 | $OCH_3$ | $OCH_3$ | $C_2H_5$ |
| 2 | $OCH_3$ | $OCH_3$ | $CH_2CH_2CH_3$ |
| 2 | $OCH_3$ | $CH_3$ | H |
| 2 | $OCH_3$ | $CH_3$ | $CH_3$ |
| 2 | $OCH_3$ | $CH_3$ | $C_2H_5$ |
| 2 | $OCH_3$ | $CH_3$ | $CH_2CH_2CH_3$ |
| 2 | $OCH_3$ | $C_2H_5$ | H |
| 2 | $OCH_3$ | $C_2H_5$ | $CH_3$ |
| 2 | $OCH_3$ | $C_2H_5$ | $C_2H_5$ |
| 2 | $OCH_3$ | $C_2H_5$ | $CH_2CH_2CH_3$ |
| 2 | $OCH_3$ | $CH(CH_3)_2$ | H |
| 2 | $OCH_3$ | $CH(CH_3)_2$ | $CH_3$ |
| 2 | $OCH_3$ | $CH(CH_3)_2$ | $C_2H_5$ |
| 2 | $OCH_3$ | $CH(CH_3)_2$ | $CH_2CH_2CH_3$ |
| 2 | $OCH_3$ | $CH_2CH_2CH_3$ | H |
| 2 | $OCH_3$ | $CH_2CH_2CH_3$ | $CH_3$ |
| 2 | $OCH_3$ | $CH_2CH_2CH_3$ | $C_2H_5$ |
| 2 | $OCH_3$ | $CH_2CH_2CH_3$ | $CH_2CH_2CH_3$ |
| 2 | $CH_3$ | H | H |
| 2 | $CH_3$ | H | $CH_3$ |
| 2 | $CH_3$ | H | $C_2H_5$ |
| 2 | $CH_3$ | H | $CH_2CH_2CH_3$ |
| 2 | $CH_3$ | Cl | H |
| 2 | $CH_3$ | Cl | $CH_3$ |
| 2 | $CH_3$ | Cl | $C_2H_5$ |
| 2 | $CH_3$ | Cl | $CH_2CH_2CH_3$ |
| 2 | $CH_3$ | $OCH_3$ | H |
| 2 | $CH_3$ | $OCH_3$ | $CH_3$ |
| 2 | $CH_3$ | $OCH_3$ | $C_2H_5$ |
| 2 | $CH_3$ | $OCH_3$ | $CH_2CH_2CH_3$ |
| 2 | $CH_3$ | $CH_3$ | H |
| 2 | $CH_3$ | $CH_3$ | $CH_3$ |
| 2 | $CH_3$ | $CH_3$ | $C_2H_5$ |

TABLE 16-continued

| | | | |
|---|---|---|---|
| 2 | $CH_3$ | $CH_3$ | $CH_2CH_2CH_3$ |
| 2 | $CH_3$ | $C_2H_5$ | H |
| 2 | $CH_3$ | $C_2H_5$ | $CH_3$ |
| 2 | $CH_3$ | $C_2H_5$ | $C_2H_5$ |
| 2 | $CH_3$ | $C_2H_5$ | $CH_2CH_2CH_3$ |
| 2 | $CH_3$ | $CH(CH_3)_2$ | H |
| 2 | $CH_3$ | $CH(CH_3)_2$ | $CH_3$ |
| 2 | $CH_3$ | $CH(CH_3)_2$ | $C_2H_5$ |
| 2 | $CH_3$ | $CH(CH_3)_2$ | $CH_2CH_2CH_3$ |
| 2 | $CH_3$ | $CH_2CH_2CH_3$ | H |
| 2 | $CH_3$ | $CH_2CH_2CH_3$ | $CH_3$ |
| 2 | $CH_3$ | $CH_2CH_2CH_3$ | $C_2H_5$ |
| 2 | $CH_3$ | $CH_2CH_2CH_3$ | $CH_2CH_2CH_3$ |
| 2 | $C_2H_5$ | H | H |
| 2 | $C_2H_5$ | H | $CH_3$ |
| 2 | $C_2H_5$ | H | $C_2H_5$ |
| 2 | $C_2H_5$ | H | $CH_2CH_2CH_3$ |
| 2 | $C_2H_5$ | Cl | H |
| 2 | $C_2H_5$ | Cl | $CH_3$ |
| 2 | $C_2H_5$ | Cl | $C_2H_5$ |
| 2 | $C_2H_5$ | Cl | $CH_2CH_2CH_3$ |
| 2 | $C_2H_5$ | $OCH_3$ | H |
| 2 | $C_2H_5$ | $OCH_3$ | $CH_3$ |
| 2 | $C_2H_5$ | $OCH_3$ | $C_2H_5$ |
| 2 | $C_2H_5$ | $OCH_3$ | $CH_2CH_2CH_3$ |
| 2 | $C_2H_5$ | $CH_3$ | H |
| 2 | $C_2H_5$ | $CH_3$ | $CH_3$ |
| 2 | $C_2H_5$ | $CH_3$ | $C_2H_5$ |
| 2 | $C_2H_5$ | $CH_3$ | $CH_2CH_2CH_3$ |
| 2 | $C_2H_5$ | $C_2H_5$ | H |
| 2 | $C_2H_5$ | $C_2H_5$ | $CH_3$ |
| 2 | $C_2H_5$ | $C_2H_5$ | $C_2H_5$ |
| 2 | $C_2H_5$ | $C_2H_5$ | $CH_2CH_2CH_3$ |
| 2 | $C_2H_5$ | $CH(CH_3)_2$ | H |
| 2 | $C_2H_5$ | $CH(CH_3)_2$ | $CH_3$ |
| 2 | $C_2H_5$ | $CH(CH_3)_2$ | $C_2H_5$ |
| 2 | $C_2H_5$ | $CH(CH_3)_2$ | $CH_2CH_2CH_3$ |
| 2 | $C_2H_5$ | $CH_2CH_2CH_3$ | H |
| 2 | $C_2H_5$ | $CH_2CH_2CH_3$ | $CH_3$ |
| 2 | $C_2H_5$ | $CH_2CH_2CH_3$ | $C_2H_5$ |
| 2 | $C_2H_5$ | $CH_2CH_2CH_3$ | $CH_2CH_2CH_3$ |
| 2 | $CH(CH_3)_2$ | H | H |
| 2 | $CH(CH_3)_2$ | H | $CH_3$ |
| 2 | $CH(CH_3)_2$ | H | $C_2H_5$ |
| 2 | $CH(CH_3)_2$ | H | $CH_2CH_2CH_3$ |
| 2 | $CH(CH_3)_2$ | Cl | H |
| 2 | $CH(CH_3)_2$ | Cl | $CH_3$ |
| 2 | $CH(CH_3)_2$ | Cl | $C_2H_5$ |
| 2 | $CH(CH_3)_2$ | Cl | $CH_2CH_2CH_3$ |
| 2 | $CH(CH_3)_2$ | $OCH_3$ | H |
| 2 | $CH(CH_3)_2$ | $OCH_3$ | $CH_3$ |
| 2 | $CH(CH_3)_2$ | $OCH_3$ | $C_2H_5$ |
| 2 | $CH(CH_3)_2$ | $OCH_3$ | $CH_2CH_2CH_3$ |
| 2 | $CH(CH_3)_2$ | $CH_3$ | H |
| 2 | $CH(CH_3)_2$ | $CH_3$ | $CH_3$ |
| 2 | $CH(CH_3)_2$ | $CH_3$ | $C_2H_5$ |
| 2 | $CH(CH_3)_2$ | $CH_3$ | $CH_2CH_2CH_3$ |
| 2 | $CH(CH_3)_2$ | $C_2H_5$ | H |
| 2 | $CH(CH_3)_2$ | $C_2H_5$ | $CH_3$ |
| 2 | $CH(CH_3)_2$ | $C_2H_5$ | $C_2H_5$ |
| 2 | $CH(CH_3)_2$ | $C_2H_5$ | $CH_2CH_2CH_3$ |
| 2 | $CH(CH_3)_2$ | $CH(CH_3)_2$ | H |
| 2 | $CH(CH_3)_2$ | $CH(CH_3)_2$ | $CH_3$ |
| 2 | $CH(CH_3)_2$ | $CH(CH_3)_2$ | $C_2H_5$ |
| 2 | $CH(CH_3)_2$ | $CH(CH_3)_2$ | $CH_2CH_2CH_3$ |
| 2 | $CH(CH_3)_2$ | $CH_2CH_2CH_3$ | H |
| 2 | $CH(CH_3)_2$ | $CH_2CH_2CH_3$ | $CH_3$ |
| 2 | $CH(CH_3)_2$ | $CH_2CH_2CH_3$ | $C_2H_5$ |
| 2 | $CH(CH_3)_2$ | $CH_2CH_2CH_3$ | $CH_2CH_2CH_3$ |
| 2 | $CH_2CH_2CH_3$ | H | H |
| 2 | $CH_2CH_2CH_3$ | H | $CH_3$ |
| 2 | $CH_2CH_2CH_3$ | H | $C_2H_5$ |
| 2 | $CH_2CH_2CH_3$ | H | $CH_2CH_2CH_3$ |
| 2 | $CH_2CH_2CH_3$ | Cl | H |
| 2 | $CH_2CH_2CH_3$ | Cl | $CH_3$ |
| 2 | $CH_2CH_2CH_3$ | Cl | $C_2H_5$ |
| 2 | $CH_2CH_2CH_3$ | Cl | $CH_2CH_2CH_3$ |
| 2 | $CH_2CH_2CH_3$ | $OCH_3$ | H |
| 2 | $CH_2CH_2CH_3$ | $OCH_3$ | $CH_3$ |
| 2 | $CH_2CH_2CH_3$ | $OCH_3$ | $C_2H_5$ |
| 2 | $CH_2CH_2CH_3$ | $OCH_3$ | $CH_2CH_2CH_3$ |
| 2 | $CH_2CH_2CH_3$ | $CH_3$ | H |
| 2 | $CH_2CH_2CH_3$ | $CH_3$ | $CH_3$ |
| 2 | $CH_2CH_2CH_3$ | $CH_3$ | $C_2H_5$ |
| 2 | $CH_2CH_2CH_3$ | $CH_3$ | $CH_2CH_2CH_3$ |
| 2 | $CH_2CH_2CH_3$ | $C_2H_5$ | H |
| 2 | $CH_2CH_2CH_3$ | $C_2H_5$ | $CH_3$ |
| 2 | $CH_2CH_2CH_3$ | $C_2H_5$ | $C_2H_5$ |
| 2 | $CH_2CH_2CH_3$ | $C_2H_5$ | $CH_2CH_2CH_3$ |
| 2 | $CH_2CH_2CH_3$ | $CH(CH_3)_2$ | H |
| 2 | $CH_2CH_2CH_3$ | $CH(CH_3)_2$ | $CH_3$ |
| 2 | $CH_2CH_2CH_3$ | $CH(CH_3)_2$ | $C_2H_5$ |
| 2 | $CH_2CH_2CH_3$ | $CH(CH_3)_2$ | $CH_2CH_2CH_3$ |
| 2 | $CH_2CH_2CH_3$ | $CH_2CH_2CH_3$ | H |
| 2 | $CH_2CH_2CH_3$ | $CH_2CH_2CH_3$ | $CH_3$ |
| 2 | $CH_2CH_2CH_3$ | $CH_2CH_2CH_3$ | $C_2H_5$ |
| 2 | $CH_2CH_2CH_3$ | $CH_2CH_2CH_3$ | $CH_2CH_2CH_3$ |
| 2 | $CH_3$ | $CH_3$ | Cl |
| 2 | $CH_3$ | $CH_3$ | $OCH_3$ |
| 2 | $CH_3$ | $CH_3$ | F |
| 2 | $CH_3$ | $CH_3$ | Br |
| 2 | $CH_3$ | $CH_3$ | $CO_2CH_3$ |
| 2 | $CH_3$ | $CH_3$ | $CO_2C_2H_5$ |
| 2 | $CH_3$ | $CH_3$ | $CH_2OCH_3$ |
| 2 | $CH_3$ | $CH_3$ | $CON(CH_3)_2$ |
| 2 | $CH_3$ | $CH_3$ | $SCH_3$ |
| 2 | $CH_3$ | $CH_3$ | $SO_2CH_3$ |
| 2 | $CH_3$ | $CH_3$ | $NO_2$ |
| 2 | $CH_3$ | $CH_3$ | $N(CH_3)_2$ |
| 2 | $CH_3$ | $CH_3$ | $NH_2$ |
| 2 | $CH_3$ | $CH_3$ | $C_6H_5$ |
| 2 | $CH_3$ | $C_6H_5$ | H |
| 2 | $C_6H_5$ | $CH_3$ | H |
| 2 | $CH_3$ | $CF_3$ | H |
| 2 | $CF_3$ | $CH_3$ | H |
| 2 | $COCH_3$ | H | H |
| 2 | $CH{=}CH_2$ | $CH_3$ | H |
| 2 | $CH_3$ | $CH{=}CH_2$ | H |
| 2 | $SCH_3$ | $CH_3$ | H |
| 2 | $CH_3$ | $SCH_3$ | H |
| 2 | $NO_2$ | $CH_3$ | H |
| 2 | $NH_2$ | $CH_3$ | H |
| 2 | CHO | $CH_3$ | H |
| 2 | $CO_2CH_3$ | H | H |
| 2 | $CH(OCH_3)_2$ | H | H |
| 2 | $COCH_3$ | H | Cl |
| 2 | $C_2H_5$ | H | Cl |
| 2 | $CO_2CH_3$ | H | Cl |

A = A-16; $R^3 = CH_3$; $R^4 = CH_3$

| n | $R^1$ | $R^2$ | $R^5$ |
|---|---|---|---|
| 2 | $CH_3$ | $CH_3$ | H |
| 2 | $C_2H_5$ | $CH_3$ | H |
| 2 | H | $CH_3$ | H |
| 2 | H | $C_2H_5$ | H |
| 2 | H | $CH_2CH_2CH_3$ | H |
| 2 | $OCH_3$ | $CH_3$ | H |
| 2 | $OCH_3$ | $C_2H_5$ | H |
| 2 | $CH_2CH_2CH_3$ | $CH_2CH_2CH_3$ | H |
| 2 | $CH_2CH{=}CH_2$ | $CH_2CH{=}CH_2$ | H |
| 2 | $CH_2C{\equiv}CH$ | $CH_2C{\equiv}CH$ | H |
| 2 | $CH(CH_3)_2$ | $CH(CH_3)_2$ | H |
| 2 | | $-(CH_2)_5-$ | H |
| 2 | | $-(CH_2)_4-$ | H |
| 2 | $CH_2CH{=}CH_2$ | $C_2H_5$ | H |
| 2 | $CH_2C{\equiv}CH$ | $C_2H_5$ | H |

TABLE 16-continued

| | | | |
|---|---|---|---|
| 2 | $OC_2H_5$ | $CH_3$ | H |
| 2 | $OC_2H_5$ | $C_2H_5$ | H |
| 2 | H | 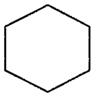 | H |
| 2 | 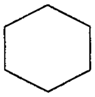 | 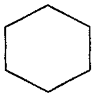 | H |
| 2 | H | $CH_2CH{=}CH_2$ | H |
| 2 | $CH_2CH_2CH_3$ | $CH_3$ | H |
| 2 | $CH_2CH{=}CH_2$ | $CH_3$ | $CH_3$ |
| 2 | $CH_2CH{=}CH_2$ | $C_2H_5$ | $CH_3$ |
| 2 | $CH_2CH{=}CH_2$ | $CH_2CH{=}CH_2$ | $CH_3$ |
| 2 | $CH_2CH_2CH_3$ | $CH_2CH_2CH_3$ | $CH_3$ |
| 2 | $CH_2CH_2CH_3$ | $C_2H_5$ | $CH_3$ |
| 2 | $-(CH_2)_5-$ | | $CH_3$ |

TABLE 17

A = A-17; $R^1 = C_2H_5$; $R^2 = C_2H_5$

| n | $R^3$ | $R^4$ | $R^5$ |
|---|---|---|---|
| 2 | H | H | H |
| 2 | H | I | H |
| 2 | H | H | $CH_3$ |
| 2 | H | H | $C_2H_5$ |
| 2 | H | H | $CH_2CH_2CH_3$ |
| 2 | H | Cl | H |
| 2 | H | Cl | $CH_3$ |
| 2 | H | Cl | $C_2H_5$ |
| 2 | H | Cl | $CH_2CH_2CH_3$ |
| 2 | H | $OCH_3$ | H |
| 2 | H | $OCH_3$ | $CH_3$ |
| 2 | H | $OCH_3$ | $C_2H_5$ |
| 2 | H | $OCH_3$ | $CH_2CH_2CH_3$ |
| 2 | H | $CH_3$ | H |
| 2 | H | $CH_3$ | $CH_3$ |
| 2 | H | $CH_3$ | $C_2H_5$ |
| 2 | H | $CH_3$ | $CH_2CH_2CH_3$ |
| 2 | H | $C_2H_5$ | H |
| 2 | H | $C_2H_5$ | $CH_3$ |
| 2 | H | $C_2H_5$ | $C_2H_5$ |
| 2 | H | $C_2H_5$ | $CH_2CH_2CH_3$ |
| 2 | H | $CH(CH_3)_2$ | H |
| 2 | H | $CH(CH_3)_2$ | $CH_3$ |
| 2 | H | $CH(CH_3)_2$ | $C_2H_5$ |
| 2 | H | $CH(CH_3)_2$ | $CH_2CH_2CH_3$ |
| 2 | H | $CH_2CH_2CH_3$ | H |
| 2 | H | $CH_2CH_2CH_3$ | $CH_3$ |
| 2 | H | $CH_2CH_2CH_3$ | $C_2H_5$ |
| 2 | H | $CH_2CH_2CH_3$ | $CH_2CH_2CH_3$ |
| 2 | Cl | H | H |
| 2 | Cl | H | $CH_3$ |
| 2 | $CF_3$ | H | $CH_3$ |
| 2 | Cl | H | $C_2H_5$ |
| 2 | $CF_3$ | H | $C_2H_5$ |
| 2 | Cl | H | $CH_2CH_2CH_3$ |
| 2 | $CF_3$ | H | $CH_2CH_2CH_3$ |
| 2 | Cl | Cl | H |
| 2 | Cl | Cl | $CH_3$ |
| 2 | $CF_3$ | $CF_3$ | $CH_3$ |
| 2 | Cl | Cl | $C_2H_5$ |
| 2 | $CF_3$ | $CF_3$ | $C_2H_5$ |
| 2 | Cl | Cl | $CH_2CH_2CH_3$ |
| 2 | $CF_3$ | $CF_3$ | $CH_2CH_2CH_3$ |
| 2 | Cl | $OCH_3$ | H |
| 2 | Cl | $OCH_3$ | $CH_3$ |

TABLE 17-continued

| | | | |
|---|---|---|---|
| 2 | Cl | $OCH_3$ | $C_2H_5$ |
| 2 | Cl | $OCH_3$ | $CH_2CH_2CH_3$ |
| 2 | Cl | $CH_3$ | H |
| 2 | $CF_3$ | $CH_3$ | H |
| 2 | Cl | $CH_3$ | $CH_3$ |
| 2 | $CF_3$ | $CH_3$ | $CH_3$ |
| 2 | Cl | $CH_3$ | $C_2H_5$ |
| 2 | $CF_3$ | $CH_3$ | $C_2H_5$ |
| 2 | Cl | $CH_3$ | $CH_2CH_2CH_3$ |
| 2 | $CF_3$ | $CH_3$ | $CH_2CH_2CH_3$ |
| 2 | Cl | $C_2H_5$ | H |
| 2 | $CF_3$ | $C_2H_5$ | H |
| 2 | Cl | $C_2H_5$ | $CH_3$ |
| 2 | Cl | $C_2H_5$ | $C_2H_5$ |
| 2 | Cl | $C_2H_5$ | $CH_2CH_2CH_3$ |
| 2 | Cl | $CH(CH_3)_2$ | H |
| 2 | Cl | $CH(CH_3)_2$ | $CH_3$ |
| 2 | Cl | $CH(CH_3)_2$ | $C_2H_5$ |
| 2 | Cl | $CH(CH_3)_2$ | $CH_2CH_2CH_3$ |
| 2 | Cl | $CH_2CH_2CH_3$ | H |
| 2 | Cl | $CH_2CH_2CH_3$ | $CH_3$ |
| 2 | $CH_3$ | H | $CF_3$ |
| 2 | $CH_3$ | Cl | $CF_3$ |
| 2 | $CH_3$ | Br | $CF_3$ |
| 2 | $CH_3$ | $CH_3$ | $CF_3$ |
| 2 | $CH_3$ | $C_2H_5$ | $CF_3$ |
| 2 | $CF_3$ | H | $CF_3$ |
| 2 | $CF_3$ | Cl | $CF_3$ |
| 2 | $CF_3$ | Br | $CF_3$ |
| 2 | Cl | $CH_2CH_2CH_3$ | $C_2H_5$ |
| 2 | Cl | $CH_2CH_2CH_3$ | $CH_2CH_2CH_3$ |
| 2 | $OCH_3$ | H | H |
| 2 | $OCH_3$ | H | $CH_3$ |
| 2 | $OCH_3$ | H | $C_2H_5$ |
| 2 | $OCH_3$ | H | $CH_2CH_2CH_3$ |
| 2 | $OCH_3$ | Cl | H |
| 2 | $OCH_3$ | Cl | $CH_3$ |
| 2 | $OCH_3$ | Cl | $C_2H_5$ |
| 2 | $OCH_3$ | Cl | $CH_2CH_2CH_3$ |
| 2 | $OCH_3$ | $OCH_3$ | H |
| 2 | $OCH_3$ | $OCH_3$ | $CH_3$ |
| 2 | $OCH_3$ | $OCH_3$ | $C_2H_5$ |
| 2 | $OCH_3$ | $OCH_3$ | $CH_2CH_2CH_3$ |
| 2 | $OCH_3$ | $CH_3$ | H |
| 2 | $OCH_3$ | $CH_3$ | $CH_3$ |
| 2 | $OCH_3$ | $CH_3$ | $C_2H_5$ |
| 2 | $OCH_3$ | $CH_3$ | $CH_2CH_2CH_3$ |
| 2 | $OCH_3$ | $C_2H_5$ | H |
| 2 | $OCH_3$ | $C_2H_5$ | $CH_3$ |
| 2 | $OCH_3$ | $C_2H_5$ | $C_2H_5$ |
| 2 | $OCH_3$ | $C_2H_5$ | $CH_2CH_2CH_3$ |
| 2 | $OCH_3$ | $CH(CH_3)_2$ | H |
| 2 | $OCH_3$ | $CH(CH_3)_2$ | $CH_3$ |
| 2 | $OCH_3$ | $CH(CH_3)_2$ | $C_2H_5$ |
| 2 | $OCH_3$ | $CH(CH_3)_2$ | $CH_2CH_2CH_3$ |
| 2 | $OCH_3$ | $CH_2CH_2CH_3$ | H |
| 2 | $OCH_3$ | $CH_2CH_2CH_3$ | $CH_3$ |
| 2 | $OCH_3$ | $CH_2CH_2CH_3$ | $C_2H_5$ |
| 2 | $OCH_3$ | $CH_2CH_2CH_3$ | $CH_2CH_2CH_3$ |
| 2 | $CH_3$ | H | H |
| 2 | $CH_3$ | H | $CH_3$ |
| 2 | $CH_3$ | Br | $CH_3$ |
| 2 | $CH_3$ | H | $C_2H_5$ |
| 2 | $CH_3$ | H | 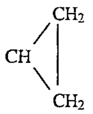 |
| 2 | $CH_3$ | H | $CH_2CH_2CH_3$ |
| 2 | $CH_3$ | Cl | H |
| 2 | $CH_3$ | Cl | $CH_3$ |
| 2 | $CH_3$ | Br | $C_2H_5$ |
| 2 | $CH_3$ | Cl | $C_2H_5$ |
| 2 | $CH_3$ | Cl | $CH_2CH_2CH_3$ |

TABLE 17-continued

| | | | |
|---|---|---|---|
| 2 | $CH_3$ | Cl | 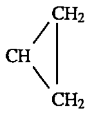 |
| 2 | $CH_3$ | $OCH_3$ | H |
| 2 | $CH_3$ | Br | 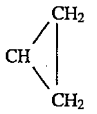 |
| 2 | $CH_3$ | $OCH_3$ | $CH_3$ |
| 2 | $CH_3$ | $OCH_3$ | $C_2H_5$ |
| 2 | $CH_3$ | $OCH_3$ | $CH_2CH_2CH_3$ |
| 2 | $CH_3$ | $CH_3$ | H |
| 2 | $CH_3$ | $CH_3$ | $CH_3$ |
| 2 | $CH_3$ | $CH_3$ | $C_2H_5$ |
| 2 | $CH_3$ | $CH_3$ | $CH_2CH_2CH_3$ |
| 2 | $CH_3$ | $C_2H_5$ | H |
| 2 | $CH_3$ | $C_2H_5$ | $CH_3$ |
| 2 | $CH_3$ | $C_2H_5$ | $C_2H_5$ |
| 2 | $CH_3$ | $C_2H_5$ | $CH_2CH_2CH_3$ |
| 2 | $CH_3$ | H | $CH_2CH(CH_3)_2$ |
| 2 | $CH_3$ | H | $CH(CH3)_2$ |
| 2 | $CH_3$ | $CH(CH_3)_2$ | H |
| 2 | $CH_3$ | $CH(CH_3)_2$ | $CH_3$ |
| 2 | $CH_3$ | $CH(CH_3)_2$ | $C_2H_5$ |
| 2 | $CH_3$ | $CH(CH_3)_2$ | $CH_2CH_2CH_3$ |
| 2 | $CH_3$ | $CH_2CH_2CH_3$ | H |
| 2 | $CH_3$ | $CH_2CH_2CH_3$ | $CH_3$ |
| 2 | $CH_3$ | $CH_2CH_2CH_3$ | $C_2H_5$ |
| 2 | $CH_3$ | $CH_2CH_2CH_3$ | $CH_2CH_2CH_3$ |
| 2 | $CH_3$ | H | $C_6H_5$ |
| 2 | $CH_3$ | Br | $C_6H_5$ |
| 2 | $CH_3$ | Cl | $C_6H_5$ |
| 2 | $CH_3$ | H | $CH(CH_3)_2$ |
| 2 | $CH_3$ | Br | $CH(CH_3)_2$ |
| 2 | $CH_3$ | Cl | $CH(CH_3)_2$ |
| 2 | $C_6H_5$ | H | $CH_3$ |
| 2 | $C_6H_5$ | Cl | $CH_3$ |
| 2 | $C_6H_5$ | Br | $CH_3$ |
| 2 | $C_2H_5$ | H | H |
| 2 | $C_2H_5$ | H | $CH_3$ |
| 2 | $C_2H_5$ | H | $C_2H_5$ |
| 2 | $C_2H_5$ | H | $CH_2CH_2CH_3$ |
| 2 | $C_2H_5$ | Cl | H |
| 2 | $C_2H_5$ | Cl | $CH_3$ |
| 2 | $C_2H_5$ | Cl | $C_2H_5$ |
| 2 | $C_2H_5$ | Cl | $CH_2CH_2CH_3$ |
| 2 | $C_2H_5$ | $OCH_3$ | H |
| 2 | $C_2H_5$ | $OCH_3$ | $CH_3$ |
| 2 | $C_2H_5$ | $OCH_3$ | $C_2H_5$ |
| 2 | $C_2H_5$ | $OCH_3$ | $CH_2CH_2CH_3$ |
| 2 | $C_2H_5$ | $CH_3$ | H |
| 2 | $C_2H_5$ | $CH_3$ | $CH_3$ |
| 2 | $C_2H_5$ | $CH_3$ | $C_2H_5$ |
| 2 | $C_2H_5$ | $CH_3$ | $CH_2CH_2CH_3$ |
| 2 | $C_2H_5$ | $C_2H_5$ | H |
| 2 | $C_2H_5$ | $C_2H_5$ | $CH_3$ |
| 2 | $C_2H_5$ | $C_2H_5$ | $C_2H_5$ |
| 2 | $C_2H_5$ | $C_2H_5$ | $CH_2CH_2CH_3$ |
| 2 | $C_2H_5$ | $CH(CH_3)_2$ | H |
| 2 | $C_2H_5$ | $CH(CH_3)_2$ | $CH_3$ |
| 2 | $C_2H_5$ | $CH(CH_3)_2$ | $C_2H_5$ |
| 2 | $C_2H_5$ | $CH(CH_3)_2$ | $CH_2CH_2CH_3$ |
| 2 | $C_2H_5$ | $CH_2CH_2CH_3$ | H |
| 2 | $C_2H_5$ | $CH_2CH_2CH_3$ | $CH_3$ |
| 2 | $C_2H_5$ | $CH_2CH_2CH_3$ | $C_2H_5$ |
| 2 | $C_2H_5$ | $CH_2CH_2CH_3$ | $CH_2CH_2CH_3$ |
| 2 | $CH(CH_3)_2$ | H | H |

TABLE 17-continued

| | | | |
|---|---|---|---|
| 2 | 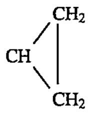 | Br | $CH_3$ |
| 2 | $CH(CH_3)_2$ | H | $CH_3$ |
| 2 | 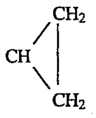 | H | $CH_3$ |
| 2 | $CH(CH_3)_2$ | H | $C_2H_5$ |
| 2 | $CH(CH_3)_2$ | H | $CH_2CH_2CH_3$ |
| 2 | $CH(CH_3)_2$ | Cl | H |
| 2 | $CH(CH_3)_2$ | Br | $CH_3$ |
| 2 | $CH(CH_3)_2$ | Cl | $CH_3$ |
| 2 | 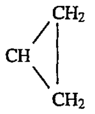 | Cl | $CH_3$ |
| 2 | $CH(CH_3)_2$ | Cl | $C_2H_5$ |
| 2 | $CH(CH_3)_2$ | Cl | $CH_2CH_2CH_3$ |
| 2 | $CH(CH_3)_2$ | $OCH_3$ | H |
| 2 | $CH(CH_3)_2$ | $OCH_3$ | $CH_3$ |
| 2 | $CH(CH_3)_2$ | $OCH_3$ | $C_2H_5$ |
| 2 | $CH(CH_3)_2$ | $OCH_3$ | $CH_2CH_2CH_3$ |
| 2 | $CH(CH_3)_2$ | $CH_3$ | H |
| 2 | $CH(CH_3)_2$ | $CH_3$ | $CH_3$ |
| 2 | $CH(CH_3)_2$ | $CH_3$ | $C_2H_5$ |
| 2 | $CH(CH_3)_2$ | $CH_3$ | $CH_2CH_2CH_3$ |
| 2 | $CH(CH_3)_2$ | $C_2H_5$ | H |
| 2 | $CH(CH_3)_2$ | $C_2H_5$ | $CH_3$ |
| 2 | $CH(CH_3)_2$ | $C_2H_5$ | $C_2H_5$ |
| 2 | $CH(CH_3)_2$ | $C_2H_5$ | $CH_2CH_2CH_3$ |
| 2 | $CH(CH_3)_2$ | $CH(CH_3)_2$ | H |
| 2 | $CH(CH_3)_2$ | $CH(CH_3)_2$ | $CH_3$ |
| 2 | $CH(CH_3)_2$ | $CH(CH_3)_2$ | $C_2H_5$ |
| 2 | $CH(CH_3)_2$ | $CH(CH_3)_2$ | $CH_2CH_2CH_3$ |
| 2 | $CH(CH_3)_2$ | $CH_2CH_2CH_3$ | H |
| 2 | $CH(CH_3)_2$ | $CH_2CH_2CH_3$ | $CH_3$ |
| 2 | $CH(CH_3)_2$ | $CH_2CH_2CH_3$ | $C_2H_5$ |
| 2 | $CH(CH_3)_2$ | $CH_2CH_2CH_3$ | $CH_2CH_2CH_3$ |
| 2 | $CH_2CH_2CH_3$ | H | H |
| 2 | $CH_2CH_2CH_3$ | H | $CH_3$ |
| 2 | $CH_2CH_2CH_3$ | H | $C_2H_5$ |
| 2 | $CH_2CH_2CH_3$ | H | $CH_2CH_2CH_3$ |
| 2 | $CH_2CH_2CH_3$ | Cl | H |
| 2 | $CH_2CH_2CH_3$ | Cl | $CH_3$ |
| 2 | $CH_2CH_2CH_3$ | Cl | $C_2H_5$ |
| 2 | $CH_2CH_2CH_3$ | Cl | $CH_2CH_2CH_3$ |
| 2 | $CH_2CH_2CH_3$ | $OCH_3$ | H |
| 2 | $CH_2CH_2CH_3$ | $OCH_3$ | $CH_3$ |
| 2 | $CH_2CH_2CH_3$ | $OCH_3$ | $C_2H_5$ |
| 2 | $CH_2CH_2CH_3$ | $OCH_3$ | $CH_2CH_2CH_3$ |
| 2 | $CH_2CH_2CH_3$ | $CH_3$ | H |
| 2 | $CH_2CH_2CH_3$ | $CH_3$ | $CH_3$ |
| 2 | $CH_2CH_2CH_3$ | $CH_3$ | $C_2H_5$ |
| 2 | $CH_2CH_2CH_3$ | $CH_3$ | $CH_2CH_2CH_3$ |
| 2 | $CH_2CH_2CH_3$ | $C_2H_5$ | H |
| 2 | $CH_2CH_2CH_3$ | $C_2H_5$ | $CH_3$ |
| 2 | $CH_2CH_2CH_3$ | $C_2H_5$ | $C_2H_5$ |
| 2 | $CH_2CH_2CH_3$ | $C_2H_5$ | $CH_2CH_2CH_3$ |
| 2 | $CH_2CH_2CH_3$ | $CH(CH_3)_2$ | H |
| 2 | $CH_2CH_2CH_3$ | $CH(CH_3)_2$ | $CH_3$ |
| 2 | $CH_2CH_2CH_3$ | $CH(CH_3)_2$ | $C_2H_5$ |
| 2 | $CH_2CH_2CH_3$ | $CH(CH_3)_2$ | $CH_2CH_2CH_3$ |
| 2 | $CH_2CH_2CH_3$ | $CH_2CH_2CH_3$ | H |
| 2 | $CH_2CH_2CH_3$ | $CH_2CH_2CH_3$ | $CH_3$ |
| 2 | $CH_2CH_2CH_3$ | $CH_2CH_2CH_3$ | $C_2H_5$ |
| 2 | $CH_2CH_2CH_3$ | $CH_2CH_2CH_3$ | $CH_2CH_2CH_3$ |
| 2 | $CH_3$ | $CH_3$ | Cl |
| 2 | $CH_3$ | $CH_3$ | $OCH_3$ |

TABLE 17-continued

| | | | |
|---|---|---|---|
| 2 | $CH_3$ | $CH_3$ | F |
| 2 | $CH_3$ | $CH_3$ | Br |
| 2 | $CH_3$ | $CH_3$ | $CO_2CH_3$ |
| 2 | $CH_3$ | $CH_3$ | $CO_2C_2H_5$ |
| 2 | $CH_3$ | $CH_3$ | $CH_2OCH_3$ |
| 2 | $CH_3$ | $CH_3$ | $CON(CH_3)_2$ |
| 2 | $CH_3$ | $CH_3$ | $SCH_3$ |
| 2 | $CH_3$ | $CH_3$ | $SO_2CH_3$ |
| 2 | $CH_3$ | $CH_3$ | $NO_2$ |
| 2 | $CH_3$ | $CH_3$ | $N(CH_3)_2$ |
| 2 | $CH_3$ | $CH_3$ | $NH_2$ |
| 2 | $CH_3$ | $CH_3$ | $C_6H_5$ |
| 2 | $CH_3$ | $C_6H_5$ | H |
| 2 | $C_6H_5$ | $CH_3$ | H |
| 2 | $CH_3$ | $CF_3$ | H |
| 2 | $CF_3$ | $CH_3$ | H |
| 2 | $COCH_3$ | H | H |
| 2 | $CH=CH_2$ | $CH_3$ | H |
| 2 | $CH_3$ | $CH=CH_2$ | H |
| 2 | $SCH_3$ | $CH_3$ | H |
| 2 | $CH_3$ | $SCH_3$ | H |
| 2 | $NO_2$ | $CH_3$ | H |
| 2 | $NH_2$ | $CH_3$ | H |
| 2 | CHO | $CH_3$ | H |
| 2 | $CO_2CH_3$ | H | H |
| 2 | $CH(OCH_3)_2$ | H | H |
| 2 | $COCH_3$ | H | Cl |
| 2 | $C_2H_5$ | H | Cl |
| 2 | $CO_2CH_3$ | H | Cl |
| A = A-17; $R^3$ = $CH_3$; $R^4$ = $CH_3$ | | | |
| n | $R^1$ | $R^2$ | $R^5$ |
| 2 | $CH_3$ | $CH_3$ | H |
| 2 | $C_2H_5$ | $CH_3$ | H |
| 2 | H | $CH_3$ | H |
| 2 | H | $C_2H_5$ | H |
| 2 | H | $CH_2CH_2CH_3$ | H |
| 2 | $OCH_3$ | $CH_3$ | H |
| 2 | $OCH_3$ | $C_2H_5$ | H |
| 2 | $CH_2CH_2CH_3$ | $CH_2CH_2CH_3$ | H |
| 2 | $CH_2CH=CH_2$ | $CH_2CH=CH_2$ | H |
| 2 | $CH_2C\equiv CH$ | $CH_2C\equiv CH$ | H |
| 2 | $CH(CH_3)_2$ | $CH(CH_3)_2$ | H |
| 2 | $-(CH_2)_5-$ | | H |
| 2 | $-(CH_2)_4-$ | | H |
| 2 | $CH_2CH=CH_2$ | $C_2H_5$ | H |
| 2 | $CH_2C\equiv CH$ | $C_2H_5$ | H |
| 2 | $OC_2H_5$ | $CH_3$ | H |
| 2 | $OC_2H_5$ | $C_2H_5$ | H |
| 2 | H | 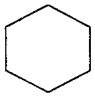 | H |
| 2 | 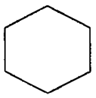 | 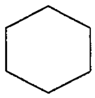 | H |
| 2 | H | $CH_2CH=CH_2$ | H |
| 2 | $CH_2CH_2CH_3$ | $CH_3$ | H |
| 2 | $CH_2CH=CH_2$ | $CH_3$ | $CH_3$ |
| 2 | $CH_2CH=CH_2$ | $C_2H_5$ | $CH_3$ |
| 2 | $CH_2CH=CH_2$ | $CH_2CH=CH_2$ | $CH_3$ |
| 2 | $CH_2CH_2CH_3$ | $CH_2CH_2CH_3$ | $CH_3$ |
| 2 | $CH_2CH_2CH_3$ | $C_2H_5$ | $CH_3$ |
| 2 | $-(CH_2)_5-$ | | $CH_3$ |

TABLE 18

| A = A-18; $R^1$ = $C_2H_5$; $R^2$ = $C_2H_5$ | | |
|---|---|---|
| n | $R^3$ | $R^4$ |
| 2 | H | H |
| 2 | H | Cl |
| 2 | H | $OCH_3$ |
| 2 | H | $CH_3$ |
| 2 | H | $C_2H_5$ |
| 2 | H | $CH(CH_3)_2$ |
| 2 | H | $CH_2CH_2CH_3$ |
| 2 | Cl | Cl |
| 2 | Cl | $OCH_3$ |
| 2 | Cl | $CH_3$ |
| 2 | Cl | $C_2H_5$ |
| 2 | Cl | $CH(CH_3)_2$ |
| 2 | Cl | $CH_2CH_2CH_3$ |
| 2 | $OCH_3$ | $OCH_3$ |
| 2 | $OCH_3$ | $CH_3$ |
| 2 | $OCH_3$ | $C_2H_5$ |
| 2 | $OCH_3$ | $CH(CH_3)_2$ |
| 2 | $OCH_3$ | $CH_2CH_2CH_3$ |
| 2 | $CH_3$ | $CH_3$ |
| 2 | $CH_3$ | $C_2H_5$ |
| 2 | $CH_3$ | $CH(CH_3)_2$ |
| 2 | $CH_3$ | $CH_2CH_2CH_3$ |
| 2 | $C_2H_5$ | $C_2H_5$ |
| 2 | $C_2H_5$ | $CH(CH_3)_2$ |
| 2 | $C_2H_5$ | $CH_2CH_2CH_3$ |
| 2 | $CH(CH_3)_2$ | $CH(CH_3)_2$ |
| 2 | $CH(CH_3)_2$ | $CH_2CH_2CH_3$ |
| 2 | $CH_2CH_2CH_3$ | $CH_2CH_2CH_3$ |
| 2 | $CH_3$ | $C_6H_5$ |
| 2 | $CH_3$ | $CF_3$ |
| 2 | $COCH_3$ | H |
| 2 | $CH=CH_2$ | $CH_3$ |
| 2 | $SCH_3$ | $CH_3$ |
| 2 | $NO_2$ | $CH_3$ |
| 2 | $NH_2$ | $CH_3$ |
| 2 | CHO | $CH_3$ |
| 2 | $CO_2CH_3$ | H |
| 2 | $CH(OCH_3)_2$ | H |
| A = A-18; $R^3$ = $CH_3$; $R^4$ = $CH_3$ | | |
| n | $R^1$ | $R^2$ |
| 2 | $CH_3$ | $CH_3$ |
| 2 | $C_2H_5$ | $CH_3$ |
| 2 | H | $CH_3$ |
| 2 | H | $C_2H_5$ |
| 2 | H | $CH_2CH_2CH_3$ |
| 2 | $OCH_3$ | $CH_3$ |
| 2 | $OCH_3$ | $C_2H_5$ |
| 2 | $CH_2CH_2CH_3$ | $CH_2CH_2CH_3$ |
| 2 | $CH_2CH=CH_2$ | $CH_2CH=CH_2$ |
| 2 | $CH_2C\equiv CH$ | $CH_2C\equiv CH$ |
| 2 | $CH(CH_3)_2$ | $CH(CH_3)_2$ |
| 2 | $-(CH_2)_5-$ | |
| 2 | $-(CH_2)_4-$ | |
| 2 | $CH_2CH=CH_2$ | $C_2H_5$ |
| 2 | $CH_2C\equiv CH$ | $C_2H_5$ |
| 2 | $OC_2H_5$ | $CH_3$ |
| 2 | $OC_2H_5$ | $C_2H_5$ |
| 2 | H | 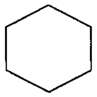 |

TABLE 18-continued

| | | |
|---|---|---|
| 2 | 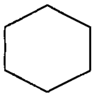 | 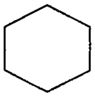 |
| 2 | H | $CH_2CH=CH_2$ |
| 2 | $CH_2CH_2CH_3$ | $CH_3$ |

TABLE 19

| A = A-19; $R^1$ = $C_2H_5$; $R^2$ = $C_2H_5$ | | |
|---|---|---|
| n | $R^3$ | $R^5$ |
| 2 | H | H |
| 2 | H | Cl |
| 2 | H | $OCH_3$ |
| 2 | H | $CH_3$ |
| 2 | H | $C_2H_5$ |
| 2 | H | $CH(CH_3)_2$ |
| 2 | H | $CH_2CH_2CH_3$ |
| 2 | Cl | H |
| 2 | Cl | Cl |
| 2 | Cl | $OCH_3$ |
| 2 | Cl | $CH_3$ |
| 2 | Cl | $C_2H_5$ |
| 2 | Cl | $CH(CH_3)_2$ |
| 2 | Cl | $CH_2CH_2CH_3$ |
| 2 | $OCH_3$ | H |
| 2 | $OCH_3$ | Cl |
| 2 | $OCH_3$ | $OCH_3$ |
| 2 | $OCH_3$ | $CH_3$ |
| 2 | $OCH_3$ | $C_2H_5$ |
| 2 | $OCH_3$ | $CH(CH_3)_2$ |
| 2 | $OCH_3$ | $CH_2CH_2CH_3$ |
| 2 | $CH_3$ | H |
| 2 | $CH_3$ | Cl |
| 2 | $CH_3$ | $OCH_3$ |
| 2 | $CH_3$ | $CH_3$ |
| 2 | $CH_3$ | $C_2H_5$ |
| 2 | $CH_3$ | $CH(CH_3)_2$ |
| 2 | $CH_3$ | $CH_2CH_2CH_3$ |
| 2 | $C_2H_5$ | H |
| 2 | $C_2H_5$ | Cl |
| 2 | $C_2H_5$ | $OCH_3$ |
| 2 | $C_2H_5$ | $CH_3$ |
| 2 | $C_2H_5$ | $C_2H_5$ |
| 2 | $C_2H_5$ | $CH(CH_3)_2$ |
| 2 | $C_2H_5$ | $CH_2CH_2CH_3$ |
| 2 | $CH(CH_3)_2$ | H |
| 2 | $CH(CH_3)_2$ | Cl |
| 2 | $CH(CH_3)_2$ | $OCH_3$ |
| 2 | $CH(CH_3)_2$ | $CH_3$ |
| 2 | $CH(CH_3)_2$ | $C_2H_5$ |
| 2 | $CH(CH_3)_2$ | $CH(CH_3)_2$ |
| 2 | $CH(CH_3)_2$ | $CH_2CH_2CH_3$ |
| 2 | $CH_2CH_2CH_3$ | H |
| 2 | $CH_2CH_2CH_3$ | Cl |
| 2 | $CH_2CH_2CH_3$ | $OCH_3$ |
| 2 | $CH_2CH_2CH_3$ | $CH_3$ |
| 2 | $CH_2CH_2CH_3$ | $C_2H_5$ |
| 2 | $CH_2CH_2CH_3$ | $CH(CH_3)_2$ |
| 2 | $CH_2CH_2CH_3$ | $CH_2CH_2CH_3$ |
| 2 | $CH_3$ | $C_6H_5$ |
| 2 | $C_6H_5$ | $CH_3$ |
| 2 | $CH_3$ | $CF_3$ |
| 2 | $CF_3$ | $CH_3$ |
| 2 | $COCH_3$ | H |
| 2 | $CH=CH_2$ | $CH_3$ |
| 2 | $CH_3$ | $CH=CH_2$ |
| 2 | $SCH_3$ | $CH_3$ |
| 2 | $CH_3$ | $SCH_3$ |
| 2 | $NO_2$ | $CH_3$ |
| 2 | $NH_2$ | $CH_3$ |
| 2 | CHO | $CH_3$ |

TABLE 19-continued

| | | |
|---|---|---|
| 2 | $CO_2CH_3$ | H |
| 2 | $CH(OCH_3)_2$ | H |

| A = A-19; $R^3$ = $CH_3$; $R^5$ = $CH_3$ | | |
|---|---|---|
| n | $R^1$ | $R^2$ |
| 2 | $CH_3$ | $CH_3$ |
| 2 | $C_2H_5$ | $CH_3$ |
| 2 | H | $CH_3$ |
| 2 | H | $C_2H_5$ |
| 2 | H | $CH_2CH_2CH_3$ |
| 2 | $OCH_3$ | $CH_3$ |
| 2 | $OCH_3$ | $C_2H_5$ |
| 2 | $CH_2CH_2CH_3$ | $CH_2CH_2CH_3$ |
| 2 | $CH_2CH=CH_2$ | $CH_2CH=CH_2$ |
| 2 | $CH_2C\equiv CH$ | $CH_2C\equiv CH$ |
| 2 | $CH(CH_3)_2$ | $CH(CH_3)_2$ |
| 2 | $-(CH_2)_5-$ | |
| 2 | $-(CH_2)_4-$ | |
| 2 | $CH_2CH=CH_2$ | $C_2H_5$ |
| 2 | $CH_2C\equiv CH$ | $C_2H_5$ |
| 2 | $OC_2H_5$ | $CH_3$ |
| 2 | $OC_2H_5$ | $C_2H_5$ |
| 2 | H | 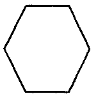 |
| 2 | 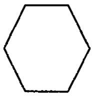 | 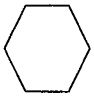 |
| 2 | H | $CH_2CH=CH_2$ |
| 2 | $CH_2CH_2CH_3$ | $CH_3$ |

TABLE 20

| A = A-20; $R^1$ = $C_2H_5$; $R^2$ = $C_2H_5$ | | |
|---|---|---|
| n | $R^3$ | $R^5$ |
| 2 | H | H |
| 2 | H | Cl |
| 2 | H | $OCH_3$ |
| 2 | H | $CH_3$ |
| 2 | H | $C_2H_5$ |
| 2 | H | $CH(CH_3)_2$ |
| 2 | H | $CH_2CH_2CH_3$ |
| 2 | Cl | H |
| 2 | Cl | Cl |
| 2 | Cl | $OCH_3$ |
| 2 | Cl | $CH_3$ |
| 2 | Cl | $C_2H_5$ |
| 2 | Cl | $CH(CH_3)_2$ |
| 2 | Cl | $CH_2CH_2CH_3$ |
| 2 | $OCH_3$ | H |
| 2 | $OCH_3$ | Cl |
| 2 | $OCH_3$ | $OCH_3$ |
| 2 | $OCH_3$ | $CH_3$ |
| 2 | $OCH_3$ | $C_2H_5$ |
| 2 | $OCH_3$ | $CH(CH_3)_2$ |
| 2 | $OCH_3$ | $CH_2CH_2CH_3$ |
| 2 | $CH_3$ | H |
| 2 | $CH_3$ | Cl |
| 2 | $CH_3$ | $OCH_3$ |
| 2 | $CH_3$ | $CH_3$ |

TABLE 20-continued

| | | |
|---|---|---|
| 2 | $CH_3$ | $C_2H_5$ |
| 2 | $CH_3$ | $CH(CH_3)_2$ |
| 2 | $CH_3$ | $CH_2CH_2CH_3$ |
| 2 | $C_2H_5$ | H |
| 2 | $C_2H_5$ | Cl |
| 2 | $C_2H_5$ | $OCH_3$ |
| 2 | $C_2H_5$ | $CH_3$ |
| 2 | $C_2H_5$ | $C_2H_5$ |
| 2 | $C_2H_5$ | $CH(CH_3)_2$ |
| 2 | $C_2H_5$ | $CH_2CH_2CH_3$ |
| 2 | $CH(CH_3)_2$ | H |
| 2 | $CH(CH_3)_2$ | Cl |
| 2 | $CH(CH_3)_2$ | $OCH_3$ |
| 2 | $CH(CH_3)_2$ | $CH_3$ |
| 2 | $CH(CH_3)_2$ | $C_2H_5$ |
| 2 | $CH(CH_3)_2$ | $CH(CH_3)_2$ |
| 2 | $CH(CH_3)_2$ | $CH_2CH_2CH_3$ |
| 2 | $CH_2CH_2CH_3$ | H |
| 2 | $CH_2CH_2CH_3$ | Cl |
| 2 | $CH_2CH_2CH_3$ | $OCH_3$ |
| 2 | $CH_2CH_2CH_3$ | $CH_3$ |
| 2 | $CH_2CH_2CH_3$ | $C_2H_5$ |
| 2 | $CH_2CH_2CH_3$ | $CH(CH_3)_2$ |
| 2 | $CH_2CH_2CH_3$ | $CH_2CH_2CH_3$ |
| 2 | $CH_3$ | $C_6H_5$ |
| 2 | $C_6H_5$ | $CH_3$ |
| 2 | $CH_3$ | $CF_3$ |
| 2 | $CF_3$ | $CH_3$ |
| 2 | $COCH_3$ | H |
| 2 | $CH{=}CH_2$ | $CH_3$ |
| 2 | $CH_3$ | $CH{=}CH_2$ |
| 2 | $SCH_3$ | $CH_3$ |
| 2 | $CH_3$ | $SCH_3$ |
| 2 | $NO_2$ | $CH_3$ |
| 2 | $NH_2$ | $CH_3$ |
| 2 | CHO | $CH_3$ |
| 2 | $CO_2CH_3$ | H |
| 2 | $CH(OCH_3)_2$ | H |

A = A-20; $R^3 = CH_3$; $R^5 = CH_3$

| n | $R^1$ | $R^2$ |
|---|---|---|
| 2 | $CH_3$ | $CH_3$ |
| 2 | $C_2H_5$ | $CH_3$ |
| 2 | H | $CH_3$ |
| 2 | H | $C_2H_5$ |
| 2 | H | $CH_2CH_2CH_3$ |
| 2 | $OCH_3$ | $CH_3$ |
| 2 | $OCH_3$ | $C_2H_5$ |
| 2 | $CH_2CH_2CH_3$ | $CH_2CH_2CH_3$ |
| 2 | $CH_2CH{=}CH_2$ | $CH_2CH{=}CH_2$ |
| 2 | $CH_2C{\equiv}CH$ | $CH_2C{\equiv}CH$ |
| 2 | $CH(CH_3)_2$ | $CH(CH_3)_2$ |
| 2 | $-(CH_2)_5-$ | |
| 2 | $-(CH_2)_4-$ | |
| 2 | $CH_2CH{=}CH_2$ | $C_2H_5$ |
| 2 | $CH_2C{\equiv}CH$ | $C_2H_5$ |
| 2 | $OC_2H_5$ | $CH_3$ |
| 2 | $OC_2H_5$ | $C_2H_5$ |
| 2 | H | 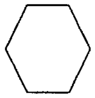 |
| 2 | 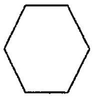 | 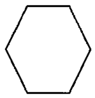 |
| 2 | H | $CH_2CH{=}CH_2$ |

TABLE 20-continued

| | | |
|---|---|---|
| 2 | $CH_2CH_2CH_3$ | $CH_3$ |

Formulation

Compounds of this invention will generally be used in formulation with an agriculturally suitable carrier comprising a liquid or solid diluent or an organic solvent. Use formulations include dusts, granules, pellets, solutions, suspensions, emulsions, wettable powders, emulsifiable concentrates, dry flowables and the like, consistent with the physical properties of the active ingredient, mode of application and environmental factors such as soil type, moisture and temperature. Sprayable formulations can be extended in suitable media and used at spray volumes from about one to several hundred liters per hectare. High strength compositions are primarily used as intermediates for further formulation. The formulations will typically contain effective amounts of active ingredient, diluent and surfactant within the following approximate ranges which add up 100 weight percent.

| | Weight Percent | | |
|---|---|---|---|
| | Active Ingredient | Diluent | Surfactant |
| Wettable Powders | 25–90 | 0–74 | 1–10 |
| Oil Suspensions, Emulsions, Solutions, (including Emulsifiable Concentrates) | 5–50 | 40–95 | 0–15 |
| Dusts | 1–25 | 70–99 | 0–5 |
| Granules and Pellets | 0.01–99 | 5–99.99 | 0–15 |
| High Strength Compositions | 90–99 | 0–10 | 0–2 |

Typical solid diluents are described in Watkins, et at., *Handbook of Insecticide Dust Diluents and Carriers,* 2nd Ed., Dotland Books, Caldwell, N.J. Typical liquid diluents and solvents are described in Marsden, *Solvents Guide,* 2nd Ed., Interscience, New York, 1950. *McCutcheon's Detergents and Emulsifiers Annual,* Allured Publ. Corp., Ridgewood, N.J., as well as Sisely and Wood, *Encyclopedia of Surface Active Agents,* Chemical Publ. Co., Inc., New York, 1964, list surfactants and recommended uses. All formulations can contain minor amounts of additives to reduce foam, caking, corrosion, microbiological growth, etc.

Solutions are prepared by simply mixing the ingredients. Fine solid compositions are made by blending and, usually, grinding as in a hammer mill or fluid energy mill. Water-dispersible granules can be produced be agglomerating a free powder composition; see for example, Cross et at., *Pesticide Formulations,* Washington, D.C., 1988, pp 251–259. Suspensions are prepared by wet-milling; see. for example, U.S. Pat. No. 3,060,084. Granules and pellets can be made by spraying the active material upon proformed granular carriers or by agglomeration techniques. See Browning, "Agglomeration", *Chemical Engineering,* Dec. 4, 1967, pp 147–48, *Perry's Chemical Engineer's Handbook,* 4th Ed., McGraw-Hill, New York, 1963. pages 8–57 and following, and WO 91/13546. Pellets can be prepared as described in U.S. Pat. No. 4,172,714. Water-dispersible and water-soluble granules can also be prepared as taught in DE 3,246,493.

For further information regarding the an of formulation, see U.S. Pat. No. 3,235,361, Col. 6, line 16 through Col. 7, line 19 and Examples 10–41; U.S. Pat. No. 3,309,192, Col. 5, line 43 through Col. 7, line 62 and Examples 8, 12, 15, 39, 41, 52, 53, 58,132, 138–140, 162–164, 166, 167 and 169–182; U.S. Pat. No. 2,891,855, Col. 3, line 66 through Col. 5, line 17 and Examples 1–4; Klingman, *Weed Control as a Science,* John Wiley and Sons, Inc., New York, 1961, pp 81–96; and Hance et al., *Weed Control Handbook,* 8th Ed., Blackwell Scientific Publications, Oxford, 1989.

In the following Examples, all percentages are by weight and all formulations are worked up in conventional ways. Compound numbers refer to compounds in Index Table A.

| Example A | |
|---|---|
| High Strength Concentrate | |
| Compound 1 | 98.5% |
| silica aerogel | 0.5% |
| synthetic amorphous fine silica | 1.0% |
| **Example B** | |
| Wettable Powder | |
| Compound 1 | 65.0% |
| dodecylphenol polyethylene glycol ether | 2.0% |
| sodium ligninsulfonate | 4.0% |
| sodium silicoaluminate | 6.0% |
| montmorillonite (calcined) | 23.0% |
| **Example C** | |
| Granule | |
| Compound 1 | 10.0% |
| attapulgite granules (low volatile matter, 0.71/0.30 mm; U.S.S. No. 25–50 sieves) | 90.0% |
| **Example D** | |
| Extruded Pellet | |
| Compound 1 | 25.0% |
| anhydrous sodium sulfate | 10.0% |
| crude calcium ligninsulfonate | 5.0% |
| sodium alkylnaphthalenesulfonate | 1.0% |
| calcium/magnesium bentonite | 59.0% |

Utility

Test results indicate compounds of this invention are active postemergence and, in particular, preemergence herbicides. Many compounds in this invention are useful for the control of selected grass and broadleaf weeds with tolerance to important agronomic crops such as barley (*Hordeum vulgare*), corn (*Zea mays*), cotton (*Gossypium hirsutum*), rape (*Brassica napus*), rice (*Oryza sativa*), sorghum (*Sorghum bicolor*), soybean (*Glycine max*), sugar beet (*Beta vulgaris*), and wheat (*Triticum aestivum*), and to vegetable crops. Grass and broadleaf weed species controlled include, but are not limited to, barnyardgrass (*Echinochloa crusgali*), blackgrass (*Alopecurus myosuroides*), chickweed (*Stellaria media*), crabgrass (Digitaria spp.), foxtail (Setaria spp.), lambsquarters (Chenopodium spp.), and wild oats (*Avena fatua*).

Compounds 15 and 18 demonstrated excellent control of weeds including pigweed, grabgrass, giant foxtail, green foxtail, fall panicum and wild proso with outstanding crop tolerance to cotton and soybeans in Table C. Compounds 30 and 38 demonstrated control of important weeds such as lambsquarter, barnyardgrass, crabgrass, giant foxtail, blackgrass and wild oats with excellent tolerance to crops including corn, soybean, cotton and wheat in Table B.

These compounds also have utility for weed control of selected vegetation in specified areas such as around storage tanks, parking lots, highways, and railways: in fallow crop areas: and in citrus and plantation crops such as banana, coffee, oil palm, and rubber. Alternatively, these compounds are useful to modify plant growth.

Effective rates of application for compounds of this invention are determined by a number of factors. These factors include: formulation selected, method of application, mount and type of vegetation present, growing conditions, etc. In general terms, the subject compounds should be applied at rates from 0.03 to 20 kg/ha with a preferred rate range of 0.05 to 2 kg/ha. One skilled in the an can easily determine effective application rates necessary for desired level of weed control.

Compounds of this invention can be used alone or in combination with other commercial herbicides, insecticides or fungicities. A mixture of one or more of the following herbicides with a compound of titis invention may be particularly useful for weed control. Examples of other herbicides with which compounds of this invention can be formulated are: acetochlor, acifluoffen, acrolein, 2-propenal, alachlor, ametryn, amidosulfuron, ammonium sulfamate, amitrole, anilofos, asulam, atrazine, barban. benefta, bensulfuron methyl, bensulide, bentazon, benzofiuor, benzoylprop, bifenox, bromacil, bromoxynil, bromoxynil heptanoate, bromoxynil octanoate, butachlor, buthidazole, butralin, butrate, cacodylic acid, 2-chloro-N,N-di-2-propenylacetamide, 2-chloroallyl diethyldithiocarbamate, chloramben, chlorbromuron, chloridazon, chlorimuron ethyl, chlormethoxynil, chlomitrofen, chloroxuron, chlorpropharn, chlorsulfuron, chlortoluron, cinmethylin, cinosulfuron, clethodim, clomazone, cloproxydim, clopyralid, calcium salt of methylarsonic acid, cyanazine, cycloate, cycluron, cyperquat, cyprazine, cyprazole, cypromid, dalapon, dazomet, dimethyl 2,3,5,6-tetrachloro-1,4-benzenedicarboxylate, desmedipham, desmetryn, dicamba, dichlebenil, dichlorprop, diclofop, diethatyl, difenzoquat, diflufenican, dimepiperate, dmitramine, dmoseb, diphenamid, dipropetryn, diquat, diuron, 2-methyl-4,6-dmitrophenol, disodium salt of methylarsonic acid, dymron, endothall, S-ethyl dipropylcarbamothioate, esprocarb, ethalfluralin, ethametsulfuron methyl, ethofumesate, fenac, fenoxaprop, fentuon, salt of fenuron and trichloroacetic acid, flareprop, fluazkfop, fluazkfop-P, fluchloralin, flumesulam, flumipropyn, fiuometuron, fiuorochloridone, fluorodffen, fluoroglycofen, fiupoxam, fluffdone, fluroxypyr, fluzasulfuron, fomesafen, losamine, glyphosate, haloxyfop, hexaflurate, hexazinone, imazamethabenz, irnazapyr, imazaquin, imazamethabenz methyl, imazethapyr, imazosulfuron, ioxynil, isopropalin, isoproturon, isouron, isoxaben, karbutilate, lactofen, lenacil, linuron, metobenzuron, metsulfuron methyl, methylarsonic acid, monoammonium salt of methylarsonic acid, (4-chloro-2-methylphenoxy)acetic acid, S,S'-dimethyl- 2-(difluoromethyl)4-(2-methylpropyl)-6-(triftuoromethyl)-3,5-pyridmedicarbothioate, mecoprop, mefenacet, mefluidide, methalpropalin, methabenzthiazuron, metham, methazole, methoxuron, metolachlor, metribuzin, 1,2-dihydropyridazine-3,6-dione, molinate, monolinuron, monuron, monuron salt and trichloroacetic acid, monosodium salt of methylarsonic acid, napropamide, naptalam, neburon, nicosulfuron, nitralin, nitrofen, nitrofluorfen, norca, norflurazon, oryzalin, oxadiazon, oxyfluorfen, paraquat, pebulate, pendimethalm, perfluidone, phenmedipham, picloram, 5-[2-chloro-4-

(trifluoromethyl)phenoxy]-2-nitroacctophenone oxime-O-acctic acid methyl ester, pretilachlor, primisulfuron, procyazine, profluralm, prometon, prometryn, pronamide, propachlor, propanil, propazine, propham, prosulfalin, prynachlor, pyrazolatc, pyrazon, pyrazosulfuron ethyl, quinchlorac, quizalofop ethyl, rimsulfuron, secbumeton, scthoxydim, siduron, simazme, 1-(a,a-dimethylbenzyl)-3-(4-methylphenyl)urea, sulfometuron methyl, trichloroacetic acid, tebuthiuron, terbacil, terbuchlor, terbuthylazine, terbutol, terbutryn, thifensulfuron methyl, thiobencarb, tri-allate, trialkoxydim, triasulfuron, tribenuron methyl, triclopyr, tridiphane, trifluralin, trimemron, (2,4-dichlorophenoxy)acetic acid, 4-(2,4-dichlorophenoxy)butanoic acid, vernolate, and xylachlor.

In certain instances, combinations with other herbicides having a similiar spectrum of control but a different mode of action will be particularly advantageous for resistance management.

Selective herbicidal properties of the subject compounds were discovered in greenhouse tests as described below.

INDEX TABLE A

| CMPD | A | X | $R^1$ | $R^2$ | $R^3$ | $R^4$ | $R^5$ | n | m.p. (°C.) |
|---|---|---|---|---|---|---|---|---|---|
| 1 | A-4 | $NCH_3$ | $C_2H_5$ | $C_2H_5$ | $CH_3$ | $CH_3$ | | 2 | oil |
| 2 | A-4 | $NC_2H_5$ | $C_2H_5$ | $C_2H_5$ | $CH_3$ | $CH_3$ | | 2 | 90–96 |
| 3 | A-4 | O | $C_2H_5$ | $C_2H_5$ | $CH_3$ | $CH_3$ | | 2 | 108–110 |
| 4 | A-4 | $NC_6H_5$ | $C_2H_5$ | $C_2H_5$ | $CH_3$ | $CH_3$ | | 2 | oil |
| 5 | A-4 | $NCH_2CF_3$ | $C_2H_5$ | $C_2H_5$ | $CH_3$ | $CH_3$ | | 2 | oil |
| 6 | A-4 | $NCH_2CO_2C_2H_5$ | $C_2H_5$ | $C_2H_5$ | $CH_3$ | $CH_3$ | | 2 | oil |
| 7 | A-4 | $NCH_2CH_2CN$ | $C_2H_5$ | $C_2H_5$ | $CH_3$ | $CH_3$ | | 2 | oil |
| 8 | A-4 | $NC(O)N(C_2H_5)_2$ | $C_2H_5$ | $C_2H_5$ | $CH_3$ | $CH_3$ | | 2 | oil |
| 9 | A-4 | $NC_2H_5$ | $CH_3$ | $CH_3$ | $CH_3$ | $CH_3$ | | 2 | oil |
| 10 | A-4 | $NCH_2CH_2CH_3$ | $C_2H_5$ | $C_2H_5$ | $CH_3$ | $CH_3$ | | 2 | oil |
| 11 | A-4 | $NCH_2CH_2CH_2CH_3$ | $C_2H_5$ | $C_2H_5$ | $CH_3$ | $CH_3$ | | 2 | oil |
| 12 | A-4 | $NCH_2CH(CH_3)_2$ | $C_2H_5$ | $C_2H_5$ | $CH_3$ | $CH_3$ | | 2 | oil |
| 13 | A-4 | $NCH_2C_6H_5$ | $C_2H_5$ | $C_2H_5$ | $CH_3$ | $CH_3$ | | 2 | 118–120 |
| 14 | A-1 | S | $C_2H_5$ | $C_2H_5$ | $C(O)CH_3$ | H | Cl | 2 | 128–130 |
| 15 | A-4 | $NCH_2CF_3$ | $C_2H_5$ | $C_2H_5$ | Cl | $CH_3$ | | 2 | 103–105 |
| 16 | A-4 | $NCH_2CH_2CH_3$ | $C_2H_5$ | $C_2H_5$ | Cl | $CH_3$ | | 2 | oil |
| 17 | A-4 | $NCH_2CH_2CH_2CH_3$ | $C_2H_5$ | $C_2H_5$ | Cl | $CH_3$ | | 2 | oil |
| 18 | A-4 | $NC_2H_5$ | $C_2H_5$ | $C_2H_5$ | Cl | $CH_3$ | | 2 | 88–90 |
| 19 | A-4 | 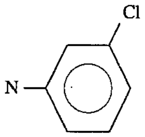 | $C_2H_5$ | $C_2H_5$ | $CH_3$ | $CH_3$ | | 2 | oil |
| 20 | A-4 | 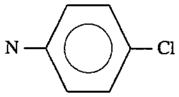 | $C_2H_5$ | $C_2H_5$ | $CH_3$ | $CH_3$ | | 2 | oil |
| 21 | A-4 | 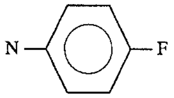 | $C_2H_5$ | $C_2H_5$ | $CH_3$ | $CH_3$ | | 2 | oil |
| 22 | A-4 | 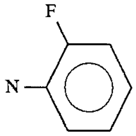 | $C_2H_5$ | $C_2H_5$ | $CH_3$ | $CH_3$ | | 2 | oil |
| 23 | A-4 | 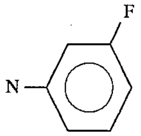 | $C_2H_5$ | $C_2H_5$ | $CH_3$ | $CH_3$ | | 2 | oil |
| 24 | A-2 | O | $C_2H_5$ | $C_2H_5$ | $CH_3$ | $CH_3$ | H | 2 | oil |
| 25 | A-4 | $NCH_2CH_2Cl$ | $C_2H_5$ | $C_2H_5$ | $CH_3$ | $CH_3$ | | 2 | oil |
| 26 | A-4 | $NCH_2CH_2Br$ | $C_2H_5$ | $C_2H_5$ | $CH_3$ | $CH_3$ | | 2 | 70–72 |
| 27 | A-6 | S | $C_2H_5$ | $C_2H_5$ | | H | Br | 2 | 110–111 |
| 28 | A-4 | $NCH_2CH=CH_2$ | $C_2H_5$ | $C_2H_5$ | $CH_3$ | $CH_3$ | | 2 | 102–104 |
| 29 | A-4 | $NCH=CH_2$ | $C_2H_5$ | $C_2H_5$ | $CH_3$ | $CH_3$ | | 2 | oil |
| 30 | A-4 | $NCH_3$ | $C_2H_5$ | $C_2H_5$ | $C_2H_5$ | $CH_3$ | | 2 | oil |
| 31 | A-3 | $NCH_3$ | $C_2H_5$ | $C_2H_5$ | $CHF_2$ | $CH_3$ | | 1 | oil |
| 32 | A-3 | $NCH_3$ | $C_2H_5$ | $C_2H_5$ | $CHF_2$ | $CH_3$ | | 2 | 89–91 |
| 33 | A-4 | $NCH_2CH_2OCH_3$ | $C_2H_5$ | $C_2H_5$ | $CH_3$ | $CH_3$ | | 2 | 83–85 |
| 34 | A-4 | $NCH_2CF_3$ | $C_2H_5$ | $C_2H_5$ | $C_2H_5$ | $C_2H_5$ | | 2 | oil |
| 35 | A-4 | $NCH_3$ | $C_2H_5$ | $C_2H_5$ | $C_2H_5$ | $C_2H_5$ | | 2 | oil |
| 36 | A-4 | $NC_2H_5$ | $C_2H_5$ | $C_2H_5$ | $C_2H_5$ | $C_2H_5$ | | 2 | oil |

INDEX TABLE A-continued

| | | | | | | | | | |
|---|---|---|---|---|---|---|---|---|---|
| 37 | A-4 | $NCH_3$ | $C_2H_5$ | $C_2H_5$ | $CH_3$ | $C_2H_5$ | | 2 | oil |
| 38 | A-4 | $NCH_2CF_3$ | $C_2H_5$ | $C_2H_5$ | $C_2H_5$ | $CH_3$ | | 2 | 95–96 |
| 39 | A-4 | $NCH_2CH_2CH_3$ | $C_2H_5$ | $C_2H_5$ | $C_2H_5$ | $C_2H_5$ | | 2 | oil |
| 40 | A-6 | S | $C_2H_5$ | $C_2H_5$ | | H | $NO_2$ | 2 | 115–118 |
| 41 | A-4 | $NCH(CH_3)_2$ | $C_2H_5$ | $C_2H_5$ | $CH_3$ | $CH_3$ | | 2 | oil |
| 42 | A-4 | 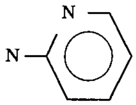 | $C_2H_5$ | $C_2H_5$ | $CH_3$ | $CH_3$ | | 2 | 97–99 |
| 43 | A-17 | | $C_2H_5$ | $C_2H_5$ | $CH_3$ | H | $CH_3$ | 2 | 86–88 |
| 44 | A-4 | $NCH_2CF_3$ | $C_2H_5$ | $C_2H_5$ | $CH_3$ | $C_2H_5$ | | 2 | oil |
| 45 | A-15 | | $C_2H_5$ | $C_2H_5$ | H | H | H | 2 | oil |
| 46 | A-17 | | $C_2H_5$ | $C_2H_5$ | $CH_3$ | Br | $CH_3$ | 2 | 93–95 |
| 47 | A-15 | | $C_2H_5$ | $C_2H_5$ | $CH_3$ | $CH_3$ | 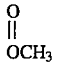 | 2 | 86–89 |
| 48 | A-17 | | $C_2H_5$ | $C_2H_5$ | H | I | H | 2 | 109–111 |
| 49 | A-17 | | $C_2H_5$ | $C_2H_5$ | $C_2H_5$ | H | $C_2H_5$ | 2 | 70–71 |
| 50 | A-17 | | $C_2H_5$ | $C_2H_5$ | H | H | H | 2 | 110–112 |
| 51 | A-15 | | $C_2H_5$ | $C_2H_5$ | $CH_3$ | $CH_3$ | $C_2H_5$ | 2 | oil |
| 52 | A-1 | NH | $C_2H_5$ | $C_2H_5$ | $CH_3$ | $C_2H_5$ | $CH_3$ | 2 | oil |
| 53 | A-17 | | $C_2H_5$ | $C_2H_5$ | $CH_3$ | H | 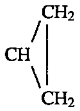 | 2 | 73–76 |
| 54 | A-17 | | $C_2H_5$ | $C_2H_5$ | 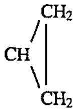 | H | $CH_3$ | 2 | 93–95 |
| 55 | A-17 | | $C_2H_5$ | $C_2H_5$ | $CH_3$ | H | $C_6H_5$ | 2 | 117–119 |
| 56 | A-4 | $NCH(CH_3)_2$ | $C_2H_5$ | $C_2H_5$ | $C_2H_5$ | CH3 | | 2 | oil |
| 57 | A-4 | $NCH(CH_3)_2$ | $C_2H_5$ | $C_2H_5$ | $CH_3$ | $C_2H_5$ | | 2 | oil |
| 58 | A-2 | $NCH_3$ | $C_2H_5$ | $C_2H_5$ | $CH_3$ | $CH_3$ | H | 2 | oil |
| 59 | A-4 | $NCH_2CF_3$ | $C_2H_5$ | $C_2H_5$ | Cl | $C_2H_5$ | | 2 | 78–80 |
| 60 | A-3 | $NCH_3$ | $C_2H_5$ | $C_2H_5$ | $CH_2Br$ | $CH_3$ | | 2 | oil |
| 61 | A-3 | $NCH_3$ | $C_2H_5$ | $C_2H_5$ | Br | Br | | 2 | 93–94 |
| 62 | A-3 | $NCH_3$ | $C_2H_5$ | $C_2H_5$ | Br | Br | | 1 | oil |
| 63 | A-12 | S | $C_2H_5$ | $C_2H_5$ | | | $CO_2CH_3$ | 2 | 105–107 |
| 64 | A-12 | S | $C_2H_5$ | $C_2H_5$ | | | $CO_2CH_3$ | 1 | oil |
| 65 | A-9 | S | $C_2H_5$ | $C_2H_5$ | $CO_2C_2H_5$ | | | 1 | oil |
| 66 | A-9 | S | $C_2H_5$ | $C_2H_5$ | $CO_2C_2H_5$ | | | 2 | oil |
| 67 | A-6 | $NCH_3$ | $C_2H_5$ | $C_2H_5$ | | Br | Br | 1 | oil |
| 68 | A-6 | $NCH_3$ | $C_2H_5$ | $C_2H_5$ | | Br | Br | 2 | oil |
| 69 | A-16 | | $C_2H_5$ | $C_2H_5$ | $CH_3$ | H | H | 2 | oil |
| 70 | A-16 | | $C_2H_5$ | $C_2H_5$ | $CH_3$ | H | $CH_3$ | 2 | oil |
| 71 | A-16 | | $C_2H_5$ | $C_2H_5$ | $C_2H_5$ | H | $CH_3$ | 2 | 70–72 |
| 72 | A-19 | | $C_2H_5$ | $C_2H_5$ | H | | H | 2 | 111–113 |
| 73 | A-16 | | $C_2H_5$ | $C_2H_5$ | $C_2H_5$ | H | H | 2 | oil |
| 74 | A-4 | $NC_2H_5$ | $C_2H_5$ | $C_2H_5$ | Cl | | $C_2H_5$ | 2 | 67–68 |
| 92 | A-17 | | $C_2H_5$ | $C_2H_5$ | $CH_3$ | $C_2H_5$ | $CH_3$ | 2 | 64–66 |
| 93 | A-4 | $NCH_2CH_3$ | $C_2H_5$ | $C_2H_5$ | Cl | $CH_3$ | | 1 | oil |
| 94 | A-17 | | $C_2H_5$ | $C_2H_5$ | $CH_3$ | H | $CH(CH_3)_2$ | 2 | 64–66 |
| 95 | A-17 | | $C_2H_5$ | $C_2H_5$ | $CH_3$ | H | $CH_2CH(CH_3)_2$ | 2 | oil |
| 96 | A-17 | | $C_2H_5$ | $C_2H_5$ | $CH_3$ | H | $C_2H_5$ | 2 | oil |
| 97 | A-4 | $NCH_2CH_2CH_3$ | $C_2H_5$ | $C_2H_5$ | $C_2H_5$ | $CH_3$ | | 2 | oil |
| 98 | A-4 | $NCH_2CF_3$ | $C_2H_5$ | $C_2H_5$ | $OCH_3$ | $CH_3$ | | 2 | oil |
| 99 | A-4 | $NCH_3$ | $C_2H_5$ | $C_2H_5$ | Cl | $CH_3$ | | 2 | oil |
| 100 | A-4 | $NCH_3$ | $C_2H_5$ | $C_2H_5$ | $OCH_3$ | $CH_3$ | | 2 | oil |
| 101 | A-7 | $NCH_3$ | $C_2H_5$ | $C_2H_5$ | Cl | | $CHF_2$ | 2 | 106–107 |
| 102 | A-7 | $NCH_3$ | $C_2H_5$ | $C_2H_5$ | Cl | | $CHF_2$ | 1 | oil |
| 103 | A-7 | $NCH_3$ | $C_2H_5$ | $C_2H_5$ | $CHF_2$ | | $CH_2CH_2CH_3$ | 2 | 97–98 |

| Compound | Spectra Data |
|---|---|
| 1 | (NMR, $CDCl_3$): δ 1.3 (t, 6H); 2.45 (s, 3H); 2.57 (s, 3H); 3.6 (bq, 4H); 3.75 (s, 3H); 8.8 (s, 1H) |
| 4 | (NMR, $CDCl_3$): δ 1.3 (t, 6H); 254 (s, 3H); 2.59 (s, 3H); 3.4–3.8 (m, 4H); 7.3–7.6 (m, 5H); 8.85 (s, 1H) |
| 5 | (NMR, $CDCl_3$): δ 1.29 (t, 6H); 2.47 (s, 3H); 2.64 (s, 3H); 3.6 (m, 4H); 4.6 (q, 2H); 8.83 (s, 1H) |

INDEX TABLE A-continued

| | |
|---|---|
| 6 | (NMR, $CDCl_3$): δ 1.1–1.4 (m, 9H); 2.46 (s, 3H); 2.55 (s, 3H); 3.4–3.7 (m, 4H); 4.22 (q, 2H); 4.8 (s, 2H); 8.82 (s, 1H) |
| 7 | (NMR, $CDCl_3$): δ 1.29 (t, 6H); 2.45 (s, 3H); 2.68 (s, 3H); 2.96 (t, 2H); 3.6 (m, 4H); 4.29 (t, 2H); 8.83 (s, 1H) IR, Nujol): 2237 $cm^{-1}$ |
| 8 | (NMR, $CDCl_3$): δ 1.30 (m, 12H); 2.49 (s, 3H); 2.68 (s, 3H); 3–3.7 (m, 8H); 8.84 (s, 1H) |
| 9 | (NMR, $CDCl_3$): δ 1.4 (t, 3H); 2.46 (s, 3H); 2.58 (s, 3H); 3.2 (bs, 3H); 3.3 (bs, 3H); 4.05 (q, 2H); 8.79 (s, 1H) |
| 10 | (NMR, $CDCl_3$): δ 0.92 (t, 3H); 1.29 (t, 6H); 1.8 (m, 2H); 2.45 (s, 3H); 2.57 (s, 3H); 3.6 (m, 4H); 3.95 (t, 2H); 8.8 (s, 1H) |
| 11 | (NMR, $CDCl_3$): δ 0.94 (t, 3H); 1.29 (m, 8H); 1.79 (m, 2H); 2.45 (s, 3H); 2.57 (s, 3H); 3.58 (m, 4H); 4 (t, 2H); 8.81 (s, 1H) |
| 12 | (NMR, $CDCl_3$): δ 0.9 (d, 6H); 1.29 (t, 6H); 2.2 (m, 1H); 2.45 (s, 3H); 2.57 (s, 3H); 3.58 (m, 4H); 3.8 (d, 2H); 8.8 (s, 1H) |
| 16 | (NMR, $CDCl_3$): δ 0.93 (t, 3H); 1.29 (t, 6H); 1.87 (m, 2H); 2.5 (s, 3H); 3.6 (m, 4H); 4.07 (t, 2H); 8.84 (s, 1H) |
| 17 | (NMR, $CDCl_3$): δ 0.98 (t, 3H); 1.3 (m, 8H); 1.8 (m, 2H); 2.5 (s, 3H); 3.6 (m, 4H); 4.1 (t, 2H); 8.84 (s, 1H) |
| 18 | (NMR, $CDCl_3$): δ 1.29 (t, 6H); 1.43 (t, 3H); 2.5 (s, 3H); 3.6 (m, 4H); 4.15 (q, 2H); 8.84 (s, 1H) |
| 19 | (NMR, $CDCl_3$): δ 1.31 (t, 6H); 2.54 (s, 3H); 2.61 (s, 3H); 3.6 (m, 4H); 7.2–7.5 (m, 4H); 8.82 (s, 1H) |
| 20 | (NMR, $CDCl_3$): δ 1.31 (t, 6H); 2.54 (s, 3H); 2.59 (s, 3H); 3.6 (m, 4H); 7.34 (d, 2H); 7.48 (d, 2H); 8.82 (s, 1H) |
| 21 | (NMR, $CDCl_3$): δ 1.3 (t, 6H); 2.53 (s, 3H); 2.57 (s, 3H); 3.6 (m, 4H); 7.1–7.4 (m, 4H); 8.82 (s, 1H) |
| 22 | (NMR, $CDCl_3$): δ 1.3 (t, 6H); 2.5 (s, 3H); 2.54 (s, 3H); 3.6 (bs, 4H); 7.2–7.6 (m, 4H); 8.87 (s, 1H) |
| 23 | (NMR, $CDCl_3$): δ 1.31 (t, 6H); 2.54 (s, 3H); 2.62 (s, 3H); 3.6 (m, 4H); 7.1–7.6 (m, 4H); 8.82 (s, 1H) |
| 24 | (NMR, $CDCl_3$): δ 1.3 (t, 6H); 2.17 (d, 3H); 2.65 (s, 3H); 3.6 (bs, 4H); 7.1 (bs, 1H); 8.82 (s, 1H) |
| 25 | (NMR, $CDCl_3$): δ 1.29 (t, 6H); 2.46 (s, 3H); 2.63 (s, 3H); 3.58 (bs, 4H); 3.85 (t, 2H); 4.3 (t, 2H); 8.82 (s, 1H) |
| 29 | (NMR, $CDCl_3$): δ 1.28 (m, 6H); 2.5 (s, 3H); 2.64 (s, 3H); 3.4–3.7 (m, 4H); 5.07 (d, 1H); 5.85 (d, 1H); 6.93 (dd, 1H); 8.82 (s, 1H) |
| 30 | (NMR, $CDCl_3$): δ 1.2–1.4 (m, 9H); 2.45 (s, 3H); 3 (q, 2H); 3.43–3.7 (m, 4H); 3.77 (s, 3H); 8.81 (s, 1H) |
| 31 | (NMR, $CDCl_3$): δ 1.25 (m, 6H); 2.36 (s, 3H); 3.58 (m, 4H); 4.09 (s, 3H); 6.99 (t, 1H); 8.9 (s, 1H) |
| 34 | (NMR, $CDCl_3$): δ 1.2–1.4 (m, 12H); 2.92 (q, 2H); 3.05 (q, 2H); 3.6 (m, 4H); 4.61 (q, 2H); 8.83 (s, 1H) |
| 35 | (NMR, $CDCl_3$): δ 1.1–1.4 (m, 12H); 2.82 (q, 2H); 2.98 (q, 2H); 3.4–3.7 (m, 4H); 3.71 (s, 1H) |
| 36 | (NMR, $CDCl_3$): δ 1.15–1.4 (m, 12H); 1.44 (t, 3H); 2.82–3.1 (m, 4H); 3.6 (m, 4H); 4.05 (q, 2H); 8.81 (s, 1H) |
| 37 | (NMR, $CDCl_3$): δ 1.18–1.4 (m, 9H); 2.58 (s, 3H); 2.9 (q, 2H); 3.6 (m, 4H); 3.76 (s, 3H); 8.8 (s, 1H) |
| 39 | (NMR, $CDCl_3$): δ 0.95 (t, 3H); 1.1–1.4 (m, 12H); 1.88 (m, 2H); 2.82–3.1 (m, 4H); 3.6 (m, 4H); 3.95 (t, 2H); 8.81 (s, 1H) |
| 41 | (NMR, $CDCl_3$): δ 1.29 (t, 6H); 1.45 (d, 6H); 2.46 (s, 3H); 2.58 (s, 3H); 3.6 (m, 4H); 4.4 (m, 1H); 8.82 (s, 1H) |
| 44 | (NMR, $CDCl_3$): δ 1.28 (m, 9H); 2.64 (s, 3H); 2.9 (q, 2H); 3.58 (m, 4H); 4.63 (q, 2H): 8.84 (s, 1H) |
| 45 | (NMR, $CDCl_3$): δ 1.24 (t, 6H); 3.5 (q, 4H); 6.42 (bs, 2H); 7.3 (bs, 2H); 9.08 (s, 1H) |
| 51 | 0.94 (t, 3H); 1.21 (t, 6H); 1.88 (s, 3H); 2.23 (q, 2H); 2.27 (s, 3H); 3.5 (m, 4H), 6.87 (s, 1H), 8.74 (s, 1H) |
| 52 | (NMR, $CDCl_3$): δ 1.05 (t, 3H); 1.2 (m, 6H); 2.08 (s, 3H); 2.19 (s, 3H); 2.39 (q, 2H); 3.5 (m, 4H); 7.87 (bs, 1H); 8.69 (s, 1H) |
| 56 | (NMR, $CDCl_3$): δ 1.2–1.3 (m, 9H); 1.47 (d, 6H); 2.47 (s, 3H); 3.02 (q, 2H); 3.5–3.7 (m, 4H); 4.43 (m, 1H); 8.82 (s, 1H) |
| 57 | (NMR, $CDCl_3$): δ 3.5–3.7 (m, 4H); 4.43 (m, 1H); 8.81 (s, 1H) |
| 58 | (NMR, $CDCl_3$): δ 1.3 (m, 6H); 2.23 (s, 3H); 2.53 (s, 3H); 3.48 (s, 3H); 3.6 (m, 4H); 5.32 (s, 1H); 8.78 (s, 1H) |
| 60 | (NMR, $CDCl_3$): δ 1.29 (m, 6H); 2.28 (s, 3H); 3.6 (m, 4H); 4.2 (s, 3H); 4.69 (s, 2H); 8.87 (s, 1H) |
| 62 | (NMR, $CDCl_3$): δ 1.25 (bs, 6H); 3.58 (bs, 4H); 4.2 (s, 3H); 8.7 (s, 1H). (IR, Nujol): 1720 $cm^{-1}$, 1081 $cm^{-1}$ |
| 64 | (NMR, $CDCl_3$): δ 1.28 (t, 6H); 3.6 (bs, 4H); 4.09 (s, 3H); 8.9 (s, 1H) |
| 65 | (NMR, $CDCl_3$): δ 1.3 (m, 6H); 1.4 (t, 3H); 3.5 (q, 4H); 4.4 (q. 2H); 8.8 (s, 1H) |
| 66 | (NMR, $CDCl_3$): δ 1.25 (bd, 6H); 1.38 (t, 3H); 3.58 (bs, 4H); 4.45 (q, 2H); 8.82 (s, 1H) |
| 67 | (NMR, $CDCl_3$): δ 1.28 (t, 6H); 3.6 (bd, 4H); 4.05 (s, 3H); 8.9 (s, 1H). (IR, neat): 1744 $cm^{-1}$; 1073 $cm^{-1}$; |

INDEX TABLE A-continued

| | |
|---|---|
| 68 | (NMR, $CDCl_3$): δ 1.3 (t, 6H); 3.6 (bd, 4H); 4.15 (s, 3H); 8.8 (s, 1H). (IR, Nujol): 1728 $cm^{-1}$; 1376 $cm^{-1}$; 1170 $cm^{-1}$ |
| 69 | (NMR, $CDCl_3$): δ 1.3 (t, 6H); 2.65 (s, 3H); 3.55 (bs, 4H); 6.95 (s, 1H); 7.4 (s, 1H); 8.9 (s, 1H) |
| 70 | (NMR, $CDCl_3$): δ 1.29 (t, 5H); 2.14 (s, 3H); 2.64 (s, 3H); 3.55 (bs, 4H); 7.07 (s, 1H); 8.76 (s, 1H) |
| 73 | (NMR, $CDCl_3$): δ 1.28 (t, 6H); 1.35 (t, 3H); 3.04 (q, 2H); 3.5 (bs, 4H); 6.97 (s, 1H); 7.40 (s, 1H); 8.88 (s, 1H) |
| 93 | (NMR, $CDCl_3$): δ 1.28 (m, 6H); 1.43 (t, 3H); 2.33 (s, 3H); 3.4–3.8 (m, 4H); 4.15 (q, 2H); 8.9 (s, 1H) |
| 95 | (NMR, $CDCl_3$): δ 0.86 (d, 6H); 1.28 (t, 6H); 1.87 (m, 1H); 2.43 (d, 2H); 2.62 (s, 3H); 3.58 (m, 4H); 6.04 (s, 1H); 8.81 (s, 1H) |
| 96 | (NMR, $CDCl_3$): δ 1.18 (t, 3H); 1.28 (t, 6H); 2.6 (m, 5H); 3.58 (m, 4H); 6.08 (s, 1H); 8.83 (s, 1H) |
| 97 | (NMR, $CDCl_3$): δ 0.95 (t, 3H); 1.29 (m, 9H); 1.9 (m, 2H); 2.46 (s, 3H); 3 (q, 2H); 3.6 (m, 4H); 3.94 (t, 2H); 8.82 (s, 1H) |
| 98 | (NMR, $CDCl_3$): δ 1.29 (t, 6H); 2.43 (s, 3H); 3.6 (m, 4H); 4.31 (s, 3H); 4.51 (q, 2H); 8.86 (s, 1H) |
| 99 | (NMR, $CDCl_3$): δ 1.30 (t, 6H); 2.50 (s, 3H); 3.6 (m, 4H); 3.82 (s, 3H); 8.84 (s, 1H) |
| 100 | (NMR, $CDCl_3$): δ 1.29 (t, 6H); 2.42 (s, 3H); 3.45–3.75 (m, 7H); 4.21 (s, 3H); 8.83 (s, 1H) |
| 102 | (NMR, $CDCl_3$): δ 1.27 (bs, 6H); 3.6 (bs, 4H); 4.1 (s, 3H); 6.7 (t, 1H); 8.95 (s, 1H) |

INTERMEDIATE TABLE

| CMPD | A | X | $R^1$ | $R^2$ | $R^3$ | $R^4$ | $R^5$ | n | m.p. (°C.) |
|---|---|---|---|---|---|---|---|---|---|
| 75 | A-4 | $NCH_3$ | $C_2H_5$ | $C_2H_5$ | $CH_3$ | $CH_3$ | | 0 | oil |
| 76 | A-4 | $NC_2H_5$ | $C_2H_5$ | $C_2H_5$ | $CH_3$ | $CH_3$ | | 0 | 67–69 |
| 77 | A-4 | $NC_6H_5$ | $C_2H_5$ | $C_2H_5$ | $CH_3$ | $CH_3$ | | 0 | oil |
| 78 | A-4 | $NCH_2CF_3$ | $C_2H_5$ | $C_2H_5$ | $CH_3$ | $CH_3$ | | 0 | oil |
| 79 | A-4 | $NCH_2C_6H_5$ | $C_2H_5$ | $C_2H_5$ | $CH_3$ | $CH_3$ | | 0 | oil |
| 80 | A-4 | $NCH_2CO_2C_2H_5$ | $C_2H_5$ | $C_2H_5$ | $CH_3$ | $CH_3$ | | 0 | oil |
| 81 | A-4 | $NC_2H_5$ | $CH_3$ | $CH_3$ | $CH_3$ | $CH_3$ | | 0 | oil |
| 82 | A-4 | $NCH_2CH_2CN$ | $C_2H_5$ | $C_2H_5$ | $CH_3$ | $CH_3$ | | 0 | 95–97 |
| 83 | A-4 | $NCH_2CH_2CH_3$ | $C_2H_5$ | $C_2H_5$ | $CH_3$ | $CH_3$ | | 0 | 81–83 |
| 84 | A-4 | $NCH_2CH_2CH_2CH_3$ | $C_2H_5$ | $C_2H_5$ | $CH_3$ | $CH_3$ | | 0 | oil |
| 85 | A-4 | $NCH_2CH(CH_3)_2$ | $C_2H_5$ | $C_2H_5$ | $CH_3$ | $CH_3$ | | 0 | oil |
| 86 | A-4 | $NCH_2CF_3$ | $C_2H_5$ | $C_2H_5$ | Cl | $CH_3$ | | 0 | 112–114 |
| 87 | A-4 | O | $C_2H_5$ | $C_2H_5$ | $CH_3$ | $CH_3$ | | 0 | oil |
| 88 | A-1 | S | $C_2H_5$ | $C_2H_5$ | $C(O)CH_3$ | H | Cl | 0 | 103–105 |
| 89 | A-1 | $NC_2H_5$ | $C_2H_5$ | $C_2H_5$ | Cl | $CH_3$ | | 0 | 88–90 |
| 90 | A-4 | $NCH_2CH_2CH_3$ | $C_2H_5$ | $C_2H_5$ | Cl | $CH_3$ | | 0 | oil |
| 91 | A-4 | $NCH_2CH_2CH_2CH_3$ | $C_2H_5$ | $C_2H_5$ | Cl | $CH_3$ | | 0 | oil |

| Compound | Spectra Data |
|---|---|
| 75 | (NMR, $CDCl_3$): δ 1.2 (t, 6H); 2.24 (s, 3H); 2.30 (s, 3H); 3.5 (q, 4H); 3.76 (s, 3H); 8.7 (s, 1H) |
| 77 | (NMR, $CDCl_3$): δ 1.2 (m, 6H); 2.34 (s, 3H); 2.39 (s, 3H); 3.43 (q, 4H); 7.45 (m, 5H); 8.72 (s, 1H) |
| 78 | (NMR, $CDCl_3$): δ 1.1–1.2 (m, 6H); 2.26 (s, 3H); 2.37 (s, 3H); 3.3–3.6 (q, 4H); 4.6 (q, 2H); 8.7 (s, 1H) |
| 79 | (NMR, $CDCl_3$): δ 1.1 (m, 6H); 2.25 (s, 3H); 2.29 (s, 3H); 3.47 (q, 4H); 5.26 (s, 2H); 7–7.4 (m, 5H); 8.69 (s, 1H) |
| 80 | (NMR, $CDCl_3$): δ 1–1.35 (m, 9H); 2.26 (s, 3H); 2.29 (s, 3H); 3.5 (bq, 4H); 4.23 (q, 2H); 4.81 (s, 2H); 8.69 (s, 1H) |
| 81 | (NMR, $CDCl_3$): δ 1.4 (t, 3H); 2.26 (s, 3H); 2.32 (s, 3H); 3.17 (bs, 6H); 4.07 (q, 2H); 8.66 (s, 1H) |
| 84 | (NMR, $CDCl_3$): δ 0.94 (t, 3H); 1.15 (m, 6H); 1.3 (m, 2H); 1.8 (m, 2H); 2.25 (s, 3H); 2.3 (s, 3H); 3.47 (q, 4H); 4 (t, 2H); 8.89 (s, 1H) |
| 85 | (NMR, $CDCl_3$): δ 0.9 (d, 6H); 1.18 (t, 6H); 2.2 (m, 1H); 2.25 (s, 3H); 2.29 (s, 3H); 3.43 (q, 4H); 3.8 (d, 2H); 8.69 (s, 1H) |
| 87 | (NMR, $CDCl_3$): δ 1.2 (m, 6H); 2.27 (s, 3H); 2.48 (s, 3H); 3.48 (q, 4H); 8.72 (s, 1H) |
| 89 | (NMR, $CDCl_3$): δ 1.2 (m, 6H); 1.4 (t, 3H); 2.28 (s, 3H); 3.5 (m, 4H); 4.17 (q, 2H); 8.7 (s, 1H) |
| 90 | (NMR, $CDCl_3$): δ 0.94 (t, 3H); 1.2 (m, 6H); 1.87 (m, 2H); 2.28 (s, 3H); 3.45 (q, 4H); 4.07 (t, 2H); 8.7 (s, 1H) |
| 91 | (NMR, $CDCl_3$): δ 0.95 (t, 3H); 1.2 (m, 6H); 1.3 (m, 2H); 1.8 (m, 2H); 2.28 (s, 3H); 3.45 (q, 4H); 4.1 (t, 2H); 8.7 (s, 1H) |

TEST A

Seeds of barnyardgrass (*Echmochloa crusgalli*), cheatgrass (*Bromus secalinus*), cocklebur (*Xanthium pensylvanicum*), crabgrass (Digitaria spp.), giant foxtaft (*Setaria faberii*), morningglory (Ipomoea spp.), sorghum (*Sorghum bicolor*), velvetled (*Abutilon theophrasti*), and wild oat (*Avena farua*) were planted into a sandy loam soft and treated preemergence with test chemicals dissolved in a nonphytotoxic solvent. At the same time, these crop and weed species were also treated postemergence with test chemicals. Plants ranged in height from two to eighteen cm and were in the two to three leaf stage for the postemergence treatment. Treated plants and untreated controls were maintained in a greenhouse for approximately eleven days, after which all treated plants were compared to untreated controls and visually evaluated for injury. Plant response ratings, summarized in Table A, are based on a 0 to 10 scale where 0 is no effect and 10 is complete control. A dash (–) response means no test results.

TABLE A

| | COMPOUND | | | | | |
|---|---|---|---|---|---|---|
| Rate (2000 g/ha) | 1 | 2 | 3 | 4 | 6 | 13 |
| POSTEMERGENCE | | | | | | |
| Barnyardgrass | 8 | 8 | 8 | 9 | 7 | 7 |
| Cheatgrass | 8 | 8 | 3 | 4 | 0 | 2 |
| Cocklebur | 4 | 5 | 1 | 2 | 0 | 0 |
| Crabgrass | 8 | 7 | 9 | 9 | 7 | 2 |
| Giant foxtail | 8 | 8 | 6 | 9 | 2 | 7 |
| Morningglory | 7 | 2 | 9 | 2 | 7 | 7 |
| Sorghum | 8 | 8 | 7 | 1 | 5 | 3 |
| Velvetleaf | 7 | 7 | 8 | 7 | 5 | 5 |
| Wild oat | 7 | 7 | 7 | 5 | 2 | 2 |
| PREEMERGENCE | | | | | | |
| Barnyardgrass | 10 | 10 | 10 | 10 | 9 | 9 |
| Cheatgrass | 10 | 9 | 9 | 8 | 9 | 8 |
| Cocklebur | 5 | 8 | 0 | 2 | 0 | 0 |

TABLE A-continued

| | COMPOUND | | | | | |
|---|---|---|---|---|---|---|
| Rate (2000 g/ha) | 1 | 2 | 3 | 4 | 6 | 13 |
| Crabgrass | 10 | 10 | 10 | 5 | 9 | 9 |
| Giant foxtail | 10 | 10 | 9 | 10 | 10 | 10 |
| Morningglory | 9 | 10 | 9 | 8 | 1 | 0 |
| Sorghum | 10 | 10 | 10 | 9 | 9 | 9 |
| Velvetleaf | 9 | 10 | 10 | 1 | 0 | 0 |
| Wild oat | 10 | 9 | 10 | 9 | 9 | 9 |

TEST B

Seeds of barley (*Hordeum vulgare*), bayardgrass (*Echinochloa crusgalli*), bedstraw (*Galium aparine*), blackgrass (*Alopecurus myosuroides*), cheatgrass (*Bromus secalinus*), chickweed (*Stellaria media*), cocklebur (*Xanthium pensylvanicum*), corn (*Zea mays*), cotton (*Gossypium hirsutum*), crategrass (Digitaria spp.), giant foxtail (*Setaria faberii*), lambsquarters (*Chenopodium album*), morningglory (*Ipomoea hederacea*), rape (*Brassica napus*), rice (*Oryza sativa*), sorghum (*Sorghum bicolor*), soybean (*Glycine max*), sugar beet (*Beta vulgaris*), velvetleaf (*Abutilon theophrasti*), wheat (*Triticum aestivum*), wild buckwheat (*Polygonum convolvulus*) and wild oat (*Avena farua*) and purple nutsedge (*Cyperus rotundus*) tubers were planted and treated preemergence with test chemicals dissolved in a non-phytotoxic solvent. At the same time, these crop and weed species were also treated with postemergence applications of test chemicals. Plants ranged in height from two to eighteen cm (one to four leaf stage) for postemergence treatments. Treated plants and controls were maintained in a greenhouse for twelve to sixteen days, after which all species were compared to controls and visually evaluated. Plant response ratings, summarized in Table B, are based on a scale of 0 to i0 where 0 is no effect and 10 is complete control. A dash (–) response means no test result.

TABLE B

| | COMPOUND | |
|---|---|---|
| Rate (2000 g/ha) | 27 | 40 |
| POSTEMERGENCE | | |
| Barley | 2 | 0 |
| Barnyardgrass | 7 | 0 |
| Bedstraw | 2 | 0 |
| Blackgrass | 2 | 0 |
| Cheatgrass | 0 | 0 |
| Chickweed | 2 | 0 |
| Cocklebur | 2 | 0 |
| Corn | 4 | 0 |
| Cotton | 1 | 4 |
| Crabgrass | 4 | 0 |
| Giant foxtail | 1 | 0 |
| Lambsquarters | 1 | 0 |
| Morningglory | 1 | 0 |
| Nutsedge | 0 | 0 |
| Rape | 5 | 0 |
| Rice | 8 | 0 |
| Sorghum | 1 | 0 |
| Soybean | 3 | 1 |
| Sugar beet | 5 | 0 |
| Velvetleaf | 1 | 0 |
| Wheat | 2 | 0 |
| Wild buckwheat | 1 | — |
| Wild oat | 0 | 0 |

TABLE B-continued

| PREEMERGENCE | | |
|---|---|---|
| Barley | 0 | 0 |
| Barnyardgrass | 10 | 0 |
| Bedstraw | 7 | 0 |
| Blackgrass | 9 | 0 |
| Cheatgrass | 4 | 0 |
| Chickweed | 3 | 0 |
| Cocklebur | 0 | 0 |
| Corn | 7 | 0 |
| Cotton | 2 | 0 |
| Crabgrass | 9 | 0 |
| Giant foxtail | 9 | 0 |
| Lambsquarters | 9 | 0 |
| Morningglory | 0 | 0 |
| Nutsedge | 3 | 0 |
| Rape | 1 | 0 |
| Rice | 2 | 0 |
| Sorghum | 8 | 0 |
| Soybean | 0 | 0 |
| Sugar beet | 2 | 0 |
| Velvetleaf | 1 | 0 |
| Wheat | 0 | 0 |
| Wild buckwheat | 10 | 0 |
| Wild oat | 9 | 0 |

| | COMPOUND | | | | | | | | | | | | | | | | | | | | | | | |
|---|---|---|---|---|---|---|---|---|---|---|---|---|---|---|---|---|---|---|---|---|---|---|---|---|
| Rate (400 g/ha) | 1 | 2 | 3 | 4 | 5 | 6 | 7 | 8 | 9 | 10 | 11 | 13 | 14 | 15 | 16 | 17 | 18 | 19 | 20 | 21 | 22 | 23 | 24 | 25 |
| POSTEMERGENCE | | | | | | | | | | | | | | | | | | | | | | | | |
| Barley | 6 | 4 | 4 | 0 | 0 | 0 | 0 | 0 | 3 | 0 | 0 | 0 | 0 | 0 | 0 | 0 | 0 | 0 | 0 | 0 | 0 | 0 | 0 | 0 |
| Barnyardgrass | 9 | 9 | 9 | 9 | 9 | 5 | 6 | 9 | 9 | 9 | 9 | 4 | 6 | 9 | 9 | 3 | 9 | 0 | 0 | 8 | 8 | 8 | 9 | 8 |
| Bedstraw | 6 | 5 | 2 | 4 | 5 | 5 | 4 | 1 | 0 | 1 | 0 | 3 | 0 | 0 | 0 | 3 | 0 | 3 | 3 | 2 | 5 | 7 | 3 | 5 |
| Blackgrass | 6 | 8 | 9 | 5 | 8 | 0 | 2 | 2 | 9 | 6 | 2 | 0 | 0 | 9 | 7 | 10 | 10 | 0 | 0 | 7 | 7 | 7 | 5 | 9 |
| Cheatgrass | 1 | 1 | 2 | 2 | 0 | 0 | 0 | 0 | 0 | 0 | 0 | 0 | 0 | 0 | 0 | 0 | 2 | 0 | 0 | 0 | 1 | 0 | 0 | 1 |
| Chickweed | 2 | 5 | — | 3 | 3 | 0 | 2 | — | — | 0 | 0 | 0 | 0 | 0 | 2 | 0 | 0 | 0 | 0 | 0 | 1 | 2 | 2 | 0 |
| Cocklebur | 1 | 1 | 1 | 2 | 0 | 1 | 1 | — | 1 | 0 | 0 | 0 | — | 0 | 1 | 0 | 1 | 0 | 1 | 1 | 1 | 0 | 0 | 0 |
| Corn | 9 | 8 | 8 | 2 | 0 | 0 | 1 | 4 | 4 | 3 | 0 | 0 | 0 | 0 | 0 | 0 | 4 | 0 | 1 | 0 | 0 | 0 | 4 | 0 |
| Cotton | 4 | 2 | 2 | 1 | 4 | 0 | 5 | 5 | 4 | 1 | 0 | 5 | 0 | 2 | 5 | 5 | 5 | 0 | 0 | 0 | 0 | 2 | 0 | 3 |
| Crabgrass | 6 | 8 | 8 | 1 | 1 | 0 | 0 | 1 | 3 | 6 | 0 | 0 | 4 | 2 | 7 | 5 | 8 | 0 | 1 | 7 | 8 | 3 | 4 | 6 |
| Giant foxtail | 5 | 6 | 0 | 3 | 1 | 0 | 0 | 1 | 7 | 3 | 0 | 0 | 3 | 2 | 2 | 1 | 7 | 0 | 0 | 2 | 7 | 0 | 1 | 3 |
| Lambsquarters | 1 | 2 | 6 | 3 | 7 | 0 | 4 | 6 | 0 | 0 | 2 | 0 | 0 | 0 | 0 | 0 | — | 2 | 1 | — | 2 | — | 1 | — |
| Morningglory | 1 | 5 | 5 | 9 | 5 | 0 | 3 | 3 | 1 | 5 | 1 | 1 | 1 | 8 | 6 | 3 | 7 | 2 | 2 | 5 | 3 | 2 | 1 | 0 |
| Nutsedge | 0 | — | — | 0 | 4 | 0 | 0 | — | — | 3 | 0 | 0 | 0 | 0 | 0 | 0 | 0 | 1 | 0 | 4 | 0 | 0 | 0 | 0 |
| Rape | 4 | 1 | 0 | 0 | 0 | 0 | 1 | 0 | 0 | 2 | 0 | 0 | 0 | 0 | 0 | 2 | 3 | 0 | 2 | 0 | 5 | 2 | 0 | 2 |
| Rice | 5 | 8 | 9 | 3 | 5 | 0 | 1 | 2 | 5 | 2 | 0 | 0 | 0 | 3 | 3 | 2 | 4 | 0 | 0 | 0 | 4 | 2 | 4 | 3 |
| Sorghum | 5 | 5 | 3 | 0 | 0 | 0 | 0 | 2 | 0 | 0 | 0 | 0 | 0 | 0 | 0 | 0 | 2 | 0 | 0 | 0 | 0 | 0 | 3 | 0 |
| Soybean | 4 | 1 | 5 | 2 | 3 | 0 | 4 | 2 | 1 | 3 | 2 | 3 | 0 | 3 | 4 | 2 | 7 | 1 | 0 | 1 | 2 | 2 | 1 | 3 |
| Sugar beet | 5 | 8 | 2 | 0 | 0 | 2 | 0 | 0 | 0 | 2 | 1 | 0 | 0 | 2 | 0 | 2 | 3 | 0 | 3 | 2 | 0 | 2 | 2 | 4 |
| Velvetleaf | 2 | 5 | 5 | 7 | 4 | 0 | 3 | 1 | 0 | 0 | 0 | 0 | 2 | 2 | 0 | 0 | 2 | 1 | 1 | 3 | 5 | 2 | 1 | 2 |
| Wheat | 6 | 6 | 5 | 0 | 0 | 0 | 0 | 0 | 6 | 2 | 0 | 0 | 0 | 0 | 0 | 0 | 0 | 0 | 0 | 0 | 0 | 0 | 2 | 3 |
| Wild buckwheat | — | — | — | 1 | 0 | 0 | — | — | — | 1 | 0 | 4 | 0 | 0 | 0 | 0 | 0 | 0 | 0 | 0 | 1 | 1 | 1 | 1 |
| Wild oat | 6 | 3 | 3 | 0 | 0 | 0 | 0 | 2 | 2 | 0 | 0 | 0 | 0 | 0 | 0 | 0 | 0 | 0 | 0 | 2 | 1 | 0 | 0 | 2 |

| | COMPOUND | | | | | | | | | | | | | | | | | | | | | | | |
|---|---|---|---|---|---|---|---|---|---|---|---|---|---|---|---|---|---|---|---|---|---|---|---|---|
| Rate (400 g/ha) | 26 | 27 | 28 | 29 | 30 | 31 | 32 | 33 | 34 | 35 | 36 | 37 | 38 | 39 | 40 | 41 | 42 | 43 | 44 | 45 | 46 | 47 | 48 | 49 |
| POSTEMERGENCE | | | | | | | | | | | | | | | | | | | | | | | | |
| Barley | 0 | 0 | 2 | 3 | 6 | 4 | 0 | 0 | 2 | 3 | 0 | 3 | 2 | 0 | 0 | 2 | 2 | 0 | 3 | 3 | 0 | 0 | 0 | 3 |
| Barnyardgrass | 6 | 6 | 8 | 9 | 9 | 9 | 9 | 9 | 8 | 9 | 9 | 9 | 9 | 9 | 0 | 7 | 9 | 0 | 9 | 9 | 9 | 3 | 0 | 8 |
| Bedstraw | 4 | 0 | 2 | 5 | 5 | 5 | 4 | 2 | — | 3 | 3 | 5 | 6 | 5 | 0 | 4 | 5 | 0 | 3 | 1 | 2 | 0 | 0 | 3 |
| Blackgrass | 5 | 0 | 5 | 9 | 8 | 9 | 0 | 2 | 1 | 9 | 8 | 9 | 5 | 8 | 0 | 6 | 7 | 0 | 3 | 6 | 1 | — | 0 | 2 |
| Cheatgrass | 0 | 0 | 0 | 2 | 3 | 3 | 0 | 2 | 4 | 4 | 2 | 5 | 4 | 3 | 0 | 0 | 3 | 0 | 1 | 1 | 1 | 2 | 2 | 0 |
| Chickweed | 2 | 0 | 3 | 0 | 4 | 1 | 0 | 1 | 1 | 0 | 0 | 4 | 3 | 1 | — | 1 | 4 | 0 | 2 | 0 | 0 | 0 | 4 | 5 |
| Cocklebur | 1 | 0 | 1 | 0 | 1 | 0 | 0 | 0 | 0 | 0 | 1 | 0 | 1 | 0 | 0 | 1 | 0 | 0 | 0 | 0 | 0 | 0 | 0 | 2 |
| Corn | 6 | 2 | 6 | 5 | 7 | 8 | 3 | 4 | 5 | 5 | 6 | 7 | 8 | 6 | 0 | 4 | 6 | 0 | 6 | 4 | 2 | 2 | 0 | 3 |
| Cotton | 3 | 0 | 4 | 5 | 5 | 9 | 2 | 2 | 0 | 6 | 5 | 3 | 1 | 0 | 0 | 3 | 2 | 0 | 1 | 2 | 2 | 2 | 0 | 2 |
| Crabgrass | 6 | 0 | 8 | 9 | 9 | 9 | 9 | 9 | 9 | 8 | 9 | 9 | 9 | 9 | 0 | 2 | 6 | 0 | 5 | 7 | 2 | 2 | 0 | 8 |
| Giant foxtail | 6 | 2 | 8 | 9 | 9 | 9 | 9 | 9 | 9 | 9 | 9 | 9 | 9 | 9 | 0 | 6 | 7 | 0 | 4 | 5 | 0 | 2 | 0 | 9 |
| Lambsquarters | 1 | 0 | 4 | 1 | 1 | 1 | 1 | — | 3 | 2 | 0 | — | 3 | 0 | 0 | 2 | 1 | 0 | — | 3 | 2 | 0 | 0 | 0 |
| Morningglory | 3 | 0 | 2 | 2 | 3 | 3 | 2 | 2 | 1 | 2 | 9 | 5 | 5 | 3 | 0 | 2 | 6 | 0 | 5 | 0 | 0 | 0 | 0 | 3 |
| Nutsedge | 0 | 0 | 0 | 0 | 6 | 0 | 2 | 0 | 0 | 0 | 5 | 2 | 0 | 0 | 0 | 0 | 0 | 0 | 3 | 0 | 0 | 0 | 0 | 0 |
| Rape | 0 | 0 | 0 | 0 | 0 | 0 | 1 | 0 | 0 | 0 | 0 | 0 | 3 | 0 | 0 | 2 | 0 | 0 | 0 | 0 | 0 | 0 | 0 | 4 |
| Rice | 6 | 6 | 8 | 2 | 8 | 8 | 7 | 6 | 8 | 7 | 8 | 8 | 7 | 5 | 0 | 5 | 5 | 0 | 3 | 5 | 3 | 2 | 0 | 9 |
| Sorghum | 3 | 0 | 3 | 4 | 8 | 8 | 5 | 7 | 1 | 7 | 6 | 6 | 6 | 4 | 0 | 6 | 7 | 0 | 4 | 6 | 2 | 2 | 0 | 6 |

TABLE B-continued

| | | | | | | | | | | | | | | | | | | | | | | | | |
|---|---|---|---|---|---|---|---|---|---|---|---|---|---|---|---|---|---|---|---|---|---|---|---|---|
| Soybean | 7 | 0 | 3 | 3 | 7 | 6 | 2 | 2 | 7 | 6 | 3 | 6 | 5 | 6 | 0 | 6 | 2 | 0 | 5 | 4 | 2 | 0 | 0 | 4 |
| Sugar beet | 0 | 0 | 0 | 0 | 0 | 0 | 2 | 0 | 2 | 0 | 0 | 0 | 5 | 0 | 0 | 0 | 0 | 0 | 0 | 0 | 0 | 0 | 0 | 6 |
| Velvetleaf | 3 | 0 | 6 | 0 | 2 | 1 | 1 | 1 | 1 | 2 | 5 | 2 | 1 | 1 | 0 | 2 | 2 | 0 | 2 | 0 | 0 | 0 | 0 | 2 |
| Wheat | 0 | 0 | 2 | 2 | 6 | 7 | 0 | 0 | 0 | 5 | 2 | 6 | 2 | 2 | 0 | 2 | 6 | 0 | 7 | 3 | 0 | 0 | 0 | 4 |
| Wild buckwheat | 0 | 0 | 0 | 0 | 1 | 1 | 0 | 0 | 0 | — | 0 | 2 | 4 | 0 | 0 | 5 | 0 | 0 | 1 | 0 | 0 | 0 | 0 | 0 |
| Wild oat | 1 | 0 | 0 | 0 | 1 | 2 | 0 | 0 | 2 | 0 | 0 | 5 | 0 | 1 | 0 | 0 | 2 | 0 | 1 | 0 | 3 | 0 | 0 | 3 |

| | COMPOUND | | | | | | | | | | | | | | | | | | | | | | | |
|---|---|---|---|---|---|---|---|---|---|---|---|---|---|---|---|---|---|---|---|---|---|---|---|---|
| Rate (400 g/ha) | 50 | 51 | 52 | 53 | 54 | 55 | 56 | 57 | 58 | 59 | 61 | 62 | 63 | 64 | 65 | 66 | 67 | 68 | 69 | 70 | 71 | 72 | 73 | 74 |
| POSTEMERGENCE | | | | | | | | | | | | | | | | | | | | | | | | |
| Barley | 2 | 0 | 0 | 0 | 0 | 0 | 0 | 0 | 2 | 0 | 0 | 0 | 0 | 0 | 0 | 0 | 0 | 0 | 0 | 0 | 0 | 0 | 0 | 1 |
| Barnyardgrass | 9 | 0 | 0 | 9 | 8 | 0 | 9 | 9 | 8 | 9 | 7 | 7 | 0 | 0 | 0 | 0 | 3 | 1 | 0 | 2 | 0 | 0 | 0 | 9 |
| Bedstraw | — | 0 | 0 | 4 | 0 | 3 | 7 | 0 | 6 | — | 3 | 3 | 0 | 1 | 0 | 0 | 0 | 1 | 0 | 0 | 0 | 0 | 0 | 5 |
| Blackgrass | 9 | 0 | 0 | 7 | 9 | 0 | 8 | 0 | 2 | 3 | — | 4 | 0 | 0 | 0 | 0 | 0 | 0 | 0 | 3 | 0 | 0 | 0 | 9 |
| Cheatgrass | 2 | 2 | 0 | 0 | 0 | 2 | 0 | 0 | 2 | 0 | 0 | 0 | 0 | 0 | 0 | 0 | 0 | 0 | 0 | 0 | 0 | 0 | 0 | 3 |
| Chickweed | 7 | — | — | 7 | 0 | — | — | — | — | 0 | 3 | 0 | 0 | 2 | 0 | 0 | 0 | 3 | 0 | 0 | 0 | 0 | 0 | — |
| Cocklebur | 0 | 0 | 0 | 4 | 2 | 0 | 5 | 2 | 1 | 0 | 0 | 0 | 0 | 0 | 0 | 0 | 0 | 0 | 0 | 1 | 0 | 0 | 0 | 1 |
| Corn | 7 | 1 | 0 | 4 | 1 | 0 | 9 | 7 | 2 | 4 | 0 | 3 | 0 | 0 | 0 | 0 | 0 | 0 | 0 | 2 | 0 | 0 | 0 | 7 |
| Cotton | 0 | 0 | 0 | 3 | 3 | 1 | 6 | 4 | 5 | 6 | 0 | 1 | 0 | 0 | 0 | 0 | 0 | 2 | 0 | 5 | 0 | 0 | 0 | 2 |
| Crabgrass | 9 | 2 | 0 | 9 | 9 | 0 | 9 | 9 | 3 | 7 | 1 | 3 | 0 | 0 | 0 | 0 | 0 | 3 | 0 | 2 | 0 | 0 | 0 | 9 |
| Giant foxtail | 8 | 0 | 0 | 8 | 9 | 0 | 9 | 8 | 2 | 4 | 0 | 3 | 0 | 0 | 0 | 0 | 0 | 0 | 0 | 2 | 0 | 0 | 0 | 8 |
| Lambsquarters | 1 | 0 | 0 | 0 | 5 | 0 | 9 | 0 | 4 | 1 | 0 | 0 | 0 | 0 | 0 | 0 | 0 | 0 | 0 | 0 | 0 | 0 | 0 | 1 |
| Morningglory | 2 | 2 | 1 | 5 | 3 | 0 | 5 | 2 | 2 | 3 | 2 | 2 | 0 | 0 | 0 | 0 | 2 | 0 | 0 | 1 | 0 | 0 | 0 | 7 |
| Nutsedge | 5 | 0 | 0 | 5 | 5 | 0 | 8 | 2 | 3 | 7 | 0 | 0 | 0 | 0 | 0 | 0 | 0 | 0 | 0 | 2 | 0 | 0 | 0 | 5 |
| Rape | 0 | 0 | 0 | 0 | 0 | 0 | 0 | 5 | 1 | 1 | 0 | 0 | 0 | 0 | 0 | 0 | 0 | 0 | 0 | 0 | 0 | 0 | 0 | 1 |
| Rice | 8 | 0 | 0 | 8 | 9 | 2 | 9 | 7 | 5 | 5 | 0 | 4 | 0 | 0 | 0 | 0 | 0 | 2 | 0 | 2 | 0 | 0 | 0 | 7 |
| Sorghum | 8 | 0 | 0 | 7 | 3 | 1 | 7 | 6 | 2 | 2 | 3 | 6 | 0 | 0 | 0 | 0 | 0 | 0 | 0 | 2 | 0 | 0 | 0 | 3 |
| Soybean | 1 | 0 | 0 | 4 | 2 | 1 | 7 | 3 | 1 | 4 | 0 | 2 | 0 | 0 | 0 | 0 | 2 | 2 | 0 | 4 | 0 | 0 | 0 | 1 |
| Sugar beet | 0 | 0 | 0 | 0 | 0 | 0 | 1 | 2 | 2 | 0 | 3 | 0 | 0 | 0 | 0 | 0 | 0 | 0 | 0 | 0 | 0 | 0 | 0 | 2 |
| Velvetleaf | 0 | 0 | 0 | 2 | 3 | 0 | 6 | 2 | 1 | 1 | 0 | 1 | 0 | 0 | 0 | 0 | 0 | 0 | 0 | 2 | 0 | 0 | 0 | 2 |
| Wheat | 8 | 0 | 0 | 0 | 4 | 0 | 0 | 0 | 0 | 0 | 0 | 0 | 0 | 0 | 0 | 0 | 0 | 0 | 0 | 0 | 0 | 0 | 0 | 2 |
| Wild buckwheat | 0 | 0 | 0 | 0 | 0 | 4 | 2 | 0 | 7 | 1 | 0 | 0 | 0 | 0 | 0 | 0 | 0 | 0 | 0 | 0 | 0 | 0 | 0 | 3 |
| Wild oat | 2 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |

| | COMPOUND | | | | | | | | | | | | | | | | | | | | | | | |
|---|---|---|---|---|---|---|---|---|---|---|---|---|---|---|---|---|---|---|---|---|---|---|---|---|
| Rate (400 g/ha) | 1 | 2 | 3 | 4 | 5 | 6 | 7 | 8 | 9 | 10 | 11 | 13 | 14 | 15 | 16 | 17 | 18 | 19 | 20 | 21 | 22 | 23 | 24 | 25 |
| PREEMERGENCE | | | | | | | | | | | | | | | | | | | | | | | | |
| Barley | 1 | 3 | 0 | 2 | 0 | 0 | 0 | 0 | 0 | 0 | 0 | 0 | 0 | 0 | 0 | 0 | 0 | 0 | 0 | 0 | 0 | 0 | 0 | 0 |
| Barnyardgrass | 10 | 10 | 10 | 9 | 10 | 3 | 10 | 10 | 10 | 10 | 10 | 7 | 9 | 9 | 9 | 9 | 9 | 5 | 5 | 10 | 10 | 10 | 10 | 10 |
| Bedstraw | 0 | 5 | 7 | 8 | 0 | 0 | 6 | 0 | 6 | 10 | 3 | 0 | 4 | 10 | 3 | 0 | 9 | 5 | 2 | 2 | 3 | 3 | 6 | 10 |
| Blackgrass | 9 | 10 | 10 | 8 | 10 | 0 | 6 | 10 | 9 | 10 | 9 | 9 | 2 | 10 | 10 | 10 | 10 | 8 | 5 | 8 | 9 | 9 | 9 | 10 |
| Cheatgrass | 9 | 10 | 5 | 4 | 5 | 0 | 2 | 1 | 3 | 8 | 7 | 0 | 7 | 9 | 4 | 5 | 5 | 1 | 2 | 3 | 4 | 6 | 2 | 6 |
| Chickweed | 10 | 10 | — | — | — | 0 | 10 | 10 | 10 | 10 | 5 | 3 | 0 | 9 | 10 | 5 | 10 | 5 | 5 | 4 | 4 | 7 | 2 | 5 |
| Cocklebur | 0 | 3 | 3 | 3 | 0 | 0 | 0 | 0 | — | 7 | 0 | 0 | 0 | 0 | 10 | 0 | 0 | 0 | 0 | 0 | 0 | 0 | 0 | 0 |
| Corn | 8 | 9 | 7 | 1 | 8 | 1 | 2 | 1 | 10 | 6 | 5 | 1 | 0 | 0 | 0 | 0 | 7 | 2 | 1 | 3 | 7 | 2 | 2 | 6 |
| Cotton | 1 | 6 | 9 | 0 | 0 | 0 | 4 | 1 | 0 | 0 | 0 | 1 | 0 | 0 | 0 | 0 | 2 | 0 | 0 | 0 | 2 | 0 | 0 | 1 |
| Crabgrass | 10 | 10 | 9 | 9 | 8 | 9 | 10 | 9 | 9 | 10 | 10 | 9 | 10 | 10 | 10 | 10 | 10 | 10 | 9 | 10 | 10 | 10 | 10 | 10 |
| Giant foxtail | 9 | 10 | 1 | 8 | 9 | 2 | 10 | 10 | 9 | 10 | 9 | 7 | 9 | 10 | 10 | 9 | 9 | 7 | 7 | 10 | 9 | 10 | 10 | 10 |
| Lambsquarters | 10 | 10 | 10 | 9 | 9 | 0 | 10 | 10 | 10 | 10 | 9 | — | — | 10 | 10 | 10 | 10 | 5 | 6 | 8 | 2 | 8 | 7 | 9 |
| Morningglory | 1 | 5 | 1 | 0 | 0 | 0 | 0 | 0 | 0 | 0 | 0 | 2 | 0 | 0 | 0 | 0 | 0 | 0 | 0 | 0 | 0 | 1 | 0 | 0 |
| Nutsedge | 0 | 0 | 0 | 7 | 4 | 0 | 6 | 0 | 0 | 0 | — | 0 | 0 | 0 | 9 | 0 | 5 | 0 | 0 | 0 | 0 | 0 | 0 | 9 |
| Rape | 2 | 5 | 6 | 2 | 0 | 0 | 0 | 0 | 0 | 1 | 1 | 0 | 0 | 0 | 5 | 0 | 2 | 0 | 0 | 2 | 0 | 0 | 1 | 0 |
| Rice | 8 | 4 | 7 | 0 | 2 | 0 | 6 | 3 | 7 | 1 | 0 | 0 | 0 | 0 | 0 | 0 | 3 | 0 | 0 | 0 | 2 | 2 | 4 | 1 |
| Sorghum | 7 | 5 | 3 | 2 | 8 | 0 | 7 | 3 | 1 | 8 | 4 | 1 | 0 | 6 | 9 | 6 | 4 | 0 | 2 | 4 | 4 | 4 | 3 | 5 |
| Soybean | 1 | 3 | 0 | 1 | 0 | 0 | 0 | 0 | 0 | 0 | 0 | 1 | 0 | 0 | 0 | 0 | 1 | 0 | 0 | 0 | 4 | 0 | 1 | 1 |
| Sugar beet | 5 | 5 | 8 | 2 | 1 | 0 | 0 | 2 | 0 | 2 | 2 | 0 | 0 | 0 | 6 | 0 | 9 | 2 | 2 | 5 | 6 | 5 | 7 | 5 |
| Velvetleaf | 5 | 8 | 3 | 0 | 2 | 1 | 3 | 1 | 0 | 0 | 0 | 1 | 0 | 5 | 2 | 0 | 4 | 0 | 1 | 0 | 0 | 1 | 2 | 0 |
| Wheat | 0 | 0 | 2 | 0 | 0 | 0 | 0 | 0 | 2 | 0 | 1 | 0 | 0 | 0 | 0 | 0 | 0 | 0 | 0 | 2 | 2 | 1 | 0 | 4 |
| Wild buckwheat | — | 0 | — | — | — | 0 | 4 | 0 | 0 | — | 0 | 0 | 0 | 10 | 10 | 10 | 9 | 0 | 0 | 0 | 0 | 0 | 0 | 4 |
| Wild oat | 9 | 10 | 9 | 9 | 9 | 0 | 9 | 3 | 8 | 9 | 7 | 4 | 4 | 10 | 9 | 3 | 10 | 2 | 2 | 7 | 7 | 2 | 3 | 9 |

| | COMPOUND | | | | | | | | | | | | | | | | | | | | | | | |
|---|---|---|---|---|---|---|---|---|---|---|---|---|---|---|---|---|---|---|---|---|---|---|---|---|
| Rate (400 g/ha) | 26 | 27 | 28 | 29 | 30 | 31 | 32 | 33 | 34 | 35 | 36 | 37 | 38 | 39 | 40 | 41 | 42 | 43 | 44 | 45 | 46 | 47 | 48 | 49 |
| PREEMERGENCE | | | | | | | | | | | | | | | | | | | | | | | | |
| Barley | 0 | 0 | 1 | 0 | 9 | 0 | 0 | 0 | 1 | 0 | 0 | 0 | 1 | 0 | 0 | 0 | 0 | 0 | 0 | 0 | 0 | 0 | 0 | 2 |
| Barnyardgrass | 10 | 7 | 10 | 10 | 10 | 10 | 10 | 9 | 10 | 10 | 10 | 10 | 10 | 10 | 0 | 10 | 9 | 0 | 7 | 5 | 9 | 9 | 1 | 10 |
| Bedstraw | 2 | 0 | 4 | 3 | 5 | 8 | 7 | 2 | 5 | 0 | 5 | 7 | 9 | 5 | 0 | 2 | 3 | — | 8 | 0 | 5 | 0 | — | — |
| Blackgrass | 10 | 7 | 10 | 8 | 9 | 9 | 9 | 5 | 9 | 10 | 10 | 10 | 9 | 9 | 0 | 9 | 7 | 0 | 9 | 10 | 9 | 5 | 0 | 8 |
| Cheatgrass | 6 | 2 | 9 | 6 | 9 | 7 | 8 | 5 | 7 | 7 | 7 | 9 | 9 | 8 | 0 | 7 | 5 | 0 | 7 | 2 | 3 | 2 | 0 | 2 |
| Chickweed | 9 | 0 | 9 | 5 | 9 | 7 | 3 | 0 | 4 | 7 | 8 | 9 | 9 | 7 | 0 | 8 | — | — | 3 | — | — | — | 0 | 7 |

TABLE B-continued

| | | | | | | | | | | | | | | | | | | | | | | | | |
|---|---|---|---|---|---|---|---|---|---|---|---|---|---|---|---|---|---|---|---|---|---|---|---|---|
| Cocklebur | — | 0 | 4 | 0 | 2 | 1 | 0 | 0 | 0 | 0 | 0 | 1 | 0 | 1 | 0 | — | 2 | 0 | 0 | 2 | 3 | 0 | 0 | 0 |
| Corn | 8 | 3 | 2 | 7 | 9 | 9 | 7 | 7 | 7 | 9 | 8 | 8 | 9 | 9 | 0 | 10 | 8 | 0 | 5 | 5 | 2 | 0 | 0 | 3 |
| Cotton | 2 | 0 | 0 | 0 | 8 | 2 | 9 | 2 | 5 | 5 | 7 | 8 | 6 | 5 | 0 | 3 | 0 | 0 | 2 | 0 | 0 | 0 | 0 | 0 |
| Crabgrass | 10 | 9 | 10 | 10 | 10 | 10 | 10 | 10 | 10 | 10 | 10 | 10 | 10 | 10 | 0 | 10 | 9 | 0 | 10 | 9 | 9 | 8 | 5 | 10 |
| Giant foxtail | 10 | 2 | 10 | 10 | 10 | 10 | 10 | 9 | 10 | 10 | 10 | 10 | 10 | 10 | 0 | 10 | 9 | 0 | 10 | 6 | 10 | 9 | 1 | 10 |
| Lambsquarters | 8 | 0 | 9 | 9 | 9 | 8 | 10 | 3 | 6 | 9 | 9 | 9 | 10 | 9 | 0 | 8 | 7 | 0 | 8 | 4 | 8 | 5 | 0 | 10 |
| Morningglory | 0 | 0 | 0 | 6 | 5 | 6 | 4 | 0 | 5 | 3 | 5 | 5 | 1 | 2 | 0 | 2 | 0 | 0 | 0 | 0 | 0 | 0 | 0 | 2 |
| Nutsedge | 7 | 0 | 0 | 0 | 4 | 0 | 0 | 0 | 2 | 5 | 5 | 5 | 7 | 3 | 0 | 4 | 6 | 0 | 8 | 0 | 0 | 0 | 0 | 0 |
| Rape | 1 | 0 | 3 | 2 | 6 | 5 | 3 | 0 | 1 | 3 | 5 | 4 | 9 | 4 | 0 | 1 | 1 | 0 | 3 | 0 | 1 | 1 | 0 | 2 |
| Rice | 0 | 0 | 1 | 2 | 7 | 2 | 1 | 2 | 3 | 2 | 4 | 6 | 6 | 2 | 0 | 4 | 0 | 0 | 2 | 0 | 0 | 0 | 0 | 2 |
| Sorghum | 8 | 2 | 6 | 9 | 9 | 9 | 9 | 6 | 9 | 9 | 9 | 9 | 9 | 9 | 0 | 2 | 8 | 0 | 6 | 0 | 5 | 0 | 0 | 10 |
| Soybean | 2 | 0 | 0 | 1 | 8 | 3 | 2 | 2 | 3 | 2 | 4 | 6 | 6 | 5 | 0 | 8 | 0 | 0 | 2 | 0 | 2 | 0 | 0 | 0 |
| Sugar beet | 6 | 0 | 2 | 7 | 6 | 6 | 3 | 0 | 0 | 5 | 7 | 7 | 9 | 3 | 0 | 5 | 5 | 0 | 0 | 0 | 0 | 1 | 0 | 8 |
| Velvetleaf | 3 | 0 | 0 | 1 | 5 | 1 | 1 | 0 | 2 | 1 | 3 | 5 | 7 | 1 | 0 | 1 | 0 | 0 | 0 | 1 | 0 | 0 | 0 | 2 |
| Wheat | 0 | 0 | 3 | 1 | 5 | 0 | 1 | 0 | 2 | 0 | 1 | 1 | 1 | 0 | 0 | 3 | 2 | 0 | 2 | 0 | 0 | 2 | 0 | 2 |
| Wild buckwheat | 5 | 2 | 5 | 5 | 7 | 8 | 10 | 0 | 5 | 7 | 1 | 7 | 10 | 6 | 0 | 5 | 6 | 0 | — | 0 | 0 | 0 | — | — |
| Wild oat | 8 | 0 | 9 | 6 | 9 | 9 | 9 | 4 | 7 | 9 | 9 | 8 | 9 | 9 | 0 | 10 | 6 | 0 | 8 | 9 | 9 | 3 | 0 | 5 |

| | COMPOUND | | | | | | | | | | | | | | | | | | | | | | | |
|---|---|---|---|---|---|---|---|---|---|---|---|---|---|---|---|---|---|---|---|---|---|---|---|---|
| Rate (400 g/ha) | 50 | 51 | 52 | 53 | 54 | 55 | 56 | 57 | 58 | 59 | 61 | 62 | 63 | 64 | 65 | 66 | 67 | 68 | 69 | 70 | 71 | 72 | 73 | 74 |
| PREEMERGENCE | | | | | | | | | | | | | | | | | | | | | | | | |
| Barley | 2 | 0 | 0 | 0 | 0 | 0 | 2 | 3 | 0 | 0 | 0 | 0 | 0 | 0 | 0 | 0 | 0 | 0 | 0 | 0 | 0 | 0 | 0 | 2 |
| Barnyardgrass | 10 | 0 | 3 | 10 | 9 | 7 | 10 | 10 | 0 | 10 | 3 | 5 | 0 | 0 | 0 | 0 | 5 | 8 | 0 | 0 | 0 | 0 | 0 | 10 |
| Bedstraw | 9 | — | — | 9 | 8 | 7 | — | 1 | 0 | 2 | 0 | 0 | 0 | 0 | 0 | — | 0 | 0 | 0 | 0 | 0 | 0 | 0 | 5 |
| Blackgrass | 9 | 0 | 0 | 9 | 0 | 2 | 10 | 10 | 9 | 8 | 9 | 10 | 2 | 2 | 0 | 2 | 0 | 9 | 0 | 0 | 0 | 0 | 0 | 9 |
| Cheatgrass | 7 | 0 | 0 | 2 | 2 | 3 | 3 | 9 | 3 | 7 | 2 | 0 | 0 | 0 | 0 | 0 | 0 | 0 | 0 | 0 | 0 | 0 | 0 | 8 |
| Chickweed | 5 | 0 | 0 | 3 | 4 | 5 | 9 | 10 | 7 | 3 | 0 | 8 | 0 | 0 | 0 | 0 | 0 | 3 | 0 | 0 | 0 | 0 | 0 | 10 |
| Cocklebur | 0 | 0 | 0 | 0 | 0 | 0 | 0 | 1 | 0 | 0 | 0 | 0 | 0 | 0 | 0 | 0 | 0 | 0 | 0 | 0 | 0 | 0 | 0 | 0 |
| Corn | 5 | 0 | 2 | 3 | 1 | 1 | 4 | 4 | 2 | 1 | 0 | 0 | 0 | 0 | 0 | 0 | 0 | 0 | 0 | 0 | 0 | 0 | 0 | 7 |
| Cotton | 0 | 0 | 0 | 0 | 0 | 0 | 0 | 0 | 5 | 4 | 0 | 0 | 0 | 0 | 0 | 0 | 0 | 0 | 0 | 0 | 0 | 0 | 0 | 3 |
| Crabgrass | 10 | 0 | 3 | 10 | 10 | 9 | 10 | 10 | 9 | 9 | 9 | 10 | 0 | 7 | 0 | 0 | 9 | 9 | 0 | 0 | 0 | 0 | 0 | 9 |
| Giant foxtail | 9 | 2 | 4 | 10 | 10 | 9 | 10 | 10 | 7 | 9 | 9 | 10 | 0 | 0 | 0 | 0 | 4 | 8 | 0 | 0 | 0 | 0 | 0 | 10 |
| Lambsquarters | 8 | — | 0 | 10 | 10 | 9 | 10 | 10 | 10 | 8 | 0 | 10 | 0 | 0 | 0 | 0 | 0 | 7 | 0 | 0 | 0 | 0 | 0 | 10 |
| Morningglory | 0 | 0 | 2 | 1 | 1 | 2 | 4 | 5 | 0 | 0 | 0 | 0 | 0 | 0 | 0 | 0 | 0 | 0 | 0 | 0 | 0 | 0 | 0 | 5 |
| Nutsedge | 0 | 0 | 0 | 0 | 0 | 0 | 0 | 2 | 4 | 0 | 0 | 0 | 0 | 0 | 0 | 0 | 0 | 0 | 0 | 0 | — | 0 | 0 | 2 |
| Rape | 0 | 6 | 0 | 2 | 0 | 3 | 7 | 9 | 0 | 7 | 0 | 0 | 0 | 0 | 0 | 0 | 0 | 0 | 0 | 0 | 0 | 0 | 0 | 7 |
| Rice | 7 | 0 | 1 | 2 | 0 | 0 | 1 | 2 | 0 | 0 | 0 | 0 | 0 | 0 | 0 | 0 | 0 | 0 | 0 | 0 | 0 | 0 | 0 | 2 |
| Sorghum | 8 | 0 | 1 | 7 | 3 | 2 | 9 | 9 | 0 | 4 | 0 | 0 | 0 | 0 | 0 | 0 | 0 | 0 | 0 | 0 | 0 | 0 | 0 | 9 |
| Soybean | 2 | 0 | 0 | 1 | 0 | 0 | 2 | 3 | 0 | 0 | 0 | 0 | 0 | 0 | 0 | 0 | 0 | 0 | 0 | 0 | 0 | 0 | 0 | 2 |
| Sugar beet | 0 | — | 0 | 10 | 3 | 2 | 7 | 4 | 0 | 2 | 0 | 0 | 0 | 0 | 0 | 0 | 0 | 1 | 0 | 0 | 0 | 0 | 0 | 7 |
| Velvetleaf | 2 | 0 | 0 | 2 | 1 | 1 | 1 | 2 | 0 | 2 | 0 | 0 | 0 | 0 | 0 | 0 | 0 | 0 | 0 | 0 | 0 | 0 | 0 | 1 |
| Wheat | 6 | 0 | 0 | 0 | 2 | 0 | 4 | 0 | 0 | 0 | 0 | 2 | 0 | 0 | 0 | 0 | 0 | 0 | 0 | 0 | 0 | 0 | 0 | 3 |
| Wild buckwheat | 8 | 4 | — | 10 | 10 | 10 | — | 4 | 0 | 0 | 0 | 0 | 0 | 0 | 0 | 0 | 0 | 0 | 0 | 0 | — | 0 | 0 | 10 |
| Wild oat | 9 | 0 | 0 | 7 | 6 | 0 | 7 | 6 | 2 | 9 | 0 | 5 | 0 | 0 | 0 | 0 | 0 | 2 | 0 | 0 | 0 | 0 | 0 | 9 |

| Rate (200 g/ha) | COMPOUND 60 |
|---|---|
| POSTEMERGENCE | |
| Barley | 0 |
| Barnyardgrass | 0 |
| Bedstraw | 3 |
| Blackgrass | 0 |
| Cheatgrass | 0 |
| Chickweed | — |
| Cocklebur | 0 |
| Corn | 0 |
| Cotton | 0 |
| Crabgrass | 2 |
| Giant foxtail | 0 |
| Lambsquarters | 0 |
| Morningglory | 0 |
| Nutsedge | 0 |
| Rape | 0 |
| Rice | 0 |
| Sorghum | 0 |
| Soybean | 0 |
| Sugar beet | 0 |
| Velvetleaf | 0 |
| Wheat | 0 |
| Wild buckwheat | 5 |
| Wild oat | 0 |
| PREEMERGENCE | |
| Barley | 0 |

TABLE B-continued

| | |
|---|---|
| Barnyardgrass | 3 |
| Bedstraw | 0 |
| Blackgrass | 0 |
| Cheatgrass | 0 |
| Chickweed | 0 |
| Cocklebur | 0 |
| Corn | 0 |
| Cotton | 0 |
| Crabgrass | 3 |
| Giant foxtail | 2 |
| Lambsquarters | 0 |
| Morningglory | 0 |
| Nutsedge | 0 |
| Rape | 0 |
| Rice | 0 |
| Sorghum | 0 |
| Soybean | 0 |
| Sugar beet | 0 |
| Velvetleaf | 0 |
| Wheat | 0 |
| Wild buckwheat | — |
| Wild oat | 0 |

| | COMPOUND | | | | | | | | | | | | | | | | | | | | | | | |
|---|---|---|---|---|---|---|---|---|---|---|---|---|---|---|---|---|---|---|---|---|---|---|---|---|
| Rate (100 g/ha) | 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 | 24 |
| POSTEMERGENCE | | | | | | | | | | | | | | | | | | | | | | | | |
| Barley | 0 | 2 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| Barnyardgrass | 3 | 5 | 8 | 1 | 2 | 0 | 0 | 2 | 0 | 6 | 0 | 2 | 0 | 0 | 5 | 1 | 1 | 8 | 0 | 0 | 1 | 1 | 0 | 2 |
| Bedstraw | 2 | 1 | 0 | 0 | 1 | 0 | 1 | 0 | 0 | 0 | 0 | 0 | 2 | 0 | 0 | 0 | 0 | 0 | 2 | 2 | 2 | — | — | 1 |
| Blackgrass | 0 | 2 | 2 | 2 | 0 | 0 | 2 | 0 | 1 | 0 | 0 | 0 | 0 | 0 | 0 | 0 | 7 | — | 0 | 0 | 1 | 1 | 2 | 0 |
| Cheatgrass | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| Chickweed | 1 | 2 | 0 | 0 | 0 | 0 | — | 0 | 0 | 0 | 0 | 0 | 0 | 0 | 0 | 0 | 0 | 0 | 0 | 0 | 0 | 0 | 0 | 0 |
| Cocklebur | 0 | 0 | 0 | 0 | 0 | 0 | 0 | 1 | — | 0 | 0 | 1 | 0 | 0 | 0 | 0 | 0 | 0 | 0 | 0 | 0 | 0 | 0 | 0 |
| Corn | 2 | 3 | 1 | 0 | 0 | 0 | 1 | 1 | 1 | 0 | 0 | 0 | 0 | 0 | 0 | 0 | 0 | 2 | 0 | 0 | 0 | 0 | 0 | 0 |
| Cotton | 0 | 0 | 0 | 0 | 2 | 0 | — | 1 | 3 | 2 | 0 | 1 | 0 | 0 | 4 | 2 | 1 | 4 | 0 | 0 | 0 | 0 | 0 | 0 |
| Crabgrass | 0 | 5 | 6 | 0 | 0 | 0 | 0 | 0 | 0 | 0 | 0 | 0 | 0 | 0 | 1 | 5 | 2 | 2 | 0 | 0 | 2 | 1 | 1 | 1 |
| Giant foxtail | 0 | 0 | 0 | 0 | 0 | 0 | 0 | 0 | 0 | 0 | 0 | 1 | 0 | 0 | 0 | 1 | 0 | 4 | 0 | 0 | 0 | 0 | 0 | 0 |
| Lambsquarters | 1 | — | 2 | 0 | 0 | 0 | 0 | 2 | 0 | 0 | 0 | 0 | 0 | 0 | 0 | — | 0 | 4 | 0 | 0 | 0 | — | 1 | 0 |
| Morningglory | 1 | 4 | 3 | 2 | 0 | 0 | 1 | 1 | 0 | 2 | 0 | 3 | 0 | 0 | 7 | 2 | 2 | 3 | 2 | 1 | 1 | 1 | 1 | 0 |
| Nutsedge | 0 | 0 | 0 | — | 0 | 0 | 0 | — | 0 | 0 | 0 | 0 | 0 | 0 | 0 | 0 | 0 | 0 | 0 | 0 | 0 | 0 | 0 | 0 |
| Rape | 1 | 0 | 0 | 0 | 0 | 0 | 0 | 0 | 0 | 0 | 0 | 0 | 0 | 0 | 0 | 0 | 0 | 4 | 0 | 0 | 0 | 0 | 0 | 0 |
| Rice | 0 | 0 | 3 | 0 | 0 | 0 | 1 | 0 | 0 | 0 | 0 | 0 | 0 | 0 | 3 | 2 | 2 | 3 | 0 | 0 | 0 | 0 | 0 | 0 |
| Sorghum | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| Soybean | 1 | 1 | 2 | 1 | 3 | 0 | 2 | 1 | 0 | 2 | 0 | 1 | 0 | 0 | 3 | 3 | 2 | 5 | 1 | 1 | 1 | 1 | 1 | 0 |
| Sugar beet | 1 | 0 | 0 | 0 | 0 | 0 | 0 | 0 | 0 | 1 | 0 | 0 | 0 | 0 | 0 | 0 | 0 | 3 | 0 | 0 | 0 | 0 | 0 | 0 |
| Velvetleaf | 0 | 1 | 3 | 2 | 3 | 0 | 1 | 0 | 0 | 0 | 0 | 0 | 0 | 0 | 0 | — | 0 | 0 | 1 | 1 | 0 | 1 | 0 | 0 |
| Wheat | 0 | 2 | 0 | 0 | 0 | 0 | — | 0 | — | 0 | 0 | 0 | 0 | 0 | 0 | 0 | 0 | 0 | 0 | 0 | 0 | 0 | 0 | 0 |
| Wild buckwheat | — | — | — | 0 | — | 0 | — | — | — | 0 | 0 | 0 | 0 | 0 | 0 | 0 | 0 | 0 | 0 | 0 | 0 | 0 | 0 | 0 |
| Wild oat | 0 | 1 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |

| | COMPOUND | | | | | | | | | | | | | | | | | | | | | | | |
|---|---|---|---|---|---|---|---|---|---|---|---|---|---|---|---|---|---|---|---|---|---|---|---|---|
| Rate (100 g/ha) | 25 | 26 | 28 | 29 | 30 | 31 | 32 | 33 | 34 | 35 | 36 | 37 | 38 | 39 | 41 | 42 | 43 | 44 | 45 | 46 | 47 | 48 | 49 | 50 |
| POSTEMERGENCE | | | | | | | | | | | | | | | | | | | | | | | | |
| Barley | 0 | 0 | 0 | 0 | 2 | 2 | 0 | 0 | 0 | 0 | 0 | 0 | 0 | 0 | 0 | 0 | 0 | 0 | 0 | 0 | 0 | 0 | 0 | 0 |
| Barnyardgrass | 1 | 0 | 2 | 2 | 9 | 9 | 8 | 0 | 0 | 7 | 2 | 8 | 7 | 2 | 6 | 5 | 0 | 0 | 4 | 1 | 0 | 0 | 4 | 8 |
| Bedstraw | 3 | 2 | 0 | 3 | 1 | 1 | 3 | 1 | 1 | 2 | 2 | 2 | 3 | 2 | 2 | 3 | 0 | 2 | 0 | 1 | 0 | 0 | 0 | — |
| Blackgrass | 1 | 0 | 0 | 2 | 5 | 3 | 0 | 0 | 1 | 0 | 1 | 1 | 3 | 2 | 0 | 2 | 0 | 0 | 1 | 0 | 0 | 0 | 0 | 3 |
| Cheatgrass | 0 | 0 | 0 | 0 | 2 | 0 | 0 | 0 | 0 | 0 | 0 | 2 | 3 | 0 | 0 | 2 | 0 | 0 | 0 | 0 | 0 | 0 | 0 | 0 |
| Chickweed | 0 | 0 | 2 | 0 | 0 | 0 | 0 | 0 | 0 | 0 | 0 | 0 | 2 | 0 | 0 | 0 | 0 | 0 | 0 | 0 | 0 | 0 | 0 | 0 |
| Cocklebur | 0 | 1 | 0 | 0 | 0 | 0 | 0 | 0 | 0 | 0 | 0 | 0 | — | 0 | 0 | 0 | 0 | 0 | 0 | 0 | 0 | 0 | 0 | 0 |
| Corn | 0 | 0 | 0 | 1 | 2 | 0 | 0 | 0 | 0 | 3 | 1 | 4 | 2 | 2 | 4 | 2 | 0 | 0 | 2 | 0 | 0 | 0 | 2 | 2 |
| Cotton | 0 | 5 | 2 | 0 | 7 | 1 | 0 | 2 | 0 | 2 | 0 | 0 | 0 | 0 | 3 | 0 | 0 | 0 | 1 | 0 | 0 | 0 | 0 | 0 |
| Crabgrass | 0 | 3 | 7 | 6 | 6 | 8 | 6 | 1 | 4 | 2 | 2 | 4 | 5 | — | 0 | 2 | 0 | 2 | 0 | 0 | 0 | 0 | 9 | 7 |
| Giant foxtail | 2 | 0 | 2 | 1 | 5 | 7 | 8 | 0 | 2 | 1 | 2 | 2 | 5 | 4 | 2 | 4 | 0 | 0 | 0 | 0 | 0 | 0 | 6 | 7 |
| Lambsquarters | 0 | 0 | 0 | 0 | 1 | 0 | 0 | 0 | — | 0 | 0 | 0 | — | — | — | 0 | 0 | — | 0 | 0 | 0 | 0 | 0 | 0 |
| Morningglory | 0 | 2 | 2 | 2 | 2 | 1 | 1 | 1 | 1 | 1 | 5 | 3 | 0 | 2 | 1 | 6 | 0 | 4 | 0 | 0 | 0 | 0 | 0 | 0 |
| Nutsedge | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| Rape | 0 | 0 | 0 | 0 | 0 | 0 | 0 | 0 | 0 | 0 | 0 | 0 | 1 | 0 | 0 | 0 | 0 | 0 | 0 | 0 | 0 | 0 | 0 | 0 |
| Rice | 0 | 0 | 1 | 0 | 5 | 2 | 1 | 1 | 2 | 2 | 2 | 2 | 3 | 2 | 3 | 3 | 0 | 2 | 2 | 0 | 0 | 0 | 5 | 4 |
| Sorghum | 0 | 0 | 0 | 0 | 2 | 1 | 2 | 0 | 0 | 1 | 0 | 2 | 2 | 0 | — | 2 | 0 | 0 | 3 | 0 | 0 | 0 | 1 | 3 |
| Soybean | 0 | 4 | 2 | 0 | 4 | 2 | 0 | 1 | 3 | 3 | 2 | 3 | 2 | 1 | 3 | 2 | 0 | 3 | 3 | 0 | 0 | 0 | 1 | 0 |
| Sugar beet | 0 | 0 | 0 | 0 | 0 | 0 | 0 | 0 | 0 | 0 | 0 | 0 | 2 | 0 | 0 | 0 | 0 | 0 | 0 | 0 | 0 | 0 | 0 | 0 |
| Velvetleaf | 0 | 0 | 1 | 0 | 2 | 0 | 0 | 0 | 1 | 0 | 0 | 0 | 1 | 0 | 2 | 0 | 0 | 2 | 0 | 0 | 0 | 0 | 1 | 0 |

TABLE B-continued

| | | | | | | | | | | | | | | | | | | | | | | | | |
|---|---|---|---|---|---|---|---|---|---|---|---|---|---|---|---|---|---|---|---|---|---|---|---|---|
| Wheat | 0 | 0 | 0 | 0 | 2 | 2 | 0 | 0 | 0 | 0 | 0 | 0 | 0 | 0 | 0 | 3 | 0 | 0 | 0 | 0 | 0 | 0 | 0 | 2 |
| Wild buckwheat | 0 | 0 | 0 | 0 | 0 | 0 | 0 | 0 | 0 | 0 | 0 | 0 | 0 | 0 | 0 | 0 | — | 0 | 0 | 0 | 0 | 0 | 0 | 0 |
| Wild oat | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |

| | COMPOUND | | | | | | | | | | | | | | | | | | | | | | |
|---|---|---|---|---|---|---|---|---|---|---|---|---|---|---|---|---|---|---|---|---|---|---|---|
| Rate (100 g/ha) | 51 | 52 | 53 | 54 | 55 | 56 | 57 | 58 | 59 | 61 | 62 | 63 | 64 | 65 | 66 | 67 | 68 | 69 | 70 | 71 | 72 | 73 | 74 |
| POSTEMERGENCE | | | | | | | | | | | | | | | | | | | | | | | |
| Barley | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| Barnyardgrass | 0 | 0 | 6 | 0 | 0 | 7 | 2 | 1 | 0 | 0 | 0 | 0 | 0 | 0 | 0 | 0 | 0 | 0 | 2 | 0 | 0 | 0 | 6 |
| Bedstraw | 0 | 0 | 2 | 0 | 2 | 5 | 0 | — | 2 | 3 | 1 | 0 | 0 | 0 | 0 | 0 | 0 | 0 | 0 | 0 | 0 | 0 | 4 |
| Blackgrass | 0 | 0 | 2 | 2 | 0 | 2 | 0 | 0 | 1 | 2 | 2 | 0 | 0 | 0 | 0 | 0 | 0 | 0 | 0 | 0 | 0 | 0 | 2 |
| Cheatgrass | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| Chickweed | 0 | 0 | — | — | 3 | — | — | — | 0 | 1 | 0 | 0 | 0 | 0 | 0 | 0 | 0 | 0 | 0 | 0 | 0 | 0 | — |
| Cocklebur | 0 | 0 | 2 | 0 | 0 | 2 | 0 | 3 | 0 | 0 | 0 | 0 | 0 | 0 | 0 | 0 | 0 | 0 | 2 | 0 | 0 | 0 | 0 |
| Corn | 0 | 0 | 2 | 0 | 0 | 4 | 4 | 0 | 0 | 0 | 0 | 0 | 0 | 0 | 0 | 0 | 0 | 0 | 1 | 0 | 0 | 0 | 2 |
| Cotton | 0 | 0 | 0 | 0 | 0 | 1 | 2 | 0 | 2 | 0 | 0 | 0 | 0 | 0 | 0 | 0 | 0 | 0 | — | 0 | 0 | 0 | 2 |
| Crabgrass | 0 | 0 | 8 | 5 | 0 | 8 | 3 | 0 | 3 | 0 | 0 | 0 | 0 | 0 | 0 | 0 | 0 | — | 2 | 0 | 0 | 0 | 4 |
| Giant foxtail | 0 | 0 | 5 | 3 | 0 | 7 | 1 | 0 | 0 | 0 | 0 | 0 | 0 | 0 | 0 | 0 | 0 | 0 | 1 | 0 | 0 | 0 | 2 |
| Lambsquarters | 0 | 0 | 7 | 0 | 0 | 2 | 0 | 0 | 1 | 0 | 0 | 0 | 0 | 0 | 0 | 0 | 0 | 0 | 0 | 0 | 0 | 0 | 1 |
| Morningglory | 0 | 0 | 2 | 1 | 0 | 5 | 2 | 3 | 2 | 2 | 2 | 0 | 0 | 0 | 0 | 2 | 0 | 0 | 1 | 0 | 0 | 0 | 5 |
| Nutsedge | 0 | 0 | 0 | 0 | 0 | 2 | 0 | 0 | 0 | 0 | 0 | 0 | 0 | 0 | 0 | 0 | 0 | 0 | 0 | 0 | 0 | 0 | 0 |
| Rape | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| Rice | 0 | 0 | 7 | 5 | 0 | 6 | 1 | 0 | 1 | 0 | 0 | 0 | 0 | 0 | 0 | 0 | 0 | 0 | 2 | 0 | 0 | 0 | 3 |
| Sorghum | 0 | 0 | 4 | 1 | 0 | 2 | 3 | 0 | 0 | 0 | 0 | 0 | 0 | 0 | 0 | 0 | 0 | 0 | 2 | 0 | 0 | 0 | 1 |
| Soybean | 0 | 0 | 1 | 0 | 0 | 5 | 1 | 1 | 1 | 0 | 0 | 0 | 0 | 0 | 0 | 2 | 0 | 0 | 2 | 0 | 0 | 0 | 4 |
| Sugar beet | 0 | 0 | 0 | 0 | 0 | 0 | 1 | 0 | 0 | 2 | 0 | 0 | 0 | 0 | 0 | 0 | 0 | 0 | — | 0 | 0 | 0 | 0 |
| Velvetleaf | 0 | 0 | 0 | 0 | 0 | 2 | 1 | 3 | 1 | 0 | 0 | 0 | 0 | 0 | 0 | 0 | 0 | 0 | 2 | 0 | 0 | 0 | 1 |
| Wheat | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| Wild buckwheat | 0 | 0 | 0 | 0 | 0 | — | 0 | 2 | 0 | 0 | 0 | 0 | 0 | 0 | 0 | 0 | 0 | 0 | 0 | 0 | 0 | 0 | 0 |
| Wild oat | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |

| | COMPOUND | | | | | | | | | | | | | | | | | | | | | | | |
|---|---|---|---|---|---|---|---|---|---|---|---|---|---|---|---|---|---|---|---|---|---|---|---|---|
| Rate (100 g/ha) | 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 | 24 |
| PREEMERGENCE | | | | | | | | | | | | | | | | | | | | | | | | |
| Barley | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| Barnyardgrass | 6 | 6 | 10 | 2 | 9 | 1 | 6 | 2 | 6 | 9 | 9 | 0 | 1 | 0 | 8 | 6 | 2 | 5 | 1 | 0 | 2 | 6 | 3 | 5 |
| Bedstraw | 0 | 0 | 7 | — | 0 | 0 | 0 | 0 | 4 | 10 | — | 3 | 0 | 0 | 3 | 3 | 0 | 6 | 0 | 0 | 0 | 0 | 0 | 0 |
| Blackgrass | 2 | 3 | 10 | 4 | 8 | 0 | 3 | 4 | 6 | 10 | 10 | 10 | 5 | — | 10 | 7 | 9 | 10 | 2 | 3 | 5 | 5 | 1 | 6 |
| Cheatgrass | 0 | 2 | 0 | 2 | 0 | 0 | 1 | 1 | 1 | 5 | 0 | 0 | 0 | 0 | 3 | 0 | 2 | 2 | 0 | 0 | 0 | 0 | 1 | 0 |
| Chickweed | 0 | 2 | — | — | 0 | 0 | 10 | 0 | 4 | 8 | 0 | 0 | 0 | 0 | 9 | 0 | 0 | 10 | 0 | 0 | 0 | 0 | 0 | 0 |
| Cocklebur | 0 | 2 | 0 | 0 | 0 | 0 | 0 | 0 | 0 | 0 | — | 0 | 0 | 0 | 0 | 0 | 0 | 0 | 0 | — | 0 | 0 | 0 | 0 |
| Corn | 0 | 2 | 0 | 0 | 2 | 0 | 0 | 0 | 10 | 0 | 0 | 0 | 0 | 0 | 0 | 0 | 0 | 0 | 0 | 0 | 0 | 2 | 0 | 0 |
| Cotton | 0 | 0 | 0 | 0 | 0 | 0 | 2 | 0 | 0 | 0 | 0 | 0 | 0 | 0 | 0 | 0 | 0 | 0 | 0 | 0 | 0 | 0 | 0 | 0 |
| Crabgrass | 8 | 10 | 9 | 5 | 6 | 2 | 5 | 2 | 4 | 10 | 9 | 6 | 8 | 6 | 9 | 9 | 9 | 9 | 7 | 9 | 8 | 9 | 9 | 5 |
| Giant foxtail | 3 | 7 | 0 | 2 | 6 | 0 | 1 | 3 | 1 | 9 | 9 | 6 | 0 | 6 | 9 | 7 | 6 | 9 | 2 | 6 | 3 | 3 | 2 | 2 |
| Lambsquarters | 10 | 10 | 9 | 0 | 8 | — | 10 | 10 | 10 | 9 | 0 | 8 | 0 | 0 | 10 | 5 | 10 | 10 | 0 | 0 | 2 | 2 | 0 | 0 |
| Morningglory | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| Nutsedge | 0 | 0 | 0 | 0 | — | 0 | — | 0 | 0 | 0 | 0 | 0 | — | 0 | — | 0 | 0 | 0 | 0 | 0 | 0 | 0 | 0 | 0 |
| Rape | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| Rice | 2 | 0 | 2 | 0 | 0 | 0 | 2 | 2 | 2 | 0 | 0 | 0 | 0 | 0 | 0 | 0 | 0 | 0 | 0 | 0 | 0 | 0 | 0 | 0 |
| Sorghum | 3 | 2 | 0 | 0 | 0 | 0 | 0 | 0 | 0 | 2 | 0 | 0 | 0 | 0 | 0 | 0 | 0 | 2 | 0 | 0 | 0 | 0 | 0 | 0 |
| Soybean | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| Sugar beet | 0 | 2 | 0 | 0 | 0 | 0 | 0 | 0 | 0 | 0 | 0 | 0 | 0 | 0 | 0 | 0 | 0 | 1 | 0 | 0 | 2 | 2 | 0 | 6 |
| Velvetleaf | 0 | 1 | 0 | 0 | 0 | 0 | 0 | 0 | 0 | 0 | 0 | 0 | 0 | 0 | 3 | 2 | 0 | 2 | 0 | 0 | 0 | 0 | 0 | 0 |
| Wheat | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| Wild buckwheat | — | 0 | — | — | — | 0 | 0 | 0 | — | — | — | 3 | 0 | 0 | 0 | 3 | 0 | 2 | 0 | 0 | 0 | 0 | 0 | 0 |
| Wild oat | 7 | 8 | 5 | 6 | 4 | 0 | 3 | 2 | 2 | 7 | 0 | 3 | 0 | 0 | 8 | 9 | 2 | 4 | 0 | 0 | 0 | 0 | 2 | 0 |

| | COMPOUND | | | | | | | | | | | | | | | | | | | | | | | |
|---|---|---|---|---|---|---|---|---|---|---|---|---|---|---|---|---|---|---|---|---|---|---|---|---|
| Rate (100 g/ha) | 25 | 26 | 28 | 29 | 30 | 31 | 32 | 33 | 34 | 35 | 36 | 37 | 38 | 39 | 41 | 42 | 43 | 44 | 45 | 46 | 47 | 48 | 49 | 50 |
| PREEMERGENCE | | | | | | | | | | | | | | | | | | | | | | | | |
| Barley | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| Barnyardgrass | 7 | 9 | 3 | 8 | 9 | 9 | 9 | 5 | 8 | 8 | 9 | 9 | 10 | 9 | 7 | 7 | 0 | 2 | 2 | 8 | 2 | 0 | 8 | 7 |
| Bedstraw | 0 | 0 | 2 | 0 | 0 | 0 | 0 | 0 | 0 | 0 | — | 3 | 7 | 0 | 0 | 0 | 0 | 0 | 0 | 0 | — | — | 0 | 2 |
| Blackgrass | 3 | 7 | 9 | 4 | 9 | 2 | 9 | 0 | 8 | 5 | 8 | 8 | 9 | 7 | 9 | 8 | 0 | 6 | 2 | 2 | 0 | 0 | 3 | 7 |
| Cheatgrass | 0 | 2 | 2 | 3 | 5 | 0 | 0 | 2 | 2 | 6 | 6 | 4 | 7 | 6 | 6 | 5 | 0 | 0 | 0 | 0 | 0 | 0 | 2 | 7 |
| Chickweed | 1 | 5 | 4 | 7 | — | 0 | 2 | 0 | 0 | 2 | 4 | 3 | 8 | 0 | 0 | — | 0 | — | — | 0 | 0 | 0 | 0 | — |
| Cocklebur | 0 | — | 0 | 0 | 0 | 0 | 0 | 0 | 0 | 0 | 0 | 0 | 0 | 0 | 0 | 0 | 0 | 0 | 0 | 0 | 0 | 0 | — | 0 |
| Corn | 1 | 1 | 0 | 3 | 0 | 0 | 0 | 3 | 2 | 2 | 2 | 2 | 8 | 3 | 2 | 0 | 0 | 0 | 0 | 0 | 0 | 0 | 0 | 0 |
| Cotton | 0 | 1 | 0 | 0 | 0 | 0 | 2 | — | — | 2 | 5 | — | 0 | 0 | 0 | 0 | 0 | 0 | 0 | 0 | 0 | 0 | 0 | 0 |

TABLE B-continued

| | | | | | | | | | | | | | | | | | | | | | | | | |
|---|---|---|---|---|---|---|---|---|---|---|---|---|---|---|---|---|---|---|---|---|---|---|---|---|
| Crabgrass | 9 | 9 | 10 | 9 | 10 | 9 | 10 | 9 | 9 | 9 | 9 | 10 | 10 | 10 | 10 | 8 | 0 | 10 | 6 | 8 | 5 | 4 | 10 | 7 |
| Giant foxtail | 3 | 7 | 6 | 9 | 10 | 9 | 9 | 9 | 9 | 9 | 9 | 10 | 9 | 9 | 9 | 7 | 0 | 9 | 3 | 4 | 4 | 0 | 9 | 8 |
| Lambsquarters | 2 | 5 | 5 | 7 | 9 | 0 | 8 | 0 | 5 | — | — | 9 | 9 | 7 | 2 | 5 | 0 | 4 | 0 | 0 | 0 | 0 | 8 | 2 |
| Morningglory | 0 | 0 | 0 | 0 | 2 | 0 | 1 | 0 | 2 | 0 | 2 | 3 | 0 | 2 | 0 | 0 | 0 | 0 | 0 | 0 | 0 | 0 | 0 | 0 |
| Nutsedge | 4 | 7 | 0 | 0 | 0 | 0 | 0 | 0 | 0 | 0 | 0 | 2 | 0 | 0 | 10 | 0 | 0 | 0 | 0 | 0 | — | 0 | 0 | 0 |
| Rape | 0 | 0 | 0 | 0 | 2 | 0 | 0 | 0 | 0 | 1 | 0 | 0 | 3 | 1 | 0 | 1 | 0 | 0 | 0 | 0 | 0 | 0 | 0 | 0 |
| Rice | 0 | 0 | 0 | 0 | 0 | 4 | 5 | 0 | 0 | 2 | 0 | 3 | 0 | 0 | 2 | 0 | 0 | 0 | 0 | 0 | 0 | 0 | 0 | 4 |
| Sorghum | 0 | 2 | 2 | 2 | 8 | 6 | 7 | 2 | 2 | 4 | 2 | 8 | 8 | 3 | 1 | 0 | 0 | 0 | 0 | 0 | 0 | 0 | 0 | 5 |
| Soybean | 0 | 0 | 0 | 0 | 0 | 0 | 0 | 0 | 0 | .2 | 2 | 3 | 1 | 2 | 0 | 0 | 0 | 1 | 0 | 0 | 0 | 0 | 0 | 0 |
| Sugar beet | 0 | 2 | 0 | 0 | 5 | 0 | 0 | 0 | 0 | 2 | 3 | 6 | 5 | 1 | 2 | 4 | 0 | 0 | 0 | 0 | 0 | 0 | 0 | 0 |
| Velvetleaf | 0 | 1 | 0 | 0 | 2 | 0 | 0 | 0 | 0 | 0 | 0 | 1 | 2 | 1 | 0 | 0 | 0 | 0 | 0 | 0 | 0 | 0 | 0 | 0 |
| Wheat | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| Wild buckwheat | 0 | 0 | 0 | 0 | 0 | 7 | 0 | — | 0 | 0 | 0 | 0 | 6 | 3 | 0 | 0 | 0 | 5 | — | 0 | 0 | — | 0 | 0 |
| Wild oat | 2 | 5 | 0 | 4 | 7 | 3 | 7 | 0 | 2 | 7 | 4 | 4 | 9 | 5 | 8 | 4 | 0 | 2 | 0 | 6 | 0 | 0 | 0 | 5 |

| | COMPOUND | | | | | | | | | | | | | | | | | | | | | | |
|---|---|---|---|---|---|---|---|---|---|---|---|---|---|---|---|---|---|---|---|---|---|---|---|
| Rate (100 g/ha) | 51 | 52 | 53 | 54 | 55 | 56 | 57 | 58 | 59 | 61 | 62 | 63 | 64 | 65 | 66 | 67 | 68 | 69 | 70 | 71 | 72 | 73 | 74 |
| PREEMERGENCE | | | | | | | | | | | | | | | | | | | | | | | |
| Barley | 0 | 0 | 0 | 0 | 0 | 2 | 0 | 0 | 0 | 0 | 0 | 0 | 0 | 0 | 0 | 0 | 0 | 0 | 0 | 0 | 0 | 0 | 0 |
| Barnyardgrass | 0 | 2 | 9 | 5 | 2 | 9 | 4 | 0 | 7 | 0 | 2 | 0 | 0 | 0 | 0 | 0 | 1 | 0 | 0 | 0 | 0 | 0 | 5 |
| Bedstraw | — | 0 | 10 | 5 | 2 | — | 0 | — | — | 0 | 0 | 0 | 0 | — | 0 | 0 | 0 | 0 | 0 | 0 | 0 | 0 | — |
| Blackgrass | 0 | 0 | 2 | 0 | 2 | 6 | 5 | 0 | 2 | 6 | 6 | 0 | 0 | 0 | 0 | 0 | 9 | 0 | 0 | 0 | 0 | 0 | 3 |
| Cheatgrass | 0 | 0 | 2 | 0 | 2 | 3 | 6 | 0 | 0 | 0 | 0 | 0 | 0 | 0 | 0 | 0 | 0 | 0 | 0 | 0 | 0 | 0 | 2 |
| Chickweed | 0 | 0 | 2 | 0 | 0 | 3 | 5 | 0 | 0 | 0 | 0 | 0 | 0 | 0 | 0 | 0 | 0 | 0 | 0 | 0 | 0 | 0 | 9 |
| Cocklebur | — | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| Corn | 0 | 0 | 0 | 0 | 0 | 2 | 0 | 0 | 0 | 0 | 0 | 0 | 0 | 0 | 0 | 0 | 0 | 0 | 0 | 0 | 0 | 0 | 1 |
| Cotton | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| Crabgrass | 0 | 0 | 9 | 8 | 8 | 10 | 7 | 5 | 8 | 2 | 6 | 0 | 4 | 0 | 0 | 6 | 8 | 0 | 0 | 0 | 0 | 0 | 9 |
| Giant foxtail | 0 | 0 | 8 | 5 | 9 | 9 | 3 | 7 | 5 | 3 | 3 | 0 | 0 | 0 | 0 | 2 | 2 | 0 | 0 | 0 | 0 | 0 | 9 |
| Lambsquarters | — | 0 | 10 | 2 | 4 | 9 | 8 | 5 | — | 0 | 4 | 0 | 0 | — | 0 | 0 | 0 | 0 | 0 | 0 | 0 | 0 | 8 |
| Morningglory | 0 | 0 | 0 | 0 | 0 | 2 | 1 | 0 | 0 | 0 | 0 | 0 | 0 | 0 | 0 | 0 | 0 | 0 | 0 | 0 | 0 | 0 | 4 |
| Nutsedge | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| Rape | 0 | 0 | 0 | 0 | 0 | 0 | 0 | 0 | 0 | 0 | 0 | 0 | 0 | — | 0 | 0 | 0 | 0 | 0 | 0 | 0 | 0 | 0 |
| Rice | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| Sorghum | 0 | 0 | 0 | 0 | 0 | 6 | 0 | 0 | 0 | 0 | 0 | 0 | 0 | 0 | 0 | 0 | 0 | 0 | 0 | 0 | 0 | 0 | 2 |
| Soybean | 0 | 0 | 0 | 0 | 0 | 1 | 0 | 0 | 0 | 0 | 0 | 0 | 0 | 0 | 0 | 0 | 0 | 0 | 0 | 0 | 0 | 0 | 0 |
| Sugar beet | 3 | 0 | 10 | 0 | 0 | 1 | — | — | 0 | 0 | 0 | 0 | 0 | 0 | 0 | 0 | 0 | 0 | 0 | 0 | 0 | 0 | 2 |
| Velvetleaf | 0 | 0 | 0 | 0 | 0 | 2 | 1 | 0 | 0 | 0 | 0 | 0 | 0 | 0 | 0 | 0 | 0 | 0 | 0 | 0 | 0 | 0 | 0 |
| Wheat | 0 | 0 | 3 | 0 | 0 | 0 | 0 | 0 | 0 | 0 | 0 | 0 | 0 | 0 | 0 | 0 | 0 | 0 | 0 | 0 | 0 | 0 | 0 |
| Wild buckwheat | — | — | 10 | 10 | 0 | 3 | — | 0 | 0 | 0 | 0 | 0 | 0 | — | 0 | 0 | 0 | 0 | 0 | 0 | 0 | 0 | 8 |
| Wild oat | 0 | 0 | 4 | 0 | 0 | 5 | 2 | 0 | 2 | 0 | 0 | 0 | 0 | 0 | 0 | 0 | 0 | 0 | 0 | 0 | 0 | 0 | 3 |

| | COMPOUND |
|---|---|
| Rate (50 g/ha) | 60 |
| POSTEMERGENCE | |
| Barley | 0 |
| Barnyardgrass | 0 |
| Bedstraw | 2 |
| Blackgrass | 0 |
| Cheatgrass | 0 |
| Chickweed | — |
| Cocklebur | 0 |
| Corn | 0 |
| Cotton | 0 |
| Crabgrass | 0 |
| Giant foxtail | 0 |
| Lambsquarters | 0 |
| Morningglory | 0 |
| Nutsedge | 0 |
| Rape | 0 |
| Rice | 0 |
| Sorghum | 0 |
| Soybean | 0 |
| Sugar beet | 0 |
| Velvetleaf | 0 |
| Wheat | 0 |
| Wild buckwheat | 3 |
| Wild oat | 0 |
| PREEMERGENCE | |
| Barley | 0 |
| Barnyardgrass | 0 |
| Bedstraw | 0 |
| Blackgrass | 0 |

TABLE B-continued

| | |
|---|---|
| Cheatgrass | 0 |
| Chickweed | 0 |
| Cocklebur | 0 |
| Corn | 0 |
| Cotton | 0 |
| Crabgrass | 0 |
| Giant foxtail | 0 |
| Lambsquarters | 0 |
| Morningglory | 0 |
| Nutsedge | 0 |
| Rape | 0 |
| Rice | 0 |
| Sorghum | 0 |
| Soybean | 0 |
| Sugar beet | — |
| Velvetleaf | 0 |
| Wheat | 0 |
| Wild buckwheat | 0 |
| Wild oat | 0 |

TEST C

The compounds evaluated in this test were formulated in a non-phytoxic solvent and applied to the soft surface before plant seedlings emerged (proemergence application), to water that covered the soft surface (flood application), and to plants that were in the one-to-four leaf stage (postemergence application). A sandy loam soft was used for the proemergence and postemergence tests, while a silt loam soil was used in the flood test. Water depth was approximately 2.5 cm for the flood test and was maintained at this level for the duration of the test.

Plant species in the proemergence and postemergence tests consisted of barley (*Hordeum vulgare*), bedstraw (*Galium aparine*), blackgrass (*Alopecurus myosuroides*), chickweed (*Stellaria media*), corn (*Zea mays*), cotton (*Gossypium hirsutum*), crabgrass (*Digitaria sanguinalis*), downy brome (*Bromus tectorum*), giant foxtail (*Setaria faberii*), lambsquarters (*Chenopodium album*), morningglory (*Ipomoea hederacea*), pigweed (*Amaranthus retroflexus*), rape (*Brassica napus*), ryegrass (*Lolium multiflorum*), sorghum (*Sorghum bicolor*), soybean (*Glycine max*), speedwell (*Veronica persica*), sugar beet (*Beta vulgaris*), velvefleaf (*Abutilon theophrasti*), wheat (*Triticum aestivum*), wild buckwheat (*Polygonum convolvulus*), and wild oat (*Avena fatua*). All plant species were planted one day before application of the compound for the proemergence portion of this test. Plantings of these species were adjusted to produce plants of appropriate size for the postemergence portion of the test. Plant species in the flood test consisted of barnyardgrass (*Echinochloa crusgalli*), rice (*Oryza saliva*), umbrella sedge (*Cyperus difformis*) and duck salad (*Heteranthera limosa*).

All plant species were grown using normal greenhouse practices. Visual evaluations of injury expressed on treated plants, when compared to untreated controls, were recorded approximately fourteen to twenty one days after application of the test compound. Plant response ratings, summarized in Table C, were recorded on a 0 to 10 scale where 0 is no effect and I 0 is complete control. A dash (–) response means no test result.

TABLE C

| | COMPOUND | |
|---|---|---|
| Rate (1000 g/ha) | 1 | 2 |
| POSTEMERGENCE | | |
| Barley Igri | — | — |
| Bedstraw | — | — |
| Blackgrass | — | — |
| Chickweed | — | — |
| Corn | — | — |
| Cotton | — | — |
| Crabgrass | — | — |
| Downy brome | — | — |
| Duck salad | 5 | 3 |
| Giant foxtail | — | — |
| Lambsquarters | — | — |
| Morningglory | — | — |
| Pigweed | — | — |
| Rape | — | — |
| Ryegrass | — | — |
| Sorghum | — | — |
| Soybean | — | — |
| Speedwell | — | — |
| Sugar beet | — | — |
| Velvetleaf | — | — |

TABLE C-continued

| | | |
|---|---|---|
| Wheat | — | — |
| Wild buckwheat | — | — |
| Wild oat | — | — |
| Barnyardgrass | 9 | 9 |
| Rice Japonica | 8 | 8 |
| Umbrella sedge | 0 | 0 |

| | COMPOUND | |
|---|---|---|
| Rate (1000 g/ha) | 1 | 2 |
| PREEMERGENCE | | |
| Barley Igri | 3 | 2 |
| Bedstraw | 10 | 10 |
| Blackgrass | 10 | 10 |
| Chickweed | 10 | 10 |
| Corn | 8 | 7 |
| Cotton | 7 | 10 |
| Crabgrass | 10 | 10 |
| Downy brome | 7 | 10 |
| Duck salad | — | — |
| Giant foxtail | 10 | 10 |
| Lambsquarters | 10 | 10 |
| Morningglory | 10 | 10 |
| Pigweed | 10 | 10 |
| Rape | 4 | 0 |
| Ryegrass | 10 | 10 |
| Sorghum | 10 | 10 |
| Soybean | 5 | 6 |
| Speedwell | 10 | 10 |
| Sugar beet | 10 | 10 |
| Velvetleaf | 10 | 10 |
| Wheat | 6 | 5 |
| Wild buckwheat | 10 | 10 |
| Wild oat | 10 | 10 |
| Barnyardgrass | — | — |
| Rice Japonica | — | — |
| Umbrella sedge | — | — |

| | COMPOUND | | | | | | | | |
|---|---|---|---|---|---|---|---|---|---|
| Rate (500 g/ha) | 1 | 2 | 7 | 10 | 11 | 15 | 18 | 26 | 41 |
| POSTEMERGENCE | | | | | | | | | |
| Barley Igri | — | — | — | — | — | — | — | — | — |
| Bedstraw | — | — | — | — | — | — | — | — | — |
| Blackgrass | — | — | — | — | — | — | — | — | — |
| Chickweed | — | — | — | — | — | — | — | — | — |
| Corn | — | — | — | — | — | — | — | — | — |
| Cotton | — | — | — | — | — | — | — | — | — |
| Crabgrass | — | — | — | — | — | — | — | — | — |
| Downy brome | — | — | — | — | — | — | — | — | — |
| Duck salad | 4 | 0 | 0 | 9 | 9 | 9 | 9 | 0 | 2 |
| Giant foxtail | — | — | — | — | — | — | — | — | — |
| Lambsquarters | — | — | — | — | — | — | — | — | — |
| Morningglory | — | — | — | — | — | — | — | — | — |
| Pigweed | — | — | — | — | — | — | — | — | — |
| Rape | — | — | — | — | — | — | — | — | — |
| Ryegrass | — | — | — | — | — | — | — | — | — |
| Sorghum | — | — | — | — | — | — | — | — | — |
| Soybean | — | — | — | — | — | — | — | — | — |
| Speedwell | — | — | — | — | — | — | — | — | — |
| Sugar beet | — | — | — | — | — | — | — | — | — |
| Velvetleaf | — | — | — | — | — | — | — | — | — |
| Wheat | — | — | — | — | — | — | — | — | — |
| Wild buckwheat | — | — | — | — | — | — | — | — | — |
| Wild oat | — | — | — | — | — | — | — | — | — |
| Barnyardgrass | 9 | 9 | 6 | 10 | 10 | 10 | 10 | 9 | 9 |
| Rice Jamonica | 8 | 8 | 7 | 9 | 9 | 8 | 8 | 9 | 8 |
| Umbrella sedge | 0 | 0 | 0 | 9 | 9 | 9 | 9 | 7 | 8 |

TABLE C-continued

| Rate (500 g/ha) | COMPOUND 1 | 2 | 7 | 10 | 11 | 15 | 18 | 26 | 41 |
|---|---|---|---|---|---|---|---|---|---|
| PREEMERGENCE | | | | | | | | | |
| Barley Igri | 2 | 0 | 2 | 2 | 2 | 2 | 2 | 3 | 5 |
| Bedstraw | 10 | 10 | 10 | 9 | 5 | 8 | 9 | 2 | 10 |
| Blackgrass | 10 | 10 | 10 | 8 | 6 | 9 | 9 | 10 | 10 |
| Chickweed | 10 | 10 | 10 | 7 | 2 | 5 | 8 | 6 | 7 |
| Corn | 6 | 6 | 0 | 5 | 6 | 8 | 10 | 0 | 6 |
| Cotton | 6 | 6 | 7 | 0 | — | 8 | 7 | 0 | 7 |
| Crabgrass | 10 | 10 | 10 | 10 | 10 | 10 | 10 | 10 | 10 |
| Downy brome | 3 | 4 | 5 | 5 | 5 | 5 | 7 | 6 | 6 |
| Duck salad | — | — | — | — | — | — | — | — | — |
| Giant foxtail | 10 | 10 | 10 | 10 | 10 | 10 | 10 | 10 | 10 |
| Lambsquarters | 10 | 10 | 10 | 10 | 10 | 8 | 10 | 9 | 10 |
| Morningglory | 10 | 7 | 0 | 7 | 2 | 7 | 8 | 0 | 0 |
| Pigweed | 10 | 10 | 10 | 7 | 8 | 8 | 9 | 8 | 8 |
| Rape | 0 | 0 | 7 | 4 | 3 | 7 | 7 | 2 | 8 |
| Ryegrass | 10 | 10 | 7 | 8 | 8 | 9 | 9 | 9 | 9 |
| Sorghum | 10 | 10 | 9 | 10 | 10 | 10 | 10 | 10 | 10 |
| Soybean | 1 | 4 | 0 | 2 | 0 | 2 | 4 | 0 | 3 |
| Speedwell | 10 | 10 | 10 | 10 | 10 | 8 | 10 | 6 | 10 |
| Sugar beet | 10 | 9 | 9 | 8 | 5 | 7 | 9 | 6 | 7 |
| Velvetleaf | 8 | 8 | 8 | 7 | 6 | 8 | 9 | 5 | 5 |
| Wheat | 5 | 4 | 2 | 2 | 2 | 1 | 2 | 4 | 6 |
| Wild buckwheat | 10 | 9 | 8 | 8 | 0 | 5 | 8 | 0 | 6 |
| Wild oat | 10 | 10 | 10 | 8 | 6 | 7 | 9 | 9 | 9 |
| Barnyardgrass | — | — | — | — | — | — | — | — | — |
| Rice Japonica | — | — | — | — | — | — | — | — | — |
| Umbrella sedge | — | — | — | — | — | — | — | — | — |

| Rate (250 g/ha) | COMPOUND 1 | 2 | 7 | 10 | 11 | 15 | 18 | 26 | 30 | 32 | 34 | 35 | 36 | 37 | 38 | 39 | 41 | 42 | 44 |
|---|---|---|---|---|---|---|---|---|---|---|---|---|---|---|---|---|---|---|---|
| POSTEMERGENCE | | | | | | | | | | | | | | | | | | | |
| Barley Igri | — | — | — | — | — | — | — | — | — | — | — | — | — | — | — | — | — | — | — |
| Bedstraw | — | — | — | — | — | — | — | — | — | — | — | — | — | — | — | — | — | — | — |
| Blackgrass | — | — | — | — | — | — | — | — | — | — | — | — | — | — | — | — | — | — | — |
| Chickweed | — | — | — | — | — | — | — | — | — | — | — | — | — | — | — | — | — | — | — |
| Corn | — | — | — | — | — | — | — | — | — | — | — | — | — | — | — | — | — | — | — |
| Cotton | — | — | — | — | — | — | — | — | — | — | — | — | — | — | — | — | — | — | — |
| Crabgrass | — | — | — | — | — | — | — | — | — | — | — | — | — | — | — | — | — | — | — |
| Downy brome | — | — | — | — | — | — | — | — | — | — | — | — | — | — | — | — | — | — | — |
| Duck salad | 0 | 0 | 0 | 9 | 9 | 9 | 0 | 0 | 0 | 2 | 2 | 0 | 2 | 7 | 7 | 0 | 1 | 2 | 0 |
| Giant foxtail | — | — | — | — | — | — | — | — | — | — | — | — | — | — | — | — | — | — | — |
| Lambsquarters | — | — | — | — | — | — | — | — | — | — | — | — | — | — | — | — | — | — | — |
| Morningglory | — | — | — | — | — | — | — | — | — | — | — | — | — | — | — | — | — | — | — |
| Pigweed | — | — | — | — | — | — | — | — | — | — | — | — | — | — | — | — | — | — | — |
| Rape | — | — | — | — | — | — | — | — | — | — | — | — | — | — | — | — | — | — | — |
| Ryegrass | — | — | — | — | — | — | — | — | — | — | — | — | — | — | — | — | — | — | — |
| Sorghum | — | — | — | — | — | — | — | — | — | — | — | — | — | — | — | — | — | — | — |
| Soybean | — | — | — | — | — | — | — | — | — | — | — | — | — | — | — | — | — | — | — |
| Speedwell | — | — | — | — | — | — | — | — | — | — | — | — | — | — | — | — | — | — | — |
| Sugar beet | — | — | — | — | — | — | — | — | — | — | — | — | — | — | — | — | — | — | — |
| Velvetleaf | — | — | — | — | — | — | — | — | — | — | — | — | — | — | — | — | — | — | — |
| Wheat | — | — | — | — | — | — | — | — | — | — | — | — | — | — | — | — | — | — | — |
| Wild buckwheat | — | — | — | — | — | — | — | — | — | — | — | — | — | — | — | — | — | — | — |
| Wild oat | — | — | — | — | — | — | — | — | — | — | — | — | — | — | — | — | — | — | — |
| Barnyardgrass | 8 | 8 | 5 | 10 | 10 | 10 | 10 | 9 | 9 | 8 | 9 | 9 | 9 | 9 | 9 | 9 | 9 | 9 | 9 |
| Rice Japonica | 8 | 8 | 6 | 9 | 8 | 8 | 8 | 8 | 7 | 7 | 8 | 8 | 8 | 8 | 8 | 7 | 8 | 8 | 8 |
| Umbrella sedge | 0 | 0 | 0 | 9 | 9 | 9 | 9 | 0 | 0 | 3 | 8 | 5 | 9 | 9 | 9 | 3 | 0 | 0 | 0 |

| Rate (250 g/ha) | COMPOUND 1 | 2 | 7 | 10 | 11 | 15 | 18 | 26 | 30 | 32 | 34 | 35 | 36 | 37 | 38 | 39 | 41 | 42 | 44 |
|---|---|---|---|---|---|---|---|---|---|---|---|---|---|---|---|---|---|---|---|
| PREEMERGENCE | | | | | | | | | | | | | | | | | | | |
| Barley Igri | 0 | 0 | 0 | 0 | 0 | 0 | 2 | 2 | 1 | 0 | 1 | 0 | 1 | 2 | 2 | 0 | 2 | 1 | 1 |
| Bedstraw | 5 | 10 | 10 | 5 | 2 | 6 | 8 | 0 | 7 | 5 | 1 | 5 | 10 | 10 | 7 | 0 | 10 | 4 | 0 |
| Blackgrass | 10 | 10 | 8 | 7 | 4 | 9 | 9 | 10 | 10 | 10 | 4 | 10 | 10 | 9 | 9 | 10 | 10 | 9 | 9 |
| Chickweed | 10 | 10 | 10 | 5 | 0 | 3 | 7 | 5 | 10 | 5 | 4 | 9 | 5 | 10 | 7 | 7 | 5 | 9 | 5 |
| Corn | 5 | 4 | 0 | 5 | 5 | 6 | 8 | 0 | 6 | 2 | 2 | 2 | 5 | 6 | 1 | 4 | 5 | 7 | 6 |

TABLE C-continued

| | | | | | | | | | | | | | | | | | | | |
|---|---|---|---|---|---|---|---|---|---|---|---|---|---|---|---|---|---|---|---|
| Cotton | 3 | 5 | 5 | 0 | 0 | 8 | 2 | 0 | 8 | 0 | 2 | 4 | 3 | 7 | 0 | 4 | 0 | 2 | 0 |
| Crabgrass | 10 | 10 | 10 | 10 | 10 | 10 | 10 | 10 | 10 | 10 | 10 | 10 | 10 | 10 | 10 | 10 | 10 | 10 | 10 |
| Downy brome | — | 4 | 2 | 2 | 3 | 3 | 5 | 3 | 6 | 2 | 2 | 6 | 6 | 7 | 6 | 2 | 5 | 3 | 1 |
| Duck salad | — | — | — | — | — | — | — | — | — | — | — | — | — | — | — | — | — | — | — |
| Giant foxtail | 9 | 10 | 10 | 10 | 10 | 10 | 10 | 10 | 10 | 10 | 9 | 10 | 10 | 10 | 10 | 10 | 10 | 10 | 10 |
| Lambsquarters | 10 | 10 | 7 | 9 | 5 | 8 | 10 | 8 | 10 | 8 | 3 | 10 | 10 | 9 | 9 | 10 | 8 | 9 | 9 |
| Morningglory | 8 | 7 | 0 | 2 | 0 | 3 | 7 | 0 | 10 | 7 | 0 | 0 | 0 | 4 | 0 | 0 | 0 | 2 | 3 |
| Pigweed | 9 | 9 | 6 | 7 | 8 | 8 | 8 | 5 | 9 | 8 | 0 | 7 | 6 | 1 | 2 | 7 | 8 | 7 | 8 |
| Rape | 0 | 0 | 0 | 2 | 0 | 3 | 3 | 0 | 7 | 4 | 0 | 2 | 0 | 2 | 2 | 0 | 2 | 0 | 0 |
| Ryegrass | 10 | 7 | 3 | 3 | 3 | 6 | 8 | 3 | 10 | 8 | 2 | 10 | 10 | 9 | 4 | 9 | 4 | 7 | 6 |
| Sorghum | 10 | 10 | 4 | 9 | 9 | 10 | 10 | 10 | 10 | 9 | 5 | 10 | 10 | 7 | 10 | 6 | 10 | 10 | 10 |
| Soybean | 0 | 0 | 0 | 0 | 0 | 0 | 2 | 0 | 4 | 1 | 3 | 0 | 1 | 4 | 0 | 0 | 0 | 2 | 0 |
| Speedwell | 10 | 10 | 10 | 10 | 8 | — | 10 | 2 | 7 | 5 | 10 | 7 | 3 | 10 | 10 | 7 | 7 | 10 | 10 |
| Sugar beet | 9 | 9 | 7 | 7 | 2 | 7 | 9 | 3 | 8 | 5 | 3 | 7 | 2 | 8 | 6 | 2 | 6 | 10 | 3 |
| Velvetleaf | 7 | 7 | 5 | 5 | 4 | 7 | 8 | 2 | 8 | 8 | 0 | 8 | 7 | 9 | 0 | 6 | 3 | 7 | 8 |
| Wheat | 3 | 1 | 0 | 2 | 2 | 0 | 2 | 2 | 5 | 3 | 2 | 0 | 4 | 3 | 4 | 0 | 5 | 5 | 2 |
| Wild buckwheat | 5 | 9 | 7 | 5 | 0 | 5 | 7 | 0 | 5 | 0 | 0 | 3 | 2 | 6 | 4 | 0 | 3 | 1 | 0 |
| Wild oat | 8 | 7 | 4 | 7 | 2 | 7 | 9 | 9 | 10 | 9 | 0 | 1 | 7 | 7 | 5 | 7 | 7 | 9 | 9 |
| Barnyardgrass | — | — | — | — | — | — | — | — | — | — | — | — | — | — | — | — | — | — | — |
| Rice Japonica | — | — | — | — | — | — | — | — | — | — | — | — | — | — | — | — | — | — | — |
| Umbrella sedge | — | — | — | — | — | — | — | — | — | — | — | — | — | — | — | — | — | — | — |

| | COMPOUND | | | | | | | | | | | | | | | | | | | | |
|---|---|---|---|---|---|---|---|---|---|---|---|---|---|---|---|---|---|---|---|---|---|
| Rate (125 g/ha) | 1 | 2 | 3 | 5 | 7 | 10 | 11 | 15 | 18 | 26 | 30 | 32 | 34 | 35 | 36 | 37 | 38 | 39 | 41 | 42 | 44 |
| POSTEMERGENCE | | | | | | | | | | | | | | | | | | | | | |
| Barley Igri | — | — | — | — | — | — | — | — | — | — | — | — | — | — | — | — | — | — | — | — | — |
| Bedstraw | — | — | — | — | — | — | — | — | — | — | — | — | — | — | — | — | — | — | — | — | — |
| Blackgrass | — | — | — | — | — | — | — | — | — | — | — | — | — | — | — | — | — | — | — | — | — |
| Chickweed | — | — | — | — | — | — | — | — | — | — | — | — | — | — | — | — | — | — | — | — | — |
| Corn | — | — | — | — | — | — | — | — | — | — | — | — | — | — | — | — | — | — | — | — | — |
| Cotton | — | — | — | — | — | — | — | — | — | — | — | — | — | — | — | — | — | — | — | — | — |
| Crabgrass | — | — | — | — | — | — | — | — | — | — | — | — | — | — | — | — | — | — | — | — | — |
| Downy brome | — | — | — | — | — | — | — | — | — | — | — | — | — | — | — | — | — | — | — | — | — |
| Duck salad | 0 | 0 | 0 | 0 | 0 | 9 | 2 | 8 | 0 | 0 | 0 | 1 | 0 | 0 | 0 | 3 | 2 | 0 | 0 | 1 | 0 |
| Giant foxtail | — | — | — | — | — | — | — | — | — | — | — | — | — | — | — | — | — | — | — | — | — |
| Lambsquarters | — | — | — | — | — | — | — | — | — | — | — | — | — | — | — | — | — | — | — | — | — |
| Morningglory | — | — | — | — | — | — | — | — | — | — | — | — | — | — | — | — | — | — | — | — | — |
| Pigweed | — | — | — | — | — | — | — | — | — | — | — | — | — | — | — | — | — | — | — | — | — |
| Rape | — | — | — | — | — | — | — | — | — | — | — | — | — | — | — | — | — | — | — | — | — |
| Ryegrass | — | — | — | — | — | — | — | — | — | — | — | — | — | — | — | — | — | — | — | — | — |
| Sorghum | — | — | — | — | — | — | — | — | — | — | — | — | — | — | — | — | — | — | — | — | — |
| Soybean | — | — | — | — | — | — | — | — | — | — | — | — | — | — | — | — | — | — | — | — | — |
| Speedwell | — | — | — | — | — | — | — | — | — | — | — | — | — | — | — | — | — | — | — | — | — |
| Sugar beet | — | — | — | — | — | — | — | — | — | — | — | — | — | — | — | — | — | — | — | — | — |
| Velvetleaf | — | — | — | — | — | — | — | — | — | — | — | — | — | — | — | — | — | — | — | — | — |
| Wheat | — | — | — | — | — | — | — | — | — | — | — | — | — | — | — | — | — | — | — | — | — |
| Wild buckwheat | — | — | — | — | — | — | — | — | — | — | — | — | — | — | — | — | — | — | — | — | — |
| Wild oat | — | — | — | — | — | — | — | — | — | — | — | — | — | — | — | — | — | — | — | — | — |
| Barnyardgrass | 8 | 8 | 9 | 8 | 0 | 10 | 9 | 9 | 9 | 8 | 9 | 8 | 9 | 8 | 9 | 8 | 9 | 8 | 8 | 9 | 4 |
| Rice Japonica | 7 | 6 | 8 | 7 | 5 | 9 | 6 | 6 | 7 | 7 | 6 | 7 | 8 | 7 | 7 | 8 | 8 | 6 | 8 | 8 | 7 |
| Umbrella sedge | 0 | 0 | 0 | 9 | 0 | 9 | 9 | 9 | 8 | 0 | 0 | 2 | 0 | 0 | 6 | 0 | 7 | 0 | 0 | 0 | 0 |

| | COMPOUND | | | | | | | | | | | | | | | | | | | |
|---|---|---|---|---|---|---|---|---|---|---|---|---|---|---|---|---|---|---|---|---|
| Rate (125 g/ha) | 1 | 2 | 3 | 7 | 10 | 11 | 15 | 18 | 26 | 30 | 32 | 34 | 35 | 36 | 37 | 38 | 39 | 41 | 42 | 44 |
| PREEMERGENCE | | | | | | | | | | | | | | | | | | | | |
| Barley Igri | 0 | 0 | 0 | 0 | 0 | 0 | 0 | 0 | 0 | 0 | 0 | 1 | 0 | 0 | 0 | 0 | 0 | 0 | 0 | 0 |
| Bedstraw | 0 | 6 | 6 | 4 | 2 | 0 | 5 | 8 | 0 | 5 | 3 | 0 | 2 | 10 | 6 | 5 | 0 | 5 | 2 | 0 |
| Blackgrass | 2 | 10 | 10 | 5 | 5 | 3 | 8 | 9 | 9 | 10 | 10 | 2 | 9 | 7 | 9 | 9 | 7 | 9 | 9 | 9 |
| Chickweed | 5 | 8 | 9 | 9 | 3 | 0 | 0 | 6 | 2 | 9 | 3 | 1 | 5 | 5 | 9 | 6 | 2 | 2 | 9 | 2 |
| Corn | 0 | 0 | 6 | 0 | 3 | 4 | 5 | 5 | 0 | 3 | 0 | 2 | 2 | 5 | 4 | 0 | 1 | 5 | 4 | 1 |
| Cotton | 0 | 4 | 5 | 3 | 0 | 0 | 3 | 0 | 0 | 5 | 0 | 2 | 4 | 2 | 5 | 0 | 3 | 0 | 0 | 0 |
| Crabgrass | 10 | 10 | 10 | 9 | 10 | 10 | 10 | 10 | 10 | 9 | 10 | 9 | 10 | 10 | 10 | 10 | 10 | 10 | 10 | 10 |
| Downy brome | 0 | 4 | 3 | 0 | 0 | 0 | 2 | 3 | 2 | 4 | 0 | 0 | 3 | 4 | 5 | 4 | 2 | 2 | 2 | 0 |
| Duck salad | — | — | — | — | — | — | — | — | — | — | — | — | — | — | — | — | — | — | — | — |
| Giant foxtail | 9 | 10 | 4 | 8 | 10 | 10 | 10 | 10 | 10 | 10 | 10 | 6 | 10 | 10 | 10 | 8 | 8 | 10 | 10 | 9 |
| Lambsquarters | 5 | 10 | 8 | 6 | 3 | 0 | 3 | 8 | 2 | 8 | 7 | 0 | 9 | 7 | 9 | 7 | 2 | 2 | 9 | 5 |
| Morningglory | 6 | 2 | 0 | 0 | 0 | 0 | 3 | 5 | 0 | 4 | 2 | 0 | 0 | 0 | 0 | 0 | 0 | 0 | 2 | 1 |
| Pigweed | 6 | 9 | 7 | 5 | 6 | 7 | 7 | 7 | 5 | 7 | 7 | 0 | 4 | 5 | 7 | 0 | 4 | 4 | 5 | 2 |
| Rape | 0 | 0 | 0 | 0 | 0 | 0 | 0 | 2 | 0 | 2 | 0 | 0 | 0 | 0 | 2 | 0 | 0 | 0 | 0 | 0 |
| Ryegrass | 5 | 4 | 7 | 0 | 2 | 2 | 3 | 6 | 2 | 10 | 7 | 0 | 7 | 5 | 6 | 3 | 6 | 2 | 4 | 3 |
| Sorghum | 9 | 8 | 5 | 2 | 7 | 6 | 9 | 10 | 5 | 6 | 4 | 5 | 5 | 6 | 5 | 4 | 5 | 9 | 9 | 7 |

TABLE C-continued

| | | | | | | | | | | | | | | | | | | | | | |
|---|---|---|---|---|---|---|---|---|---|---|---|---|---|---|---|---|---|---|---|---|---|
| Soybean | 0 | 0 | | 0 | 0 | 0 | 0 | 0 | 0 | 0 | 1 | 0 | 2 | 0 | 0 | 2 | 0 | 0 | 0 | 0 | 0 |
| Speedwell | 10 | 10 | | 10 | 10 | 5 | 5 | — | 10 | 0 | 5 | 2 | 2 | 3 | 0 | 10 | 9 | 2 | 3 | 10 | 9 |
| Sugar beet | 6 | 8 | | 10 | 5 | 4 | 0 | 5 | 8 | 0 | 7 | 2 | 2 | 3 | 2 | 7 | 5 | 2 | 3 | 3 | 1 |
| Velvetleaf | 4 | 2 | | 0 | 5 | 3 | 2 | 6 | 5 | 2 | 7 | 7 | 0 | 8 | 0 | 7 | 0 | 5 | 0 | 5 | 3 |
| Wheat | 0 | 0 | | 5 | 0 | 0 | 0 | 0 | 1 | 0 | 2 | 0 | 1 | 0 | 2 | 2 | 2 | 0 | 4 | 3 | 0 |
| Wild buckwheat | 0 | 3 | | 4 | 6 | 3 | 0 | 3 | 5 | 0 | 2 | 0 | 0 | 2 | 0 | 5 | 3 | 0 | 2 | 0 | 0 |
| Wild oat | 0 | 4 | | 4 | 2 | 4 | 0 | 3 | 7 | 5 | 10 | 7 | 0 | 5 | 4 | 2 | 1 | 3 | 4 | 6 | 5 |
| Barnyardgrass | — | — | | — | — | — | — | — | — | — | — | — | — | — | — | — | — | — | — | — | — |
| Rice Japonica | — | — | | — | — | — | — | — | — | — | — | — | — | — | — | — | — | — | — | — | — |
| Umbrella sedge | — | — | | — | — | — | — | — | — | — | — | — | — | — | — | — | — | — | — | — | — |

| | COMPOUND | | | | | | | | | | | | | | | | | | |
|---|---|---|---|---|---|---|---|---|---|---|---|---|---|---|---|---|---|---|---|
| Rate (62 g/ha) | 3 | 5 | 7 | 10 | 11 | 15 | 18 | 26 | 30 | 32 | 34 | 35 | 36 | 37 | 38 | 39 | 41 | 42 | 44 |
| POSTEMERGENCE | | | | | | | | | | | | | | | | | | | |
| Barley Igri | — | — | — | — | — | — | — | — | — | — | — | — | — | — | — | — | — | — | — |
| Bedstraw | — | — | — | — | — | — | — | — | — | — | — | — | — | — | — | — | — | — | — |
| Blackgrass | — | — | — | — | — | — | — | — | — | — | — | — | — | — | — | — | — | — | — |
| Chickweed | — | — | — | — | — | — | — | — | — | — | — | — | — | — | — | — | — | — | — |
| Corn | — | — | — | — | — | — | — | — | — | — | — | — | — | — | — | — | — | — | — |
| Cotton | — | — | — | — | — | — | — | — | — | — | — | — | — | — | — | — | — | — | — |
| Crabgrass | — | — | — | — | — | — | — | — | — | — | — | — | — | — | — | — | — | — | — |
| Downy brome | — | — | — | — | — | — | — | — | — | — | — | — | — | — | — | — | — | — | — |
| Duck salad | 0 | 0 | 0 | 9 | 0 | 8 | 0 | 0 | 0 | 0 | 0 | 0 | 0 | 0 | 0 | 0 | 0 | 0 | 0 |
| Giant foxtail | — | — | — | — | — | — | — | — | — | — | — | — | — | — | — | — | — | — | — |
| Lambsquarters | — | — | — | — | — | — | — | — | — | — | — | — | — | — | — | — | — | — | — |
| Morningglory | — | — | — | — | — | — | — | — | — | — | — | — | — | — | — | — | — | — | — |
| Pigweed | — | — | — | — | — | — | — | — | — | — | — | — | — | — | — | — | — | — | — |
| Rape | — | — | — | — | — | — | — | — | — | — | — | — | — | — | — | — | — | — | — |
| Ryegrass | — | — | — | — | — | — | — | — | — | — | — | — | — | — | — | — | — | — | — |
| Sorghum | — | — | — | — | — | — | — | — | — | — | — | — | — | — | — | — | — | — | — |
| Soybean | — | — | — | — | — | — | — | — | — | — | — | — | — | — | — | — | — | — | — |
| Speedwell | — | — | — | — | — | — | — | — | — | — | — | — | — | — | — | — | — | — | — |
| Sugar beet | — | — | — | — | — | — | — | — | — | — | — | — | — | — | — | — | — | — | — |
| Velvetleaf | — | — | — | — | — | — | — | — | — | — | — | — | — | — | — | — | — | — | — |
| Wheat | — | — | — | — | — | — | — | — | — | — | — | — | — | — | — | — | — | — | — |
| Wild buckwheat | — | — | — | — | — | — | — | — | — | — | — | — | — | — | — | — | — | — | — |
| Wild oat | — | — | — | — | — | — | — | — | — | — | — | — | — | — | — | — | — | — | — |
| Barnyardgrass | 8 | 8 | 0 | 10 | 8 | 9 | 8 | 0 | 8 | 8 | 6 | 8 | 7 | 6 | 8 | 8 | 5 | 8 | 0 |
| Rice Japonica | 6 | 6 | 1 | 8 | 5 | 6 | 6 | 5 | 5 | 5 | 6 | 6 | 6 | 7 | 7 | 5 | 7 | 6 | 5 |
| Umbrella sedge | 0 | 0 | 0 | 9 | 9 | 9 | 8 | 0 | 0 | 0 | 0 | 0 | 0 | 0 | 0 | 0 | 0 | 0 | 0 |

| | COMPOUND | | | | | | | | | | | | | | | | | |
|---|---|---|---|---|---|---|---|---|---|---|---|---|---|---|---|---|---|---|
| Rate (62 g/ha) | 3 | 7 | 10 | 11 | 15 | 18 | 26 | 30 | 32 | 34 | 35 | 36 | 37 | 38 | 39 | 41 | 42 | 44 |
| PREEMERGENCE | | | | | | | | | | | | | | | | | | |
| Barley Igri | 0 | 0 | 0 | 0 | 0 | 0 | 0 | 0 | 0 | 0 | 0 | 0 | 0 | 0 | 0 | 0 | 0 | 0 |
| Bedstraw | 0 | 0 | 0 | 0 | 2 | 5 | 0 | 2 | 3 | 0 | 0 | 2 | 5 | 5 | 0 | 0 | 0 | 0 |
| Blackgrass | 9 | 4 | 2 | 3 | 3 | 6 | 4 | 9 | 9 | 0 | 9 | 5 | 9 | 9 | 7 | 7 | 8 | 7 |
| Chickweed | 0 | 2 | 0 | 0 | 0 | 4 | 0 | 5 | 0 | 0 | 3 | 0 | 7 | 5 | 0 | 0 | 4 | 0 |
| Corn | 4 | 0 | 2 | 3 | 4 | 4 | 0 | 1 | 0 | 0 | 0 | 2 | 2 | 0 | 0 | 2 | 1 | 0 |
| Cotton | 3 | 0 | 0 | 0 | 0 | 0 | 0 | 4 | 0 | 0 | 1 | 0 | 2 | 0 | 2 | 0 | 0 | 0 |
| Crabgrass | 9 | 4 | 9 | 9 | 9 | 10 | 8 | 9 | 9 | 6 | 10 | 9 | 9 | 9 | 6 | 9 | 9 | 9 |
| Downy brome | 0 | 0 | 0 | 0 | 0 | 0 | 0 | 2 | 0 | 0 | 2 | 2 | 2 | 2 | 0 | 0 | 1 | 0 |
| Duck salad | — | — | — | — | — | — | — | — | — | — | — | — | — | — | — | — | — | — |
| Giant foxtail | 2 | 5 | 9 | 7 | 9 | 10 | 9 | 10 | 9 | 5 | 9 | 10 | 9 | 5 | 7 | 10 | 9 | 7 |
| Lambsquarters | 0 | 0 | 0 | 0 | 3 | 8 | 0 | 8 | 5 | 0 | 5 | 3 | 7 | 7 | 0 | 0 | 8 | 3 |
| Morningglory | 0 | 0 | 0 | 0 | 0 | 2 | 0 | 2 | 0 | 0 | 0 | 0 | 0 | 0 | 0 | 0 | 1 | 1 |
| Pigweed | 7 | 0 | 6 | 7 | 7 | 7 | 0 | 5 | 6 | 0 | 2 | 4 | 7 | 0 | 2 | 0 | 2 | 0 |
| Rape | 0 | 0 | 0 | 0 | 0 | 0 | 0 | 0 | 0 | 0 | 0 | 0 | 0 | 0 | 0 | 0 | 0 | 0 |
| Ryegrass | 4 | 0 | 0 | 0 | 0 | 3 | 0 | 6 | 5 | 0 | 3 | 2 | 4 | 2 | 2 | 0 | 2 | 0 |
| Sorghum | 4 | 0 | 2 | 3 | 4 | 5 | 0 | 4 | 4 | 4 | 5 | 5 | 4 | 4 | 3 | 5 | 5 | 3 |
| Soybean | 0 | 0 | 0 | 0 | 0 | 0 | 0 | 0 | 0 | 0 | 0 | 0 | 0 | 0 | 0 | 0 | 0 | 0 |
| Speedwell | 10 | 6 | 2 | 5 | — | 9 | 0 | 0 | 0 | 0 | 2 | 0 | 5 | 9 | 0 | 0 | 9 | 9 |
| Sugar beet | 5 | 5 | 0 | 0 | 3 | 5 | 0 | 5 | 0 | 0 | 2 | 0 | 6 | 3 | 0 | 2 | 1 | 1 |
| Velvetleaf | 0 | 4 | 0 | 0 | 5 | 5 | 0 | 5 | 5 | 0 | 4 | 4 | 5 | 0 | 4 | 0 | 2 | 2 |
| Wheat | 3 | 0 | 0 | 0 | 0 | 0 | 0 | 0 | 0 | 0 | 0 | 0 | 0 | 0 | 0 | 2 | 1 | 0 |
| Wild buckwheat | 4 | 3 | 0 | 0 | 0 | 0 | 0 | 0 | 0 | 0 | 0 | 0 | 4 | 3 | 0 | 0 | 0 | 0 |
| Wild oat | 2 | 0 | 0 | 0 | 0 | 2 | 2 | 7 | 4 | 0 | 3 | 2 | 0 | 0 | 0 | 0 | 1 | 0 |
| Barnyardgrass | — | — | — | — | — | — | — | — | — | — | — | — | — | — | — | — | — | — |
| Rice Japonica | — | — | — | — | — | — | — | — | — | — | — | — | — | — | — | — | — | — |
| Umbrella sedge | — | — | — | — | — | — | — | — | — | — | — | — | — | — | — | — | — | — |

TABLE C-continued

| | COMPOUND | | | | | | | | | | | | |
|---|---|---|---|---|---|---|---|---|---|---|---|---|---|
| Rate (31 g/ha) | 3 | 5 | 10 | 30 | 32 | 34 | 35 | 36 | 37 | 38 | 39 | 42 | 44 |
| POSTEMERGENCE | | | | | | | | | | | | | |
| Barley Igri | — | — | — | — | — | — | — | — | — | — | — | — | — |
| Bedstraw | — | — | — | — | — | — | — | — | — | — | — | — | — |
| Blackgrass | — | — | — | — | — | — | — | — | — | — | — | — | — |
| Chickweed | — | — | — | — | — | — | — | — | — | — | — | — | — |
| Corn | — | — | — | — | — | — | — | — | — | — | — | — | — |
| Cotton | — | — | — | — | — | — | — | — | — | — | — | — | — |
| Crabgrass | — | — | — | — | — | — | — | — | — | — | — | — | — |
| Downy brome | — | — | — | — | — | — | — | — | — | — | — | — | — |
| Duck salad | 0 | 0 | — | 0 | 0 | 0 | 0 | 0 | 0 | 0 | 0 | 0 | 0 |
| Giant foxtail | — | — | — | — | — | — | — | — | — | — | — | — | — |
| Lambsquarters | — | — | — | — | — | — | — | — | — | — | — | — | — |
| Morningglory | — | — | — | — | — | — | — | — | — | — | — | — | — |
| Pigweed | — | — | — | — | — | — | — | — | — | — | — | — | — |
| Rape | — | — | — | — | — | — | — | — | — | — | — | — | — |
| Ryegrass | — | — | — | — | — | — | — | — | — | — | — | — | — |
| Sorghum | — | — | — | — | — | — | — | — | — | — | — | — | — |
| Soybean | — | — | — | — | — | — | — | — | — | — | — | — | — |
| Speedwell | — | — | — | — | — | — | — | — | — | — | — | — | — |
| Sugar beet | — | — | — | — | — | — | — | — | — | — | — | — | — |
| Velvetleaf | — | — | — | — | — | — | — | — | — | — | — | — | — |
| Wheat | — | — | — | — | — | — | — | — | — | — | — | — | — |
| Wild buckwheat | — | — | — | — | — | — | — | — | — | — | — | — | — |
| Wild oat | — | — | — | — | — | — | — | — | — | — | — | — | — |
| Barnyardgrass | 0 | 1 | 0 | 6 | 8 | 3 | 0 | 2 | 3 | 6 | 2 | 4 | 0 |
| Rice Japonica | 4 | 3 | 3 | 5 | 3 | 1 | 5 | 4 | 7 | 4 | 1 | 5 | 2 |
| Umbrella sedge | 0 | 0 | — | 0 | 0 | 0 | 0 | 0 | 0 | 0 | 0 | 0 | 0 |

| | COMPOUND | | | | | | | | | | |
|---|---|---|---|---|---|---|---|---|---|---|---|
| Rate (31 g/ha) | 3 | 30 | 32 | 34 | 35 | 36 | 37 | 38 | 39 | 42 | 44 |
| PREEMERGENCE | | | | | | | | | | | |
| Barley Igri | 0 | 0 | 0 | 0 | 0 | 0 | 0 | 0 | 0 | 0 | 0 |
| Bedstraw | 0 | 0 | 0 | 0 | 0 | 0 | 2 | 1 | 0 | 0 | 0 |
| Blackgrass | 4 | 9 | 9 | 0 | 5 | 2 | 3 | 4 | 3 | 3 | 3 |
| Chickweed | 0 | 4 | 0 | 0 | 0 | 0 | 2 | 0 | 0 | 0 | — |
| Corn | 0 | 0 | 0 | 0 | 0 | 0 | 0 | 0 | 0 | 0 | 0 |
| Cotton | 2 | 3 | 0 | 0 | 1 | 0 | 0 | 0 | 0 | 0 | 0 |
| Crabgrass | 8 | 9 | 6 | 2 | 9 | 9 | 8 | 6 | 5 | 9 | 8 |
| Downy brome | 0 | 0 | 0 | 0 | 0 | 0 | 0 | 0 | 0 | 0 | 0 |
| Duck salad | — | — | — | — | — | — | — | — | — | — | — |
| Giant foxtail | 0 | 7 | 5 | 0 | 7 | 5 | 5 | 2 | 5 | 8 | 2 |
| Lambsquarters | 0 | 7 | 0 | 0 | 2 | 0 | 0 | 3 | 0 | 0 | — |
| Morningglory | 0 | 0 | 0 | 0 | 0 | 0 | 0 | 0 | 0 | 0 | 0 |
| Pigweed | 5 | 4 | 4 | 0 | 0 | 0 | 2 | 0 | 0 | 0 | 0 |
| Rape | 0 | 0 | 0 | 0 | 0 | 0 | 0 | 0 | 0 | 0 | 0 |
| Ryegrass | 0 | 2 | 2 | 0 | 0 | 0 | 3 | 0 | 0 | 0 | 0 |
| Sorghum | 0 | 3 | 4 | 2 | 4 | 4 | 3 | 2 | 3 | 2 | 0 |
| Soybean | 0 | 0 | 0 | 0 | 0 | 0 | 0 | 0 | 0 | 0 | 0 |
| Speedwell | 7 | 0 | 0 | 0 | 0 | 0 | 1 | 3 | 0 | 8 | 9 |
| Sugar beet | 5 | 0 | 0 | 0 | 0 | 0 | 5 | 2 | 0 | 0 | 0 |
| Velvetleaf | 0 | 4 | 3 | 0 | 4 | 2 | 4 | 0 | 4 | 0 | 0 |
| Wheat | 0 | 0 | 0 | 0 | 0 | 0 | 0 | 0 | 0 | 0 | 0 |
| Wild buckwheat | 0 | 0 | 0 | 0 | 0 | 0 | 3 | 0 | 0 | 0 | 0 |
| Wild oat | 0 | 4 | 0 | 0 | 0 | 0 | 0 | 0 | 0 | 0 | 0 |
| Barnyardgrass | — | — | — | — | — | — | — | — | — | — | — |
| Rice Japonica | — | — | — | — | — | — | — | — | — | — | — |
| Umbrella sedge | — | — | — | — | — | — | — | — | — | — | — |

| | COMPOUND | | |
|---|---|---|---|
| Rate (16 g/ha) | 3 | 5 | 10 |
| POSTEMERGENCE | | | |
| Barley Igri | — | — | — |
| Bedstraw | — | — | — |
| Blackgrass | — | — | — |
| Chickweed | — | — | — |
| Corn | — | — | — |

TABLE C-continued

| | | | |
|---|---|---|---|
| Cotton | — | — | — |
| Crabgrass | — | — | — |
| Downy brome | — | — | — |
| Duck salad | 0 | 0 | — |
| Giant foxtail | — | — | — |
| Lambsquarters | — | — | — |
| Morningglory | — | — | — |
| Pigweed | — | — | — |
| Rape | — | — | — |
| Ryegrass | — | — | — |
| Sorghum | — | — | — |
| Soybean | — | — | — |
| Speedwell | — | — | — |
| Sugar beet | — | — | — |
| Velvetleaf | — | — | — |
| Wheat | — | — | — |
| Wild buckwheat | — | — | — |
| Wild oat | — | — | — |
| Barnyardgrass | 0 | 0 | 0 |
| Rice Japonica | 1 | 0 | 0 |
| Umbrella sedge | 0 | 0 | — |

| | COMPOUND |
|---|---|
| Rate (16 g/ha) | 3 |
| PREEMERGENCE | |
| Barley Igri | 0 |
| Bedstraw | 0 |
| Blackgrass | 0 |
| Chickweed | 0 |
| Corn | 0 |
| Cotton | 0 |
| Crabgrass | 5 |
| Downy brome | 0 |
| Duck salad | — |
| Giant foxtail | 0 |
| Lambsquarters | 0 |
| Morningglory | 0 |
| Pigweed | 0 |
| Rape | 0 |
| Ryegrass | 0 |
| Sorghum | 0 |
| Soybean | 0 |
| Speedwell | 3 |
| Sugar beet | 4 |
| Velvetleaf | 0 |
| Wheat | 0 |
| Wild buckwheat | 0 |
| Wild oat | 0 |
| Barnyardgrass | — |
| Rice Japonica | — |
| Umbrella sedge | — |

TEST D

Seeds of barnyardgrass (*Echinochloa crusgalli*), black nightshade (*Solanum prycanthum dunal*), common ragweed (*Ambrosia elatior*), corn (*Zea mays*), cotton (*Gossypium hirsutum*), crabgrass (Digitaria spp.), fall panicum (*Panicum dicholomiflorum*), giant foxtail (*Setaria faberii*), green foxtail (*Setaria viridis*), johnsongrass (*Sorghum halepense*), lambsquarter (*Chenopodium album*), pigweed (*Amaranthus retroflexus*), signalgrass (*Brachiaria platyphylla*), smartweed (*Polygonum pensylvanicum*), soybean (*Glycine max*), wild proso (*Panicum miliaceum*) and wooly cupgrass (*Eriochloa villosa*) were planted into a silt loam soil. Test chemicals, dissolved in a non-phytotoxic solvent, were then applied to the soil surface within one clay after the seeds were planted.

Treated plants and untreated controls were maintained in the greenhouse approximately 21 days, then treated plants were compared to tintreated controls and visually evaluated. Plant response ratings, summarized in Table D, are reported on a 0 to 10 scale where 0 is no effect and 10 is complete control.

TABLE D

| | COMPOUND | |
|---|---|---|
| Rate (1000 g/ha) | 3 | 10 |
| PREEMERGENCE | | |
| Barnyardgrass | 10 | 10 |
| Black Nightshade | — | 10 |
| Common Ragweed | — | 9 |
| Corn G4689A | 10 | 9 |
| Cotton | 7 | 10 |
| Crabgrass | 10 | 10 |
| Fall Panicum | 10 | 10 |
| Giant Foxtail | 7 | 10 |
| Green Foxtail | 7 | 10 |
| Johnson Grass | 10 | 10 |
| Lambsquarter | — | 10 |
| Pigweed | — | 9 |
| Signalgrass | 10 | 10 |
| Soybean | 8 | 6 |
| Wild Proso | 10 | 10 |

| | COMPOUND | | | | | | | | | | | |
|---|---|---|---|---|---|---|---|---|---|---|---|---|
| Rate (500 g/ha) | 1 | 2 | 3 | 10 | 15 | 18 | 26 | 30 | 35 | 36 | 37 | 41 |
| PREEMERGENCE | | | | | | | | | | | | |
| Barnyardgrass | 10 | 10 | 10 | 10 | 10 | 10 | 10 | 10 | 10 | 10 | 10 | 10 |
| Black Nightshade | — | — | — | 10 | 10 | 10 | 10 | 10 | 10 | 10 | 10 | 10 |
| Common Ragweed | — | — | — | 7 | 9 | 10 | 8 | 9 | 5 | 8 | 10 | 10 |
| Corn G4689A | 7 | 9 | 8 | 7 | 8 | 9 | 6 | 6 | 6 | 7 | 8 | 7 |
| Cotton | 5 | 10 | — | 10 | — | 9 | 1 | 0 | 0 | 3 | 4 | 0 |
| Crabgrass | 10 | 10 | 10 | 10 | 10 | 10 | 10 | 10 | 10 | 10 | 10 | 10 |
| Fall Panicum | 10 | 10 | 10 | 10 | 10 | 10 | 10 | — | 10 | 10 | — | 10 |
| Giant Foxtail | 10 | 10 | 2 | 10 | 10 | 10 | 10 | 10 | 10 | 10 | 10 | 10 |
| Green Foxtail | 10 | 10 | 1 | 10 | 10 | 10 | 10 | 10 | 10 | 10 | 10 | 10 |
| Johnson Grass | 10 | 10 | 10 | 10 | 10 | 10 | 10 | 10 | 10 | 10 | 10 | 10 |
| Lambsquarter | — | — | — | 9 | 10 | 10 | 9 | 7 | 9 | 10 | 10 | 9 |
| Pigweed | — | — | — | 6 | 10 | 10 | 7 | 7 | 7 | 5 | 9 | 5 |
| Signalgrass | 10 | 10 | 10 | 10 | 10 | 10 | 10 | 10 | 10 | 10 | 10 | 10 |
| Smartweed | — | — | — | — | — | — | 10 | 9 | 7 | 7 | 9 | 9 |
| Soybean | 3 | 0 | 1 | 2 | 6 | 8 | 2 | 0 | 0 | 2 | 5 | 6 |
| Wild Proso | 10 | 10 | 10 | 10 | 10 | 10 | 10 | 10 | 10 | 10 | 10 | 10 |
| Wooly Cupgrass | — | — | — | — | 9 | 10 | 8 | — | 10 | 10 | — | 10 |

| | COMPOUND | | | | | | | | | | | |
|---|---|---|---|---|---|---|---|---|---|---|---|---|
| Rate (250 g/ha) | 1 | 2 | 3 | 10 | 15 | 18 | 26 | 30 | 35 | 36 | 37 | 41 |
| PREEMERGENCE | | | | | | | | | | | | |
| Barnyardgrass | 10 | 10 | 10 | 10 | 10 | 10 | 6 | 10 | 10 | 10 | 7 | 10 |
| Black Nightshade | — | — | — | 9 | 9 | 10 | 9 | 10 | 10 | 10 | 10 | 10 |
| Common Ragweed | — | — | — | 6 | 8 | 6 | 3 | 6 | 0 | 5 | 6 | 7 |
| Corn G4689A | 4 | 6 | 7 | 2 | 4 | 7 | 1 | 5 | 2 | 2 | 6 | 6 |
| Cotton | — | 7 | 0 | 10 | — | 0 | 0 | 0 | 0 | 0 | 3 | 0 |
| Crabgrass | 10 | 10 | 10 | 10 | 10 | 10 | 9 | 10 | 10 | 8 | 10 | 8 |
| Fall Panicum | 10 | 10 | 10 | 10 | 10 | 10 | 10 | — | 10 | 10 | — | 10 |
| Giant Foxtail | 10 | 10 | 1 | 10 | 10 | 10 | 10 | 10 | 10 | 10 | 10 | 10 |
| Green Foxtail | 10 | 10 | 1 | 10 | 10 | 10 | 10 | 10 | 10 | 10 | 10 | 10 |
| Johnson Grass | 10 | 10 | 10 | 10 | 10 | 10 | 6 | 7 | 10 | 10 | 10 | 10 |
| Lambsquarter | — | — | — | 8 | 8 | 10 | 7 | 9 | 9 | 9 | 10 | 9 |
| Pigweed | — | — | — | 5 | 6 | 6 | 4 | 6 | 5 | 3 | 8 | 5 |
| Signalgrass | 10 | 10 | 8 | 10 | 10 | 10 | 7 | 10 | 10 | 10 | 9 | 10 |
| Smartweed | — | — | — | — | — | — | 6 | 5 | 6 | 5 | 6 | 6 |
| Soybean | — | — | — | 0 | 0 | 3 | 0 | 0 | 0 | 0 | 1 | 0 |
| Wild Proso | 10 | 10 | 10 | 10 | 10 | 10 | 10 | 10 | 10 | 10 | 10 | 10 |
| Wooly Cupgrass | — | — | — | — | 8 | 10 | 7 | — | 9 | 9 | — | 10 |

| | COMPOUND | | | | | | | | | | | |
|---|---|---|---|---|---|---|---|---|---|---|---|---|
| Rate (125 g/ha) | 1 | 2 | 3 | 10 | 15 | 18 | 26 | 30 | 35 | 36 | 37 | 41 |
| PREEMERGENCE | | | | | | | | | | | | |

TABLE D-continued

| | | | | | | | | | | | | |
|---|---|---|---|---|---|---|---|---|---|---|---|---|
| Barnyardarass | 10 | 9 | 10 | 5 | 10 | 10 | 5 | 8 | 8 | 9 | 8 | 8 |
| Black Nightshade | — | — | — | 8 | 9 | 9 | 9 | 9 | 9 | 9 | 9 | 9 |
| Common Ragweed | — | — | — | 0 | 7 | 5 | 0 | 1 | 0 | 0 | 6 | 0 |
| Corn G4689A | 2 | 1 | 6 | 1 | 2 | 5 | 0 | 1 | 0 | 0 | 0 | 1 |
| Cotton | — | 0 | 0 | 0 | 0 | 0 | 0 | 0 | 0 | 0 | 0 | 0 |
| Crabgrass | 10 | 10 | 10 | 9 | 10 | 10 | 6 | 10 | 8 | 7 | 10 | 7 |
| Fall Panicum | 10 | 10 | 10 | 10 | 10 | 10 | 10 | — | 10 | 10 | — | 10 |
| Giant Foxtail | 10 | 10 | 1 | 6 | 9 | 10 | 10 | 9 | 9 | 10 | 10 | 9 |
| Green Foxtail | 7 | 10 | 0 | 6 | 10 | 10 | 10 | 6 | 9 | 10 | 7 | 7 |
| Johnson Grass | 6 | 10 | 10 | 9 | 10 | 10 | 6 | 7 | 7 | 10 | 9 | 8 |
| Lambsquarter | — | — | — | 3 | 8 | 9 | 7 | 8 | 3 | 7 | 8 | 8 |
| Pigweed | — | — | — | 4 | 4 | 3 | 4 | 1 | 4 | 2 | 6 | 2 |
| Signalgrass | 8 | 9 | 0 | 10 | 10 | 10 | 5 | 10 | 7 | 10 | 7 | 9 |
| Smartweed | — | — | — | — | — | — | 3 | 2 | 3 | 5 | 6 | 5 |
| Soybean | 0 | 0 | 0 | 0 | 0 | 0 | 0 | 0 | 0 | 0 | 0 | 0 |
| Wild Proso | 9 | 10 | 10 | 8 | 10 | 10 | 8 | 9 | 9 | 9 | 10 | 8 |
| Wooly Cupgrass | — | — | — | — | 8 | 10 | 7 | — | 6 | 6 | — | 9 |

| | COMPOUND | | | | | | | | | | | |
|---|---|---|---|---|---|---|---|---|---|---|---|---|
| Rate (62 g/ha) | 1 | 2 | 3 | 10 | 15 | 18 | 26 | 30 | 35 | 36 | 37 | 41 |
| PREEMERGENCE | | | | | | | | | | | | |
| Barnyardarass | 7 | 9 | 1 | 5 | 8 | 10 | 2 | 6 | 5 | 6 | 6 | 6 |
| Black Nightshade | — | — | — | 6 | 4 | 9 | 5 | 8 | 9 | 5 | 8 | 9 |
| Common Ragweed | — | — | — | 0 | 3 | 1 | 0 | 0 | 0 | 0 | 0 | 0 |
| Corn G4689A | 1 | 1 | 0 | 0 | 2 | 0 | 0 | 0 | 0 | 0 | 0 | 0 |
| Cotton | 0 | 0 | — | — | 0 | 0 | 0 | 0 | 0 | 0 | 0 | 0 |
| Crabgrass | 6 | 10 | 4 | 4 | 10 | 9 | 3 | 6 | 7 | 4 | 6 | 4 |
| Fall Panicum | 2 | 10 | 0 | 8 | 10 | 10 | 5 | — | 10 | 10 | — | 10 |
| Giant Foxtail | 5 | 6 | 0 | 1 | 9 | 10 | 6 | 6 | 9 | 6 | 9 | 8 |
| Green Foxtail | 4 | 6 | 0 | 0 | 9 | 10 | 5 | 4 | 6 | 6 | 6 | 6 |
| Johnson Grass | 1 | 2 | 10 | 1 | 10 | 6 | 2 | 1 | 5 | 5 | 2 | 4 |
| Lambsquarter | — | — | — | 0 | 1 | 7 | 5 | 7 | 0 | 0 | 4 | 6 |
| Pigweed | — | — | — | 0 | 0 | 2 | 3 | 1 | 3 | 2 | 0 | 2 |
| Signalgrass | 0 | 7 | 0 | 0 | 10 | 10 | 1 | 8 | 5 | 3 | 1 | 8 |
| Smartweed | — | — | — | — | — | — | 0 | 1 | 2 | 0 | 3 | 0 |
| Soybean | 0 | 0 | 0 | 0 | 0 | 0 | 0 | 0 | 0 | 0 | 0 | 0 |
| Wild Proso | 5 | 10 | 1 | 4 | 9 | 9 | 5 | 8 | 6 | 7 | 8 | 5 |
| Woolu Cupgrass | — | — | — | — | 8 | 9 | 5 | — | 6 | 5 | — | 4 |

| | COMPOUND | | | | | | | | | |
|---|---|---|---|---|---|---|---|---|---|---|
| Rate (31 g/ha) | 1 | 2 | 15 | 18 | 26 | 30 | 35 | 36 | 37 | 41 |
| PREEMERGENCE | | | | | | | | | | |
| Barnyardgrass | 0 | 0 | 4 | 6 | 0 | 2 | 0 | 0 | 5 | 1 |
| Black Nightshade | — | — | 4 | 7 | 3 | 2 | 0 | 0 | 5 | 8 |
| Common Ragweed | — | — | 0 | 0 | 0 | 0 | 0 | 0 | 0 | 0 |
| Corn G4689A | 0 | 1 | 0 | 0 | 0 | 0 | 0 | 0 | 0 | 0 |
| Cotton | 0 | 0 | 0 | — | 0 | 0 | 0 | 0 | 0 | 0 |
| Crabgrass | 0 | 3 | 5 | 6 | 0 | 3 | 0 | 0 | 5 | 0 |
| Fall Panicum | 0 | 0 | 6 | 10 | 0 | — | 9 | 0 | — | 5 |
| Giant Foxtail | 0 | 0 | 4 | 6 | 0 | 0 | 3 | 0 | 1 | 2 |
| Green Foxtail | 0 | 0 | 4 | 6 | 0 | 0 | 2 | 0 | 1 | 2 |
| Johnson Grass | 0 | 0 | 0 | 5 | 2 | 0 | 0 | 3 | 1 | 4 |
| Lambsquarter | — | — | 0 | 0 | 0 | 4 | 0 | 0 | 0 | 0 |
| Pigweed | — | — | 0 | 0 | 3 | 0 | 0 | 1 | 0 | 0 |
| Signalgrass | 0 | 0 | 8 | 9 | 0 | 0 | 1 | 0 | 0 | 5 |
| Smartweed | — | — | — | — | 0 | 0 | 0 | 0 | 0 | 0 |
| Soybean | 0 | 0 | 0 | 0 | 0 | 0 | 0 | 0 | 0 | 0 |
| Wild Proso | 0 | 0 | 3 | 9 | 0 | 0 | 0 | 4 | 2 | 4 |
| Wooly Cupgrass | — | — | 1 | 9 | 0 | — | 0 | 0 | — | 1 |

TEST E

Compounds evaluated in this test were formulated in a non-phytoxic solvent and applied to the soil surface before plant seedlings emerged (preemergence application) and to plants that were in the one-to-four leaf stage (postemergence application). A sandy loam soil was used for the preemergence test while a mixture of sandy loam soil and greenhouse potting mix in a 60:40 ratio was used for the postemergence test. Test compounds were applied within approximately one day after planting seeds for the preemergence test.

Plantings of these crops and weed species were adjusted to produce plants of appropriate size for the postemergence test. All plant species were grown using normal greenhouse practices. Crop and weed species include winter barley (*Hordeum vulgare* cv. 'Igri'), blackgrass (*Alopecurus myosuroides*), chickweed (*Stellaria media*), downy brome (*Bromus rectorum*), field violet (*Viola arvensis*), galium (*Galium aparine*), green foxtail (*Setaria viridis*), kochia (*Kochia scoparia*), lambsquarters (*Chenopodium album*), speedwell (*Veronica persica*), rape (*Brassica napus*), ryegrass (*Lolium multiflorum*), sugar beet (*Beta vulgrais* cv. 'US1'), sunflower (*Helianthus annuus* cv. 'Russian Giant'), spring wheat (*Triticum aestivum* cv. 'ERA'), winter wheat (*Triticum aestivum* cv. Talent'), wild buckwheat (*Polygonum convolvulus*), wild mustard (*Sinapis arvensis*), wild oat (*Avena fatua*), and wild radish (*Raphanus raphamstrum*).

Blackgrass, galium and wild oat were treated at two growth stages. The first stage (1) was when the plants had two to three leaves. The second stage (2) was when the plants had approximately four leaves or in the initial stages of tillering. Treated plants and untreated controls were maintained in a greenhouse for approximately 21 to 28 days, after which all treated plants were compared to untreated controls and visually evaluated. Plant response ratings, summarized in Table E, axe based upon a 0 to 10 scale where 0 is no effect and 10 is complete control. A dash response (–) means no test result.

TABLE E

| | COMPOUND | |
|---|---|---|
| Rate (1000 g/ha) | 10 | 15 |
| POSTEMERGENCE | | |
| Blackgrass (1) | 2 | 8 |
| Blackgrass (2) | 2 | 7 |
| Chickweed | 2 | 0 |
| Downy brome | 3 | 2 |
| Field violet | 0 | 0 |
| Galium (1) | 4 | 3 |
| Galium (2) | 3 | 3 |
| Green foxtail | 5 | 10 |
| Kochia | 0 | 0 |
| Lambsquarters | 7 | 2 |
| Speedwell | 0 | 3 |
| Rape | 2 | 3 |
| Ryegrass | 5 | 9 |
| Sugar beet | 3 | 2 |
| Sunflower | 2 | 5 |
| Wheat (Spring) | 3 | 3 |
| Wheat (Winter) | 2 | 2 |
| Wild buckwheat | 2 | 3 |
| Wild mustard | 3 | 4 |
| Wild oat (1) | 3 | 8 |
| Wild oat (2) | 2 | 8 |
| Wild radish | — | 2 |
| Winter Barley | 2 | 0 |

| | COMPOUND | |
|---|---|---|
| Rate (1000 g/ha) | 10 | 15 |
| PREEMERGENCE | | |
| Blackgrass (1) | 10 | 10 |
| Blackgrass (2) | 10 | 10 |
| Chickweed | 10 | 10 |
| Downy brome | 10 | 8 |
| Field violet | 10 | 4 |
| Galium (1) | 10 | 10 |
| Galium (2) | 10 | 10 |

TABLE E-continued

| | | |
|---|---|---|
| Green foxtail | 10 | 10 |
| Kochia | 10 | 10 |
| Lambsquarters | 10 | — |
| Speedwell | 10 | 8 |
| Rape | 9 | 10 |
| Ryegrass | 10 | 10 |
| Sugar beet | 9 | 9 |
| Sunflower | 5 | 4i |
| Wheat (Spring) | 5 | 4 |
| Wheat (Winter) | 5 | Q |
| Wild buckwheat | 9 | 2 |
| Wild mustard | 10 | 10 |
| Wild oat (1) | 10 | 10 |
| Wild oat (2) | 10 | 10 |
| Wild radish | 7 | 5 |
| Winter Barley | 2 | 5 |

| | COMPOUND | | | | | |
|---|---|---|---|---|---|---|
| Rate (500 g/ha) | 10 | 15 | 18 | 26 | 30 | 41 |
| POSTEMERGENCE | | | | | | |
| Blackgrass (1) | 0 | 3 | — | — | — | — |
| Blackgrass (2) | 0 | 3 | — | — | — | — |
| Chickweed | 0 | 0 | — | — | — | — |
| Downy brome | 0 | 0 | — | — | — | — |
| Field violet | 0 | 0 | — | — | — | — |
| Galium (1) | 0 | 0 | — | — | — | — |
| Galium (2) | 0 | 0 | — | — | 4 | — |
| Green foxtail | 2 | 7 | — | — | — | — |
| Kochia | 0 | 0 | — | — | — | — |
| Lambsquarters | 3 | 0 | — | — | — | — |
| Speedwell | 0 | 0 | — | — | — | — |
| Rape | 0 | 0 | — | — | — | — |
| Ryegrass | 2 | 4 | — | — | — | — |
| Sugar beet | 0 | 0 | — | — | — | — |
| Sunflower | 0 | 2 | — | — | — | — |
| Wheat (Spring) | 0 | 0 | — | — | — | — |
| Wheat (Winter) | 0 | 0 | — | — | — | — |
| Wild buckwheat | 0 | 0 | — | — | — | — |
| Wild mustard | 0 | 0 | — | — | — | — |
| Wild oat (1) | 0 | 3 | — | — | — | — |
| Wild oat (2) | 0 | 2 | — | — | — | — |
| Wild radish | — | 0 | — | — | — | — |
| Winter Barley | 0 | 0 | — | — | — | — |

| | COMPOUND | | | | | |
|---|---|---|---|---|---|---|
| Rate (500 g/ha) | 10 | 15 | 18 | 26 | 30 | 41 |
| PREEMERGENCE | | | | | | |
| Blackgrass (1) | 10 | 9 | 10 | 3 | 10 | 10 |
| Blackgrass (2) | 10 | 8 | 10 | 10 | 9 | 10 |
| Chickweed | 10 | 10 | 10 | 9 | 10 | 9 |
| Downy brome | 7 | 4 | 10 | 5 | 10 | 7 |
| Field violet | 10 | 2 | 10 | 6 | 8 | 10 |
| Galium (1) | 9 | 7 | 6 | 10 | 10 | 10 |
| Galium (2) | 10 | 7 | 10 | 10 | 10 | 10 |
| Green foxtail | 10 | 10 | 10 | 10 | 10 | 10 |
| Kochia | 10 | 6 | — | — | 10 | — |
| Lambsquarters | 10 | — | — | 10 | 10 | 9 |
| Speedwell | 10 | 6 | 10 | 9 | 8 | 10 |
| Rape | 6 | 8 | 8 | 9 | 9 | 9 |
| Ryegrass | 10 | 10 | 10 | 8 | 10 | 10 |
| Sugar beet | 8 | 6 | 8 | 5 | 7 | 7 |
| Sunflower | 3 | 2 | 8 | 10 | 10 | 10 |
| Wheat (Spring) | 2 | 2 | 0 | 0 | 7 | 4 |
| Wheat (Winter) | 2 | 1 | 5 | 4 | 9 | 6 |
| Wild buckwheat | 8 | 0 | — | 5 | 7 | 6 |
| Wild mustard | 7 | 8 | 10 | 10 | 10 | 10 |
| Wild oat (1) | 10 | 9 | 10 | 10 | 10 | 10 |
| Wild oat (2) | 10 | 8 | 10 | 10 | 10 | 10 |
| Wild radish | 5 | 2 | 9 | 8 | 8 | 10 |
| Winter Barley | 0 | 2 | 0 | 2 | 4 | 5 |

TABLE E-continued

| | COMPOUND | |
|---|---|---|
| Rate (250 g/ha) | 10 | 15 |
| POSTEMERGENCE | | |
| Blackgrass (1) | 0 | 0 |
| Blackgrass (2) | 0 | 0 |
| Chickweed | 0 | 0 |
| Downy brome | 0 | 0 |
| Field violet | 0 | 0 |
| Galium (1) | 0 | 0 |
| Galium (2) | 0 | 0 |
| Green foxtail | 0 | 2 |
| Kochia | 0 | 0 |
| Lambsquarters | 0 | 0 |
| Speedwell | 0 | 0 |
| Rape | 0 | 0 |
| Ryegrass | 0 | 0 |
| Sugar beet | 0 | 0 |
| Sunflower | 0 | 0 |
| Wheat (Spring) | 0 | 0 |
| Wheat (Winter) | 0 | 0 |
| Wild buckwheat | 0 | 0 |
| Wild mustard | 0 | 0 |
| Wild oat (1) | 0 | 0 |
| Wild oat (2) | 0 | 0 |
| Wild radish | — | 0 |
| Winter Barley | 0 | 0 |

| | COMPOUND | | | | | | | |
|---|---|---|---|---|---|---|---|---|
| Rate (250 g/ha) | 10 | 15 | 18 | 26 | 30 | 37 | 38 | 41 |
| PREEMERGENCE | | | | | | | | |
| Blackgrass (1) | 8 | 6 | 9 | 3 | 9 | 7 | 8 | 6 |
| Blackgrass (2) | 8 | 5 | 10 | 5 | 9 | 10 | 6 | 10 |
| Chickweed | 10 | 8 | 10 | 8 | 7 | 7 | 3 | 7 |
| Downy brome | 5 | 2 | 0 | 3 | 9 | 7 | 6 | 5 |
| Field violet | 10 | 0 | 10 | 6 | 7 | 7 | 4 | 10 |
| Galium (1) | 7 | 3 | 4 | 9 | 10 | 0 | 9 | 7 |
| Galium (2) | 8 | 3 | 10 | 5 | 10 | 10 | 10 | 9 |
| Green foxtail | 10 | 10 | 10 | 10 | 10 | 10 | 10 | 10 |
| Kochia | 8 | 2 | — | — | 9 | — | — | — |
| Lambsquarters | 6 | — | — | 9 | 10 | 9 | 8 | 8 |
| Speedwell | 10 | 4 | 10 | 9 | 7 | 8 | 10 | 10 |
| Rape | 2 | 5 | 6 | 2 | 9 | 2 | 5 | 4 |
| Ryegrass | 9 | 8 | 10 | 4 | 10 | 10 | 10 | 10 |
| Sugar beet | 6 | 4 | 8 | — | 7 | 5 | 3 | 7 |
| Sunflower | 0 | 0 | 7 | 10 | 10 | 10 | 3 | 10 |
| Wheat (Spring) | 0 | 0 | 0 | 0 | 6 | 3 | 2 | 4 |
| Wheat (Winter) | 0 | 0 | 0 | 3 | 6 | 2 | 1 | 5 |
| Wild buckwheat | 3 | 0 | — | 5 | 5 | 2 | 0 | 3 |
| Wild mustard | 4 | 6 | 10 | 10 | 10 | 6 | 9 | 9 |
| Wild oat (1) | 7 | 4 | 5 | 9 | 7 | 8 | 10 | 7 |
| Wild oat (2) | 7 | 4 | 10 | 10 | 10 | 10 | 10 | 10 |
| Wild radish | 2 | 0 | 9 | 8 | 5 | 8 | 1 | 10 |
| Winter Barley | 0 | 0 | 0 | 0 | 4 | 0 | 2 | 5 |

| | COMPOUND | | | | | | | | |
|---|---|---|---|---|---|---|---|---|---|
| Rate (125 g/ha) | 10 | 15 | 18 | 26 | 30 | 32 | 37 | 38 | 41 |
| PREEMERGENCE | | | | | | | | | |
| Blackgrass (1) | 3 | 3 | 8 | 2 | 5 | 0 | 4 | 2 | 5 |
| Blackgrass (2) | 3 | 2 | 6 | 3 | 7 | 5 | 9 | 4 | 5 |
| Chickweed | 9 | 5 | 6 | 7 | 4 | 0 | 2 | 3 | 3 |
| Downy brome | 2 | 0 | 0 | 0 | 2 | 0 | 0 | 4 | 5 |
| Field violet | 7 | 0 | 4 | 3 | 0 | 2 | 3 | 4 | 8 |
| Galium (1) | 4 | 0 | 4 | 0 | 5 | 0 | 0 | 2 | 0 |
| Galium (2) | 4 | 0 | 5 | 3 | 6 | 0 | 4 | 2 | 0 |
| Green foxtail | 10 | 7 | 10 | 10 | 10 | 10 | 10 | 10 | 10 |
| Kochia | 3 | 0 | — | — | 8 | — | — | — | — |
| Lambsquarters | 3 | — | — | 6 | 5 | 0 | 7 | 6 | 5 |
| Speedwell | 8 | 2 | 10 | 6 | 2 | 0 | 5 | 9 | 10 |
| Rape | 0 | 2 | 5 | 0 | 3 | 0 | 0 | 0 | 2 |
| Ryegrass | 7 | 5 | 8 | 0 | 10 | 4 | 10 | 3 | 5 |
| Sugar beet | 4 | 3 | 8 | 0 | 4 | 0 | 5 | 3 | 7 |
| Sunflower | 0 | 0 | 0 | 10 | 10 | — | 4 | 0 | 3 |
| Wheat (Spring) | 0 | 0 | 0 | 0 | 5 | 1 | 0 | 1 | 4 |
| Wheat (Winter) | 0 | 0 | 0 | 1 | 3 | 0 | 0 | 0 | 4 |
| Wild buckwheat | 0 | 0 | — | 5 | 5 | 0 | 0 | 0 | 3 |
| Wild mustard | 0 | 3 | 10 | 6 | 9 | 3 | 0 | 7 | 8 |
| Wild oat (1) | 3 | 3 | 0 | 2 | 3 | 0 | 5 | 5 | 5 |
| Wild oat (2) | 3 | 2 | 9 | 0 | 7 | 1 | 8 | 8 | 7 |
| Wild radish | 0 | 0 | 8 | 4 | 2 | 0 | 0 | 1 | 7 |
| Winter Barley | 0 | 0 | 0 | 0 | 1 | 0 | 0 | 0 | 4 |

| | COMPOUND | | | | | | | | |
|---|---|---|---|---|---|---|---|---|---|
| Rate (64 g/ha) | 10 | 15 | 18 | 26 | 30 | 32 | 37 | 38 | 41 |
| PREEMERGENCE | | | | | | | | | |
| Blackgrass (1) | 0 | 0 | 6 | 0 | 3 | 0 | 0 | 0 | 3 |
| Blackgrass (2) | 0 | 0 | 4 | — | 4 | 0 | 2 | 0 | 4 |
| Chickweed | 3 | 2 | 5 | 2 | 3 | 0 | 2 | 0 | 3 |
| Downy brome | 0 | 0 | 0 | 0 | 0 | 0 | 0 | 2 | 4 |
| Field violet | 3 | 0 | 3 | 3 | 0 | 0 | 0 | 3 | 7 |
| Galium (1) | 2 | 0 | 0 | 0 | 0 | 0 | 0 | 0 | 0 |
| Galium (2) | 2 | 0 | 5 | 3 | 0 | 0 | 2 | 0 | 0 |
| Green foxtail | 7 | 4 | 10 | 10 | 10 | 9 | 10 | 10 | 10 |
| Kochia | 0 | 0 | — | — | 8 | — | — | — | — |
| Lambsquarters | 0 | — | — | 6 | 5 | 0 | 6 | 5 | 4 |
| Speedwell | 4 | 0 | 10 | 2 | 0 | 0 | 2 | 1 | 8 |
| Rape | 0 | 0 | 0 | 0 | 0 | 0 | 0 | 0 | 0 |
| Ryegrass | 4 | 2 | 0 | 0 | 1 | 2 | 3 | 0 | 4 |
| Sugar beet | 2 | 0 | 6 | 0 | 3 | 0 | 2 | 2 | 4 |
| Sunflower | 0 | 0 | 0 | 10 | 3 | 0 | — | — | — |
| Wheat (Spring) | 0 | 0 | 0 | 0 | 5 | 0 | 0 | 1 | 4 |
| Wheat (Winter) | 0 | 0 | 0 | 0 | 3 | 0 | 0 | 0 | 4 |
| Wild buckwheat | 0 | 0 | 0 | 5 | 2 | 0 | 0 | 0 | 3 |
| Wild mustard | 0 | 0 | 5 | 0 | 7 | 3 | 0 | 0 | 8 |
| Wild oat (1) | 0 | 0 | 0 | 0 | 2 | 0 | 0 | 0 | 0 |
| Wild oat (2) | 0 | 0 | 3 | 0 | 3 | 0 | 0 | 5 | 5 |
| Wild radish | 0 | 0 | 5 | 4 | 0 | 0 | 0 | 0 | 6 |
| Winter Barley | 0 | 0 | 0 | 0 | 1 | 0 | 0 | 0 | 3 |

| | COMPOUND | | | | | | | |
|---|---|---|---|---|---|---|---|---|
| Rate (32 g/ha) | 10 | 18 | 26 | 30 | 32 | 37 | 38 | 41 |
| PREEMERGENCE | | | | | | | | |
| Blackgrass (1) | 0 | 3 | 0 | 0 | 0 | 0 | 0 | 0 |
| Blackgrass (2) | 0 | 0 | 0 | 0 | 0 | 0 | 0 | 2 |
| Chickweed | 0 | — | 0 | 0 | 0 | 0 | 0 | 2 |
| Downy brome | 0 | 0 | 0 | 0 | 0 | 0 | 0 | 3 |
| Field violet | 0 | — | 2 | 0 | 0 | 0 | 0 | 6 |
| Galium (1) | 0 | 0 | 0 | 0 | 0 | 0 | 0 | 0 |
| Galium (2) | 0 | 0 | 3 | 0 | 0 | 0 | — | 0 |
| Green foxtail | 4 | 4 | 10 | 5 | 3 | 10 | 10 | 8 |
| Kochia | 0 | — | — | — | — | — | — | — |
| Lambsquarters | 0 | — | 5 | 0 | 0 | 0 | 0 | 0 |
| Speedwell | 2 | 0 | 0 | 0 | 0 | 0 | 0 | 8 |
| Rape | 0 | 0 | 0 | 0 | 0 | 0 | 0 | 0 |
| Ryegrass | 0 | 0 | 0 | 1 | 2 | 0 | 0 | 2 |
| Sugar beet | 0 | 0 | 0 | 2 | 0 | 0 | 0 | 0 |
| Sunflower | 0 | 0 | 4 | 0 | 0 | — | — | 3 |
| Wheat (Spring) | 0 | 0 | 0 | 3 | 0 | 0 | 0 | 3 |
| Wheat (Winter) | 0 | 0 | 0 | 3 | 0 | 0 | 0 | 2 |
| Wild buckwheat | 0 | 0 | 0 | 0 | 0 | 0 | 0 | 3 |
| Wild mustard | 0 | — | 0 | 2 | 2 | 0 | 0 | 0 |
| Wild oat (1) | 0 | 0 | 0 | 2 | 0 | 0 | 0 | 0 |
| Wild oat (2) | 0 | 0 | 0 | 3 | 0 | 0 | 2 | 3 |
| Wild radish | — | 0 | 4 | 0 | 0 | 0 | 0 | 6 |
| Winter Barley | 0 | 0 | 0 | 1 | 0 | 0 | 0 | 1 |

TABLE E-continued

| | COMPOUND | | |
|---|---|---|---|
| Rate (16 g/ha) | 32 | 37 | 38 |
| PREEMERGENCE | | | |
| Blackgrass (1) | 0 | 0 | 0 |
| Blackarass (2) | 0 | 0 | 0 |
| Chickweed | 0 | 0 | 0 |
| Downy brome | 0 | 0 | 0 |
| Field violet | 0 | 0 | 0 |
| Galium (1) | 0 | 0 | 0 |
| Galium (2) | 0 | 0 | 0 |
| Green foxtail | 0 | 1 | 0 |
| Lambsquarters | 0 | 0 | 0 |
| Speedwell | 0 | 0 | 0 |
| Rape | 0 | 0 | 0 |
| Ryegrass | 0 | 0 | 0 |
| Sugar beet | 0 | 0 | 0 |
| Sunflower | 0 | 3 | — |
| Wheat (Spring) | 0 | 0 | 0 |
| Wheat (Winter) | 0 | 0 | 0 |
| Wild buckwheat | 0 | 0 | 0 |
| Wild mustard | 0 | 0 | 0 |
| Wild oat (1) | 0 | 0 | 0 |
| Wild oat (2) | 0 | 0 | 0 |
| Wild radish | 0 | 0 | 0 |
| Winter Barley | 0 | 0 | 0 |

What is claimed is:

1. A compound of the formula:

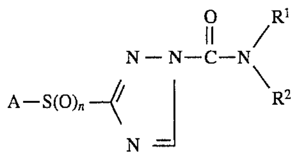

I wherein

A is a pyrazole ring substituted with 1 to 3 substituents selected from $R^3$, $R^4$, $R^5$ and $R^6$;

$R^1$ is H; $C_1$–$C_6$ alkyl optionally substituted with $C_1$–$C_3$ alkoxy or 1 to 5 halogens; C–$C_6$ cycloalkyl; $C_2$–$C_6$ alkenyl optionally substituted with 1 to 3 halogens; C–$C_6$ alkynyl; or $C_1$–$C_3$ alkoxy;

$R^2$ is $C_1$–$C_6$ alkyl optionally substituted with $C_1$–$C_3$ alkoxy or 1 to 5 halogens; C–$C_6$ cycloalkyl; $C_2$–$C_6$ alkenyl optionally substituted with 1 to 3 halogens; or C–$C_6$ alkynyl;

$R^3$, $R^4$ and $R^5$ are independently H; halogen; $C_1$–$C_6$ alkyl optionally substituted with one or more halogen, $C_1$–$C_6$ alkoxy, CN, $CO_2R^7$, $S(O)_mR^8$, $C(O)NR^9R^{10}$ or $SO_2NR^{13}R^{14}$; C–$C_6$ cycloalkyl; $C_2$–$C_6$ alkenyl; $C_2$–$C_6$ haloalkenyl; $C_2$–$C_6$ alkynyl; $C_1$–$C_6$ alkoxy; CN; $CO_2R^{11}$; $S(O)_nR^{12}$; $C(O)NR^{15}R^{16}$; $SO_2NR^{17}R^{18}$; $C(O)R^{19}$, $C(OR^{20})$ $(OR^{21})$ $R^{22}$; $CR^{23}$=$NOR^{24}$; $NO_2$; $NR^{25}R^{26}$; or phenyl or benzyl, each ring optionally substituted with 1 to 3 substituents selected from halogen, $C_1$–$C_3$ alkyl, $C_1$–$C_3$ haloalkyl and $C_1$–$C_3$ alkoxy;

$R^6$ is H; $C_1$–$C_6$ alkyl optionally substituted with one or more halogen, $C_1$–$C_6$ alkoxy, CN, $CO_2R^7$, $S(O)_mR^8$, $C(O)NR^9R^{10}$ or $SO_2NR^{13}R^{14}$; $C_2$–$C_6$ alkenyl; $C_2$–$C_6$ haloalkenyl; $C_2$–$C_6$ alkynyl; CN; $CO_2R^{11}$; $SO_2R^{12}$; $C(O)NR^{15}R^{16}$; $SO_2NR^{17}R^{18}$; or phenyl or benzyl, each ring optionally substituted with 1 to 3 substituents selected from halogen, $C_1$–$C_3$ alkyl, $C_1$–$C_3$ haloalkyl and $C_1$–$C_3$ alkoxy;

$R^7$ and $R^{11}$ are independently H, $C_1$–$C_3$ alkyl or allyl;

$R^8$ and $R^{12}$ are independently $C_1$–$C_3$ alkyl;

$R^9$, $R^{10}$, $R^{13}$, $R^{14}$, $R^{15}$, $R^{16}$, $R^{17}$ and $R^{18}$ are independently H or $C_1$–$C_3$ alkyl;

$R^{19}$, $R^{22}$ and $R^{23}$ are independently H or $C_1$–$C_3$ alkyl;

$R^{20}$ and $R^{21}$ are independently $C_1$–$C_3$ alkyl;

$R^{24}$ is H or $C_1$–$C_3$ alkyl;

$R^{25}$ and $R^{26}$ are independently H or $C_1$–$C_3$ alkyl; and m, n and p are independently 0, 1 or 2;

provided that a) $R^3$, $R^4$ and $R^5$ are independently bonded to carbon, and $R^6$ is bonded to nitrogen; and b) when $S(O)_n$ is bonded to nitrogen then n is 2.

2. A compound of claim 1 whereto n is 1 or 2.

3. A compound of claim 2 where A is

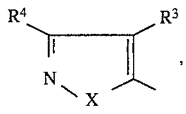

A-3

,

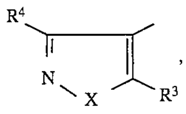

A-4

,

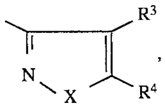

A-5

, or

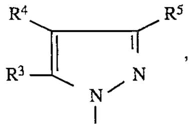

A-17

, wherein

X is $NR^6$.

4. A compound of claim 3 where n is 2 and $R^1$ and $R^2$ are independently $C_1$–$C_3$ alkyl or $C_2$–$C_3$ alkenyl.

5. A compound of claim 4 where $R^3$, $R^4$ and $R^5$ are independently H; F; Cl; Br; $C_1$–$C_3$ alkyl optionally substituted with one or more F, Cl, Br or $C_1$–$C_3$ alkoxy; cyclopropyl; $C_2$–$C_3$ alkenyl; $C_2$–$C_3$ haloalkenyl; $C_2$–$C_3$ alkynyl; $C_1$–$C_3$ alkoxy; CN; $CO_2(C_1$–$C_2$ alkyl), $S(O)_n(C_1$–$C_2$ alkyl); $C(O)NR^{15}R^{16}$; $SO_2NR^{17}R^{18}$; C(O) $R^{19}$, C $(OR^{20})$ $(OR^{21})$ $R^{22}$; $CR^{23}$=$NOR^{24}$; $NO_2$; $NR^{25}R^{26}$; or phenyl optionally substituted with 1 to 3 substituents selected from halogen, $C_1$–$C_3$ alkyl, $C_1$–$C_3$ haloalkyl and $C_1$–$C_3$ alkoxy;

$R^6$ is H, $C_1$–$C_4$ alkyl optionally substituted with one or more F, Cl, Br, $C_1$–$C_3$ alkoxy, CN, $CO_2$ $(C_1$–$C_2$ alkyl), $S(O)_m(C_1$–$C_2$ alkyl), $C(O)NR^9R^{10}$ or $SO_2NR^{13}R^{14}$; $C_2$–$C_4$ alkenyl; $C_2$–$C_4$ haloalkenyl; $C_2$–$C_4$ alkynyl; $CO_2R^{11}$; $SO_2(C_1$–$C_2$ alkyl); $C(O)NR^{15}R^{16}$; $SO_2NR^{17}R^{18}$; or phenyl or benzyl, each ring optionally substituted with 1 to 3 substituents selected from halogen, $C_1$–$C_3$ alkyl, $C_1$–$C_3$ haloalkyl and $C_1$–$C_3$ alkoxy;

$R^9$, $R^{10}$, $R^{13}$ and $R^{14}$ are independently $C_1$–$C_2$ alkyl;

$R^{11}$ is $C_1$–$C_2$ alkyl or allyl;

$R^{15}$, $R^{16}$, $R^{17}$, $R^{18}$, $R^{25}$ and $R^{26}$ are independently $C_1$–$C_3$ alkyl; and $R^{19}$, $R^{22}$ and $R^{23}$ are independently H or $C_1$–$C_2$ alkyl.

6. A compound of claim 5 where $R^1$ and $R^2$ axe independently ethyl or allyl; and $R^5$ is H, Cl, $CH_3$, $C_2H_5$ or $CF_3$.

7. A composition suitable for controlling the growth of undesired vegetation which comprises an effective mount of a compound of claim 2 and at least one of the following: surfactant, solid or liquid inert diluent.

8. A method for controlling the growth of undesired vegetation which comprises applying to the locus to be protected an effective amount of a compound of claim 2.

* * * * *